US007745587B2

(12) United States Patent
Devy et al.

(10) Patent No.: US 7,745,587 B2
(45) Date of Patent: Jun. 29, 2010

(54) ANTIBODIES THAT BIND MMP-14

(75) Inventors: Laetitia Devy, Liege (BE); Henk Pieters, Maastricht (NL); Robert C. Ladner, Ijamsville, MD (US); Rene Hoet, Maastricht (NL); Daniel T. Dransfield, Hanson, MA (US); Clive R. Wood, Boston, MA (US); Maria Henderikx, Hasselt (BE)

(73) Assignee: Dyax Corp., Cambridge, MA (US)

( * ) Notice: Subject to any disclaimer, the term of this patent is extended or adjusted under 35 U.S.C. 154(b) by 0 days.

(21) Appl. No.: 11/648,423

(22) Filed: Dec. 29, 2006

(65) Prior Publication Data

US 2007/0217997 A1  Sep. 20, 2007

Related U.S. Application Data

(60) Provisional application No. 60/755,376, filed on Dec. 30, 2005, provisional application No. 60/805,567, filed on Jun. 22, 2006, provisional application No. 60/870,566, filed on Dec. 18, 2006.

(51) Int. Cl.
C07K 16/40 (2006.01)
C07K 16/00 (2006.01)
A61K 39/395 (2006.01)

(52) U.S. Cl. .............. 530/388.26; 530/387.1; 530/387.3; 530/388.1; 424/130.1; 424/133.1; 424/141.1; 424/146.1

(58) Field of Classification Search ................ None
See application file for complete search history.

(56) References Cited

U.S. PATENT DOCUMENTS

| 6,984,619 | B1 | 1/2006 | Grdina et al. |
| 2004/0096899 | A1* | 5/2004 | Aoki et al. ............... 435/7.1 |
| 2005/0058725 | A1 | 3/2005 | McKearn et al. |
| 2005/0129615 | A1 | 6/2005 | Rozga et al. |
| 2006/0036076 | A1 | 2/2006 | Dransfield et al. |
| 2006/0275294 | A1 | 12/2006 | Omoigui |
| 2007/0117848 | A1 | 5/2007 | Puerta et al. |
| 2007/0217997 | A1 | 9/2007 | Devy et al. |
| 2008/0076120 | A1 | 3/2008 | Donaldson et al. |

FOREIGN PATENT DOCUMENTS

WO  2006065533  6/2006

OTHER PUBLICATIONS

Rudikoff et al. PNAS 1982 79:1979.*
Padlan et al. PNAS 1989, 86:5938-5942.*
Bendig Methods: A Companion to Methods in Enzymology 1995; 8:83-93.*
MacCallum et al. J. Mol. Biol. 1996, 262:732-745.*
Anilkumar et al., "Palmitoylation at Cys$^{574}$ is essential for MT1-MMP to promote cell migration,"*The FASEB Journal*, pp. 1-18, Jun. 9, 2005.

Aoki et al., "Cleavage of Apolipoprotein E by Membrane-Type Matrix Metalloproteinase-1 Abrogates Suppression of Cell Proliferation," *J. Biochem.* 137, pp. 95-99 (2005).
Bauvois, "Transmembrane proteases in cell growth and invasion: new contributors to angiogenesis?," *Oncogene*, 23, pp. 317-329, 2004.
Berno et al., "The 67 kDa laminin receptor increases tumor aggressiveness by remodeling laminin-1," *Endocrine-Related Cancer*, 12, pp. 393-406 (2005).
Butler et al., "The TIMP2 Membrane Type 1 Metalloproteinase "Receptor" Regulates the Concentration and Efficient Activation of Progelatinase A," *The Journal of Biological Chemistry*, 273(2), pp. 871-880, Jan. 9, 1998.
Cao et al., "Membrane type I-matrix metalloproteinase promotes human prostate cancer invasion and metastasis," *Thromb Haemost*, 93, p. 770-778, 2005.
Cao et al., "Membrane Type Matrix Metalloproteinase 1 Activates Pro-gelatinase A without Furin Cleavage of the N-terminal Domain," *The Journal of Biochemistry*, 271(47), pp. 30174-30180, Nov. 22, 1996.
Chang et al., "Activation Systems for Latent Matrix Metalloproteinase-2 Are Upregulated Immediately After Focal Cerebral Ischemia," *Journal of Cerebral Blood Flow & Metabolism*, 23, pp. 1408-1419, 2003.
Deryugina et al., "Unexpected Effect of Matrix Metalloproteinase Down-Regulation on Vascular Intravasation and Metastasis of Human Fibrosarcoma Cells Selected In vivo for High Rates of Dissemination," *Cancer Res.*, 65(23), pp. 10959-10969, Dec. 1, 2005.
Distler et al., "The induction of matrix metalloproteinase and cytokine expression in synovial fibroblasts stimulated with immune cell microparticles," *PNAS*, 102(8), pp. 2892-2897, Feb. 22, 2005.
Dong et al., "Expression of Membrane-Type Matrix Metalloproteinases 4, 5, and 6 in Mouse Corneas Infected with *P. aeruginosa*," *Investigative Ophthalmology & Visual Science*, 42(13), pp. 3223-3227, Dec. 2001.
Dong et al., "Matrix Metalloproteinase Activity and Osteoclasts in Experimental Prostate Cancer Bone Metastasis Tissue," *American Journal of Pathology*, 166(4), pp. 1173-1186, Apr. 2005.
El Bedoui et al., "Catechins prevent vascular smooth muscle cell invasion by inhibiting MT1-MMP activity and MMP-2 expression," *Cardiovascular Research*, 67, pp. 317-315, 2005.
Folgueras et al., "Matrix metalloproteinases in cancer: from new functions to improved inhibition strategies," *Int. J. Dev. Biol.*, 48, pp. 411-424 (2004).
Galvez et al., "Membrane Type 1-Matrix Metalloproteinase Is Regulated by Chemokines Monocyte-Chemoattractant Protein-1/CCL2 and Interleukin-8/CXCL8 in Endothelial Cells during Angiogenesis," *The Journal of Biological Chemistry*, 280(2), pp. 1292-1298, Jan. 14, 2005.
Giebel et al., "Matrix metalloproteinases in early diabetic retinopathy and their role in alteration of the blood-retinal barrier," *Laboratory Investigation*, 85, pp. 597-607, 2005.

(Continued)

*Primary Examiner*—Phillip Gambel
*Assistant Examiner*—Sharon Wen
(74) *Attorney, Agent, or Firm*—Lando & Anastasi, LLP

(57) ABSTRACT

Proteins that bind to matrix metalloproteinase 14 and methods of using such proteins are described.

32 Claims, 14 Drawing Sheets

OTHER PUBLICATIONS

Gilles et al., "Contribution of MT1-MMP and of human laminin-5 γ2 chain degradation to mammary epithelial cell migration," *Journal of Cell Science*, 114, pp. 2967-2976, 2001.

Gilles et al., "Implication of Collagen Type I-Induced Membrane-Type 1-Matrix Metalloproteinase Expression and Matrix Metalloproteinase-2 Activation in the Metastatic Progression of Breast Carcinoma," *Laboratory Investigation*, 76(5), pp. 651-660, 1997.

Goldbach-Mansky et al., "Active synovial matrix metalloproteinase-2 is associated with radiographic erosions in patients with early synovitis," *Arthritis Res.*, 2, pp. 145-153, 2000.

Grossman, "Profiling the evolution of human metastatic bladder cancer," *Urologic Oncology: Seminars and Original Investigations*, 23, p. 222, 2005.

Grossman, "Small cell carcinoma of the urinary bladder: a clinicopathologic analysis of 64 patients," *Urologic Oncology: Seminars and Original Investigations*, 23, p. 222-223, 2005.

Guo et al., "Up-Regulation of Angiopoietin-2, Matrix Metalloprotease-2, Membrane Type 1 Metalloprotease, and Laminin 5 γ 2 Correlates with the Invasiveness of Human Glioma," *American Journal of Pathology*, 166(3), pp. 877-890, Mar. 2005.

Haas, "Endothelial cell regulation of matrix metalloproteinases," *Can. J. Physiol. Pharmacol.*, 83, pp. 1-7, 2005.

Handsley et al., "Metalloproteinases and their inhibitors in tumor angiogenesis," *Int. J. Cancer*, 115, pp. 849-860, 2005.

Harrison et al., "The influence of CD44v3-v10 on adhesion, invasion and MMP-14 expression in prostate cancer cells," *Oncology Reports*, 15, pp. 199-206, 2006.

Hayashita-Kinoh et al., "Membrane-Type 5 Matrix Metalloproteinase Is Expressed in Differentiated Neurons and Regulates Axonal Growth," *Cell Growth & Differentiation*, 12, pp. 573-580, Nov. 2001.

Hernandez-Barrantes et al., "Regulation of membrane type-matrix metalloproteinases," *Cancer Biology*, 12, pp. 131-138, 2002.

Holmbeck et al., "MT1-MMP-Deficient Mice Develop Dwarfism, Osteopenia, Arthritis, and Connective Tissue Disease due to Inadequate Collagen Turnover," *Cell*, 99, pp. 81-92, Oct. 1, 1999.

Hotary et al., "Matrix Metalloproteinases (MMPs) Regulate Fibrin-invasive Activity via MT1-MMP-dependent and -independent Processes," *J. Exp. Med.*, 195(3), pp. 295-308, Feb. 4, 2002.

Hwang et al., "A proteomic approach to identify substrates of matrix metalloproteinase-14 in human plasma," *Biochimica et Biophysica Acta*, 1702, pp. 79-87, 2004.

Iida et al., "Melanoma Chondroitin Sulfate Proteoglycan Regulates Matrix Metalloproteinase-dependent Human Melanoma Invasion into Type I Collagen," *The Journal of Biological Chemistry*, 276(22), pp. 18786-18794, Jun. 1, 2001.

Itoh et al., "MT1-MMP: A Potent Modifier of Pericellular Microenvironment," *Journal of Cellular Physiology*, 206, pp. 1-8, 2006.

Jaworski et al., "Developmental regulation of membrane type-5 matrix metalloproteinase (MT5-MMP) expression in the rat nervous system," *Brain Research*, 860, pp. 174-177, 2000.

Kang et al., "Functional characterization of MT3-MMP in transfected MDCK cells: progelatinase A activation and tubulogenesis in 3-D collagen lattice," *The FASEB Journal*, 14, pp. 2559-2568, Dec. 2000.

Kevorkian et al., "Expression Profiling of Metalloproteinases and Their Inhibitors in Cartilage," *Arthritis & Rheumatism*, 50(1), pp. 131-141, Jan. 2004.

Kinoshita et al., "TIMP-2 Promotes Activation of Progelatinase A by Membrane-type 1 Matrix Metalloproteinase Immobilized on Agarose Beads," *The Journal of Biological Chemistry*, 273(26), pp. 16098-16103, Jun. 26, 1998.

Kitagawa et al., "Expression of Messenger RNAs for Membrane-Type 1, 2, and 3 Matrix Metalloproteinases in Human Renal Cell Carcinomas," *The Journal of Urology*, 162, pp. 905-909, Sep. 1999.

Kluft, "The Fibrinolytic System and Thrombotic Tendency," *Pathophysiology of Haemostasis and Thrombosis*, vol. 33, No. 5-6, pp. 425-429, Sep.-Oct. 2003/2004.

Knauper et al., "Cellular Mechanisms for Human Procollagenase-3 (MMP-13) Activation," *The Journal of Biological Chemistry*, 271(29), pp. 17124-17131, Jul. 19, 1996.

Komori et al., "Absence of mechanical allodynia and Aβ-fiber sprouting after sciatic nerve injury in mice lacking membrane-type 5 matrix metalloproteinase," *FEBS Letters*, 557, pp. 125-128, 2004.

Konaka et al., "A Human Seminoma Xenograft Model With Regional Lymph Node Metastasis," *The Journal of Urology*, 161, pp. 342-248, Jan. 1999.

Koshida et al., "Correlation Between Expression of Metastasis-Related Genes and Lymph Node Metastasis in Testicular Cancer," *Acta Urol. Jpn.*, 46(10), pp. 775-781, Oct. 2000.

Kousidou et al., "Genistein suppresses the invasive potential of human breast cancer cells through transcriptional regulation of metalloproteinases and their tissue inhibitors," *International Journal of Oncology*, 26(4), pp. 1101-1109, Apr. 2005.

Lafleur et al., "Endothelial tubulogenesis within fibrin gels specifically requires the activity of membrane-type-matrix metalloproteinases (MT-MMPs)," *Journal of Cell Science*, 115(17), pp. 3427-3438, 2002.

Lafleur et al., "Upregulation of matrix metalloproteinases (MMPs) in breast cancer xenografts: A major induction of stromal MMP-13," *Int. J. Cancer*, 114, pp. 544-554 (2005).

Lee et al., "Unveiling the Surface Epitopes That Render Tissue Inhibitor of Metalloproteinase-1 Inactive against Membrane Type 1-Matrix Metalloproteinase," *The Journal of Biological Chemistry*, 278(41), pp. 40224-40230, Oct. 10, 2003.

Llano et al., "Identification and Characterization of Human MT5-MMP, a New Membrane-bound Activator of Progelatinase A Overexpressed in Brain Tumors," *Cancer Research*, 59, pp. 2570-2576, Jun. 1, 1999.

Lopez et al., "Human Carcinoma Cell Growth and Invasiveness Is Impaired by the Propeptide of the Ubiquitous Proprotein Convertase Furin," *Cancer Research*, 65(10), pp. 4162-4171, May 15, 2005.

Manes et al., "Identification of Insulin-like Growth Factor-binding Protein-1 as a Potential Physiological Substrate for Human Stromelysin-3," *The Journal of Biological Chemistry*, 272(41), pp. 25706-25712, Oct. 10, 1997.

Maquoi et al., "Membrane Type 1 Matrix Metalloproteinase-associated Degradation of Tissue Inhibitor of Metalloproteinase 2 in Human Tumor Cell Lines," *The Journal of Biological Chemistry*, 275(15), pp. 11368-11378, Apr. 14, 2000.

May et al., "Plasminogen and matrix metalloproteinase activation by enzymatically modified low density lipoproteins in monocytes and smooth muscle cells," *Thromb. Haemost.*, 93, pp. 710-715, 2005.

Minond et al., "Matrix Metalloproteinase Triple-Helical Peptidase Activities Are Differentially Regulated by Substrate Stability," *Biochemistry*, 43, pp. 11474-11481, 2004.

Munshi et al., "Differential Regulation of Membrane Type 1-Matrix Metalloproteinase Activity by ERK ½ and p38 MAPK-modulated Tissue Inhibitor of Metalloproteinases 2 Expression Controls Transforming Growth Factor-β1-induced Pericellular Collagenolysis," *The Journal of Biological Chemistry*, 279(37), pp. 39042-39050, Sep. 10, 2004.

Murphy et al., "Role of TIMPs (tissue inhibitors of metalloproteinases) in pericellular proteolysis: the specificity is in the detail," *Biochem. Soc. Symp.*, 70, pp. 65-80, 2003.

Nuttall et al., "Elevated Membrane-Type Matrix Metalloproteinases in Gliomas Revealed by Profiling Proteases and Inhibitors in Human Cancer Cells," *Molecular Cancer Research*, vol. 1, pp. 333-345, Mar. 2003.

Ohnishi et al., "Coordinate expression of membrane type-matrix metalloproteinases-2 and 3 (MT2-MMP and MT3-MMP) and matrix metalloproteinase-2 (MMP-2) in primary and metastatic melanoma cells," *European Journal of Dermatology*, 11(5), pp. 420-423, Sep.-Oct. 2001.

Osenkowski et al., "Processing, Shedding, and Endocytosis of Membrane Type 1-Matrix Metalloproteinase (MT1-MMP)," *Journal of Cellular Physiology*, 200, pp. 2-10, 2004.

Pap et al., "Differential Expression Pattern of Membrane-Type Matrix Metalloproteinases in Rheumatoid Arthritis," *Arthritis & Rheumatism*, 43(6), pp. 1226-1232, Jun. 2000.

Pei, "Identification and Characterization of the Fifth Membrane-type Matrix Metalloproteinase MT5-MMP," *The Journal of Biological Chemistry*, 274(13), pp. 8925-8932, Mar. 26, 1999.

Philip et al., "Matrix metalloproteinase-2: Mechanism and regulation of NF-κB-mediated activation and its role in cell motility and ECM-invasion," *Glycoconjugate Journal*, 21, pp. 429-441, 2004.

Pilorget et al., "Inhibition of angiogenic properties of brain endothelial cells by platelet-derived sphingosine-1-phosphate," *Journal of Cerebral Blood Flow & Metabolism*, 25, pp. 1171-1182, 2005.

Plaisier et al., "Involvement of Membrane-Type Matrix Metalloproteinases (MT-MMPs) in Capillary Tube Formation by Human Endometrial Microvascular Endothelial Cells: Role of MT3-MMP," *The Journal of Clinical Endocrinology & Metabolism*, 89(11), pp. 5828-5836, 2004.

Rajavashisth et al., "Membrane Type 1 Matrix Metalloproteinase Expression in Human Atherosclerotic Plaques: Evidence for Activation by Proinflammatory Mediators," *Circulation*, 99, pp. 3103-3109, 1999.

Ray et al., "Induction of the MMP-14 Gene in Macrophages of the Atherosclerotic Plaque: Role of SAF-1 in the Induction Process," *Circulation Research*, 95, pp. 1082-1090, 2004.

Raymond et al., "Recanalization of arterial thrombus, and inhibition with β-radiation in a new murine carotid occlusion model: mRNA expression of angiopoietins, metalloproteinases, and their inhibitors," *Journal of Vascular Surgery*, 40(6), pp. 1190-1198, Dec. 2004.

Roebuck et al., Matrix Metalloproteinase Expression Is Related to Angiogenesis and Histologic Grade in Spindle Cell Soft Tissue Neoplasms of the Extremities, *American Journal of Clinical Pathology*, 123(3), pp. 405-414, Mar. 2005.

Romanic et al., "Upregulated expression of human membrane type-5 matrix metalloproteinase in kidneys from diabetic patients," *Am J Physiol Renal Physiol*, 281, F309-317, 2001.

Sato et al., "Roles of membrane-type matrix metalloproteinase-1 in tumor invasion and metastasis," *Cancer Sci*, 96(4), pp. 212-217, Apr. 2005.

Savinov et al., "Inhibition of Membrane Type-1 Matrix Metalloproteinase by Cancer Drugs Interferes with the Homing of Diabetogenic T Cells into the Pancreas," *The Journal of Biological Chemistry*, 280(30), pp. 27755-27758, Jul. 29, 2005.

Sekine-Aizawa et al., "Matrix metalloproteinase (MMP) system in brain: identification and characterization of brain-specific MMP highly expressed in cerebellum," *European Journal of Neuroscience*, 13, pp. 935-948, 2001.

Shofuda et al., "Expression of Three Membrane-type Matrix Metalloproteinases (MT-MMPs) in Rat Vascular Smooth Muscle Cells and Characterization of MT3-MMPs with and without Transmembrane Domain," *The Journal of Biological Chemistry*, 272(15), pp. 9749-9754, Apr. 11, 1997.

Sounni et al., "Up-regulation of Vascular Endothelial Growth Factor-A by Active Membrane-type 1 Matrix Metalloproteinase through Activation of Src-Tyrosine Kinases,", *The Journal of Biological Chemistry*, 279(14), pp. 13564-13574, Apr. 2, 2004.

Stadlmann et al., "Cytokine-regulated expression of collagenase-2 (MMP-8) is involved in the progression of ovarian cancer," *European Journal of Cancer*, 39, pp. 2499-2505, 2003.

Stawowy et al., "Furin-Like Proprotein Convertases Are Central Regulators of the Membrane Type Matrix Metalloproteinase-Pro-Matrix Metalloproteinase-2 Proteolytic Cascade in Atherosclerosis," *Circulation*, 111, pp. 2820-2827, 2005.

Strongin et al., "Mechanism of Cell Surface Activation of 72-kDA Type IV Collagenase," *The Journal of Biological Chemistry*, 270(10), pp. 5331-5338, Mar. 10, 1995.

Suenaga et al., "CD44 binding through the hemopexin-like domain is critical for its shedding by membrane-type 1 matrix metalloproteinase," *Oncogene*, 24, pp. 859-868, 2005.

Sun et al., "Expression of mRNA for Membrane-Type 1, 2, and 3 Matrix Metalloproteinases in Human Laryngeal Cancer," *Chinese Medical Sciences Journal*, 19(3), pp. 170-173, Sep. 2004.

Szabova et al., "Expression Pattern of Four Membrane-Type Matrix Metalloproteinases in the Normal and Diseased Mouse Mammary Gland," *Journal of Cellular Physiology*, 205, pp. 123-132, 2005.

Takino et al., "Identification of the Second Membrane-type Matrix Metalloproteinase (MT-MMP-2) Gene from a Human Placenta cDNA Library," *The Journal of Biological Chemistry*, 270(39), pp. 23013-23020, Sep. 29, 1995.

Tanimura et al., "Specific blockade of the ERK pathway inhibits the invasiveness of tumor cells: down-regulation of matrix metalloproteinase-3/-9/-14 and CD 44," *Biochemical and Biophysical Research Communications*, 304, pp. 801-806, 2003.

Tchetina et al., "Increased Type II Collagen Degradation and Very Early Focal Cartilage Degeneration Is Associated with Upregulation of Chondrocyte Differentiation Related Genes in Early Human Articular Cartilage Lesions," *The Journal of Rheumatology*, 32(5), pp. 876-886, 2005.

Toth et al., "Pro-MMP-9 activation by the MT1-MMP/MMP-2 axis and MMP-3: role of TIMP-2 and plasma membranes," *Biochemical and Biophysical Research Communications*, 308, pp. 386-395, 2003.

Trisciuoglio et al., "Bcl-2 Overexpression in Melanoma Cells Increases Tumor Progression-Associated Properties and In Vivo Tumor Growth," *Journal of Cellular Physiology*, 205, pp. 414-421, 2005.

Udayakumar et al., "Fibroblast Growth Factor-I Transcriptionally Induces Membrane Type-I Matrix Metalloproteinase Expression in Prostate Carcinoma Cell Line," *The Prostate*, 58, pp. 66-75, 2004.

Ueno et al., "Expression and Tissue Localization of Membrane-Types 1, 2, and 3 Matrix Metalloproteinases in Human Invasive Breast Carcinomas," *Cancer Research*, 57, pp. 2055-2060, May 15, 1997.

Uzui et al., "Increased Expression of Membrane Type 3-Matrix Metalloproteinase in Human Atherosclerotic Plaque: Role of Activated Macrophages and Inflammatory Cytokines," *Circulation*, 106, pp. 3024-3030, 2002.

Van Meter et al., "Induction of membrane-type-1 matrix metalloproteinase by epidermal growth factor-mediated signaling in gliomas," *Neuro-Oncology*, pp. 188-199, Jul. 2004.

Wan et al., "Effects of losartan on MT3-MMP and TIMP2 mRNA expressions in diabetic rat kidney," *Journal of First Military Medical University*, 24(12), pp. 1391-1394, Dec. 2004.

Wang et al., "Expression, purification and characterization of recombinant mouse MT5-MMP protein products," *FEBS Letters*, 462, pp. 261-266, 1999.

Wang et al., "The Hemopexin Domain of Membrane-type Matrix Metalloproteinase-1 (MT1-MMP) Is Not Required for Its Activation of proMMP2 on Cell Surface but Is Essential for MT1-MMP-mediated Invasion in Three-dimensional Type I Collagen," *The Journal of Biological Chemistry*, 279(49), pp. 51148-51155, Dec. 3, 2004.

Yoshiyama et al., "Expression of the membrane-type 3 matrix metalloproteinase (MT3-MMP) in human brain tissue," *Acta Neuropathol*, 96, pp. 347-350, 1998.

Zhao et al., "Differential Inhibition of Membrane Type 3 (MT3)-Matrix Metalloproteinase (MMP) and MT1-MMP by Tissue Inhibitor of Metalloproteinase (TIMP)-2 and TIMP-3 Regulates Pro-MMP-2 Activation," *The Journal of Biological Chemistry*, 279(10), pp. 8592-8601, Mar. 5, 2004.

Zucker et al., "Imaging metalloproteinase activity in vivo," *Nature Medicine*, 7(6), pp. 655-656, Jun. 2001.

Zucker et al., "Membrane Type-Matrix Metalloproteinases (MT-MMP)," *Current Topics in Developmental Biology*, 54, pp. 1-74, 2003.

Zucker et al., "Role of matrix metalloproteinases (MMPs) in colorectal cancer," Cancer and Metastasis Reviews, Vol. 23, pp. 101-117, 2004.

Galvez et al., "Membrane Type 1-Matrix Metalloproteinase Is Activated during Migration of Human Endothelial Cells and Modulates Endothelial Motility and Matrix Remodeling," The Journal of Biological Chemistry, 276(40), pp. 37491-37500, Oct. 5, 2001.

OMIM Accession No. 600754; Matrix Metalloproteinase 14; Aug. 28, 1995.

International Search Report dated May 14, 2008 from corresponding International PCT Application PCT/US2006/049556.

International Preliminary Report on Patentability and Written Opinion dated Jul. 1, 2008 from corresponding International PCT Application PCT/US2006/049556.

International Search Report dated May 15, 2009 from International Application No. PCT/US09/32384.

Liu et al., "Eradication of large colon tumor xenografts by targeted delivery of maytansinoids", Proc. Natl. Acad. Sci. USA, Aug. 1996, vol. 93, pp. 8618-8623.

International Search Report including Written Opinion dated Oct. 8, 2009 from International Application No. PCT/US09/41632.

Tornetta el al., "Isolation of human anti-idiotypic antibodies by phage display for clinical immune response assays" Journal of Immunological Methods, vol. 328, pp. 34-44, 2007.

Devy et al., "Potent and selective antibody inhibitor of human matrix metalloproteinase-14 (MMP-14) inhibits tumor growth, invasion and angiogenesis," American Society of Clinical Oncology [Online], 2007 (retrieved online on Sep. 29, 2009), retrieved from the internet at URL:http://www.asco.org/ASCOv2IMeetings/Abstracts &vmview=abst_detail_view&confID=52&abstractID=40128; abstract.

Peterson et al., "Monoclonal antibody form and function: Manufacturing the right antibodies 13-14 for treating drug abuse," The AAPS Journal, 2006, vol. 8, No. 2, pp. E383-E390; 2006.

International Search Report including Written Opinion dated Feb. 24, 2009 from International Application No. PCT/US08/87230.

International Search Report including Written Opinion dated Jun. 1, 2009 from International Application No. PCT/US08/87236.

Extended European Search Report dated Apr. 8, 2010 from European Application No. EP 06848335.3.

Li et al., "Immunological Characterization of Cell-Surface and Soluble Forms of Membrane Type 1 Matrix Metalloproteinase in Human Breast Cancer Cells and in Fibroblasts", Molecular Carcinogenesis, vol. 22, No. 2, pp. 84-94, Jun. 1, 1998.

Shinoda et al., "A Novel Matrix Metalloproteinase Inhibitor, FYK-1388 Suppresses Tumor Growth, Metastasis and Angiotenesis by Human Fibrasarcoma Cell Line", International Journal of Oncology, vol. 22, No. 2, pp. 281-288, Feb. 1, 2003.

* cited by examiner

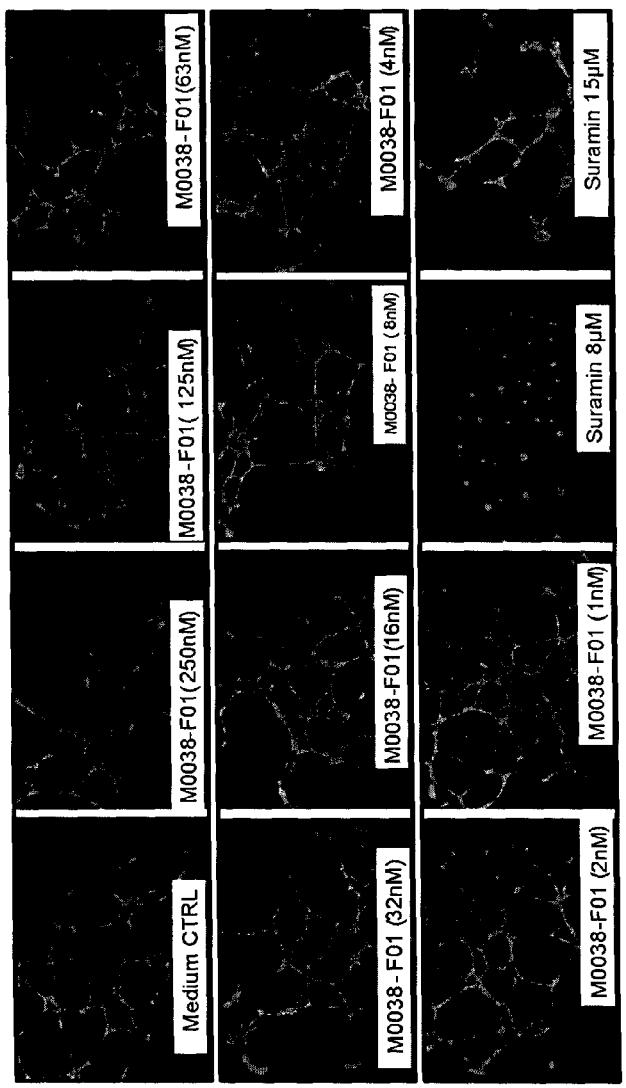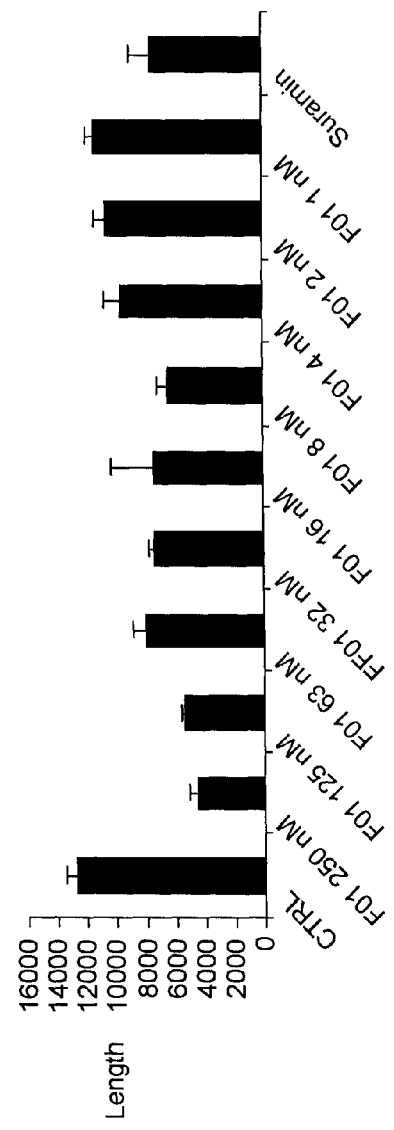

US 7,745,587 B2

ANTIBODIES THAT BIND MMP-14

CROSS-REFERENCE TO RELATED APPLICATIONS

This application claims priority to U.S. Application Ser. No. 60/755,376, filed on Dec. 30, 2005; U.S. Application Ser. No. 60/805,567, filed on Jun. 22, 2006; and U.S. Application Ser. No. 60/870,566, filed on Dec. 18, 2006. The disclosures of the prior applications are considered part of (and are incorporated by reference in) the disclosure of this application.

BACKGROUND

The membrane type (MT)- matrix metalloproteinases (MMPs) constitute a sub-group of membrane-anchored MMPs that are major mediators of pericellular proteolysis and physiological activators of pro-MMP-2. MT-MMPs activate the zymogenic form of MMP-2 (pro-MMP-2 or pro-gelatinase A) (Hernandez-Barrantes et al, 2002, Semin. Cancer Biol, 12:131-8; Zucker et al, 2003, Curr Top Dev Biol, 54: 1-74). MMP-2, in turn, can activate pro-MMP-9 (Toth et al, 2003, Biochem Biophys Res Commun, 308:386-95). The MT-MMPs comprise six members of plasma-tethered MMPs, which include four type I transmembrane enzymes (MMP-14, -15, -16, and -24) and two glycosylphosphatidylinositol-anchored enzymes (MMP-17, and -25) (Zhao et al, 2004, J Biol Chem, 279: 8592-8601). In addition to being potent extracellular matrix (ECM)-degrading enzymes, the type I transmembrane MT-MMPs can also initiate a cascade of zymogen activation on the cell surface.

SUMMARY

This disclosure relates, inter alia, to proteins that bind MMP-14, herein referred to as "MMP-14 binding proteins," and methods of identifying and using such proteins. These proteins include antibodies and antibody fragments (e.g., primate antibodies and Fabs, especially human antibodies and Fabs) that bind to and/or inhibit MMP-14 (e.g., human MMP-14). The MMP-14 binding proteins can be used in the treatment of diseases, particularly human disease, such as cancer, in which excess or inappropriate activity of MMP-14 features. In many cases, the proteins have tolerable low or no toxicity.

Some of these binding proteins also bind to and/or inhibit other type I transmembrane enzymes, such as MMP-16 and MMP-24. Ability to inhibit two or more of MMP-14, 16, and 24 is useful for treating diseases and conditions to which these MMPs collectively contribute.

In one aspect, the disclosure features a protein (e.g., an isolated protein) that binds to MMP-14 (e.g., human MMP-14) and includes at least one immunoglobulin variable region. For example, the protein includes a heavy chain (HC) immunoglobulin variable domain sequence and a light chain (LC) immunoglobulin variable domain sequence. In one embodiment, the protein binds to and inhibits MMP-14, e.g., human MMP-14.

The protein can include one or more of the following characteristics: (a) a human CDR or human framework region; (b) the HC immunoglobulin variable domain sequence comprises one or more CDRs that are at least 85, 88, 90, 92, 94, 95, 96, 97, 98, 99, or 100% identical to a CDR of a LC variable domain described herein; (c) the LC immunoglobulin variable domain sequence comprises one or more CDRs that are at least 85, 88, 90, 92, 94, 95, 96, 97, 98, 99, or 100% identical to a CDR of a HC variable domain described herein; (d) the LC immunoglobulin variable domain sequence is at least 85, 88, 90, 92, 94, 95, 96, 97, 98, 99, or 100% identical to a LC variable domain described herein; (e) the HC immunoglobulin variable domain sequence is at least 85, 88, 90, 92, 94, 95, 96, 97, 98, 99, or 100% identical to a HC variable domain described herein; (f) the protein binds an epitope bound by a protein described herein, or an epitope that overlaps with such epitope; and (g) a primate CDR or primate framework region.

The protein can bind to MMP-14, e.g., human MMP-14, with a binding affinity of at least $10^5$, $10^6$, $10^7$, $10^8$, $10^9$, $10^{10}$ and $10^{11}$ M$^{-1}$. In one embodiment, the protein binds to MMP-14 with a $K_{off}$ slower than $1\times10^{-3}$, $5\times10^{-4}$ s$^{-1}$, or $1\times10^{-4}$ s$^{-1}$. In one embodiment, the protein binds to MMP-14 with a $K_{on}$ faster than $1\times10^2$, $1\times10^3$, or $5\times10^3$ M$^{-1}$s$^{-1}$. In one embodiment, the protein inhibits human MMP-14 activity, e.g., with a Ki of less than $10^{-5}$, $10^{-6}$, $10^{-7}$, $10^{-8}$, $10^{-9}$, and $10^{-10}$ M. The protein can have, for example, an IC50 of less than 100 nM, 10 nM or 1 nM. For example, the protein modulates MMP-14 binding to proMMP-2, e.g., by inhibiting activation of proMMP-2. The protein may inhibit MMP-14 activation of pro-MMP2 in vitro in PMA-activated HT-1080 cells. The affinity of the protein for MMP-14 can be characterized by a $K_D$ of less than 100 nm, less than 10 nM, or less than 2.4 nM.

In one embodiment, the protein binds the catalytic domain of human MMP-14, e.g., the protein contacts residues in or near the active site of MMP-14.

In one embodiment, the protein also binds to MMP-16 and/or MMP-24, e.g., with a binding affinity of at least $10^5$, $10^6$, $10^7$, $10^8$, $10^9$, $10^{10}$ and $10^{11}$ M$^{-1}$. For example, the protein binds to both MMP-14 and to MMP-16 or MMP-24 with a binding affinity of at least $10^5$, $10^6$, $10^7$, $10^8$, $10^9$, $10^{10}$ and $10^{11}$ M$^{-1}$.

In a preferred embodiment, the protein is a human antibody having the light and heavy chains of antibodies picked from the list comprising M0031-C02, M0031-F01, M0033-H07, M0037-C09, M0037-D01, M0038-E06, M0038-F01, M0038-F08, M0039-H08, M0040-A06, M0040-A11, and M0043-G02. In a preferred embodiment, the protein is a human antibody having its heavy chain picked from the list comprising M0031-C02, M0031-F01, M0033-H07, M0037-C09, M0037-D01, M0038-E06, M0038-F01, M0038-F08, M0039-H08, M0040-A06, M0040-A11, and M0043-G02. In a preferred embodiment, the protein is a human antibody having its light chain picked from the list comprising M0031-C02, M0031-F01, M0033-H07, M0037-C09, M0037-D01, M0038-E06, M0038-F01, M0038-F08, M0039-H08, M0040-A06, M0040-A11, and M0043-G02. In a preferred embodiment, the protein is a human antibody having one or more heavy chain CDRs picked from the corresponding CDRs of the list of heavy chains comprising M0031-C02, M0031-F01, M0033-H07, M0037-C09, M0037-D01, M0038-E06, M0038-F01, M0038-F08, M0039-H08, M0040-A06, M0040-A11, and M0043-G02. In a preferred embodiment, the protein is a human antibody having one or more light chain CDRs picked from the corresponding CDRs of the list of heavy chains comprising M0031-C02, M0031-F01, M0033-H07, M0037-C09, M0037-D01, M0038-E06, M0038-F01, M0038-F08, M0039-H08, M0040-A06, M0040-A11, and M0043-G02.

In one embodiment, the HC and LC variable domain sequences are components of the same polypeptide chain. In another, the HC and LC variable domain sequences are components of different polypeptide chains. For example, the protein is an IgG., e.g., IgG1, IgG2, IgG3, or IgG4. The protein can be a soluble Fab. In other implementations the protein includes a Fab2', scFv, minibody, scFv::Fc fusion, Fab::HSA fusion, HSA::Fab fusion, Fab::HSA::Fab fusion, or other molecule that comprises the antigen combining site of one of the binding proteins herein. The VH and VL regions of these Fabs can be provided as IgG, Fab, Fab2, Fab2', scFv, PEGylated Fab, PEGylated scFv, PEGylated Fab2, VH:: CH1::HSA+LC, HSA::VH::CH1+LC, LC::HSA+VH::CH1, HSA::LC+VH::CH1, or other appropriate construction.

In one embodiment, the protein is a human or humanized antibody or is non-immunogenic in a human. For example, the protein includes one or more human antibody framework regions, e.g., all human framework regions. In one embodiment, the protein includes a human Fc domain, or an Fc domain that is at least 95, 96, 97, 98, or 99% identical to a human Fc domain.

In one embodiment, the protein is a primate or primatized antibody or is non-immunogenic in a human. For example, the protein includes one or more primate antibody framework regions, e.g., all primate framework regions. In one embodiment, the protein includes a primate Fc domain, or an Fc domain that is at least 95, 96, 97, 98, or 99% identical to a primate Fc domain. "Primate" includes humans (*Homo sapiens*), chimpanzees (*Pan troglodytes* and *Pan paniscus* (bonobos)), gorillas (*Gorilla gorilla*), gibons, monkeys, lemurs, aye-ayes (*Daubentonia madagascariensis*), and tarsiers.

In some embodiments, the affinity of the primate antibody for MMP-14 is characterized by a $K_D$ of less than 1.2 nM.

In certain embodiments, the protein includes no sequences from mice or rabbits (e.g., is not a murine or rabbit antibody).

In one embodiment, the protein is capable of binding to tumor cells expressing MMP-14, e.g., to HT-1080 (a human fibrosarcoma cell line), LNCaP (human prostate carcinoma), MDA-MB-231 (human, Caucasian, breast, adenocarcinoma), or PC3 (Human prostatic cancer cells) cells.

In one embodiment, protein is physically associated with a nanoparticle, and can be used to guide a nanoparticle to a cell expressing MMP-14 on the cell surface. In one embodiment, the protein causes effector cells (CDC or ADCC) to kill a cell which expresses MMP-14.

A binding protein described herein can be provided as a pharmaceutical composition, e.g., including a pharmaceutically acceptable carrier. The composition can be at least 10, 20, 30, 50, 75, 85, 90, 95, 98, 99, or 99.9% free of other protein species.

In another aspect, the disclosure features a method of detecting an MMP-14 in a sample. The method includes: contacting the sample with an MMP-14 binding protein; and detecting an interaction between the protein and the MMP-14, if present. In some embodiments, the protein includes a detectable label. An MMP-14 binding protein can be used to detect MMP-14 in a subject. The method includes: administering an MMP-14 binding protein to a subject; and detecting the protein in the subject. In some embodiments, the protein further includes a detectable label. For example, the detecting comprises imaging the subject.

In another aspect, the disclosure features a method of modulating MMP-14 activity. The method includes: contacting an MMP-14 with an MMP-14 binding protein (e.g., in a human subject), thereby modulating MMP-14 activity.

In another aspect, the disclosure features a method of treating cancer (e.g., metastatic cancer). The method includes: administering, to a subject, an MMP-14 binding protein in an amount sufficient to treat a cancer in the subject. For example, the cancer is head and neck cancer, oral cavity cancer, laryngeal cancer, chondrosarcoma, breast cancer (which may be estrogen receptor positive (ER+), estrogen receptor negative (ER−), Her2 positive (Her2+), Her2 negative (Her2−), or a combination thereof, e.g., ER+/Her2+, ER+/Her2−, ER−./ Her2+, or ER−/Her2−), laryngeal cancer, ovarian cancer, testicular carcinoma, melanoma, or brain tumors (e.g., astrocytomas, glioblastomas, gliomas).

MMP-14 binding proteins are useful to modulate metastatic activity in a subject. The protein can be administered, to the subject, an MMP-14 binding protein in an amount effective to modulate metastatic activity. For example, the protein inhibits one or more of: tumor growth, tumor embolism, tumor mobility, tumor invasiveness, and cancer cell proliferation.

The methods disclosed herein relating to the treatment cancer (e.g., treating cancer and/or modulation of metastatic activity) can further include providing to the subject a second therapy that is an anti-cancer therapy, e.g., administration of a chemotherapeutic, e.g., an agent that antagonizes signaling through a VEGF pathway, e.g., bevacizumab (AVASTIN®). In one embodiment, the second therapy includes administering 5-FU, leucovorin, and/or irinotecan. In one embodiment, the second therapy includes administering a Tie1 inhibitor (e.g., an anti-Tie1 antibody). In one embodiment, the second therapy is an inhibitor of plasmin (e.g., a kunitz domain disclosed in U.S. Pat. No. 6,010,880, such as a protein or polypeptide comprising the amino acid sequence (SEQ ID NO:5)
MHSFCAFKAETGPCRARFDRWFFNIFTRQCEEFIYGGCEGNQNRFESLEE

CKKMCTRD.

Inhibitors of MMP-14 (e.g., the MMP-14 binding proteins disclosed herein) can potentiate the activity of an agent that targets Her2 (e.g., a Her2-binding antibody such as trastuzumab). Accordingly, in one embodiment, the second therapy is an agent that binds Her2, such as a Her2-binding antibody (e.g., trastuzumab). In some such embodiments, the dose of the Her2 binding agent is reduced from the dose of the Her2 binding agent when administered not in combination with an MMP-14 binding protein (e.g., is at least 10%, 25%, 40%, or 50% less than the dose of the Her2 binding agent when administered not in combination with a MMP-14 binding protein)

In another aspect, the disclosure features a method of treating an ocular condition. The method includes: administering, to a subject, an MMP-14 binding protein in an amount sufficient to treat the ocular condition. In one embodiment, the method further includes administering a second agent an agent that antagonizes signaling through a VEGF pathway, e.g., bevacizumab or ranibizumab. In one embodiment where the second agent is a VEGF pathway inhibitor (e.g., bevacizumab or ranibizumab), the ocular condition is age-related macular degeneration, such as wet age-related macular degeneration.

In another aspect, the disclosure features a method of treating an inflammatory disease (e.g., synovitis, rheumatoid arthritis). The method includes: administering, to a subject, an MMP-14 binding protein in an amount sufficient to treat the inflammatory disease. The method can further include providing to the subject a second therapy that is an anti-inflammatory therapy. For example, particularly for rheumatoid arthritis, the second therapy comprises administering one or more of the following agents: aspirin, naproxen, ibuprofen, etodolac, cortisone (corticosteroids), antacids, sucralfate, proton-pump inhibitors, misoprostol, gold (e.g., gold salts, gold thioglucose, gold thiomalate, oral gold), methotrexate, sulfasalazine, D-penicillamine, azathioprine, cyclophosphamide, chlorambucil, cyclosporine, leflunomide, etanercept, infliximab, anakinra, adalimumab, and/or hydroxychloroquine.

In another aspect, the disclosure features a method of treating osteoarthritis. The method includes: administering, to a subject, an MMP-14 binding protein in an amount sufficient to treat the the osteoarthritis. The method can further include providing to the subject a second therapy that is an anti-osteoarthritis therapy.

In another aspect, the disclosure features a method of treating diabetes. The method includes: administering, to a subject, an MMP-14 binding protein in an amount sufficient to treat diabetes. The method can further include providing to the subject a second therapy that is a diabetes therapy. For example, the second therapy comprises administering one or more of the following agents: sulfonylureas, meglitinides, biguanides, metformin, troglitazone, pioglitazone, rosiglitazone, acarbose, pramlintide, exenatide, glyburide/metformin (GLUCOVANCE®), rosiglitazone/metformin (AVANDAMET®), and/or glipizide/metformin (METAGLIP®).

In another aspect, the disclosure features a method of treating Alzheimer's Disease. The method includes: administering, to a subject, an MMP-14 binding protein in an amount sufficient to treat Alzheimer's Disease. The method can further include providing to the subject a second therapy that is an Alzheimer's Disease therapy. For example, the second therapy comprises administering one or more of the following agents: tacrine (COGNEX®), donepezil (ARICEPT®), rivastigmine (EXELON®), galantamine (REMINYL®), memantine (NAMENDA™), nonsteroidal anti-inflammatory drugs (NSAIDS), statins, folic acid, gingko biloba, vitamin E, vitamin B6, and/or vitamin B12.

Other exemplary therapeutic methods that include administering an MMP-14 binding protein are described below. An MMP-14 binding protein described herein can be administered in combination with one or more other MMP inhibitors, e.g., small molecule inhibitors, e.g., broad specificity inhibitors. In one embodiment, the small molecule inhibitors are one or more of neovastat, marimastat, BAY 12-9566, or prinomastat. In another embodiment, the one or more MMP inhibitors include another MMP-14 binding protein.

MMP-14 binding proteins are useful for targeted delivery of an agent to a subject (e.g., a subject who has or is suspected of having a tumor), e.g., to direct the agent to a tumor in the subject. For example, an MMP-14 binding protein that is coupled to an anti-tumor agent (such as a chemotherapeutic, toxin, drug, or a radionuclide (e.g., $^{131}$I, $^{90}$Y, $^{177}$Lu)) can be administered to a subject who has or is suspected of having a tumor.

In another aspect, the disclosure features a method of imaging a subject. The method includes administering an MMP-14 binding protein to the subject. In some embodiments, the protein is one that does not substantially inhibit MMP-14 catalytic activity. The MMP-14 binding protein may include a detectable label (e.g., a radionuclide or an MRI-detectable label). In one embodiment, the subject has or is suspected of having a tumor. The method is useful for cancer diagnosis, intraoperative tumor detection, post-operative tumor detection, or monitoring tumor invasive activity.

In one aspect, the disclosure features the use of an MMP-14 binding protein described herein for the manufacture of a medicament for the treatment of a disorder described herein, e.g., a cancer (e.g., metastatic cancer, e.g., metastatic breast cancer), an inflammatory disease (e.g., synovitis, atherosclerosis), rheumatoid arthritis, osteoarthritis, an ocular condition (e.g., macular degeneration), diabetes, Alzheimer's Disease, cerebral ischemia, endometriosis, fibrin-invasive activity, or dysregulated or inappropriate angiogenesis. Still other disorders that can be treated using a medicament comprising an MMP-14 binding protein include: aortic aneurysms, periodontitis, autoimmune blistering disorders of the skin, dermal photoaging.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 6A shows photomicrographs of three dimensional cultures of HUVEC treated with vehicle, M0038 F01 at various doses, or suramin. FIG. 6B shows a graph summarizing measurements of tube length from the same experiment.

DETAILED DESCRIPTION

Figure 1A:
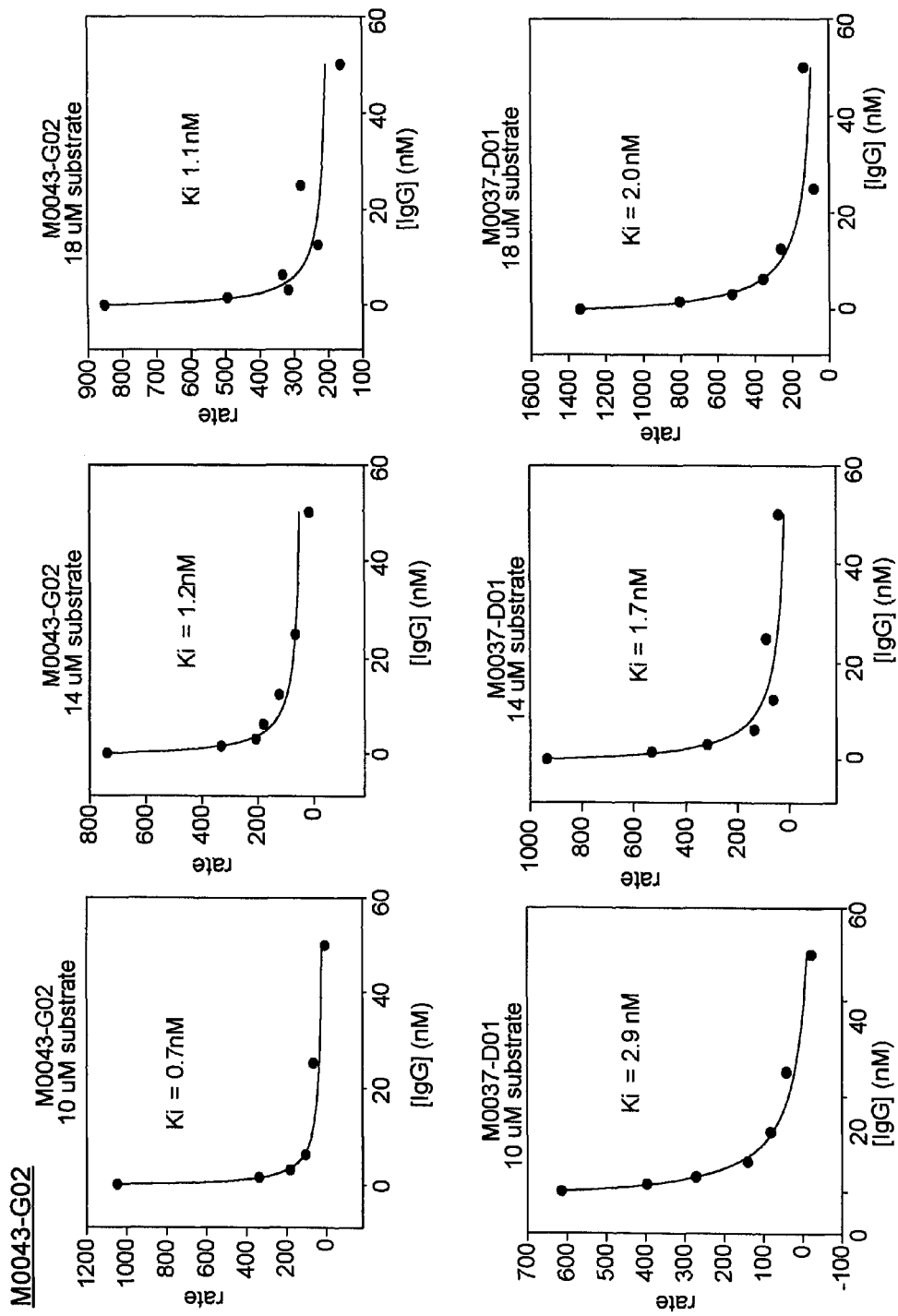
FIGS. 1A, 1B, and 1C show a series of graphs depicting the determination of Ki values of MMP-14 binding proteins.
Figure 1B:
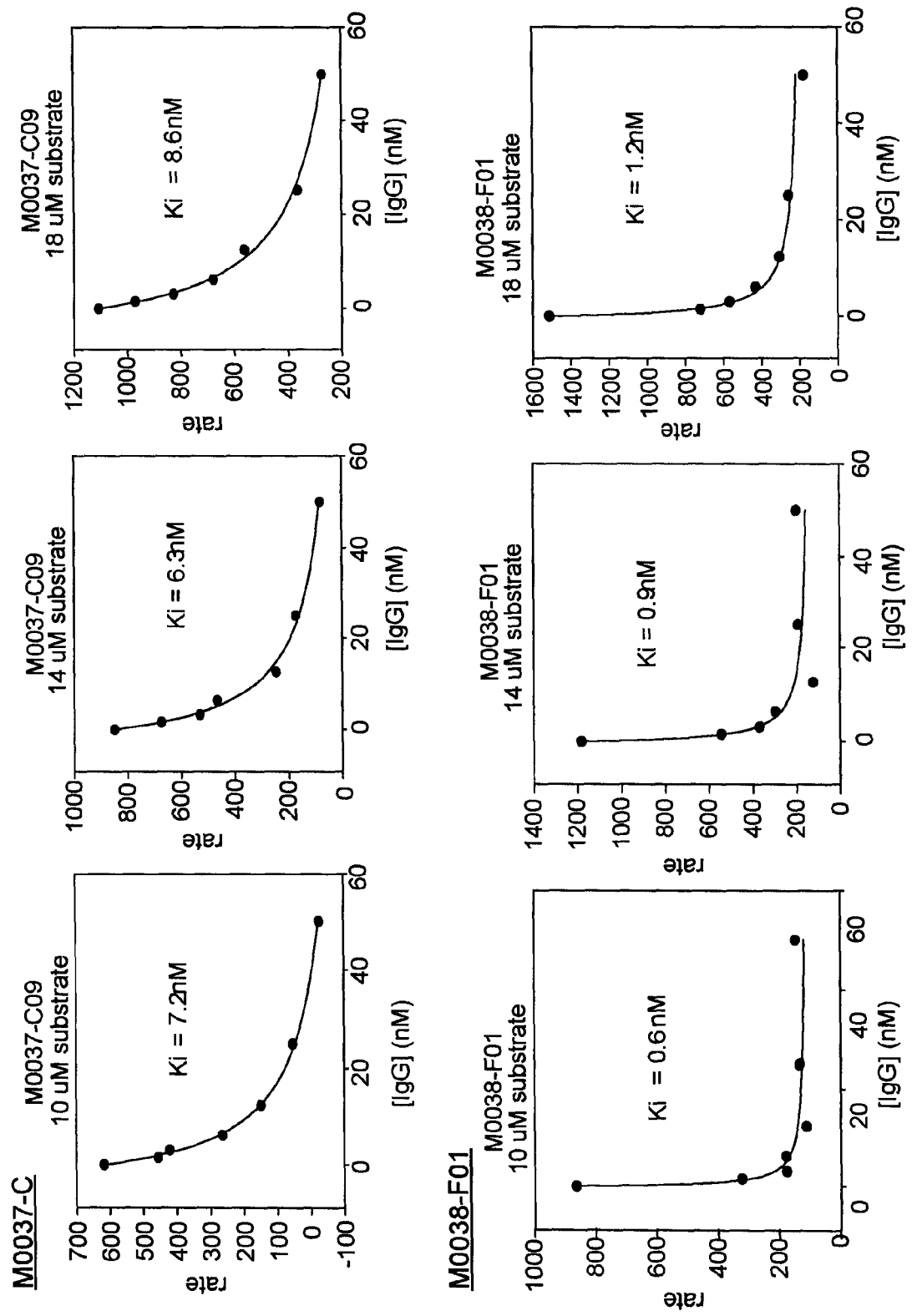
Figure 1C:
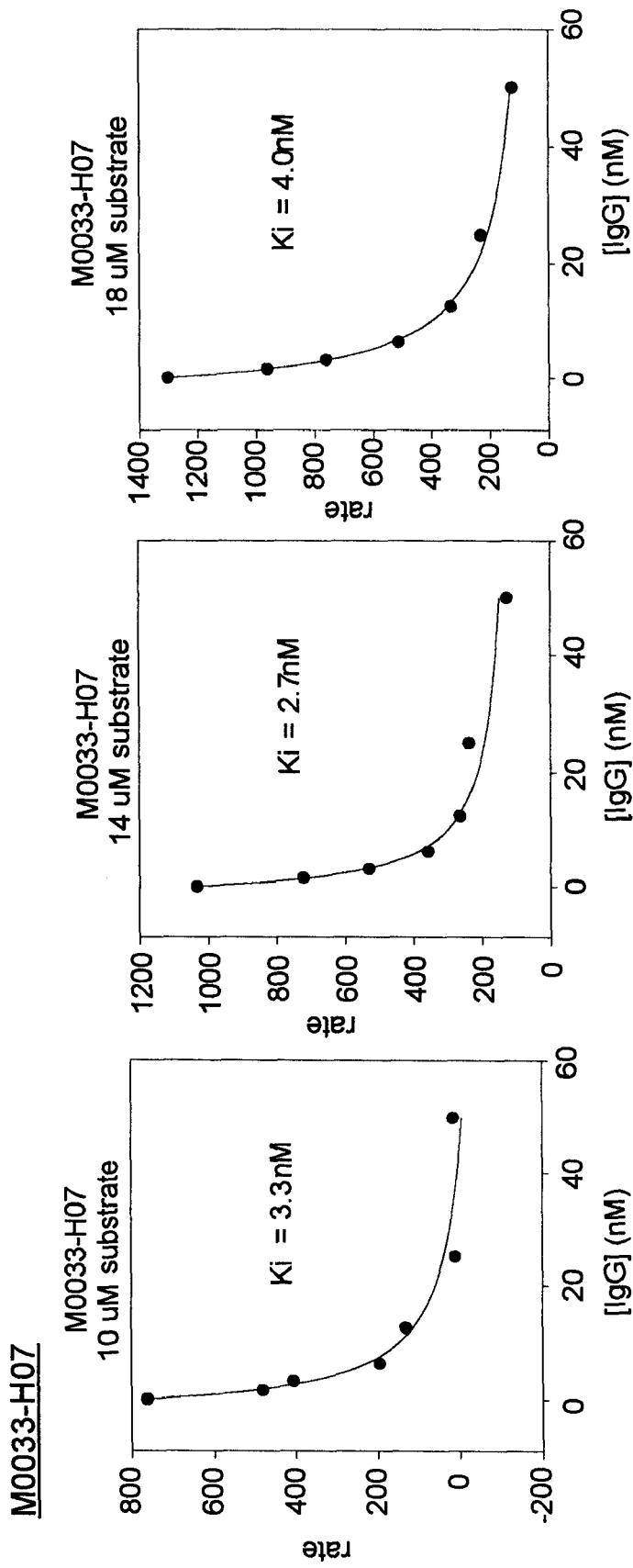

Matrix metalloproteinases function in the physiological remodeling of the extracellular matrix, e.g., during tissue morphogenesis, growth, uterine cycling and postpartum involution, tissue repair, and angiogenesis. Three proteases that have these activities are MMP-14, MMP-16, and MMP-24. The disclosure provides MMP-14 binding proteins, including MMP-14 binding proteins that inhibit MMP-14 binding activity. The MMP-14 binding proteins taught by the disclosure may also bind, and in some embodiments also inhibit, MMP-16 and/or MMP-24.

The term "binding protein" refers to a protein that can interact with a target molecule. This term is used interchangeably with "ligand." An "MMP-14 binding protein" refers to a protein that can interact with MMP-14, and includes, in particular, proteins that preferentially interact with and/or inhibit MMP-14. For example, the MMP-14 binding protein is an antibody.

The term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')$_2$, Fd fragments, Fv fragments, scFv, and domain antibodies (dAb) fragments (de Wildt et al., Eur J Immunol. 1996; 26(3):629-39.)) as well as complete antibodies. An antibody can have the structural features of IgA, IgG, IgE, IgD, IgM (as well as subtypes thereof). Antibodies may be from any source, but primate (human and non-human primate) and primatized are preferred The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al (1991) *Sequences of Proteins of Immunological Interest, Fifth Edition*, U.S. Department of Health and Human Services, NIH Publication No. 91-3242, and Chothia, C. et al. (1987) J. Mol. Biol. 196:901-917, see also www.hgmp.mrc.ac.uk). Kabat definitions are used herein. Each VH and VL is typically composed of three CDRs and four FRs, arranged from amino-terminus to carboxy-terminus in the following order: FR1, CDR1, FR2, CDR2, FR3, CDR3, FR4.

As used herein, an "immunoglobulin variable domain sequence" refers to an amino acid sequence which can form the structure of an immunoglobulin variable domain such that one or more CDR regions are positioned in a conformation suitable for an antigen binding site. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes immunoglobulin variable domain sequence can associate with another immunoglobulin variable domain sequence to form an antigen binding site, e.g., a structure that preferentially interacts with an MMP-14 protein, e.g., the MMP-14 catalytic domain.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. In IgGs, the heavy chain constant region includes three immunoglobulin domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The light chains of the immunoglobulin may be of types kappa or lambda. In one embodiment, the antibody is glycosylated. An antibody can be functional for antibody-dependent cytotoxicity and/or complement-mediated cytotoxicity.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and LC CDR3. Each of the light chain CDRs can be human. HC CDR3 can be human. One or more of the framework regions can be human, e.g., FR1, FR2, FR3, and FR4 of the HC or LC. For example, the Fc region can be human. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. In one embodiment, the framework (FR) residues of a selected Fab can be converted to the amino-acid type of the corresponding residue in the most similar primate germline gene, especially the human germline gene. One or more of the constant regions can be human or effectively human. For example, at least 70, 75, 80, 85, 90, 92, 95, 98, or 100% of an immunoglobulin variable domain, the constant region, the constant domains (CH1, CH2, CH3, CL1), or the entire antibody can be human or effectively human.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the many immunoglobulin variable region genes. Full-length immunoglobulin "light chains" (about 25 KDa or about 214 amino acids) are encoded by a variable region gene at the NH2-terminus (about 110 amino acids) and a kappa or lambda constant region gene at the COOH-terminus. Full-length immunoglobulin "heavy chains" (about 50 KDa or about 446 amino acids), are similarly encoded by a variable region gene (about 116 amino acids) and one of the other aforementioned constant region genes, e.g., gamma (encoding about 330 amino acids). The length of human HC varies considerably because HC CDR3 varies from about 3 amino-acid residues to over 35 amino-acid residues.

The term "antigen-binding fragment" of a full length antibody refers to one or more fragments of a full-length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')$_2$ fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., U.S. Pat. Nos. 5,260,203, 4,946,778, and 4,881,175; Bird et al. (1988) *Science* 242:423-426; and Huston et al. (1988) *Proc. Natl. Acad. Sci. USA* 85:5879-5883.

Antibody fragments can be obtained using any appropriate technique including conventional techniques known to those with skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition, irrespective of how the antibody was generated.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

A "humanized" immunoglobulin variable region is an immunoglobulin variable region that is modified to include a sufficient number of human framework amino acid positions such that the immunoglobulin variable region does not elicit an immunogenic response in a normal human. Descriptions of "humanized" immunoglobulins include, for example, U.S. Pat. Nos. 6,407,213 and 5,693,762.

As used herein, "binding affinity" refers to the apparent association constant or $K_a$. The $K_a$ is the reciprocal of the dissociation constant ($K_d$). A binding protein may, for example, have a binding affinity of at least $10^5$, $10^6$, $10^7$, $10^8$, $10^9$, $10^{10}$ and $10^{11}$ M$^{-1}$ for a particular target molecule, e.g., MMP-14, MMP-16, or MMP-24. Higher affinity binding of a binding protein to a first target relative to a second target can be indicated by a higher $K_a$ (or a smaller numerical value $K_d$) for binding the first target than the $K_a$ (or numerical value $K_d$) for binding the second target. In such cases, the binding protein has specificity for the first target (e.g., a protein in a first conformation or mimic thereof) relative to the second target (e.g., the same protein in a second conformation or mimic thereof; or a second protein). Differences in binding affinity (e.g., for specificity or other comparisons) can be at least 1.5, 2, 3, 4, 5, 10, 15, 20, 37.5, 50, 70, 80, 91, 100, 500, 1000, or $10^5$ fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in TRIS-buffer (50 mM TRIS, 150 mM NaCl, 5 mM CaCl$_2$ at pH7.5). These techniques can be used to measure the concentration of bound and free binding protein as a function of binding protein (or target) concentration. The concentration of bound binding protein ([Bound]) is related to the concentration of free binding protein ([Free]) and the concentration of binding sites for the binding protein on the target where (N) is the number of binding sites per target molecule by the following equation:

$$[Bound]=N\cdot[Free]/((1/K_a)+[Free]).$$

It is not always necessary to make an exact determination of $K_a$, though, since sometimes it is sufficient to obtain a quantitative measurement of affinity, e.g., determined using a method such as ELISA or FACS analysis, is proportional to $K_a$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

An "isolated composition" refers to a composition that is removed from at least 90% of at least one component of a natural sample from which the isolated composition can be obtained. Compositions produced artificially or naturally can be "compositions of at least" a certain degree of purity if the species or population of species of interests is at least 5, 10, 25, 50, 75, 80, 90, 92, 95, 98, or 99% pure on a weight-weight basis.

An "epitope" refers to the site on a target compound that is bound by a binding protein (e.g., an antibody such as a Fab or full length antibody). In the case where the target compound is a protein, the site can be entirely composed of amino acid components, entirely composed of chemical modifications of amino acids of the protein (e.g., glycosyl moieties), or composed of combinations thereof. Overlapping epitopes include at least one common amino acid residue, glycosyl group, phosphate group, sulfate group, or other molecular feature.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

In a preferred embodiment, the length of a reference sequence aligned for comparison purposes is at least 30%, preferably at least 40%, more preferably at least 50%, even more preferably at least 60%, and even more preferably at least 70%, 80%, 90%, 92%, 95%, 97%, 98%, or 100% of the length of the reference sequence. For example, the reference sequence may be the length of the immunoglobulin variable domain sequence.

As used herein, the term "substantially identical" (or "substantially homologous") is used herein to refer to a first amino acid or nucleic acid sequence that contains a sufficient number of identical or equivalent (e.g., with a similar side chain, e.g., conserved amino acid substitutions) amino acid residues or nucleotides to a second amino acid or nucleic acid sequence such that the first and second amino acid or nucleic acid sequences have (or encode proteins having) similar activities, e.g., a binding activity, a binding preference, or a biological activity. In the case of antibodies, the second antibody has the same specificity and has at least 50%, at least 25%, or at least 10% of the affinity relative to the same antigen.

Sequences similar or homologous (e.g., at least about 85% sequence identity) to the sequences disclosed herein are also part of this application. In some embodiments, the sequence identity can be about 85%, 90%, 91%, 92%, 93%, 94%, 95%, 96%, 97%, 98%, 99% or higher. In addition, substantial identity exists when the nucleic acid segments hybridize under selective hybridization conditions (e.g., highly stringent hybridization conditions), to the complement of the strand. The nucleic acids may be present in whole cells, in a cell lysate, or in a partially purified or substantially pure form.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6. Aqueous and nonaqueous methods are described in that reference and either can be used. Specific hybridization conditions referred to herein are as follows: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and (4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified. The disclosure includes nucleic acids that hybridize with low, medium, high, or very high stringency to a nucleic acid described herein or to a complement thereof, e.g., nucleic acids encoding a binding protein described herein. The nucleic acids can be the same length or within 30, 20, or 10% of the length of the reference nucleic acid. The nucleic acid can correspond to a region encoding an immunoglobulin variable domain sequence described herein.

An MMP-14 binding protein may have mutations (e.g., at least one, two, or four, and/or less than 15, 10, 5, or 3) relative to a binding protein described herein (e.g., a conservative or non-essential amino acid substitutions), which do not have a substantial effect on protein function. Whether or not a particular substitution will be tolerated, i.e., will not adversely affect biological properties, such as binding activity can be predicted, e.g., by evaluating whether the mutation is conservative or by the method of Bowie, et al. (1990) *Science* 247:1306-1310.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). It is possible for many framework and CDR amino acid residues to include one or more conservative substitutions.

Motif sequences for biopolymers can include positions which can be varied amino acids. For example, the symbol "X" in such a context generally refers to any amino acid (e.g., any of the twenty natural amino acids or any of the nineteen non-cysteine amino acids). Other allowed amino acids can also be indicated for example, using parentheses and slashes. For example, "(A/W/F/N/Q)" means that alanine, tryptophan, phenylalanine, asparagine, and glutamine are allowed at that particular position.

A "non-essential" amino acid residue is a residue that can be altered from the wild-type sequence of the binding agent, e.g., the antibody, without abolishing or more preferably, without substantially altering a biological activity, whereas changing an "essential" amino acid residue results in a substantial loss of activity.

The term "cognate ligand" refers to a naturally occurring ligand of an MMP-14, including naturally occurring variants thereof (e.g., splice variants, naturally occurring mutants, and isoforms).

Statistical significance can be determined by any art known method. Exemplary statistical tests include: the Students T-test, Mann Whitney U non-parametric test, and Wilcoxon non-parametric statistical test. Some statistically significant relationships have a P value of less than 0.05 or 0.02. Particular binding proteins may show a difference, e.g., in specificity or binding, that are statistically significant (e.g., P value<0.05 or 0.02). The terms "induce", "inhibit", "potentiate", "elevate", "increase", "decrease" or the like, e.g., which denote distinguishable qualitative or quantitative differences between two states, and may refer to a difference, e.g., a statistically significant difference, between the two states.

MMP-14 Binding Proteins

The disclosure provides proteins that bind to MMP-14 (e.g., human MMP-14) and include at least one immunoglobin variable region. For example, the MMP-14 binding protein includes a heavy chain (HC) immunoglobulin variable domain sequence and a light chain (LC) immunoglobulin variable domain sequence. A number of exemplary MMP-14 binding proteins are described herein.

The MMP-14 binding protein may be an isolated protein (e.g., at least 70, 80, 90, 95, or 99% free of other proteins).

The MMP-14 binding protein may additionally inhibit MMP-14, e.g., human MMP-14. In one embodiment, the protein binds the catalytic domain of human MMP-14, e.g., the protein contacts residues in or near the active site of MMP-14.

In certain embodiments, the MMP-14 binding protein also binds to MMP-16 and/or MMP-24. Additionally, the MMP-14 binding protein may also inhibit MMP-16 and/or MMP-24.

Exemplary MMP-14 binding proteins include M0031-C02, M0031-F01, M0033-H07, M0037-C09, M0037-D01, M0038-E06, M0038-F01, M0038-F08, M0039-H08, M0040-A06, M0040-A11, and M0043-G02.

MMP-14 binding proteins may be antibodies. MMP-14 binding antibodies may have their HC and LC variable domain sequences included in a single polypeptide (e.g., scFv), or on different polypeptides (e.g., IgG or Fab).

Matrix Metalloproteinases

MMP-14

MMP-14 is encoded by a gene designated as MMP14, matrix metalloproteinase-14 precursor. Synonyms for MMP-14 include matrix metalloproteinase 14 (membrane-inserted), membrane-type-1 matrix metalloproteinase, membrane-type matrix metalloproteinase 1, MMP-14, MMP-X1, MT1MMP, MT1-MMP, MTMMP1, MT-MMP 1.

MT-MMPs have similar structures, including a signal peptide, a prodomain, a catalytic domain, a hinge region, and a hemopexin domain (Wang, et al., 2004, J Biol Chem, 279: 51148-55). According to SwissProt entry P50281, the signal sequence of MMP-14 precursor includes amino acid residues 1-20. The pro-peptide includes residues 21-111. Cys93 is annotated as a possible cysteine switch. Residues 112 through 582 make up the mature, active protein. The catalytic domain includes residues 112-317. The hemopexin domains includes residues 318-523. The transmembrane segment comprises residues 542 through 562.

MMP-14 can be shed from cells or found on the surface of cells, tethered by a single transmembrane amino-acid sequence. See, e.g., Osnkowski et al. (2004, J Cell Physiol, 200:2-10).

An exemplary amino acid sequence of human MMP14 is shown in Table 1:

TABLE 1

Amino-acid sequence of human MMP14

MSPAPRPPRCLLLPLLTLGTALASLGSAQSSSFSPEAWLQQYGYLPPGDL
RTHTQRSPQSLSAAIAAMQKFYGLQVTGKADADTMKAMRRPRCGVPDKFG
AEIKANVRRKRYAIQGLKWQHNEITFCIQNYTPKVGEYATYEAIRKAFRV
WESATPLRFREVPYAYIREGHEKQADIMIFFAEGFHGDSTPFDGEGGFLA
HAYFPGPNIGGDTHFDSAEPWTVRNEDLNGNDIFLVAVHELGHALGLEHS
SDPSAIMAPFYQWMDTENFVLPDDDRRGIQQLYGGESGFPTKMPPQPRTT

TABLE 1-continued

Amino-acid sequence of human MMP14

SRPSVPDKPKNPTYGPNICDGNFDTVAMLRGEMFVFKERWFWRVRNNQVM
DGYPMPIGQFWRGLPASINTAYERKDGKFVFFKGDKHWVFDEASLEPGYP
KHIKELGRGLPTDKIDAALFWMPNGKTYFFRGNKYYRFNEELRAVDSEYP
KNIKVWEGIPESPRGSFMGSDEVFTYFYKGNKYWKFNNQKLKVEPGYPKS
ALRDWMGCPSGGRPDEGTEEETEVIIIEVDEEGGGAVSAAAVVLPVLLLL
LVLAVGLAVFFFRRHGTPRRLLYCQRSLLDKV (SEQ ID NO:2;
Genbank Accession No. CAA88372.1).

An exemplary amino acid sequence of mouse MMP14 is shown in Table 2.

TABLE 2

Amino-acid sequence of mouse MMP14

MSPAPRPSRSLLLPLLTLGTALASLGWAQGSNFSPEAWLQQYGYLPPGDL
RTHTQRSPQSLSAAIAAMQKFYGLQVTGKADLATMMAMRRPRCGVPDKFG
TEIKANVRRKRYAIQGLKWQHNEITFCIQNYTPKVGEYATFEAIRKAFRV
WESATPLRFREVPYAYIREGHEKQADIMILFAEGFHGDSTPFDGEGGFLA
HAYFPGPNISGDTHFDSAEPWTVQNEDLNGNDIFLVAVHELGHALGLEHS
NDPSAIMSPFYQWMDTENFVLPDDDRRGIQQLYGSKSGSPTKMPPQPRTT
SRPSVPDKPKNPAYGPNICDGNFDTVAMLRGEMFVFKERWFWRVRNNQVM
DGYPMPIGQFWRGLPASINTAYERKDGKFVFFKGDKHWVFDEASLEPGYP
KHIKELGRGLPTDKIDAALFWMPNGKTYFFRGNKYYRFNEEFRAVDSEYP
KNIKVWEGIPESPRGSFMGSDEVFTYFYKGNKYWKFNNQKLKVEPGYPKS
ALRDWMGCPSGRRPDEGTEEETEVIIIEVDEEGSGAVSAAAVVLPVLLLL
LVLAVGLAVFFFRRHGTPKRLLYCQRSLLDKV SEQ ID NO:4;
GenBank Accession No. NP_032634.2.

An exemplary MMP-14 protein can include the human or mouse MMP-14 amino acid sequence, a sequence that is 80%, 85%, 90%, 95%, 96%, 97%, 98%, or 99% identical to one of these sequences, or a fragment thereof, e.g., a fragment without the signal sequence or prodomain.

Table 3 shows a sequence alignment of the exemplary human MMP-14 (hMMP-14) amino acid sequence with the exemplary mouse MMP-14 (mMMP-14) amino acid sequence. A "-" in the mMMP14 entries indicates that the amino acid is the same as shown for hMMP14.

TABLE 3

Comparison of human and murine MMP 14

```
hMMP14:   1:  50  MSPAPRPPRC LLLPLLTLGT ALASLGSAQS SSFSPEAWLQ QYGYLPPGDL  (SEQ ID NO:1)
mMMP14:   1:  50  -------S-S ---------- ------W--G -N-------- ----------  (SEQ ID NO:3)

hMMP14:  51: 100  RTHTQRSPQS LSAAIAAMQK FYGLQVTGKA DADTMKAMRR PRCGVPDKFG
mMMP14:  51: 100  ---------- ---------- ---------- -LA--M---- ---------- hMMP14: 101: 150  AEIKANVRRK RYAIQGLKWQ HNEITFCIQN YTPKVGEYAT YEAIRKAFRV
mMMP14: 101: 150  T--------- ---------- ---------- ---------- F--------- hMMP14: 151: 200  WESATPLRFR EVPYAYIREG HEKQADIMIF FAEGFHGDST PFDGEGGFLA
mMMP14: 151: 200  ---------- ---------- ---------L ---------- ---------- hMMP14: 201: 250  HAYFPGPNIG GDTHFDSAEP WTVRNEDLNG NDIFLVAVHE LGHALGLEHS
mMMP14: 201: 250  ---------- ---------- ---Q------ ---------- ---------- hMMP14: 251: 300  SDPSAIMAPF YQWMDTENFV LPDDDRRGIQ QLYGGESGFP TKMPPQPRTT
mMMP14: 251: 300  N------S-- ---------- ---------- ----SK--S- ---------- hMMP14: 301: 350  SRPSVPDKPK NPTYGPNICD GNFDTVAMLR GEMFVFKERW FWRVRNNQVM
mMMP14: 301: 350  ---------- --A------- ---------- ---------- ---------- hMMP14: 351: 400  DGYPMPIGQF WRGLPASINT AYERKDGKFV FFKGDKHWVF DEASLEPGYP
mMMP14: 351: 400  ---------- ---------- ---------- ---------- ---------- hMMP14: 401: 450  KHIKELGRGL PTDKIDAALF WMPNGKTYFF RGNKYYRFNE ELRAVDSEYP
mMMP14: 401: 450  ---------- ---------- ---------- ---------- -F--------
```

TABLE 3-continued

Comparison of human and murine MMP 14

```
hMMP14:  451: 500  KNIKVWEGIP ESPRGSFMGS DEVFTYFYKG NKYWKFNNQK LKVEPGYPKS
mMMP14:  451: 500  ---------- ---------- ---------- ---------- ---------- hMMP14:  501: 550  ALRDWMGCPS GGRPDEGTEE ETEVIIIEVD EEGGGAVSAA AVVLPVLLLL
mMMP14:  501: 550  ---------- -R-------- ---------- ---S------ ---------- hMMP14:  551: 582  LVLAVGLAVF FFRRHGTPRR LLYCQRSLLD
mMMP14:  551: 582  ---------- --------K- ----------
```

These exemplary hMMP-14 and mMMP-14 sequences are identical at 558 of 580 positions, about 96.2% identity. Despite a relatively high degree of similarity, their activity toward different substrates, including proMMP-2 and type I collagen, varies (Wang, et al., 2004, J Biol Chem, 279:51148-55).

MMP-14-deficient mice were generated by gene targeting (Holmbeck, et al., 1999, Cell, 99:81-92). MMP-14 deficiency causes craniofacial dysmorphism, arthritis, osteopenia, dwarfism, and fibrosis of soft tissues, but the mice are viable. The expression of MMP-14 in tumors is reviewed in Sato et al. (Sato, et al., 2005, Cancer Sci, 96:212-7), Zucker et al. (Zucker and Vacirca, 2004, Cancer Metastasis Rev, 23:101-17), and Bauvois (Bauvois, 2004, Oncogene, 23:317-29). Increased expression of MT-MMPs has previously been reported to correlate with increasing grade of malignancy in gliomas, a relationship shared with alterations in epidermal growth factor receptor (EGFR) signaling. One mechanism of EGFR-mediated invasiveness in gliomas may involve the induction of MT1-MMP (Van metter et al, 2004, Neurooncol., 6(3):188-99).

MMP-14 is regulated by chemokines monocyte-chemoattractant protein-1/ccl2 and interleukin-8/CXCL8 in endothelial cells during angiogenesis (Galvez et al, 2005, J Biol Chem, 280(2):1292-8). MMP-14 activity is also regulated by ERK 1/2- and p38 MAPK-modulated TIMP-2 expression which controls TGF-beta1-induced pericellular collagenolysis (Munshi et al, 2004, J Biol Chem, 279(37):39042-50). Blockade of the ERK pathway suppress the expression of MMP-3, -9, and -14, and CD44 and markedly inhibits the invasiveness of tumor cells (Tanimura et al, 2003, Biochem Biophys Res Commun, 304(4):801-6).

During angiogenesis, MMP-14 contributes to the specific up-regulation of VEGF-A through activation of Src tyrosine kinase pathways perhaps involving the cleavage of CD44 (Sounni et al, 2004, J Biol Chem, 279(14):13564-74).

MMP-14 has a number of endogenous inhibitors. TIMP-2 binds MMP-14 and anchors MMP-14 to cell surface and acts as a "receptor" for proMMP-2 (progelatinase A), such that the latter can be activated efficiently in a localized fashion (Murphy, et al., 2003, Biochem Soc Symp, 65-80). TIMP-2, TIMP-3, and TIMP-4 inhibit MMP-14, but TIMP-1 does not (Lee, et al., 2003, J Biol Chem, 278:40224-30). TIMPs typically are slow, tight binding inhibitors.

MMP-14 activates pro-MMP-2 causing a cascade of proteolysis that facilitates the mobility and invasiveness of tumor cells (Berno, et al., 2005, Endocr Relat Cancer, 12:393-406; Anilkumar, et al., 2005, Faseb J, 19:1326-8; Itoh and Seiki, 2005, J Cell Physiol; Lopez de Cicco, et al., 2005, Cancer Res, 65:4162-71; El Bedoui, et al., 2005, Cardiovasc Res, 67:317-25; Cao, et al., 2005, Thromb Haemost, 93:770-8; Sato, et al., 2005, Cancer Sci, 96:212-7; Dong, et al., 2005, Am J Pathol, 166:1173-86; Philip, et al., 2004, Glycoconj J, 21:429-41; Guo, et al., 2005, Am J Pathol, 166:877-90; Grossman, 2005, Urol Oncol, 23:222; Gilles, et al., 2001, J Cell Sci, 114:2967-76). Studies propose that this activation process requires both active MT1-MMP and the TIMP-2-bound MT1-MMP (Strongin et al, 1995, J Biol Chem, 270, 5331-5338; Butler et al, 1998, J Biol Chem, 273: 871-80; Kinoshita et al, 1998, J Biol Chem, 273, 16098-103). The TIMP-2 in the latter complex binds, through its C-terminal domain, to the hemopexin domain of pro-MMP-2, which may localize the zymogen close to the active MT 1-MMP (Butler et al, 1998, J Biol Chem, 273: 871-80; Kinoshita et al, 1998).

In addition to proMMP-2, MMP-14 cleaves other substrates, such as collagen triple-helical structure (Minond, et al., 2004, Biochemistry, 43:11474-81), fibrin (Kluft, 2003, Pathophysiol Haemost Thromb, 33:425-9), Matrigel (Cao, et al., 2005, Thromb Haemost, 93:770-8), other extracellular matrix components (Sato, et al., 2005, Cancer Sci, 96:212-7), CD44 (Suenaga, et al., 2005, Oncogene, 24:859-68), and various other proteins (Hwang, et al., 2004, Biochim Biophys Acta, 1702:79-87). MMP-14 can promote the activation of pro-collagenase 2 and -3, a potent collagenolytic protease (Knauper et al, 1996, J Biol Chem, 271:17124-31; Woessner et Nagase, 2000).

MMP-14 has been implicated in many disease states, including, e.g.: tumor growth (Trisciuoglio, et al., 2005, J Cell Physiol), tumor embolism (Cao, et al., 1996, J Biol Chem, 271:30174-80), angiogenesis (Haas, 2005, Can J Physiol Pharmacol, 83:1-7; (Handsley and Edwards, 2005, Int J Cancer, 115:849-60; (Roebuck, et al., 2005, Am J Clin Pathol, 123:405-14; (Pilorget, et al., 2005, J Cereb Blood Flow Metab), and cell proliferation (Aoki, et al., 2005, J Biochem (Tokyo), 137:95-9). Accordingly, proteins that bind and/or inhibit MMP-14 can be used to treat and/or diagnose these conditions.

As MMP-14 is implicated in the progression of laryngeal cancer, MMP-14 may serve as a reliable marker in estimating invasive and metastatic potency of laryngeal cancer. Suppressing expression of MMP-14 may inhibit the invasion and metastases of laryngeal cancer (Sun, Li, 2004, Chin Med Sci J, 19(3):170-3). Thus, MMP-14 binding proteins can be used to treat or prevent metastatic cancers, e.g., metastatic laryngeal cancer.

MMP-14 is implicated in several non-oncological diseases including: rheumatoid arthritis (Itoh and Seiki, 2005, J Cell Physiol,; (Distler, et al., 2005, Proc Natl Acad Sci USA, 102:2892-7); osteoarthritis (Tchetina, et al., 2005, J Rheumatol, 32:876-86); diabetes (inter alia, (Savinov, et al., 2005, J Biol Chem, 280:27755-8; Giebel, et al., 2005, Lab Invest, 85:597-607; Raymond, et al., 2004, J Vasc Surg, 40:1190-8); and atherosclerosis (Stawowy, et al., 2005, Circulation, 111: 2820-7; May, et al., 2005, Thromb Haemost, 93:710-5; Rajavashisth, et al., 1999, Circulation, 99:3103-9). The role of MMPs in development, normal processes, and cancer is reviewed in Folgueras et al., Int. J. Dev. Biol. 48:411-424 (2004). Accordingly, proteins that bind and/or inhibit MMP-14 are useful to treat and/or diagnose these conditions.

MMP-16

Matrix metalloproteinase-16 (also known as MMP-16, membrane type-3 matrix metalloproteinase, or MT3-MMP) is expressed in a variety of normal (Takino et al, 1995, J Biol Chem, 270: 23013-20; Yoshiyama et al, 1998, Acta Neuropathol, 96: 347-50; Shofuda et al, 2001, 947:337-40; Nutall et al, 2003, Mol Cancer Res, 1:333-45) and tumor tissues (Nutall et al, 2003, Mol Cancer Res, 1:333-45; Kitagawa et al, 1999, J Urol, 162:905-9; Ohnishi et al, 2001, Eur J dermatol, 11:420-3). MMP-16 is involved in the remodeling of both the normal and diseased mammary gland either directly or indirectly by activation of other MMPs. Non invasive breast cancer (MCF-7) express notably less MMPs than invasive breast cancer (MDA-MB-231) (Kousidou et al. 2005, Int J Oncol, 26(4):1101-9; Szabova et al. 2005, J Cell Physiol, 205(1): 123-32). MMP-16 plays a role in extracellular matrix turnover not only by activating proMMP-2 but also by acting directly on ECM macromolecules.

MMP-16 is involved in capillary tube formation (Lafleur et al, 2002, J Cell Sci., 115(Pt 17):3427-38. et al. 2004, J Clin Endocrinol Metab, 89(11):5828-36; et al. 2002, J Cell Sci; Plaisier et al, 2004, J Clin Endocrinol Metab, 89(11):5828-36.) and matrix remodeling of blood vessels (Shofuda et al. 1997, J Biol Chem, 272(15):9749-54). MMP-16 is an alternate pro-invasive factor that drives fibrin-invasive activity (Kang et al, 2000, Faseb J, 14(15):2559-68; 2002, et al. J Exp Med, 195(3):295-308).

MMP-16 shows increased expression in osteoarthritis (at P<0.01) (Kevorkian et al. 2004, Arthritis Rheum., 50(1):131-41). MMP-16 is intensely expressed in synovium of rheumatoid arthritis patients (Pap et al. 2000, Arthritis Rheum., 43(6):1226-32). Expression of MMP-16 is also increased in human atherosclerotic plaque (Uzui et al. 2002, Circulation, 106(24):3024-30).

MMP-16 is expressed in the ovarian cancers (Stadlmann et al. 2003, Eur J Cancer, 39(17):2499-505). Expression of MMP-2, MMP-16, and VEGF is increased in testicular carcinoma (Konaka et al. 1999, J Urol, 161(1):342-8), and MMP-16 shows increased expression in the testicular cancer associated with increased metastatic potential (Koshida et al. 2000, Hinyokika Kiyo, 46(10):775-81). Expression of MMP-16 is higher in carcinomas, especially clear cell carcinoma, than in normal parenchyma.

MMP-16 is expressed in primary and metastatic melanoma cells. Double immunofluorescence demonstrates a consistent colocalization of MMP-16/MMP-2 in metastatic melanoma cells. The colocalization of MMP-16 and MMP-2 in nodular and metastatic melanoma cells indicates that MT-MMPs and MMP-2 may cooperate in the invasive and metastatic process of melanoma cells (Ohnishi et al. 2001, Eur J Dermatol, 11(5):420-3; Iida et al. 2001, J Biol Chem, 276(22):18786-94). Like MMP-14, MMP-16 is implicated in the progression of laryngeal cancer. Thus, MMP-14 binding proteins that also bind and/or inhibit MMP-16 can be used to treat or prevent metastatic cancers, e.g., metastatic laryngeal cancer.

Basal MMP-16 mRNA expression has a pattern similar to that of MMP-14 but is not up-regulated by collagen (Gilles et al. 1997, Lab Invest, 76(5):651-60). MMP-14 is implicated in collagen-stimulated MMP-2 activation. This mechanism may be employed in vivo by both tumor-associated fibroblasts and EMT-derived carcinoma cells to facilitate increased invasion and/or metastasis. In human invasive breast carcinomas, there is a correlation between the expression of MMP-14 and -16, immunolocalization of MMP-14 and proMMP-2 activation (Ueno et al. 1997, Cancer Res, 57(10):2055-60). MMP-16 and TIMP-2 mRNA expressions are significantly increased in diabetic rat kidneys (Wan et al. 2004, Di Yi Jun Yi Da Xue Xue Bao. 24(12):1391-4).

MMP-24

Matrix metalloproteinase-24 (also known as MMP-24, membrane type-5 matrix metalloproteinase, or MT5-MMP) has been identified and cloned from a human brain cDNA library (Llano et al., 1999, Cancer Res, 59(11):2570-6). While sharing similar domain structure with other MT-MMPs, the cytoplasmic tail of MMP-24 is the most divergent, having only 50% identity with those of MMP-14 and -16 (Pei D, 1999, J Biol Chem, 274, 8925-32). MMP-24 is expressed predominantly in the brain and at low levels in the kidney, pancreas, and lung. MMP-24 has been shown to play a role in axonal growth (Hayashita-Kinoh et al., 2001, Cell Growth Differ, 12, 573-58). Human MMP-24 gene maps to 20q11.2, a region frequently amplified in tumors from diverse sources, suggesting that MMP-24 may play a role in the progression of cancer. The catalytic domain of MMP-24 exhibits a potent proteolytic activity against proMMP-2, leading to the generation of the Mr 62,000 active form of this enzyme. MMP-24 may contribute to the activation of proMMP-2 in tumor tissues, in which it is overexpressed, thereby facilitating tumor progression (Pei D, 1999, J Biol Chem, 274, 8925-32).

MMP-24 transcripts are detected at high levels compared to normal brain tissue in a series of brain tumors, including astrocytomas, glioblastomas and gliomas (Van metter et al, 2004, Neuro-oncol, 3:188-99). MMP-24 is predominantly expressed in the brain. (Brain Res. 2000 Mar. 31; 860(1-2): 174; Biol Chem. 1999 Mar. 26; 274(13):8925-32; Lett. 1999 Dec. 3; 462(3):261-6).

MMP-24 mRNA levels are higher in a series of brain tumors, including astrocytomas and glioblastomas, as compared to levels in normal brain tissue (Llano et al., 1999, Cancer Res, 59(11):2570-6).

MMP-24-deficient mice are born without obvious morphological abnormalities. No apparent histological defects are observed in the nervous system. However, MMP-24 deficient mice do not develop neuropathic pain with mechanical allodynia after sciatic nerve injury, though responses to acute noxious stimuli are normal (Uekita et al, FEBS Lett. 2004 Jan. 16, 557(1-3):125-8).

MMP-24 expression is increased in infected corneas. There is good correlation between the overexpression of MMP-24 in the infected corneas and the inflammatory response. Inflammatory cells such as macrophages and PMNs may play a role in the upregulation of MT-MMPs during corneal infection, which in turn can cause the destruction of corneal tissue (Dong et al, Invest Ophthalmol Vis Sci. 2001 December; 42(13):3223-7).

MMP-24 expression is increased in diabetes. MMP-24 plays a role in the pathogenesis of renal tubular atrophy and end-stage renal disease (Romanic et al, 2001, Am J Physiol Renal Physiol, August; 281(2):F309-17).

MMP-24 is co-localized with senile plaques in Alzheimer brain, indicating possible roles in regulating patho-physiological processes associated with advanced age (Sekine-Aizawa, 2001, Eur J Neurosci, 13(5):935-48).

Display Libraries

A display library is a collection of entities; each entity includes an accessible polypeptide component and a recoverable component that encodes or identifies the polypeptide component. The polypeptide component is varied so that different amino acid sequences are represented. The polypeptide component can be of any length, e.g. from three amino acids to over 300 amino acids. A display library entity can include more than one polypeptide component, for example, the two polypeptide chains of an sFab. In one exemplary implementation, a display library can be used to identify proteins that bind to MMP-14. In a selection, the polypeptide component of each member of the library is probed with MMP-14 (e.g., the catalytic domain of MMP-14 or other fragment) and if the polypeptide component binds to the MMP-14, the display library member is identified, typically by retention on a support.

Retained display library members are recovered from the support and analyzed. The analysis can include amplification and a subsequent selection under similar or dissimilar conditions. For example, positive and negative selections can be alternated. The analysis can also include determining the amino acid sequence of the polypeptide component and purification of the polypeptide component for detailed characterization.

A variety of formats can be used for display libraries. Examples include the following.

Phage Display: The protein component is typically covalently linked to a bacteriophage coat protein. The linkage results from translation of a nucleic acid encoding the protein component fused to the coat protein. The linkage can include a flexible peptide linker, a protease site, or an amino acid incorporated as a result of suppression of a stop codon. Phage display is described, for example, in U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; WO 90/02809; de Haard et al. (1999) *J. Biol. Chem* 274:18218-30; Hoogenboom et al. (1998) *Immunotechnology* 4:1-20; Hoogenboom et al. (2000) *Immunol Today* 2:371-8 and Hoet et al. (2005) *Nat Biotechnol.* 23(3)344-8. Bacteriophage displaying the protein component can be grown and harvested using standard phage preparatory methods, e.g. PEG precipitation from growth media. After selection of individual display phages, the nucleic acid encoding the selected protein components can be isolated from cells infected with the selected phages or from the phage themselves, after amplification. Individual colonies or plaques can be picked, the nucleic acid isolated and sequenced.

Other Display Formats. Other display formats include cell based display (see, e.g., WO 03/029456), protein-nucleic acid fusions (see, e.g., U.S. Pat. No. 6,207,446), ribosome display (See, e.g., Mattheakis et al. (1994) *Proc. Natl. Acad. Sci. USA* 91:9022 and Hanes et al. (2000) *Nat Biotechnol.* 18:1287-92; Hanes et al. (2000) *Methods Enzymol.* 328:404-30; and Schaffitzel et al. (1999) *J Immunol Methods.* 231(1-2):119-35), and *E. coli* periplasmic display (*J Immunol Methods.* 2005 Nov. 22; PMID: 16337958).

Scaffolds. Scaffolds useful for display include: antibodies (e.g., Fab fragments, single chain Fv molecules (scFV), single domain antibodies, camelid antibodies, and camelized antibodies); T-cell receptors; MHC proteins; extracellular domains (e.g., fibronectin Type III repeats, EGF repeats); protease inhibitors (e.g., Kunitz domains, ecotin, BPTI, and so forth); TPR repeats; trifoil structures; zinc finger domains; DNA-binding proteins; particularly monomeric DNA binding proteins; RNA binding proteins; enzymes, e.g., proteases (particularly inactivated proteases), RNase; chaperones, e.g., thioredoxin and heat shock proteins; intracellular signaling domains (such as SH2 and SH3 domains); linear and constrained peptides; and linear peptide substrates. Display libraries can include synthetic and/or natural diversity. See, e.g., US 2004-0005709.

Display technology can also be used to obtain binding proteins (e.g., antibodies) that bind particular epitopes of a target. This can be done, for example, by using competing non-target molecules that lack the particular epitope or are mutated within the epitope, e.g., with alanine. Such non-target molecules can be used in a negative selection procedure as described below, as competing molecules when binding a display library to the target, or as a pre-elution agent, e.g., to capture in a wash solution dissociating display library members that are not specific to the target.

Iterative Selection. In one preferred embodiment, display library technology is used in an iterative mode. A first display library is used to identify one or more binding proteins for a target. These identified binding proteins are then varied using a mutagenesis method to form a second display library. Higher affinity binding proteins are then selected from the second library, e.g., by using higher stringency or more competitive binding and washing conditions.

In some implementations, the mutagenesis is targeted to regions at the binding interface. If, for example, the identified binding proteins are antibodies, then mutagenesis can be directed to the CDR regions of the heavy or light chains as described herein. Further, mutagenesis can be directed to framework regions near or adjacent to the CDRs. In the case of antibodies, mutagenesis can also be limited to one or a few of the CDRs, e.g., to make precise step-wise improvements. Exemplary mutagenesis techniques include: error-prone PCR, recombination, DNA shuffling, site-directed mutagenesis and cassette mutagenesis.

In one example of iterative selection, the methods described herein are used to first identify a protein from a display library that binds MMP-14 with at least a minimal binding specificity for a target or a minimal activity, e.g., an equilibrium dissociation constant for binding of less than 1 nM, 10 nM, or 100 nM. The nucleic acid sequence encoding the initial identified proteins are used as a template nucleic acid for the introduction of variations, e.g., to identify a second protein that has enhanced properties (e.g., binding affinity, kinetics, or stability) relative to the initial protein.

Off-Rate Selection. Since a slow dissociation rate can be predictive of high affinity, particularly with respect to interactions between polypeptides and their targets, the methods described herein can be used to isolate binding proteins with a desired (e.g., reduced) kinetic dissociation rate for a binding interaction to a target.

To select for slow dissociating binding proteins from a display library, the library is contacted to an immobilized target. The immobilized target is then washed with a first solution that removes non-specifically or weakly bound biomolecules. Then the bound binding proteins are eluted with a second solution that includes a saturating amount of free target or a target specific high-affinity competing monoclonal antibody, i.e., replicates of the target that are not attached to the particle. The free target binds to biomolecules that dissociate from the target. Rebinding is effectively prevented by the saturating amount of free target relative to the much lower concentration of immobilized target.

The second solution can have solution conditions that are substantially physiological or that are stringent. Typically, the solution conditions of the second solution are identical to the solution conditions of the first solution. Fractions of the second solution are collected in temporal order to distinguish early from late fractions. Later fractions include biomolecules that dissociate at a slower rate from the target than biomolecules in the early fractions.

Further, it is also possible to recover display library members that remain bound to the target even after extended incubation. These can either be dissociated using chaotropic conditions or can be amplified while attached to the target. For example, phage bound to the target can be contacted to bacterial cells.

Selecting or Screening for Specificity. The display library screening methods described herein can include a selection or screening process that discards display library members that bind to a non-target molecule. Examples of non-target molecules include streptavidin on magnetic beads, blocking agents such as bovine serum albumin, non-fat bovine milk, any capturing or target immobilizing monoclonal antibody, or non-transfected cells which do not express the human MMP-14 target.

In one implementation, a so-called "negative selection" step is used to discriminate between the target and related non-target molecule and a related, but distinct non-target molecules. The display library or a pool thereof is contacted to the non-target molecule. Members of the sample that do not bind the non-target are collected and used in subsequent selections for binding to the target molecule or even for subsequent negative selections. The negative selection step can be prior to or after selecting library members that bind to the target molecule.

In another implementation, a screening step is used. After display library members are isolated for binding to the target molecule, each isolated library member is tested for its ability to bind to a non-target molecule (e.g., a non-target listed above). For example, a high-throughput ELISA screen can be used to obtain this data. The ELISA screen can also be used to obtain quantitative data for binding of each library member to the target as well as for cross species reactivity to related targets or subunits of the target (e.g., mouse MMP-14) and also under different condition such as pH6 or pH 7.5. The non-target and target binding data are compared (e.g., using a computer and software) to identify library members that specifically bind to the target.

Other Exemplary Expression Libraries

Other types of collections of proteins (e.g., expression libraries) can be used to identify proteins with a particular property (e.g., ability to bind MMP-14 and/or ability to modulate MMP-14), including, e.g., protein arrays of antibodies (see, e.g., De Wildt et al. (2000) Nat. Biotechnol. 18:989-994), lambda gt11 libraries, two-hybrid libraries and so forth.

Exemplary Libraries

It is possible to immunize a non-human primate and recover primate antibody genes that can be displayed on phage (see below). From such a library, one can select antibodies that bind the antigen used in immunization. See, for example, Vaccine. (2003) 22(2):257-67 or Immunogenetics. (2005) 57(10):730-8. Thus one could obtain primate antibodies that bind and inhibit MMP-14 by immunizing a chimpanzee or macaque and using a variety of means to select or screen for primate antibodies that bind and inhibit MMP-14. One can also make chimeras of primatized Fabs with human constant regions, see Curr Opin Mol Ther. (2004) 6(6):675-83. "PRIMATIZED antibodies, genetically engineered from cynomolgus macaque monkey and human components, are structurally indistinguishable from human antibodies. They may, therefore, be less likely to cause adverse reactions in humans, making them potentially suited for long-term, chronic treatment" Curr Opin Investig Drugs. (2001) 2(5): 635-8.

One exemplary type of library presents a diverse pool of polypeptides, each of which includes an immunoglobulin domain, e.g., an immunoglobulin variable domain. Of interest are display libraries where the members of the library include primate or "primatized" (e.g., such as human, non-human primate or "humanized",) immunoglobin domains (e.g., immunoglobin variable domains) or chimeric primatized Fabs with human constant regions. Human or humanized immunoglobin domain libraries may be used to identify human or "humanized" antibodies that, for example, recognize human antigens. Because the constant and framework regions of the antibody are human, these antibodies may avoid themselves being recognized and targeted as antigens when administered to humans. The constant regions may also be optimized to recruit effector functions of the human immune system. The in vitro display selection process surmounts the inability of a normal human immune system to generate antibodies against self-antigens.

A typical antibody display library displays a polypeptide that includes a VH domain and a VL domain. An "immunoglobulin domain" refers to a domain from the variable or constant domain of immunoglobulin molecules. Immunoglobulin domains typically contain two β-sheets formed of about seven β-strands, and a conserved disulphide bond (see, e.g., A. F. Williams and A. N. Barclay, 1988, *Ann. Rev. Immunol.* 6:381-405). The display library can display the antibody as a Fab fragment (e.g., using two polypeptide chains) or a single chain Fv (e.g., using a single polypeptide chain). Other formats can also be used.

As in the case of the Fab and other formats, the displayed antibody can include one or more constant regions as part of a light and/or heavy chain. In one embodiment, each chain includes one constant region, e.g., as in the case of a Fab. In other embodiments, additional constant regions are displayed.

Antibody libraries can be constructed by a number of processes (see, e.g., de Haard et al., 1999, *J. Biol. Chem.* 274: 18218-30; Hoogenboom et al., 1998, *Immunotechnology* 4:1-20; Hoogenboom et al., 2000, *Immunol. Today* 21:371-378, and Hoet et al. (2005) *Nat Biotechnol.* 23(3)344-8. Further, elements of each process can be combined with those of other processes. The processes can be used such that variation is introduced into a single immunoglobulin domain (e.g., VH or VL) or into multiple immunoglobulin domains (e.g., VH and VL). The variation can be introduced into an immunoglobulin variable domain, e.g., in the region of one or more of CDR1, CDR2, CDR3, FR1, FR2, FR3, and FR4, referring to such regions of either and both of heavy and light chain variable domains. The variation(s) may be introduced into all three CDRs of a given variable domain, or into CDR1 and CDR2, e.g., of a heavy chain variable domain. Any combination is feasible. In one process, antibody libraries are constructed by inserting diverse oligonucleotides that encode CDRs into the corresponding regions of the nucleic acid. The oligonucleotides can be synthesized using monomeric nucleotides or trinucleotides. For example, Knappik et al., 2000, *J. Mol. Biol.* 296:57-86 describe a method for constructing CDR encoding oligonucleotides using trinucleotide synthesis and a template with engineered restriction sites for accepting the oligonucleotides.

In another process, an animal, e.g. a rodent, is immunized with MMP-14. The animal is optionally boosted with the antigen to further stimulate the response. Then spleen cells are isolated from the animal, and nucleic acid encoding VH and/or VL domains is amplified and cloned for expression in the display library.

In yet another process, antibody libraries are constructed from nucleic acid amplified from naïve germline immunoglobulin genes. The amplified nucleic acid includes nucleic acid encoding the VH and/or VL domain. Sources of immunoglobulin-encoding nucleic acids are described below. Amplification can include PCR, e.g., with primers that anneal to the conserved constant region, or another amplification method.

Nucleic acid encoding immunoglobulin domains can be obtained from the immune cells of, e.g., a primate (e.g., a human), mouse, rabbit, camel, or rodent. In one example, the cells are selected for a particular property. B cells at various stages of maturity can be selected. In another example, the B cells are naïve.

In one embodiment, fluorescent-activated cell sorting (FACS) is used to sort B cells that express surface-bound IgM, IgD, or IgG molecules. Further, B cells expressing different isotypes of IgG can be isolated. In another preferred embodiment, the B or T cell is cultured in vitro. The cells can be stimulated in vitro, e.g., by culturing with feeder cells or by adding mitogens or other modulatory reagents, such as antibodies to CD40, CD40 ligand or CD20, phorbol myristate acetate, bacterial lipopolysaccharide, concanavalin A, phytohemagglutinin, or pokeweed mitogen.

In another embodiment, the cells are isolated from a subject that has a disease of condition described herein, e.g., a cancer (e.g., metastatic cancer, e.g., metastatic breast cancer), an inflammatory disease (e.g., synovitis, atherosclerosis), rheumatoid arthritis, osteoarthritis, an ocular condition (e.g., macular degeneration), diabetes, Alzheimer's Disease, cerebral ischemia, endometriosis, fibrin-invasive activity, angiogenesis, or capillary tube formation In another embodiment, the cells are isolated from a transgenic non-human animal that includes a human immunoglobulin locus.

In one preferred embodiment, the cells have activated a program of somatic hypermutation. Cells can be stimulated to undergo somatic mutagenesis of immunoglobulin genes, for example, by treatment with anti-immunoglobulin, anti-CD40, and anti-CD38 antibodies (see, e.g., Bergthorsdottir et al., 2001, *J. Immunol.* 166:2228). In another embodiment, the cells are naïve.

The nucleic acid encoding an immunoglobulin variable domain can be isolated from a natural repertoire by the following exemplary method. First, RNA is isolated from the immune cell. Full length (i.e., capped) mRNAs are separated (e.g. by degrading uncapped RNAs with calf intestinal phosphatase). The cap is then removed with tobacco acid pyrophosphatase and reverse transcription is used to produce the cDNAs.

The reverse transcription of the first (antisense) strand can be done in any manner with any suitable primer. See, e.g., de Haard et al., 1999, *J. Biol. Chem.* 274:18218-30. The primer binding region can be constant among different immunoglobulins, e.g., in order to reverse transcribe different isotypes of immunoglobulin. The primer binding region can also be specific to a particular isotype of immunoglobulin. Typically, the primer is specific for a region that is 3' to a sequence encoding at least one CDR. In another embodiment, poly-dT primers may be used (and may be preferred for the heavy-chain genes).

A synthetic sequence can be ligated to the 3' end of the reverse transcribed strand. The synthetic sequence can be used as a primer binding site for binding of the forward primer during PCR amplification after reverse transcription. The use of the synthetic sequence can obviate the need to use a pool of different forward primers to fully capture the available diversity.

The variable domain-encoding gene is then amplified, e.g., using one or more rounds. If multiple rounds are used, nested primers can be used for increased fidelity. The amplified nucleic acid is then cloned into a display library vector.

Secondary Screening Methods

After selecting candidate library members that bind to a target, each candidate library member can be further analyzed, e.g., to further characterize its binding properties for the target, e.g., MMP-14, or for binding to other protein, e.g., another metalloproteinase. Each candidate library member can be subjected to one or more secondary screening assays. The assay can be for a binding property, a catalytic property, an inhibitory property, a physiological property (e.g., cytotoxicity, renal clearance, immunogenicity), a structural property (e.g., stability, conformation, oligomerization state) or another functional property. The same assay can be used repeatedly, but with varying conditions, e.g., to determine pH, ionic, or thermal sensitivities.

As appropriate, the assays can use a display library member directly, a recombinant polypeptide produced from the nucleic acid encoding the selected polypeptide, or a synthetic peptide synthesized based on the sequence of the selected polypeptide. In the case of selected Fabs, the Fabs can be evaluated or can be modified and produced as intact IgG proteins. Exemplary assays for binding properties include the following.

ELISA. Binding proteins can be evaluated using an ELISA assay. For example, each protein is contacted to a microtitre plate whose bottom surface has been coated with the target, e.g., a limiting amount of the target. The plate is washed with buffer to remove non-specifically bound polypeptides. Then the amount of the binding protein bound to the target on the plate is determined by probing the plate with an antibody that can recognize the binding protein, e.g., a tag or constant portion of the binding protein. The antibody is linked to a detection system (e.g., an enzyme such as alkaline phosphatase or horse radish peroxidase (HRP) which produces a colorimetric product when appropriate substrates are provided).

Homogeneous Binding Assays. The ability of a binding protein described herein to bind a target can be analyzed using a homogenous assay, i.e., after all components of the assay are added, additional fluid manipulations are not required. For example, fluorescence resonance energy transfer (FRET) can be used as a homogenous assay (see, for example, Lakowicz et al., U.S. Pat. No. 5,631,169; Stavrianopoulos, et al., U.S. Pat. No. 4,868,103). A fluorophore label on the first molecule (e.g., the molecule identified in the fraction) is selected such that its emitted fluorescent energy can be absorbed by a fluorescent label on a second molecule (e.g., the target) if the second molecule is in proximity to the first molecule. The fluorescent label on the second molecule fluoresces when it absorbs to the transferred energy. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A binding event that is configured for monitoring by FRET can be conveniently measured through standard fluorometric detection means, e.g., using a fluorimeter. By titrating the amount of the first or second binding molecule, a binding curve can be generated to estimate the equilibrium binding constant.

Another example of a homogenous assay is ALPHAS-CREEN™ (Packard Bioscience, Meriden Conn.). ALPHAS-CREEN™ uses two labeled beads. One bead generates singlet oxygen when excited by a laser. The other bead generates a light signal when singlet oxygen diffuses from the first bead and collides with it. The signal is only generated when the two beads are in proximity. One bead can be attached to the display library member, the other to the target. Signals are measured to determine the extent of binding.

Surface Plasmon Resonance (SPR). The interaction of binding protein and a target can be analyzed using SPR. SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules. Methods for using SPR are described, for example, in U.S. Pat. No. 5,641,640; Raether, 1988, Surface Plasmons Springer Verlag; Sjolander and Urbaniczky, 1991, Anal. Chem. 63:2338-2345; Szabo et al., 1995, Curr. Opin. Struct. Biol. 5:699-705 and on-line resources provide by BIAcore International AB (Uppsala, Sweden).

Information from SPR can be used to provide an accurate and quantitative measure of the equilibrium dissociation constant ($K_d$), and kinetic parameters, including $K_{on}$ and $K_{off}$, for the binding of a binding protein to a target. Such data can be used to compare different biomolecules. For example, selected proteins from an expression library can be compared to identify proteins that have high affinity for the target or that have a slow $K_{off}$. This information can also be used to develop structure-activity relationships (SAR). For example, the kinetic and equilibrium binding parameters of matured versions of a parent protein can be compared to the parameters of the parent protein. Variant amino acids at given positions can be identified that correlate with particular binding parameters, e.g., high affinity and slow $K_{off}$. This information can be combined with structural modeling (e.g., using homology modeling, energy minimization, or structure determination by x-ray crystallography or NMR). As a result, an understanding of the physical interaction between the protein and its target can be formulated and used to guide other design processes.

Cellular Assays. Binding proteins can be screened for ability to bind to cells which transiently or stably express and display the target of interest on the cell surface. For example, MMP-14 binding proteins can be fluorescently labeled and binding to MMP-14 in the presence of absence of antagonistic antibody can be detected by a change in fluorescence intensity using flow cytometry e.g., a FACS machine.

Other Exemplary Methods for Obtaining MMP-14 Binding Antibodies

In addition to the use of display libraries, other methods can be used to obtain a MMP-14 binding antibody. For example, MMP-14 protein or a region thereof can be used as an antigen in a non-human animal, e.g., a rodent.

In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies (Mabs) derived from the genes with the desired specificity may be produced and selected. See, e.g., XENOMOUSE™, Green et al., 1994, Nat. Gen. 7:13-21; U.S. 2003-0070185, WO 96/34096, published Oct. 31, 1996, and PCT Application No. PCT/US96/05928, filed Apr. 29, 1996.

In another embodiment, a monoclonal antibody is obtained from the non-human animal, and then modified, e.g., humanized or deimmunized. Winter describes a CDR-grafting method that may be used to prepare the humanized antibodies (UK Patent Application GB 2188638A, filed on Mar. 26, 1987; U.S. Pat. No. 5,225,539. All of the CDRs of a particular human antibody may be replaced with at least a portion of a non-human CDR or only some of the CDRs may be replaced with non-human CDRs. It is only necessary to replace the number of CDRs required for binding of the humanized antibody to a predetermined antigen.

Humanized antibodies can be generated by replacing sequences of the Fv variable region that are not directly involved in antigen binding with equivalent sequences from human Fv variable regions. General methods for generating humanized antibodies are provided by Morrison, S. L., 1985, Science 229:1202-1207, by Oi et al., 1986, BioTechniques 4:214, and by Queen et al. U.S. Pat. No. 5,585,089, U.S. Pat. No. 5,693,761 and U.S. Pat. No. 5,693,762. Those methods include isolating, manipulating, and expressing the nucleic acid sequences that encode all or part of immunoglobulin Fv variable regions from at least one of a heavy or light chain. Numerous sources of such nucleic acid are available. For example, nucleic acids may be obtained from a hybridoma producing an antibody against a predetermined target, as described above. The recombinant DNA encoding the humanized antibody, or fragment thereof, can then be cloned into an appropriate expression vector.

Reducing Immunogenicity of MMP-14 Binding Proteins

Immunoglobin MMP-14 binding proteins (e.g., IgG or Fab MMP-14 binding proteins) may be modified to reduce immunogenicity. Reduced immunogenicity is desirable in MMP-14 binding proteins intended for use as therapeutics, as it reduces the chance that the subject will develop an immune response against the therapeutic molecule. Techniques useful for reducing immunogenicity of MMP-14 binding proteins include deletion/modification of potential human T cell epitopes and 'germlining' of sequences outside of the CDRs (e.g., framework and Fc).

An MMP-14-binding antibody may be modified by specific deletion of human T cell epitopes or "deimmunization" by the methods disclosed in WO 98/52976 and WO 00/34317. Briefly, the heavy and light chain variable regions of an antibody are analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the VH and VL sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable regions, or preferably, by single amino acid substitutions. As far as possible conservative substitutions are made, often but not exclusively, an amino acid common at this position in human germline antibody sequences may be used. Human germline sequences are disclosed in Tomlinson, I. A. et al., 1992, J. Mol. Biol. 227:776-798; Cook, G. P. et al., 1995, Immunol. Today Vol. 16 (5): 237-242; Chothia, D. et al., 1992, J. Mol. Bio. 227:799-817. The V BASE directory provides a comprehensive directory of human immunoglobulin variable region sequences (compiled by Tomlinson, I. A. et al. MRC Centre for Protein Engineering, Cambridge, UK). After the deimmunizing changes are identified, nucleic acids encoding $V_H$ and $V_L$ can be constructed by mutagenesis or other synthetic methods (e.g., de novo synthesis, cassette replacement, and so forth).

Mutagenized variable sequence can, optionally, be fused to a human constant region, e.g., human IgG1 or κ constant regions.

In some cases a potential T cell epitope will include residues which are known or predicted to be important for antibody function. For example, potential T cell epitopes are usually biased towards the CDRs. In addition, potential T cell epitopes can occur in framework residues important for antibody structure and binding. Changes to eliminate these potential epitopes will in some cases require more scrutiny, e.g., by making and testing chains with and without the change. Where possible, potential T cell epitopes that overlap the CDRs were eliminated by substitutions outside the CDRs. In some cases, an alteration within a CDR is the only option, and thus variants with and without this substitution should be tested. In other cases, the substitution required to remove a potential T cell epitope is at a residue position within the framework that might be critical for antibody binding. In these cases, variants with and without this substitution should be tested. Thus, in some cases several variant deimmunized heavy and light chain variable regions were designed and various heavy/light chain combinations tested in order to identify the optimal deimmunized antibody. The choice of the final deimmunized antibody can then be made by considering the binding affinity of the different variants in conjunction with the extent of deimmunization, i.e., the number of potential T cell epitopes remaining in the variable region. Deimmunization can be used to modify any antibody, e.g., an antibody that includes a non-human sequence, e.g., a synthetic antibody, a murine antibody other non-human monoclonal antibody, or an antibody isolated from a display library.

MMP-14 binding antibodies are "germlined" by reverting one or more non-germline amino acids in framework regions to corresponding germline amino acids of the antibody, so long as binding properties are substantially retained. Similar methods can also be used in the constant region, e.g., in constant immunoglobulin domains.

Antibodies that bind to MMP-14, e.g., an antibody described herein, may be modified in order to make the variable regions of the antibody more similar to one or more germline sequences. For example, an antibody can include one, two, three, or more amino acid substitutions, e.g., in a framework, CDR, or constant region, to make it more similar to a reference germline sequence. One exemplary germlining method can include identifying one or more germline sequences that are similar (e.g., most similar in a particular database) to the sequence of the isolated antibody. Mutations (at the amino acid level) are then made in the isolated antibody, either incrementally or in combination with other mutations. For example, a nucleic acid library that includes sequences encoding some or all possible germline mutations is made. The mutated antibodies are then evaluated, e.g., to identify an antibody that has one or more additional germline residues relative to the isolated antibody and that is still useful (e.g., has a functional activity). In one embodiment, as many germline residues are introduced into an isolated antibody as possible.

In one embodiment, mutagenesis is used to substitute or insert one or more germline residues into a framework and/or constant region. For example, a germline framework and/or constant region residue can be from a germline sequence that is similar (e.g., most similar) to the non-variable region being modified. After mutagenesis, activity (e.g., binding or other functional activity) of the antibody can be evaluated to determine if the germline residue or residues are tolerated (i.e., do not abrogate activity). Similar mutagenesis can be performed in the framework regions.

Selecting a germline sequence can be performed in different ways. For example, a germline sequence can be selected if it meets a predetermined criteria for selectivity or similarity, e.g., at least a certain percentage identity, e.g., at least 75, 80, 85, 90, 91, 92, 93, 94, 95, 96, 97, 98, 99, or 99.5% identity. The selection can be performed using at least 2, 3, 5, or 10 germline sequences. In the case of CDR1 and CDR2, identifying a similar germline sequence can include selecting one such sequence. In the case of CDR3, identifying a similar germline sequence can include selecting one such sequence, but may including using two germline sequences that separately contribute to the amino-terminal portion and the carboxy-terminal portion. In other implementations more than one or two germline sequences are used, e.g., to form a consensus sequence.

In one embodiment, with respect to a particular reference variable domain sequence, e.g., a sequence described herein, a related variable domain sequence has at least 30, 40, 50, 60, 70, 80, 90, 95 or 100% of the CDR amino acid positions that are not identical to residues in the reference CDR sequences, residues that are identical to residues at corresponding positions in a human germline sequence (i.e., an amino acid sequence encoded by a human germline nucleic acid).

In one embodiment, with respect to a particular reference variable domain sequence, e.g., a sequence described herein, a related variable domain sequence has at least 30, 50, 60, 70, 80, 90 or 100% of the FR regions identical to FR sequence from a human germline sequence, e.g., a germline sequence related to the reference variable domain sequence.

Accordingly, it is possible to isolate an antibody which has similar activity to a given antibody of interest, but is more similar to one or more germline sequences, particularly one or more human germline sequences. For example, an antibody can be at least 90, 91, 92, 93, 94, 95, 96, 97, 98, 99, or 99.5% identical to a germline sequence in a region outside the CDRs (e.g., framework regions). Further, an antibody can include at least 1, 2, 3, 4, or 5 germline residues in a CDR region, the germline residue being from a germline sequence of similar (e.g., most similar) to the variable region being modified. Germline sequences of primary interest are human germline sequences. The activity of the antibody (e.g., the binding activity as measured by $K_A$) can be within a factor or 100, 10, 5, 2, 0.5, 0.1, and 0.001 of the original antibody.

Germline sequences of human immunoglobin genes have been determined and are available from a number of sources, including the international ImMunoGeneTics information system® (IMGT), available via the world wide web at imgt-.cines.fr, and the V BASE directory (compiled by Tomlinson, I. A. et al. MRC Centre for Protein Engineering, Cambridge, UK, available via the world wide web at vbase.mrc-cpe.cam.ac.uk).

Exemplary germline reference sequences for $V_{kappa}$ include: O12/O2, O18/O8, A20, A30, L14, L1, L15, L4/18a, L5/L19, L8, L23, L9, L24, L11, L12, O11/O1, A17, A1, A18, A2, A19/A3, A23, A27, A11, L2/L16, L6, L20, L25, B3, B2, A26/A10, and A14. See, e.g., Tomlinson et al., 1995, *EMBO J.* 14(18):4628-3.

A germline reference sequence for the HC variable domain can be based on a sequence that has particular canonical structures, e.g., 1-3 structures in the H1 and H2 hypervariable loops. The canonical structures of hypervariable loops of an immunoglobulin variable domain can be inferred from its sequence, as described in Chothia et al., 1992, *J. Mol. Biol.* 227:799-817; Tomlinson et al., 1992, *J. Mol. Biol.* 227:776-798); and Tomlinson et al., 1995, *EMBO J.* 14(18):4628-38. Exemplary sequences with a 1-3 structure include: DP-1, DP-8, DP-12, DP-2, DP-25, DP-15, DP-7, DP-4, DP-31, DP-32, DP-33, DP-35, DP-40, 7-2, hv3005, hv3005f3, DP-46, DP-47, DP-58, DP-49, DP-50, DP-51, DP-53, and DP-54.

Protein Production

Standard recombinant nucleic acid methods can be used to express a protein that binds to MMP-14. Generally, a nucleic acid sequence encoding the protein is cloned into a nucleic acid expression vector. Of course, if the protein includes multiple polypeptide chains, each chain can be cloned into an expression vector, e.g., the same or different vectors, that are expressed in the same or different cells.

Antibody Production. Some antibodies, e.g., Fabs, can be produced in bacterial cells, e.g., *E. coli* cells. For example, if the Fab is encoded by sequences in a phage display vector that includes a suppressible stop codon between the display entity and a bacteriophage protein (or fragment thereof), the vector nucleic acid can be transferred into a bacterial cell that cannot suppress a stop codon. In this case, the Fab is not fused to the gene III protein and is secreted into the periplasm and/or media.

Antibodies can also be produced in eukaryotic cells. In one embodiment, the antibodies (e.g., scFv's) are expressed in a yeast cell such as *Pichia* (see, e.g., Powers et al., 2001, *J. Immunol. Methods.* 251:123-35), *Hanseula*, or *Saccharomyces*.

In one preferred embodiment, antibodies are produced in mammalian cells. Preferred mammalian host cells for expressing the clone antibodies or antigen-binding fragments thereof include Chinese Hamster Ovary (CHO cells) (including dhfr-CHO cells, described in Urlaub and Chasin, 1980, *Proc. Natl. Acad. Sci. USA* 77:4216-4220, used with a DHFR selectable marker, e.g., as described in Kaufman and Sharp, 1982, *Mol. Biol.* 159:601 621), lymphocytic cell lines, e.g., NS0 myeloma cells and SP2 cells, COS cells, HEK293T cells (*J. Immunol. Methods* (2004) 289(1-2):65-80.), and a cell from a transgenic animal, e.g., a transgenic mammal. For example, the cell is a mammary epithelial cell.

In addition to the nucleic acid sequence encoding the diversified immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

In an exemplary system for recombinant expression of an antibody, or antigen-binding portion thereof, a recombinant expression vector encoding both the antibody heavy chain and the antibody light chain is introduced into dhfr⁻ CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G coupled matrix.

For antibodies that include an Fc domain, the antibody production system may produce antibodies in which the Fc region is glycosylated. For example, the Fc domain of IgG molecules is glycosylated at asparagine 297 in the CH2 domain. This asparagine is the site for modification with biantennary-type oligosaccharides. It has been demonstrated that this glycosylation is required for effector functions mediated by Fcg receptors and complement C1q (Burton and Woof, 1992, *Adv. Immunol.* 51:1-84; Jefferis et al., 1998, *Immunol. Rev.* 163:59-76). In one embodiment, the Fc domain is produced in a mammalian expression system that appropriately glycosylates the residue corresponding to asparagine 297. The Fc domain can also include other eukaryotic post-translational modifications.

Antibodies can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

Characterization of MMP-14 Binding Proteins

Binding of MMP-14 binding proteins to cells expressing MMP-14 can be characterized in a number assays known in the art, including FACS (Fluorescence Activated Cell Sorting), immunofluorescence, and immunocytochemistry. MMP-14 binding protein is contacted with cells and/or tissues which express or contain MMP-14, and binding is detected in accordance with the method being used. For example, a fluorescent detection system (e.g., fluorescent-labeled secondary antibody) employed for FACS and immunofluorescence analysis, or a enzymatic system is used for immunocytochemistry are generally used in these assayscan be performed on non-perm. MMP-14 binding proteins can be characterized as to cellular binding by FACS (Fluorescence Activated Cell Sorting) using cells expressing MMP-14. Individual cells held in a thin stream of fluid are passed through one or more laser beams cause light to scatter and fluorescent dyes to emit light at various frequencies. Photomultiplier tubes (PMT) convert light to electrical signals and cell data is collected. Forward and side scatter are used for preliminary identification of cells. Forward and side scatter are used to exclude debris and dead cells. Fluorescent labeling allows investigation of cell structure and function. Cell autofluorescence is generated by labeling cell structures with fluorescent dyes. FACS collects fluorescence signals in one to several channels corresponding to different laser excitation and fluorescence emission wavelength. Immunofluorescence, the most widely used application, involves the staining of cells with antibodies conjugated to fluorescent dyes such as fluorescein and phycoerythrin (PE). This method can be used to label MMP-14 on the cell surface of MDA-MB-231 cells using biotinylated MMP-14 binding proteins. Biotin is used in this two-step detection systems in concert with conjugated steptavidin. Biotin is typically conjugated to proteins via primary amines (i.e., lysines). Usually, between 1.5 and 3 biotin molecules are conjugated to each antibody. A second fluorescently conjugated antibody (streptavidin/PE) is added which is specific for biotin.

MMP-14 binding proteins can be characterized in cultured cells expressing the MMP-14 antigen. The method generally used is immunocytochemistry. Immunocytochemistry involves the use of antibodies that recognize parts of the receptor that are exposed to the outside environment when expressed at the cell surface (the 'primary antibody'). If the experiment is carried out in intact cells, such an antibody will only bind to surface expressed receptors. Biotinylated or non-biotinylated MMP-14 binding proteins can be used. The secondary antibody is then either a streptavidin/HRP antibody (for biotinylated MMP-14 binding protein) or an anti-human IgG/HRP (for non-biotinylated MMP-14 binding protein). The staining can then be detected using an inverted microscope. The assay can be performed in the absence of MMP-14 binding protein and in presence of 10 µg/mL of MMP-14 binding protein.

MMP-14 binding proteins can be characterized in assays that measure their modulatory activity toward MMP-14 or fragments thereof in vitro or in vivo. For example, MMP-14 can be combined with a substrate such as Mca-Pro-Leu-Ala-Cys(Mob)-Trp-Ala-Arg-Dap(Dnp)-NH$_2$ under assay conditions permitting cleavage by MMP-14. The assay is performed in the absence of the MMP-14 binding protein, and in the presence of increasing concentrations of the MMP-14 binding protein. The concentration of binding protein at which 50% of the MMP-14 activity (e.g., binding to the substrate) is inhibited is the IC$_{50}$ value (Inhibitory Concentration 50%) or EC$_{50}$ (Effective Concentration 50%) value for that binding protein. Within a series or group of binding proteins, those having lower IC$_{50}$ or EC$_{50}$ values are considered more potent inhibitors of MMP-14 than those binding proteins having higher IC$_{50}$ or EC$_{50}$ values. Exemplary binding proteins have an IC$_{50}$ value of less than 800 nM, 400 nM, 100 nM, 25 nM, 5 nM, or 1 nM, e.g., as measured in an in vitro assay for inhibition of MMP-14 activity when the MMP-14 is at 2 pM.

MMP-14 binding proteins may also be characterized with reference to the activity of MMP-14 on its substrates (e.g., activation of cell surface pro-MMP-2). Cleavage of cell surface pro-MMP-2 by MMP-14 releases active MMP-2, which can be detected by zymography. The method is based on a SDS gel impregnated with a protein substrate, which is degraded by the proteases resolved during the incubation period. Coomassie blue staining of the gels reveals proteolytic fragments as white bands on a dark blue background. Within a certain range, the band intensity can be related linearly to the amount of the protease loaded. Cells expressing both MMP-14 and MMP-2 are used in this assay. The assay is performed in the absence of the MMP-14 binding protein, and in the presence of increasing concentrations of the MMP-14 binding protein. The concentration of binding protein at which 50% of the MMP-2 activity (e.g., binding to the substrate) is inhibited is the IC$_{50}$ value (Inhibitory Concentration 50%) or EC$_{50}$ (Effective Concentration 50%) value for that binding protein. Within a series or group of binding proteins, those having lower IC$_{50}$ or EC$_{50}$ values are considered more potent inhibitors of MMP-14 than those binding proteins having higher IC$_{50}$ or EC$_{50}$ values. Exemplary binding proteins have an IC$_{50}$ value of less than 800 nM, 400 nM, 100 nM, 25 nM, 5 nM, or 1 nM, e.g., as measured in an in vitro assay for inhibition of MMP-14 activity.

The binding proteins can also be evaluated for selectivity toward MMP-14. For example, a MMP-14 binding protein can be assayed for its potency toward MMP-14 and a panel of MMPs and other enzymes, e.g., MMP-1, -2, -3, -7, -8, -9, -12, -13, -16, -17, -24, and TACE, and an IC$_{50}$ value or EC$_{50}$ value can be determined for each MMP. In one embodiment, a compound that demonstrates a low IC$_{50}$ value or EC$_{50}$ value for the MMP-14, and a higher IC$_{50}$ value or EC$_{50}$ value, e.g., at least 2-, 5-, or 10-fold higher, for another MMP within the test panel (e.g., MMP-1, -10) is considered to be selective toward MMP-14.

MMP-14 binding proteins can be evaluated for their ability to inhibit MMP-14 in a cell based assay. The expansion of tumor cells inside a three-dimensional collagen-matrix can be significantly enhanced in response to MMP-14 overexpression (Hotary et al., 2003 Cell 114:33-45). Addition of an MMP-14 binding protein to this assay can be used to determine the inhibitory properties and other characteristics of the protein.

A pharmacokinetics study in rat, mice, or monkey can be performed with MMP-14 binding proteins for determining MMP-14 half-life in the serum. Likewise, the effect of the binding protein can be assessed in vivo, e.g., in an animal model for a disease, for use as a therapeutic, for example, to treat a disease or condition described herein, e.g., a cancer (e.g., metastatic cancer, e.g., metastatic breast cancer), an inflammatory disease (e.g., synovitis, atherosclerosis), rheumatoid arthritis, osteoarthritis, an ocular condition (e.g., macular degeneration), diabetes, Alzheimer's Disease, cerebral ischemia, endometriosis, fibrin-invasive activity, angiogenesis, or capillary tube formation.

Pharmaceutical Compositions

In another aspect, the disclosure provides compositions, e.g., pharmaceutically acceptable compositions or pharmaceutical compositions, which include an MMP-14-binding protein, e.g., an antibody molecule, other polypeptide or peptide identified as binding to MMP-14 described herein. The MMP-14 binding protein can be formulated together with a pharmaceutically acceptable carrier. Pharmaceutical compositions include therapeutic compositions and diagnostic compositions, e.g., compositions that include labeled MMP-14 binding proteins for in vivo imaging.

A pharmaceutically acceptable carrier includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal, or epidermal administration (e.g., by injection or infusion), although carriers suitable for inhalation and intranasal administration are also contemplated. Depending on the route of administration, the MMP-14 binding protein may be coated in a material to protect the compound from the action of acids and other natural conditions that may inactivate the compound.

A pharmaceutically acceptable salt is a salt that retains the desired biological activity of the parent compound and does not impart any undesired toxicological effects (see e.g., Berge, S. M., et al., 1977, *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous, and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids, and the like. Base addition salts include those derived from alkaline earth metals, such as sodium, potassium, magnesium, calcium, and the like, as well as from nontoxic organic amines, such as N,N'-dibenzylethylenediamine, N-methylglucamine, chloroprocaine, choline, diethanolamine, ethylenediamine, procaine, and the like.

The compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form can depend on the intended mode of administration and therapeutic application. Many compositions are in the form of injectable or infusible solutions, such as compositions similar to those used for administration of humans with antibodies. An exemplary mode of administration is parenteral (e.g., intravenous, subcutaneous, intraperitoneal, intramuscular). In one embodiment, the MMP-14 binding protein is administered by intravenous infusion or injection. In another preferred embodiment, the MMP-14 binding protein is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion.

The composition can be formulated as a solution, microemulsion, dispersion, liposome, or other ordered structure suitable to high drug concentration. Sterile injectable solutions can be prepared by incorporating the binding protein in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

An MMP-14 binding protein can be administered by a variety of methods, although for many applications, the preferred route/mode of administration is intravenous injection or infusion. For example, for therapeutic applications, the MMP-14 binding protein can be administered by intravenous infusion at a rate of less than 30, 20, 10, 5, or 1 mg/min to reach a dose of about 1 to 100 mg/m$^2$ or 7 to 25 mg/m$^2$. The route and/or mode of administration will vary depending upon the desired results. In certain embodiments, the active compound may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are available. See, e.g., Sustained and Controlled Release Drug Delivery Systems, J. R. Robinson, ed., 1978, Marcel Dekker, Inc., New York.

Pharmaceutical compositions can be administered with medical devices. For example, in one embodiment, a pharmaceutical composition disclosed herein can be administered with a device, e.g., a needleless hypodermic injection device, a pump, or implant.

In certain embodiments, an MMP-14 binding protein can be formulated to ensure proper distribution in vivo. For example, the blood-brain barrier (BBB) excludes many highly hydrophilic compounds. To ensure that the therapeutic compounds disclosed herein cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties that are selectively transported into specific cells or organs, thus enhance targeted drug delivery (see, e.g., V. V. Ranade, 1989, *J. Clin. Pharmacol.* 29:685).

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms can be dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody disclosed herein is 0.1-20 mg/kg, more preferably 1-10 mg/kg. An anti-MMP-14 antibody can be administered, e.g., by intravenous infusion, e.g., at a rate of less than 30, 20, 10, 5, or 1 mg/min to reach a dose of about 1 to 100 mg/m$^2$ or about 5 to 30 mg/m$^2$. For binding proteins smaller in molecular weight than an antibody, appropriate amounts can be proportionally less. Dosage values may vary with the type and severity of the condition to be alleviated. For a particular subject, specific dosage regimens can be adjusted over time according to the individual need and the professional judgment of the person administering or supervising the administration of the compositions.

The pharmaceutical compositions disclosed herein may include a "therapeutically effective amount" or a "prophylactically effective amount" of an MMP-14 binding protein disclosed herein. A "therapeutically effective amount" refers to an amount effective, at dosages and for periods of time necessary, to achieve the desired therapeutic result. A therapeutically effective amount of the composition may vary according to factors such as the disease state, age, sex, and weight of the individual, and the ability of the protein to elicit a desired response in the individual. A therapeutically effective amount is also one in which any toxic or detrimental effects of the composition is outweighed by the therapeutically beneficial effects.

A "therapeutically effective dosage" preferably modulates a measurable parameter, e.g., levels of circulating IgG antibodies by a statistically significant degree or at least about 20%, more preferably by at least about 40%, even more preferably by at least about 60%, and still more preferably by at least about 80% relative to untreated subjects. The ability of a compound to modulate a measurable parameter, e.g., a disease-associated parameter, can be evaluated in an animal model system predictive of efficacy in human disorders and conditions, e.g., a cancer (e.g., metastatic cancer, e.g., metastatic breast cancer), an inflammatory disease (e.g., synovitis, atherosclerosis), rheumatoid arthritis, osteoarthritis, an ocular condition (e.g., macular degeneration), diabetes, Alzheimer's Disease, cerebral ischemia, endometriosis, fibrin-invasive activity, angiogenesis, or capillary tube formation. Alternatively, this property of a composition can be evaluated by examining the ability of the compound to modulate a parameter in vitro.

A "prophylactically effective amount" refers to an amount effective, at dosages and for periods of time necessary, to achieve the desired prophylactic result. Typically, because a prophylactic dose is used in subjects prior to or at an earlier stage of disease, the prophylactically effective amount will be less than the therapeutically effective amount.

Stabilization and Retention

In one embodiment, an MMP-14 binding protein is physically associated with a moiety that improves its stabilization and/or retention in circulation, e.g., in blood, serum, lymph, or other tissues, e.g., by at least 1.5, 2, 5, 10, or 50 fold. For example, an MMP-14 binding protein can be associated with a polymer, e.g., a substantially non-antigenic polymers, such as polyalkylene oxides or polyethylene oxides. Suitable polymers will vary substantially by weight. Polymers having molecular number average weights ranging from about 200 to about 35,000 (or about 1,000 to about 15,000, and 2,000 to about 12,500) can be used. For example, an MMP-14 binding protein can be conjugated to a water soluble polymer, e.g., hydrophilic polyvinyl polymers, e.g. polyvinylalcohol and polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

An MMP-14 binding protein can also be associated with a carrier protein, e.g., a serum albumin, such as a human serum albumin. For example, a translational fusion can be used to associate the carrier protein with the MMP-14 binding protein.

Kits

An MMP-14 binding protein described herein can be provided in a kit, e.g., as a component of a kit. For example, the kit includes (a) an MMP-14 binding protein, e.g., a composition that includes an MMP-14 binding protein, and, optionally (b) informational material. The informational material can be descriptive, instructional, marketing or other material that relates to the methods described herein and/or the use of an MMP-14 binding protein for the methods described herein.

The informational material of the kits is not limited in its form. In one embodiment, the informational material can include information about production of the compound, molecular weight of the compound, concentration, date of expiration, batch or production site information, and so forth. In one embodiment, the informational material relates to using the binding protein to treat, prevent, or diagnosis of disorders and conditions, e.g., a cancer (e.g., metastatic cancer, e.g., metastatic breast cancer), an inflammatory disease (e.g., synovitis, atherosclerosis), rheumatoid arthritis, osteoarthritis, an ocular condition (e.g., macular degeneration), diabetes, Alzheimer's Disease, cerebral ischemia, endometriosis, fibrin-invasive activity, angiogenesis, or capillary tube formation.

In one embodiment, the informational material can include instructions to administer an MMP-14 binding protein in a suitable manner to perform the methods described herein, e.g., in a suitable dose, dosage form, or mode of administration (e.g., a dose, dosage form, or mode of administration described herein). In another embodiment, the informational material can include instructions to administer an MMP-14 binding protein to a suitable subject, e.g., a human, e.g., a human having, or at risk for, a disorder or condition described herein, e.g., a cancer (e.g., metastatic cancer, e.g., metastatic breast cancer), an inflammatory disease (e.g., synovitis, atherosclerosis), rheumatoid arthritis, osteoarthritis, an ocular condition (e.g., macular degeneration), diabetes, Alzheimer's Disease, cerebral ischemia, endometriosis, fibrin-invasive activity, angiogenesis, or capillary tube formation. For example, the material can include instructions to administer an MMP-14 binding protein to a patient with a disorder or condition described herein, e.g., a cancer (e.g., metastatic cancer, e.g., metastatic breast cancer), an inflammatory disease (e.g., synovitis, atherosclerosis), rheumatoid arthritis, osteoarthritis, an ocular condition (e.g., macular degeneration), diabetes, Alzheimer's Disease, cerebral ischemia, endometriosis, fibrin-invasive activity, angiogenesis, or capillary tube formation. The informational material of the kits is not limited in its form. In many cases, the informational material, e.g., instructions, is provided in print but may also be in other formats, such as computer readable material.

An MMP-14 binding protein can be provided in any form, e.g., liquid, dried or lyophilized form. It is preferred that an MMP-14 binding protein be substantially pure and/or sterile. When an MMP-14 binding protein is provided in a liquid solution, the liquid solution preferably is an aqueous solution, with a sterile aqueous solution being preferred. When an MMP-14 binding protein is provided as a dried form, reconstitution generally is by the addition of a suitable solvent. The solvent, e.g., sterile water or buffer, can optionally be provided in the kit.

The kit can include one or more containers for the composition containing an MMP-14 binding protein. In some embodiments, the kit contains separate containers, dividers or compartments for the composition and informational material. For example, the composition can be contained in a bottle, vial, or syringe, and the informational material can be contained association with the container. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of an MMP-14 binding protein. For example, the kit includes a plurality of syringes, ampules, foil packets, or blister packs, each containing a single unit dose of an MMP-14 binding protein. The containers of the kits can be air tight, waterproof (e.g., impermeable to changes in moisture or evaporation), and/or light-tight.

The kit optionally includes a device suitable for administration of the composition, e.g., a syringe, inhalant, dropper (e.g., eye dropper), swab (e.g., a cotton swab or wooden swab), or any such delivery device. In one embodiment, the device is an implantable device that dispenses metered doses of the binding protein. The disclosure also features a method of providing a kit, e.g., by combining components described herein.

Treatments

Proteins that bind to MMP-14 and identified by the method described herein and/or detailed herein have therapeutic and prophylactic utilities, particularly in human subjects. These binding proteins are administered to a subject to treat, prevent, and/or diagnose a variety of disorders, including e.g., a cancer (e.g., metastatic cancer, e.g., metastatic breast cancer), an inflammatory disease (e.g., synovitis, atherosclerosis), rheumatoid arthritis, osteoarthritis, an ocular condition (e.g., macular degeneration), diabetes, Alzheimer's Disease, cerebral ischemia, endometriosis, fibrin-invasive activity, angiogenesis, or capillary tube formation, or even to cells in culture, e.g. in vitro or ex vivo. Treating includes administering an amount effective to alleviate, relieve, alter, remedy, ameliorate, improve or affect the disorder, the symptoms of the disorder or the predisposition toward the disorder. The treatment may also delay onset, e.g., prevent onset, or prevent deterioration of a disease or condition.

Exemplary disorders include a cancer (e.g., metastatic cancer, e.g., metastatic breast cancer), an inflammatory disease (e.g., synovitis, atherosclerosis), rheumatoid arthritis, osteoarthritis, an ocular condition (e.g., macular degeneration), diabetes, Alzheimer's Disease, cerebral ischemia, endometriosis, fibrin-invasive activity, angiogenesis, or capillary tube formation. Some of these disorders are discussed above. Still other disorders that can be treated using an MMP-14 binding protein include: aortic aneurysms, periodontitis, autoimmune blistering disorders of the skin, dermal photoaging.

As used herein, an amount of an target-binding agent effective to prevent a disorder, or a prophylactically effective amount of the binding agent refers to an amount of a target binding agent, e.g., an MMP-14 binding protein, e.g., an anti-MMP-14 antibody described herein, which is effective, upon single- or multiple-dose administration to the subject, for preventing or delaying the occurrence of the onset or recurrence of a disorder, e.g., a disorder described herein.

A binding agent described herein can be used to reduce angiogenesis in a subject, e.g., to treat a cancer (e.g., a solid tumor) or an angiogenesis-associated disorder. The method includes administering the binding to the subject, e.g., in an amount effective to modulate angiogenesis, a symptom of the disorder, or progression of the disorder. The agent (e.g., an MMP-14 binding protein, e.g., an anti-MMP-14 antibody) may be administered multiple times (e.g., at least two, three, five, or ten times) before a therapeutically effective amount is attained. Methods of administering MMP-14 binding proteins and other agents are also described in "Pharmaceutical Compositions." Suitable dosages of the molecules used can depend on the age and weight of the subject and the particular drug used. The binding proteins can be used as competitive agents to inhibit, reduce an undesirable interaction, e.g., between a natural or pathological agent and the MMP-14. The dose of the MMP-14 binding protein can be the amount sufficient to block 90%, 95%, 99%, or 99.9% of the activity of MMP-14 in the patient, especially at the site of disease. Depending on the disease, this may require 0.1, 1.0, 3.0, 6.0, or 10.0 mg/Kg. For an IgG having a molecular mass of 150,000 g/mole (two binding sites), these doses correspond to approximately 18 nM, 180 nM, 540 nM, 1.08 µM, and 1.8 µM of binding sites for a 5 L blood volume.

In one embodiment, the MMP-14 binding proteins are used to inhibit an activity (e.g., inhibit at least one activity of, reduce proliferation, migration, growth or viability) of a cell, e.g., a cancer cell in vivo. The binding proteins can be used by themselves or conjugated to an agent, e.g., a cytotoxic drug, cytotoxin enzyme, or radioisotope. This method includes: administering the binding protein alone or attached to an agent (e.g., a cytotoxic drug), to a subject requiring such treatment. For example, MMP-14 binding proteins that do not substantially inhibit MMP-14 may be used to deliver nanoparticles containing agents, such as toxins, to MMP-14 associated cells or tissues, e.g., tumors.

Because the MMP-14 binding proteins recognize MMP-14-expressing cells and can bind to cells that are associated with (e.g., in proximity of or intermingled with) cancer cells, e.g., cancerous lung, liver, colon, breast, ovarian, epidermal, laryngeal, and cartilage cells, and particularly metastatic cells thereof, MMP-14 binding proteins can be used to inhibit (e.g., inhibit at least one activity, reduce growth and proliferation, or kill) any such cells and inhibit carcinogenesis. Reducing MMP-14 activity near a cancer can indirectly inhibit (e.g., inhibit at least one activity, reduce growth and proliferation, or kill) the cancer cells which may be dependent on the MMP-14 activity for metastasis, activation of growth factors, and so forth.

Alternatively, the binding proteins bind to cells in the vicinity of the cancerous cells, but are sufficiently close to the cancerous cells to directly or indirectly inhibit (e.g., inhibit at least one activity, reduce growth and proliferation, or kill) the cancers cells. Thus, the MMP-14 binding proteins (e.g., modified with a toxin, e.g., a cytotoxin) can be used to selectively inhibit cells in cancerous tissue (including the cancerous cells themselves and cells associated with or invading the cancer).

The binding proteins may be used to deliver an agent (e.g., any of a variety of cytotoxic and therapeutic drugs) to cells and tissues where MMP-14 is present. Exemplary agents include a compound emitting radiation, molecules of plants, fungal, or bacterial origin, biological proteins, and mixtures thereof. The cytotoxic drugs can be intracellularly acting cytotoxic drugs, such as toxins short range radiation emitters, e.g., short range, high energy α-emitters.

To target MMP-14 expressing cells, particularly cancerous cells, a prodrug system can be used. For example, a first binding protein is conjugated with a prodrug which is activated only when in close proximity with a prodrug activator. The prodrug activator is conjugated with a second binding protein, preferably one which binds to a non competing site on the target molecule. Whether two binding proteins bind to competing or non competing binding sites can be determined by conventional competitive binding assays. Exemplary drug prodrug pairs are described in Blakely et al., (1996) Cancer Research, 56:3287 3292.

The MMP-14 binding proteins can be used directly in vivo to eliminate antigen-expressing cells via natural complement-dependent cytotoxicity (CDC) or antibody dependent cellular cytotoxicity (ADCC). The binding proteins described herein can include complement binding effector domain, such as the Fc portions from IgG1, -2, or -3 or corresponding portions of IgM which bind complement. In one embodiment, a population of target cells is ex vivo treated with a binding agent described herein and appropriate effector cells. The treatment can be supplemented by the addition of complement or serum containing complement. Further, phagocytosis of target cells coated with a binding protein described herein can be improved by binding of complement proteins. In another embodiment target, cells coated with the binding protein which includes a complement binding effector domain are lysed by complement.

Methods of administering MMP-14 binding proteins are described in "Pharmaceutical Compositions." Suitable dosages of the molecules used will depend on the age and weight of the subject and the particular drug used. The binding proteins can be used as competitive agents to inhibit or reduce an undesirable interaction, e.g., between a natural or pathological agent and the MMP-14.

The MMP-14 binding protein can be used to deliver macro and micromolecules, e.g., a gene into the cell for gene therapy purposes into the endothelium or epithelium and target only those tissues expressing the MMP-14. The binding proteins may be used to deliver a variety of cytotoxic drugs including therapeutic drugs, a compound emitting radiation, molecules of plants, fungal, or bacterial origin, biological proteins, and mixtures thereof. The cytotoxic drugs can be intracellularly acting cytotoxic drugs, such as short range radiation emitters, including, for example, short range, high energy α emitters, as described herein.

In the case of polypeptide toxins, recombinant nucleic acid techniques can be used to construct a nucleic acid that encodes the binding protein (e.g., antibody or antigen-binding fragment thereof) and the cytotoxin (or a polypeptide component thereof) as translational fusions. The recombinant nucleic acid is then expressed, e.g., in cells and the encoded fusion polypeptide isolated.

Alternatively, the MMP-14 binding protein can be coupled to high energy radiation emitters, for example, a radioisotope, such as $^{131}$I, a γ-emitter, which, when localized at a site, results in a killing of several cell diameters. See, e.g., S. E. Order, "Analysis, Results, and Future Prospective of the Therapeutic Use of Radiolabeled Antibody in Cancer Therapy", *Monoclonal Antibodies for Cancer Detection and Therapy*, R. W. Baldwin et al. (eds.), pp 303 316 (Academic Press 1985). Other suitable radioisotopes include a emitters, such as $^{212}$Bi, $^{213}$Bi, and $^{211}$At, and b emitters, such as $^{186}$Re and $^{90}$Y. Moreover, $^{177}$Lu may also be used as both an imaging and cytotoxic agent.

Radioimmunotherapy (RIT) using antibodies labeled with $^{131}$I, $^{90}$Y, and $^{177}$Lu is under intense clinical investigation. There are significant differences in the physical characteristics of these three nuclides and as a result, the choice of radionuclide is very critical in order to deliver maximum radiation dose to a tissue of interest. The higher beta energy particles of $^{90}$Y may be good for bulky tumors. The relatively low energy beta particles of $^{131}$I are ideal, but in vivo dehalogenation of radioiodinated molecules is a major disadvantage for internalizing antibody. In contrast, $^{177}$Lu has low energy beta particle with only 0.2-0.3 mm range and delivers much lower radiation dose to bone marrow compared to $^{90}$Y. In addition, due to longer physical half-life (compared to $^{90}$Y), the residence times are higher. As a result, higher activities (more mCi amounts) of $^{177}$Lu labeled agents can be administered with comparatively less radiation dose to marrow. There have been several clinical studies investigating the use of $^{177}$Lu labeled antibodies in the treatment of various cancers. (Mulligan T et al., 1995, *Clin. Canc. Res.* 1: 1447-1454; Meredith R F, et al., 1996, *J. Nucl. Med.* 37:1491-1496; Alvarez R D, et al., 1997, *Gynecol. Oncol.* 65: 94-101).

Exemplary Diseases and Conditions

The MMP-14 binding proteins described herein are useful to treat diseases or conditions in which MMP-14 is implicated, e.g., a disease or condition described herein, or to treat one or more symptoms associated therewith. In some embodiments, the MMP-14 binding protein (e.g., MMP-14 binding IgG or Fab) inhibits MMP-14 activity, and may further inhibit, MMP-16, and/or MMP-24. MMP-14 binding proteins which inhibit MMP-16 and/or MMP-24 are particularly useful for the treatment of disorders in which these metalloproteases are also implicated.

Examples of such diseases and conditions include a cancer (e.g., metastatic cancer, e.g., metastatic breast cancer), inflammatory disease (e.g., synovitis, rheumatoid arthritis, osteoarthritis), atherosclerosis, ocular conditions (e.g., macular degeneration), diabetes, Alzheimer's Disease, cerebral ischemia, endometriosis, fibrin-invasive activity, angiogenesis, and capillary tube formation. A therapeutically effective amount of a MMP-14 binding protein is administered to a subject having or suspected of having a disorder in which MMP-14 is implicated, thereby treating (e.g., ameliorating or improving a symptom or feature of a disorder, slowing, stabilizing or halting disease progression) the disorder.

The MMP-14 binding protein is administered in a therapeutically effective amount. A therapeutically effective amount of an MMP-14 binding protein is the amount which is effective, upon single or multiple dose administration to a subject, in treating a subject, e.g., curing, alleviating, relieving or improving at least one symptom of a disorder in a subject to a degree beyond that expected in the absence of such treatment. A therapeutically effective amount of the composition may vary according to factors such as the disease state, age, sex, and weight of the individual, and the ability of the compound to elicit a desired response in the individual. A therapeutically effective amount is also one in which any toxic or detrimental effects of the composition is outweighed by the therapeutically beneficial effects.

A therapeutically effective amount can be administered, typically an amount of the compound which is effective, upon single or multiple dose administration to a subject, in treating a subject, e.g., curing, alleviating, relieving or improving at least one symptom of a disorder in a subject to a degree beyond that expected in the absence of such treatment. A therapeutically effective amount of the composition may vary according to factors such as the disease state, age, sex, and weight of the individual, and the ability of the compound to elicit a desired response in the individual. A therapeutically effective amount is also one in which any toxic or detrimental effects of the composition is outweighed by the therapeutically beneficial effects. A therapeutically effective dosage preferably modulates a measurable parameter, favorably, relative to untreated subjects. The ability of a compound to inhibit a measurable parameter can be evaluated in an animal model system predictive of efficacy in a human disorder.

Dosage regimens can be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Cancer

Matrix metalloproteases (MMPs), such as MMP-14, MMP-16, and MMP-24, are believed to contribute to cancer by cleaving components of the ECM and basement membranes, thereby allowing cancer cells to penetrate and infiltrate the subjacent stromal matrix. Additionally, a number of growth-factor receptors, cell adhesion molecules, chemokines, cytokines, apoptotic ligands, and angiogenic factors are substrates of MMPs. Hence, MMP activity may cause activation of growth factors, suppression of tumor cell apoptosis, destruction of chemokine gradients developed by host immune response, or release of angiogenic factors. MMPs may facilitate tumor growth by promoting the release of cell proliferation factors such as insulin-like growth factors which are bound to specific binding proteins (IGFBPs) (Manes et al., 1997 J. Biol. Chem. 272: 25706-25712).

Collagenases, including MMP-2, have been found at elevated levels in melanoma and in cancers of the colon, breast, lung, prostate, and bladder. Usually, these elevated levels correlate with higher tumor grade and invasiveness. MMP-2 levels are significantly elevated in the serum of patients with metastatic lung cancer, and in those patients with high levels, response to chemotherapy is diminished.

Likewise, MMP-14, which cleaves proMMP-2 to release active MMP-2, is elevated in numerous cancers and can contribute to the growth of tumors, tumor embolism, and the mobility, invasiveness and metastasis of cancer (e.g., CNS tumors (e.g., gliomas), head and neck cancer, oral cavity cancer, laryngeal cancer, chondrosarcoma, breast cancer).

MMP-16 and MMP-24 are also elevated in numerous cancers and can contribute to both the growth of tumors and the invasiveness and metastasis of cancer (e.g., breast cancer, laryngeal cancer, ovarian cancer, testicular carcinoma, melanoma, brain tumors (e.g., astrocytomas, glioblastomas, gliomas).

Accordingly, the disclosure provides methods of treating (e.g., slowing, eliminating, or reversing tumor growth, preventing or reducing, either in number or size, metastases, reducing or eliminating tumor cell invasiveness, providing an increased interval to tumor progression, or increasing disease-free survival time) cancer (e.g., breast cancer, including Her2+, Her2−, ER+, ER−, Her2+/ER+, Her2+/ER−, Her2−/ER+, and Her2−/ER− breast cancer), head and neck cancer, oral cavity cancer, laryngeal cancer, chondrosarcoma, ovarian cancer, testicular carcinoma, melanoma, brain tumors (e.g., astrocytomas, glioblastomas, gliomas)) by administering an effective amount of an MMP-14 binding protein (e.g., an anti-MMP-14 IgG or Fab). In some embodiments, the MMP-14 binding protein inhibits MMP-14 activity. The MMP-14 binding protein may further inhibit MMP-16 and/or MMP-24.

In certain embodiments, the MMP-14 binding protein is administered as a single agent treatment. In other embodiments, the MMP-14 binding protein is administered in combination with a an additional anti-cancer agent.

Also provided are methods of preventing or reducing risk of developing cancer, by administering an effective amount of an MMP-14 binding protein to a subject at risk of developing cancer, thereby reducing the subject's risk of developing a cancer.

The disclosure further provides methods of modulating (e.g. reducing or preventing) angiogenesis at a tumor site by administering an effective amount of an MMP-14 binding protein, thereby reducing or preventing angiogenesis at the tumor site. The MMP-14 binding protein may be administered as a single agent therapy or in combination with additional agents.

Also provided are methods for reducing extracellular matrix (ECM) degradation by a tumor, comprising administering an effective amount of an MMP-14 binding protein to a subject, thereby reducing ECM degradation by a tumor in the subject.

The disclosed methods are useful in the prevention and treatment of solid tumors, soft tissue tumors, and metastases thereof. Solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine. Additional exemplary solid tumors include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastrointestinal system carcinomas, colon carcinoma, pancreatic cancer, breast cancer, genitourinary system carcinomas, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, endocrine system carcinomas, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Metastases of the aforementioned cancers can also be treated or prevented in accordance with the methods described herein.

Guidance for determination of a therapeutically effective amount for treatment of cancer may be obtained by reference to in vivo models of the cancer to be treated. For example, the amount of a MMP-14 binding protein that is a therapeutically effective amount in a rodent or Libechov minipig model of cancer may be used to guide the selection of a dose that is a therapeutically effective amount. A number of rodent models of human cancers are available, including nude mouse/tumor xenograft systems (e.g., melanoma xenografts; see, e.g., Trikha et al. Cancer Research 62:2824-2833 (2002)) and murine models of breast cancer or glioma (e.g., Kuperwasser et al., Cancer Research 65, 6130-6138, (2005); Bradford et al., Br J Neurosurg. 3(2):197-210 (1989)). A melanoblastoma-bearing Libechov minipig (MeLiM) is available as an animal model of melanoma (e.g., Boisgard et al., Eur J Nucl Med Mol Imaging 30(6):826-34 (2003)).

Synovitis

Synovitis is a condition characterized by inflammation of the synovium, a tissue normally only a few cell layers thick. In synovitis, the synovium can become thickened, more cellular, and engorged with fluid. Synovitis can cause pain and inflammation within the affected joint, and is commonly seen in arthritic conditions (e.g., rheumatoid arthritis).

Active synovial MMP-2 is associated with radiographic erosions in patients with early synovitis (Goldbach-Mansky et al, 2000, Arthritis Res, 2:145-153). Synovial tissue expressions of MMP-2, MMP-14, and TIMP-2 are virtually undetectable in normal synovial tissue samples. The synovial tissue samples of patients with erosive disease have significantly higher levels of active MMP-2 than did those of patients without erosions. This may reflect augmented activation of MMP-2 by the relatively high levels of MMP-14 and low levels of TIMP-2 seen in these tissues. Thus, active MMP-2 can contribute to the development and/or progression of rheumatoid arthritis and osteoarthritis.

The disclosure provides methods of treating (e.g., ameliorating, stabilizing, reducing, or eliminating a symptom of synovitis such as pain, joint swelling, synovial thickening, increased synovial fluid) synovitis by administering a therapeutically effective amount of a MMP-14 binding protein. Also provided are methods which combine MMP-14 binding protein therapy with additional therapies. Current therapies for synovitis include anti-inflammatory medications (e.g. NSAIDS and ibuprofen), cortisone injections into the joint, and surgical treatment (e.g., synovectomy). One or more of these treatments can be used in combination with an MMP-14 binding protein (e.g., an inhibitory MMP-14 binding protein, e.g., an anti-MMP-14 IgG or Fab) to treat this condition.

Guidance for determination of a therapeutically effective amount of an MMP-14 binding protein may be obtained from an animal model of synovitis. Rodent models of synovitis are available, including a rat model of synovitis-like inflammation (Cirino et al., J Rheumatol. 21(5):824-9 (1994)), and a model of carrageenan synovitis in male Wistar rats (Walsh et al. Lab Invest. 78(12):1513-21 (1998)).

Rheumatoid Arthritis and Associated Conditions

Rheumatoid arthritis (RA) is an autoimmune, chronic inflammatory disease that causes joint swelling and pain and normally results in joint destruction. RA generally follows a relapsing/remitting course, with "flares" of disease activity interspersed with remissions of disease symptoms. RA is associated with a number of additional inflammatory disorders, including Sjogren's syndrome (dry eyes and mouth caused by inflammation of tear and saliva glands), pleuritis (inflammation of the pleura that causes pain upon deep breath and coughing), rheumatoid nodules (nodular sites of inflammation that develop within the lungs), pericarditis (inflammation of the pericardium that causes pain when lying down or leaning forward), Felty syndrome (splenomegaly and leucopenia observed in conjunction with RA, making the subject prone to infection), and vasculitis (an inflammation of the blood vessels which can block blood flow). MMP-14 and MMP-16 have been implicated in rheumatoid arthritis.

Symptoms of active RA include fatigue, lack of appetite, low grade fever, muscle and joint aches, and stiffness. Muscle and joint stiffness are usually most notable in the morning and after periods of inactivity. During flares, joints frequently become red, swollen, painful, and tender, generally as a consequence of synovitis.

Treatment for rheumatoid arthritis involves a combination of medications, rest, joint strengthening exercises, and joint protection. Two classes of medications are used in treating rheumatoid arthritis: anti-inflammatory "first-line drugs," and Disease-Modifying Antirheumatic Drugs (DMARDs)." The first-line drugs, include NSAIDS (e.g., aspirin, naproxen, ibuprofen, and etodolac) and cortisone (corticosteroids). DMARDS, such as gold (e.g., gold salts, gold thioglucose, gold thiomalate, oral gold), methotrexate, sulfasalazine, D-penicillamine, azathioprine, cyclophosphamide, chlorambucil, and cyclosporine, leflunomide, etanercept, infliximab, anakinra, and adalimumab, and hydroxychloroquine, promote disease remission and prevent progressive joint destruction, but they are not anti-inflammatory agents.

The disclosure provides methods of treating (e.g., ameliorating, stabilizing, or eliminating one or more symptoms or ameliorating or stabilizing the subject's score on a RA scale) rheumatoid arthritis by administering a therapeutically effective amount of a MMP-14 binding protein to a subject having or suspected of having RA. Additionally provides are methods of treating RA by administering a therapeutically effective amount of a MMP-14 binding protein and at least one NSAID and/or DMARDS.

Further provided are methods of treating (e.g., ameliorating, stabilizing, or eliminating one or more symptoms) rheumatoid arthritis associated disorders (Sjogren's syndrome, pleuritis, pulmonary rheumatoid nodules, pericarditis, Felty syndrome, and vasculitis) by administering a therapeutically effective amount of an MMP-14 binding protein.

Scales useful for assessing RA and symptoms of RA include the Rheumatoid Arthritis Severity Scale (RASS; Bardwell et al., (2002) *Rheumatology* 41(1):38-45), SF-36 Arthritis Specific Health Index (ASHI; Ware et al., (1999) *Med. Care.* 37(5 Suppl):MS40-50), Arthritis Impact Measurement Scales or Arthritis Impact Measurement Scales 2 (AIMS or AIMS2; Meenan et al. (1992) *Arthritis Rheum.* 35(1):1-10); the Stanford Health Assessment Questionnaire (HAQ), HAQII, or modified HAQ (see, e.g., Pincus et al. (1983) *Arthritis Rheum.* 26(11):1346-53).

Guidance for the determination of the dosage that delivers a therapeutically effective amount of a MMP-14 binding protein may be obtained from animal models of rheumatoid arthritis, such as collagen-induced arthritis (CIA), which is induced, typically in rodents, by immunization with autologous or heterologous type II collagen in adjuvant (Williams et al. Methods Mol Med. 98:207-16 (2004)).

Atherosclerosis

Induction of MMP-14 is linked to the rupture of atherosclerotic plaques associated with acute coronary syndrome (ACS) (Ray et al, 2004, Circ Res, 95:1082-90). MMP-14 can cause highly focal degradation of the fibrous cap structure of atherosclerotic plaques because of its cell membrane location and the ability to activate several other members of the MMP family including MMP-2. Accordingly, the disclosure provides methods of treating (e.g., eliminating, ameliorating, or stabilizing a symptom of atherosclerosis, reducing or stabilizing the size or number of atherosclerotic plaques, including plaques in coronary arteries, carotid arteries, and the aorta, reducing or stabilizing arterial stenosis, including coronary artery and carotid artery stenosis, or reducing risk of myocardial infarction) atherosclerosis in a subject having or suspected of having atherosclerosis by administering a therapeutically effective amount of a MMP-14 binding protein (e.g., an inhibitory MMP-14 binding protein, e.g., an anti-MMP-14 IgG or Fab).

Current treatments for atherosclerosis include cholestyramine, colestipol, nicotinic acid, gemfibrozil, probucol, atorvastatin, lovastatin, aspirin, ticlopidine, clopidogrel (inhibitors of platelet clumping) and anti-coagulants. The disclosure also includes methods of treating atherosclerosis by administering a therapeutically effective amount of a MMP-14 binding protein (e.g., an inhibitory MMP-14 binding protein, e.g., an anti-MMP-14 IgG or Fab) in addition to another atherosclerosis therapy (e.g., cholestyramine, colestipol, nicotinic acid, gemfibrozil, probucol, atorvastatin, lovastatin, aspirin, ticlopidine, clopidogrel, or anti-coagulants).

Guidance for determining the dosage of MMP-14 binding protein that provides a therapeutically effective amount of the MMP-14 binding protein may be obtained from an animal model of atherosclerosis, such as a hypercholesterolaemic rabbit (Booth et al. NMR Biomed. 3(2):95-100 (1990)), or a apoE-knockout mouse (Ozaki et al., J Clin Invest. 110(3): 331-340 (2002)).

Ocular Conditions

Macular Degeneration. Macular degeneration progressively destroys the macula, the central portion of the retina, impairing central vision, leading to difficulty with reading, driving, and/or other daily activities that require fine central vision. While there are a number of different forms of macular degeneration, the most common is age-related macular degeneration (AMD). AMD presents as either "dry" or "wet", with the wet type being far more common. In wet AMD, fluid leaking from newly formed subretinal blood vessels (subretinal neovascularization) distorts the macula and impairs vision. Symptoms of AMD include loss or impairment in central vision (generally slowing in dry AMD and rapidly in wet AMD) and abnormal visual perception of straight lines (e.g., straight lines appear wavy). Supplements of zinc and the antioxidants vitamin C, vitamin E and beta-carotene reportedly slow the progression of wet AMD.

The disclosure provides methods of treating (e.g., ameliorating vision, stabilizing vision degradation, or reducing the rate of vision degradation) AMD (wet AMD or dry AMD) by administering a therapeutically effective amount of a MMP-14 binding protein (e.g., an inhibitory MMP-14 binding protein, e.g., an anti-MMP-14 IgG or Fab) to a subject having or suspected of having AMD. Also provided are methods of treating AMD by administering a therapeutically effective amount of a MMP-14 binding protein with another AMD treatment (e.g., zinc, vitamin C, vitamin E and/or beta-carotene).

Guidance regarding the efficacy and dosage an MMP-14 binding protein which will deliver a therapeutically effective amount of the protein can be obtained from an animal model of macular degeneration, e.g., a Coturnix coturnix japonica (Japanese quail) model of macular degeneration (U.S. Pat. No. 5,854,015), or wound creation on the Bruch's membrane of a C57BL/6J mouse, e.g., with a krypton laser (US App. No. 20030181531).

Corneal Disease. Peak expression of MMP-14 and -16 shows a good correlation with the overall inflammatory response in intracorneal diseases (Dong et al. 2000, Invest Ophthalmol Vis Sci, 41(13):4189-94). Keratoconus is a progressive disease where the cornea thins and changes shape. The resulting distortion (astigmatism) frequently causes nearsightedness. Keratoconus may also cause swelling and scarring of the cornea and vision loss.

The disclosure provides methods of treating (e.g., improving or stabilizing vision, or improving, stabilizing, reducing eliminating, or preventing corneal scarring) keratoconus in a subject having or suspected of having keratoconus by administering an effective amount of a MMP-14 binding protein (e.g., an inhibitory MMP-14 binding protein, e.g., an anti-MMP-14 IgG or Fab).

Guidance regarding the efficacy and dosage an MMP-14 binding protein which will deliver a therapeutically effective amount of the protein can be obtained from an animal model of keratoconus, e.g., the inbred SKC mouse line, which serves as a model for a subset of keratoconus (Tachibana et al. Investig Ophthalmol Visual Sci, 43:51-57 (2002)).

Corneal Infection. Also provided are methods of treating (e.g., preventing, reducing, stabilizing or eliminatnig corneal scarring as a result of the infection) corneal infection by administering an effective amount of a MMP-14 binding protein (e.g., an inhibitory MMP-14 binding protein, e.g., an anti-MMP-14 IgG or Fab) to a subject having or suspected of having a corneal infection. Additionally, methods are provided for treatment of corneal infection by administering a MMP-14 binding protein and a therapeutic agent which treats the infectious agent (e.g., an antibiotic or anti-viral agent).

Guidance regarding the efficacy and dosage an MMP-14 binding protein which will deliver a therapeutically effective amount of the protein can be obtained from an animal model of corneal infection, e.g., a rabbit model of experimental keratomycosis, in which keratitis is induced with a standardized inoculum of Candida albicans (SC 5314) placed on a debrided cornea (Goldblum et al. Antimicrob Agents Chemother 49:1359-1363 (2005)).

Osteoarthritis

Osteoarthritis, also known as degenerative arthritis, is characterized by the breakdown and eventual loss of the cartilage of one or more joints. Osteoarthritis commonly affects the hands, feet, spine, and large weight-bearing joints, such as the hips and knees. MMP-14 and MMP-16 have been implicated in osteoarthritis. The disclosure provides methods of treating (e.g., stabilizing, reducing, or eliminating joint pain, stabilizing or improving performance on general health or osteoarthritis scales) osteoarthritis by administering a therapeutically effective amount of a MMP-14 binding protein (e.g., an inhibitory MMP-14 binding protein, e.g., an anti-MMP-14 IgG or Fab) to a subject having or suspected of having osteoarthritis.

Current medical treatment of osteoarthritis includes conservative measures (e.g., rest, weight reduction, physical and occupational therapy) and medications such as acetaminophen, pain-relieving creams applied to the skin over the joints such as capsaicin, salycin, methyl salicylate, and menthol, nonsteroidal anti-inflammatory drugs (NSAIDs) such as aspirin, ibuprofen, nabumetone, and naproxen, and Cox-2 inhibitors. The disclosure further provides methods of treating osteoarthritis by administering a therapeutically effective amount of a MMP-14 binding protein (e.g., an inhibitory MMP-14 binding protein, e.g., an anti-MMP-14 IgG or Fab) and another osteoarthritis therapy (e.g. acetaminophen, a topical pain-relieving cream, a nonsteroidal anti-inflammatory drug (NSAID) such as aspirin, ibuprofen, nabumetone, or naproxen, or a Cox-2 inhibitor).

Scales useful for the assessment of osteoarthritis include the Knee Injury and Osteoarthritis Outcome Score (KOOS; Roos et al. (1998) *J. Orthop. Sports Phys. Ther.* 28(2):88-96), Western Ontario and McMaster Universities Osteoarthrtis Index (WOMAC; Roos et al. (2003) *Health Qual. Life Outcomes* 1(1):17), and the 36-item Short Form General Health Scale (SF-36 GHS), as well as other assessment tools known in the art.

Guidance regarding the efficacy and dosage an MMP-14 binding protein which will deliver a therapeutically effective amount of the protein can be obtained from an animal model of osteoarthritis, e.g., injection of mono-iodoacetate (MIA) into the femorotibial joint of rodents which promotes loss of articular cartilage similar to that noted in human osteoarthritis (Guzman et al. Toxicol Pathol. 31(6):619-24 (2003)), or transection of the anterior cruciate ligament (ACL) in canines to induce osteoarthritis (Fife and Brandt J Clin Invest. 84(5): 1432-1439 (1989)).

Diabetes

There are two major types of diabetes mellitus, called type 1 (sometimes known as insulin dependent diabetes mellitus (IDDM), or juvenile onset diabetes mellitus) and type 2 (sometimes known as non-insulin dependent diabetes mellitus (NIDDM) or adult onset diabetes mellitus). MMP-14 and MMP-24 have been implicated in diabetes. Pro-MMP2 is efficiently activated in the fibrovascular tissues of proliferative diabetic retinopathy (PDR), probably through interaction with MMP-14 and TIMP2, suggesting that MMP2 and MT1-

MMP may be involved in the formation of the fibrovascular tissues and in the pathogenesis of PDR.

The disclosure provides methods of treating (e.g., reducing or eliminating dependence on exogenous insulin, reducing fasting serum glucose levels, e.g., 6 hour fasting serum glucose, to below 150, 140, 130, 126, 120, 110, or 100 mg/dL) diabetes (type 1 or type 2) by administering a therapeutically effective amount of a MMP-14 binding protein (e.g., an inhibitory MMP-14 binding protein, e.g., an anti-MMP-14 IgG or Fab) to a subject having or suspected of having diabetes mellitus.

The disclosure further provides methods of treating diabetes by administering a therapeutically effective amount of a MMMP-14 binding protein in addition to another diabetes mellitus treatment agent. A number of additional treatment agents are known, including agents that increase the insulin output by the pancreas (e.g., sulfonylureas (e.g., chlorpropamide and tolbutamide, glyburide, glipizide, and glimepiride) and meglitinides (e.g., repaglinide and nateglinide), agents that decrease hepatic glucose production (e.g., biguanides, metformin), insulin sensitizing agents (e.g., troglitazone, pioglitazone, rosiglitazone), agents that decrease the absorption of carbohydrates from the intestine (e.g., acarbose), agents that effect glycemic control (e.g., pramlintide, exenatide), and combination medications such as glyburide/metformin (GLUCOVANCE®), rosiglitazone/metformin (AVANDAMET®), and glipizide/metformin (METAGLIP®).

Also provided are methods of treating disorders secondary to diabetes, such as proliferative diabetic retinopathy (PDR) and microangiopathy. Accordingy, the disclosure provides a method of treating (e.g., preventing, stabilizing, reducing, or eliminating vision deterioration) PDR by administering a therapeutically effective amount of a MMP-14 binding protein (e.g., an inhibitory MMP-14 binding protein, e.g., an anti-MMP-14 IgG or Fab) to a subject having or suspected of having PDR. Also provided are methods of treating (e.g., preventing, stabilizing, reducing, or eliminating a symptom) microangiopathy by administering a MMP-14 binding protein (e.g., an inhibitory MMP-14 binding protein, e.g., an anti-MMP-14 IgG or Fab) to a subject having or suspected of having microangiopathy.

Guidance regarding the efficacy and dosage an MMP-14 binding protein which will deliver a therapeutically effective amount of the protein can be obtained from an animal model of diabetes, e.g., the ob/ob mouse (Kerouz et al. J. Clin. Invest. 100:3164-3172 (1997)), the db/db mouse (Koenig and Cerami Proc Natl Acad Sci USA. 72(9): 3687-3691 (1975)), the Zucker fatty rat (Orci et al. Proc Natl Acad Sci USA. 87(24):9953-7 (1990)), or rats made diabetic by daily low-dose intraperitoneal streptozotocin (STZ) (Nie et al. J Clin Invest. 105:955-965 (2000)).

Alzheimer's Disease

Alzheimer's Disease (AD) is a progressive, neurodegenerative disease characterized in the brain by abnormal clumps (amyloid plaques) and tangled bundles of fibers (neurofibrillary tangles) composed of misplaced proteins. Symptoms of AD include memory loss, language deterioration, impaired ability to mentally manipulate visual information, poor judgment, confusion, restlessness, and mood swings. Eventually AD destroys cognition, personality, and the ability to function. The early symptoms of AD, which include forgetfulness and loss of concentration, are often missed because they resemble natural signs of aging. Current medical treatments for AD include as tacrine (COGNEX®), donepezil (ARICEPT®), rivastigmine (EXELON®), and galantamine (REMINYL®), memantine (NAMENDA™), other drugs that may affect AD progression include nonsteroidal anti-inflammatory drugs (NSAIDS), statins, folic acid, gingko biloba, and vitamins E, B6, and B12.

The disclosure provides methods of treating (e.g., stabilizing, ameliorating, eliminating, or preventing a symptom of AD or slowing or eliminating disease progression) by administering a therapeutically effective amount of a MMP-14 binding protein (e.g., an inhibitory MMP-14 binding protein, e.g., an anti-MMP-14 IgG or Fab) to a subject having or suspected of having AD. Also provided are methods for treatment of AD by administering to a subject having or suspected of having AD a therapeutically effective amount of a MMP-14 binding protein and an additional AD treatment (e.g., tacrine COGNEX®), donepezil (ARICEPT®), rivastigmine (EXELON®), and galantamine (REMINYL®), memantine (NAMENDA™)).

Guidance regarding the efficacy and dosage an MMP-14 binding protein which will deliver a therapeutically effective amount of the protein can be obtained from an animal model of AD. For example, transgenic mice expressing a human or mouse APP or presenilin can be used. Some of these transgenic mice develop a progressive neurologic disorder generally within a year from birth (see, e.g., U.S. Pat. Nos. 5,877,399; 6,037,521; 5,894,078; 5,850,003; and 5,898,094). Certain transgenic animal models have been described, for example, in U.S. Pat. Nos. 5,612,486; 5,387,742; 5,720,936; 5,877,015, and 5,811,633, and in Ganes et. al. (1995) Nature 373:523.

Mammary Gland Remodeling

Mammary morphogenesis involves epithelial "invasion" of adipose tissue, a process akin to invasion by breast cancer cells, although the former is a highly regulated developmental process. Mammary gland branching morphogenesis is dependent, in part, on the extracellular matrix (ECM), ECM-receptors (e.g., integrins), ECM-degrading enzymes (e.g., MMPs) and MMP inhibitors (tissue inhibitors of metalloproteinases (TIMPs)). Increased MMP-14 expression is associated with increased mammary carcinogenesis and MMP-2 contributes to mammary gland branching morphogenesis during puberty. Accordingly, provided herein are methods of inhibiting inappropriate mammary gland remodeling and for prophylaxis or treatment of precancerous lesions/activity in breast tissue.

The disclosure provides methods of inhibiting (e.g., preventing, reducing, or eliminating) inappropriate mammary gland remodeling by administering a therapeutically effective amount of a MMP-14 binding protein (e.g., an inhibitory MMP-14 binding protein, e.g., an anti-MMP-14 IgG or Fab) to a subject having or suspected of having inappropriate mammary gland remodeling. Also provided are methods for prophylaxis or treatment (e.g., reducing risk of developing breast cancer, or preventing, eliminating, reducing, or stabilizing precancerous breast lesions) precancerous breast lesions or activity by administering a therapeutically effective amount of a MMP-14 binding protein (e.g., an inhibitory MMP-14 binding protein, e.g., an anti-MMP-14 IgG or Fab) to a subject having or suspected of having breast tissue precancerous lesions or activity.

Guidance regarding the efficacy and dosage an MMP-14 binding protein which will deliver a therapeutically effective amount of the protein can be obtained from an animal model of mammary carcinogenesis, such as transgenic mice over-expressing MMP-14 in mammary gland under the control of the mouse mammary tumor virus long terminal repeat-promoter (Ha et al. Cancer Research 61:984-990, (2001)), or transgenic mice model in which rat stromelysin-1 expression is augmented in breast tissue (Lochter et al. J Biol Chem 272:5007-5015 (1997)) can be used.

Cerebral Ischemia Expression of MMP-2, MMP-14 and MMP-16 are increased within 1 hour after middle cerebral artery occlusion in the ischemic core (Chang et al. 2003, J Cereb Blood Flow Metab., 23(12):1408-19). The expression patterns are consistent with secretion of proMMP-2 and its activators in the ischemic core, perhaps from separate cell compartments. The rapid and coordinate appearance of pro-MMP-2 and its activation apparatus suggest that in the primate striatum this protease may participate in matrix injury during focal cerebral ischemia.

The disclosure provides methods of treating (e.g., reducing or eliminating a symptom of cerebral ischemia, such as a deficit/impairment in speech, movement, vision, or understanding) cerebral ischemia by administering a therapeutically effective amount of a MMP-14 binding protein (e.g., an inhibitory MMP-14 binding protein, e.g., an anti-MMP-14 IgG or Fab) to a subject having or suspected of having cerebral ischemia.

Current medical treatment of cerebral ischemia includes anticoagulation with heparin and heparin-like agents (low molecular heparin and heparinoid), and aspirin. The disclosure further provides methods of treating cerebral ischemia by administering a therapeutically effective amount of a MMP-14 binding protein (e.g., an inhibitory MMP-14 binding protein, e.g., an anti-MMP-14 IgG or Fab) and an additional cerebral ischemia treatment to a subject having or suspected of having cerebral ischemia.

Guidance regarding the efficacy and dosage an MMP-14 binding protein which will deliver a therapeutically effective amount of the protein can be obtained from an animal model of cerebral ischemia, e.g., acute stroke model middle cerebral artery occlusion (MCAO) and the direct distal MCAO model (Schneider et al. J. Clin. Invest. 115:2083-2098 (2005); Taguchi et al. J. Clin. Invest. 114:330-338 (2004)).

Endometriosis

Endometriosis involves the proliferation of endometrial tissue outside of the endometrial cavity, typically throughout the peritoneum, and can cause significant pain (e.g., pelvic pain, pain upon defecation, dyspareunia) and infertility. Lesions may be "classical" (pigmented, e.g., dark blue, dark brown, or black and may be cystic) or "non-classical" (generally non-pigmented). Non-classical lesions are commonly found in patients with more 'aggressive' disease (e.g., significant pain). MMP-2 and MMP-14 mRNA expression levels in clinically aggressive pigmented lesions are significantly higher than those in normal eutopic endometrium.

Current endometriosis treatments include progestational agents, including acetate, norethynodrel, megestrol acetate, dydrogesterone, norethisterone, and lynestrenol; danazol, a synthetic, 3-isoxazole derivative of 17 ethinyl-testosterone, gonadotropin-releasing hormone (GnRH), destruction of lesions, e.g., with laparoscopy.

The disclosure provides methods for treating (e.g., reducing, stabilizing, or eliminating a symptom of endometriosis such as pain or infertility) endometriosis in a subject having or suspected of having endometriosis by administering a therapeutically effective amount of a MMP-14 binding protein (e.g., an inhibitory MMP-14 binding protein, e.g., an anti-MMP-14 IgG or Fab). Also provided are methods for treating endometriosis by in a subject having or suspected of having endometriosis by administering a therapeutically effective amount of a MMP-14 binding protein and an additional endometriosis treatment (e.g., a progestational agent (acetate, norethynodrel, megestrol acetate, dydrogesterone, norethisterone, and lynestrenol), danazol, gonadotropin-releasing hormone (GnRH), or laparoscopic lesion removal/destruction).

Guidance regarding the efficacy and dosage an MMP-14 binding protein which will deliver a therapeutically effective amount of the protein can be obtained from an animal model of endometriosis, e.g., surgically-induced endometriosis involving autotransplantation of biopsies of uterus into the abdomen (Berkley et al. (2004) *Proc. Natl. Acad. Sci. USA* 101:11094-98).

Fibrin-Invasive Activity

Cross-linked fibrin is deposited in tissues surrounding wounds, inflammatory sites, or tumors and serves not only as a supporting substratum for trafficking cells, but also as a structural barrier to invasion. Invading cells can use proteinases to access the fibrin matrix with proteolysis purposefully restricted to the pericellular milieu of the ingressing cells. MMP-14 may participate fibrin-invasive events, as fibroblasts from MMP-14-null mice display an early defect in invasion. However, MMP-14-deleted fibroblasts can circumvent this early deficiency and exhibit compensatory fibrin-invasive activity. The MMP-14-independent process is sensitive to MMP inhibitors that target membrane-anchored MMPs (Hotary et al., 2002 J Exp Med. 195(3):295-308).

The disclosure provides methods of modulating fibrin invasive activity by administering a therapeutically effective amount of a MMP-14 binding protein (e.g., a Fab or IgG, that inhibits MMP-14) to a subject in need of fibrin invasive activity modulation. In some embodiments, the MMP-14 binding protein further binds MMP-16, or further binds and inhibits MMP-16.

Guidance regarding the efficacy and dosage an MMP-14 binding protein which will deliver a therapeutically effective amount of the protein can be obtained from a model of fibrin invasive activity, e.g., a cell invasion assay (Trikha et al. Cancer Research 62:2824-2833 (2002)).

Angiogenesis and Capillary Tube Formation

The role of MMPs in angiogenesis is dual and complex. The relevance of these enzymes as positive regulators of tumor angiogenesis has been largely demonstrated. However MMPs have also been reported to act as inhibitors of angiogenesis, by recent descriptions of mechanisms by which these enzymes negatively regulate angiogenesis have contributed to increase the functional complexity of this proteolytic system in cancer. A number of MMPs are able to cleave the precursors of angiostatin and endostatin, and generate the active forms of these endogenous inhibitors of angiogenesis (Cornelius et al., 1998; Ferreras et al., 2000). Human endothelial cell (EC) tube formation induced by the chemokines CCL2 and CXCL8 is highly dependent on MMP-14 activity.

The disclosure provides methods of modulating (e.g., inhibiting) inappropriate angiogenesis or capillary tube formation by administering a therapeutically effective amount of a MMP-14 binding protein (e.g., an anti-MMP-14 IgG or Fab that inhibits MMP-14) to a subject in need of modulation of inappropriate angiogenesis or capillary tube formation. Also provided are methods in which inappropriate angiogenesis or capillary tube formation is modulated by administering a MMP-14 binding protein and an additional angiogenesis or capillary tube formation modulating agent, such as a VEGF or Tie1 inhibitor.

Guidance regarding the efficacy and dosage an MMP-14 binding protein which will deliver a therapeutically effective amount of the protein can be obtained from a model of angiogenesis, e.g., a Matrigel-based angiogenesis assay in nude rats, or in a model of capillary tube formation, e.g., endothelial MC-based sprouting assay (Trikha et al. Cancer Research 62:2824-2833 (2002)) or a capillary tube formation assay or an angiogenesis assay as described in U.S. Ser. No. 11/199,739 and PCT/US2005/0284, both filed Aug. 9, 2005.

Combination Therapies

The MMP-14 binding proteins described herein, e.g., anti-MMP-14 Fabs or IgGs, can be administered in combination with one or more of the other therapies for treating a disease or condition associated with MMP-14 activity, e.g., a disease or condition described herein. For example, an MMP-14 binding protein can be used therapeutically or prophylactically with surgery, another MMP-14 inhibitor, e.g., a small molecule inhibitor, another anti-MMP-14 Fab or IgG (e.g., another Fab or IgG described herein), peptide inhibitor, or small molecule inhibitor. Examples of MMP-14 inhibitors that can be used in combination therapy with an MMP-14 binding protein described herein include neovastat, marimastat, BAY 12-9566 and prinomastat.

One or more small-molecule MMP inhibitors can be used in combination with one or more MMP-14 binding proteins described herein. For example, the combination can result in a lower dose of the small-molecule inhibitor being needed, such that side effects are reduced.

The MMP-14 binding proteins described herein can be administered in combination with one or more of the other therapies for treating cancers, including, but not limited to: surgery; radiation therapy, and chemotherapy. For example, proteins that inhibit MMP-14 or that inhibit a downstream event of MMP-14 activity (e.g., cleavage of pro-MMP-2 to MMP-2) can also be used in combination with other anti-cancer therapies, such as radiation therapy, chemotherapy, surgery, or administration of a second agent. For example, the second agent can be a Tie-1 inhibitor (e.g., Tie-1 binding proteins; see e.g., U.S. Ser. No. 11/199,739 and PCT/US2005/0284, both filed Aug. 9, 2005). As another example, the second agent can be one that targets or negatively regulates the VEGF signaling pathway. Examples of this latter class include VEGF antagonists (e.g., anti-VEGF antibodies such as bevacizumab) and VEGF receptor antagonists (e.g., anti-VEGF receptor antibodies). One particularly preferred combination includes bevacizumab. As a further example, the second agent is an inhibitor of plasmin, such as a kunitz domain-containing protein or polypeptide (e.g., a plasmin-inhibiting kunitz domain disclosed in U.S. Pat. No. 6,010,880, such as a protein or polypeptide comprising the amino acid sequence MHSFCAFKAETGPCRARFDRWFFNIF-TRQCEEFIYGGCEGNQNRFESLEECKKMCTRD (SEQ ID NO:)). As another example, the second agent is an agent that binds to Her2, such as a Her2-binding antibody (e.g., trastuzumab). The combination can further include 5-FU and leucovorin, and/or irinotecan.

Ihibitors of MMP-14 (e.g., the MMP-14 binding proteins disclosed herein) can potentiate the activity of an agent that targets Her2 (e.g., a Her2-binding antibody such as trastuzumab). Accordingly, in one combination therapy for the treatment of breast cancer, the second therapy is an agent that binds Her2, such as a Her2-binding antibody (e.g., trastuzumab). When an MMP-14 binding protein is used in a combination therapy with a Her2 binding agent, the dose of the Her2 binding agent may be reduced from the dose of the Her2 binding agent when administered not in combination with an MMP-14 binding protein (e.g., is at least 10%, 25%, 40%, or 50% less than the dose of the Her2 binding agent when administered not in combination with a MMP-14 binding protein). For example, the dose of trastuzumab, when administered in a combination therapy with an MMP-14 binding protein is less than about 4.0, 3.6, 3.0, 2.4, or 2 mg/kg as an initial (loading) dose, and less than about 2.0, 1.8, 1.5, 1.2, or 1 mg/kg in subsequent doses.

The MMP-14 binding proteins described herein can also be administered in combination with one or more other therapies for treating ocular disorders, such as surgical or medical (e.g., administration of a second agent) therapies. For example, in treatment of age-related macular degeneration (e.g., wet age-related macular degeneration), an MMP-14 binding protein may be administered in conjunction with (e.g., before, during, or after) laser surgery (laser photocoagulation or photocoagulation therapy). As another example, the MMP-14 binding protein can be administered in combination with a second agent, such as a VEGF antagonist (e.g., an anti-VEGF antibody such as bevacizumab or ranibizumab) or a VEGF receptor antagonist (e.g., anti-VEGF receptor antibodies).

The term "combination" refers to the use of the two or more agents or therapies to treat the same patient, wherein the use or action of the agents or therapies overlap in time. The agents or therapies can be administered at the same time (e.g., as a single formulation that is administered to a patient or as two separate formulations administered concurrently) or sequentially in any order. Sequential administrations are administrations that are given at different times. The time between administration of the one agent and another agent can be minutes, hours, days, or weeks. The use of an MMP-14 binding protein described herein can also be used to reduce the dosage of another therapy, e.g., to reduce the side-effects associated with another agent that is being administered, e.g., to reduce the side-effects of an anti-VEGF antibody such as bevacizumab. Accordingly, a combination can include administering a second agent at a dosage at least 10, 20, 30, or 50% lower than would be used in the absence of the MMP-14 binding protein.

In addition, a subject can be treated for an angiogenesis-associated disorder, e.g., a cancer, by administering to the subject a first and second agent. For example, the first agent modulates early stage angiogenesis and the second agent modulates a subsequent stage of angiogenesis or also modulates early stage angiogenesis. The first and second agents can be administered using a single pharmaceutical composition or can be administered separately. In one embodiment, the first agent is a VEGF pathway antagonist (e.g., an inhibitor of a VEGF (e.g., VEGF-A, -B, or -C) or a VEGF receptor (e.g., KDR or VEGF receptor III (Flt4)) or a bFGF pathway antagonist (e.g., an antibody that binds to bFGF or a bFGF receptor). Other VEGF pathway antagonists are also described, herein and elsewhere. In one embodiment, the second agent inhibits or decreases the mobility or invasiveness of tumor cells. For example, the second agent comprises an MMP-14 binding protein. For example, the second agent is an MMP-14 binding protein described herein.

Once a tumor reaches a certain size (e.g., ~1-2 mm), the tumor requires new vasculature prior to increasing its mass. An early stage of tumor angiogenesis can include a signal from the tumor, e.g., secretion of VEGF, to stimulate the growth of new blood vessels from the host and infiltration of the tumor by the vessels. VEGF can, for example, stimulate proliferation of endothelial cells that are then assembled into blood vessels. A late stage of tumor growth can include metastasis, mobility and invasiveness of tumor cells. This mobility and invasiveness may involve the action of matrix metalloproteinases, e.g., MMP-14, MMP-16, or MMP-24. Thus, an effective therapy to treat angiogenesis-related disorders can involve a combination of an agent that modulates an early stage angiogenesis (e.g., VEGF pathway antagonists, e.g., anti-VEGF (e.g., bevacizumab) or anti-VEGF receptor (e.g., anti-KDR) antibodies; or antagonists of other pro-angiogenic pathways, e.g., anti-bFGF antibodies or anti-bFGF receptor (e.g., anti-bFGF receptor-1, -2, -3) antibodies) and an agent that modulates a late stage of tumor growth can include metastasis, mobility and invasiveness of tumor cells s (e.g., antagonists of MMP-14, MMP-16, or MMP-24 (e.g., anti-MMP-14 antibodies (e.g., an antibody disclosed herein)), of MMP-16 (e.g., anti-MMP-14 antibodies that cross react with MMP-16), or of MMP-24 (e.g., anti-MMP-14 antibodies that cross react with MMP-24). One or more of these agents can be used in combination. One or more of these agents may also be used in combination with other anti-cancer therapies, such as radiation therapy or chemotherapy.

Exemplary VEGF receptor antagonists include inhibitors of a VEGF (e.g., VEGF-A, -B, or -C, for example bevacizumab), modulators of VEGF expression (e.g., INGN-241, oral tetrathiomolybdate, 2-methoxyestradiol, 2-methoxyestradiol nanocrystal dispersion, bevasiranib sodium, PTC-299, Veglin), inhibitors of a VEGF receptor (e.g., KDR or VEGF receptor III (Flt4), for example anti-KDR antibodies, VEGFR2 antibodies such as CDP-791, IMC-1121B, VEGFR2 blockers such as CT-322), VEGFR3 antibodies such as mF4-31C1 from Imclone Systems, modulators of VEGFR expression (e.g., VEGFR1 expression modulator Sirna-027) or inhibitors of VEGF receptor downstream signaling.

Exemplary inhibitors of VEGF include bevacizumab, pegaptanib, ranibizumab, NEOVASTAT®, AE-941, VEGF Trap, and PI-88.

Exemplary VEGF receptor antagonists include inhibitors of VEGF receptor tyrosine kinase activity. 4-[4-(1-Amino-1-methylethyl)phenyl]-2-[4-(2-morpholin-4-yl-ethyl)phenylamino]pyrimidine-5-carbonitrile (JNJ-17029259) is one of a structural class of 5-cyanopyrimidines that are orally available, selective, nanomolar inhibitors of the vascular endothelial growth factor receptor-2 (VEGF-R2). Additional examples include: PTK-787/ZK222584(Astra-Zeneca), SU5416, SU11248 (Pfizer), and ZD6474 ([N-(4-bromo-2-fluorophenyl)-6-methoxy-7-[(1-methylpiperidin-4-yl)methoxy]quinazolin-4-amine]), vandetanib, cediranib, AG-013958, CP-547632, E-7080, XL-184, L-21649, and ZK-304709. Other VEGF antagonist agents are broad specificity tyrosine kinase inhibitors, e.g., SU6668 (see, e.g., Bergers, B. et al., 2003 J. Clin. Invest. 111:1287-95), sorafenib, sunitinib, pazopanib, vatalanib, AEE-788, AMG-706, axitinib, BIBF-1120, SU-14813, XL-647, XL-999, ABT-869, BAY-57-9352, BAY-73-4506, BMS-582664, CEP-7055, CHIR-265, OSI-930, and TKI-258. Also useful are agents that down regulate VEGF receptors on the cell surface, such as fenretinide, and agents which inhibit VEGF receptor downstream signaling, such as squalamine The second agent or therapy can also be another anti-cancer agent or therapy. Non-limiting examples of anti-cancer agents include, e.g., anti-microtubule agents, topoisomerase inhibitors, antimetabolites, mitotic inhibitors, alkylating agents, intercalating agents, agents capable of interfering with a signal transduction pathway, agents that promote apoptosis, radiation, and antibodies against other tumor-associated antigens (including naked antibodies, immunotoxins and radioconjugates). Examples of the particular classes of anti-cancer agents are provided in detail as follows: antitubulin/antimicrotubule, e.g., paclitaxel, vincristine, vinblastine, vindesine, vinorelbin, taxotere; topoisomerase I inhibitors, e.g., irinotecan, topotecan, camptothecin, doxorubicin, etoposide, mitoxantrone, daunorubicin, idarubicin, teniposide, amsacrine, epirubicin, merbarone, piroxantrone hydrochloride; antimetabolites, e.g., 5 fluorouracil (5 FU), methotrexate, 6 mercaptopurine, 6 thioguanine, fludarabine phosphate, cytarabine/Ara C, trimetrexate, gemcitabine, acivicin, alanosine, pyrazofurin, N-Phosphoracetyl-L-Asparate=PALA, pentostatin, 5 azacitidine, 5 Aza 2' deoxycytidine, ara A, cladribine, 5 fluorouridine, FUDR, tiazofurin, N-[5-[N-(3,4-dihydro-2-methyl-4-oxoquinazolin-6-ylmethyl)-N-methylamino]-2-thenoyl]-L-glutamic acid; alkylating agents, e.g., cisplatin, carboplatin, mitomycin C, BCNU=Carmustine, melphalan, thiotepa, busulfan, chlorambucil, plicamycin, dacarbazine, ifosfamide phosphate, cyclophosphamide, nitrogen mustard, uracil mustard, pipobroman, 4 ipomeanol; agents acting via other mechanisms of action, e.g., dihydrolenperone, spiromustine, and desipeptide; biological response modifiers, e.g., to enhance anti-tumor responses, such as interferon; apoptotic agents, such as actinomycin D; and anti-hormones, for example anti-estrogens such as tamoxifen or, for example antiandrogens such as 4'-cyano-3-(4-fluorophenylsulphonyl)-2-hydroxy-2-methyl-3'-(trifluoromethyl)propionanilide.

A combination therapy can include administering an agent that reduces the side effects of other therapies. The agent can be an agent that reduces the side effects of anti-cancer treatments. For example, the agent can be leucovorin.

Combination therapies that include administering an MMP-14 binding protein or other binding protein described herein can also be used to treat a subject having or at risk for another angiogenesis related disorder (e.g., a disorder other than cancer, e.g., disorders that include undesired endothelial cell proliferation or undesirable inflammation, e.g., rheumatoid arthritis).

Diagnostic Uses

Proteins that bind to MMP-14 and identified by the method described herein and/or detailed herein have in vitro and in vivo diagnostic utilities. The MMP-14 binding proteins described herein (e.g., the proteins that bind and inhibit, or the proteins that bind but do not inhibit MMP-14) can be used, e.g., for in vivo imaging, e.g., during a course of treatment for a disease or condition in which MMP-14 is active, e.g., a disease or condition described herein, or in diagnosing a disease or condition described herein.

In one aspect, the disclosure provides a diagnostic method for detecting the presence of an MMP-14, in vitro or in vivo (e.g., in vivo imaging in a subject). The method can include localizing MMP-14 within a subject or within a sample from a subject. With respect to sample evaluation, the method can include, for example: (i) contacting a sample with MMP-14 binding protein; and (ii) detecting location of the MMP-14 binding protein in the sample.

An MMP-14 binding protein can also be used to determine the qualitative or quantitative level of expression of MMP-14 in a sample. The method can also include contacting a reference sample (e.g., a control sample) with the binding protein, and determining a corresponding assessment of the reference sample. A change, e.g., a statistically significant change, in the formation of the complex in the sample or subject relative to the control sample or subject can be indicative of the presence of MMP-14 in the sample. In one embodiment, the MMP-14 binding protein does not cross react with another metalloproteinase.

The MMP-14 binding proteins are also useful for in vivo tumor imaging. Better clinical endpoints are needed to monitor the efficacy of drugs, such as MMP-inhibitors, that are designed to block enzymatic function (Zucker et al, 2001, Nature Medicine 7:655-656). Imaging of tumors in vivo by using labeled MMP-14 binding proteins could be of help to target the delivery of the binding protein to tumors for cancer diagnosis, intraoperative tumor detection, and for investigations of drug delivery and tumor physiology. MMP-14 binding proteins can be used to monitor native enzymatic activity in vivo at invasive sites. Another exemplary method includes: (i) administering the MMP-14 binding protein to a subject; and (iii) detecting location of the MMP-14 binding protein in the subject. The detecting can include determining location or time of formation of the complex.

The MMP-14 binding protein can be directly or indirectly labeled with a detectable substance to facilitate detection of the bound or unbound antibody. Suitable detectable substances include various enzymes, prosthetic groups, fluorescent materials, luminescent materials and radioactive materials.

Complex formation between the MMP-14 binding protein and MMP-14 can be detected by evaluating the binding protein bound to the MMP-14 or unbound binding protein. Conventional detection assays can be used, e.g., an enzyme-linked immunosorbent assays (ELISA), a radioimmunoassay (RIA) or tissue immunohistochemistry. Further to labeling the MMP-14 binding protein, the presence of MMP-14 can be assayed in a sample by a competition immunoassay utilizing standards labeled with a detectable substance and an unlabeled MMP-14 binding protein. In one example of this assay, the biological sample, the labeled standards, and the MMP-14 binding protein are combined and the amount of labeled standard bound to the unlabeled binding protein is determined. The amount of MMP-14 in the sample is inversely proportional to the amount of labeled standard bound to the MMP-14 binding protein.

Fluorophore and chromophore labeled proteins can be prepared. Because antibodies and other proteins absorb light having wavelengths up to about 310 nm, the fluorescent moieties should be selected to have substantial absorption at wavelengths above 310 nm and preferably above 400 nm. A variety of suitable fluorescers and chromophores are described by Stryer, 1968, *Science* 162:526 and Brand, L. et al., 1972, *Annu. Rev. Biochem.* 41:843 868. The proteins can be labeled with fluorescent chromophore groups by conventional procedures such as those disclosed in U.S. Pat. Nos. 3,940,475, 4,289,747, and 4,376,110. One group of fluorescers having a number of the desirable properties described above is the xanthene dyes, which include the fluoresceins and rhodamines. Another group of fluorescent compounds are the naphthylamines. Once labeled with a fluorophore or chromophore, the protein can be used to detect the presence or localization of the MMP-14 in a sample, e.g., using fluorescent microscopy (such as confocal or deconvolution microscopy).

Histological Analysis. Immunohistochemistry can be performed using the proteins described herein. For example, in the case of an antibody, the antibody can be synthesized with a label (such as a purification or epitope tag), or can be detectably labeled, e.g., by conjugating a label or label-binding group. For example, a chelator can be attached to the antibody. The antibody is then contacted to a histological preparation, e.g., a fixed section of tissue that is on a microscope slide. After an incubation for binding, the preparation is washed to remove unbound antibody. The preparation is then analyzed, e.g., using microscopy, to identify if the antibody bound to the preparation.

Of course, the antibody (or other polypeptide or peptide) can be unlabeled at the time of binding. After binding and washing, the antibody is labeled in order to render it detectable.

Protein Arrays. The MMP-14 binding protein can also be immobilized on a protein array. The protein array can be used as a diagnostic tool, e.g., to screen medical samples (such as isolated cells, blood, sera, biopsies, and the like). Of course, the protein array can also include other binding proteins, e.g., that bind to MMP-14 or to other target molecules.

Methods of producing polypeptide arrays are described, e.g., in De Wildt et al., 2000, *Nat. Biotechnol.* 18:989-994; Lueking et al., 1999, *Anal. Biochem.* 270:103-111; Ge, 2000, *Nucleic Acids Res.* 28, e3, I-VII; MacBeath and Schreiber, 2000, *Science* 289:1760-1763; WO 01/40803 and WO 99/51773A1. Polypeptides for the array can be spotted at high speed, e.g., using commercially available robotic apparati, e.g., from Genetic MicroSystems or BioRobotics. The array substrate can be, for example, nitrocellulose, plastic, glass, e.g., surface-modified glass. The array can also include a porous matrix, e.g., acrylamide, agarose, or another polymer.

For example, the array can be an array of antibodies, e.g., as described in De Wildt, supra. Cells that produce the proteins can be grown on a filter in an arrayed format. Polypeptide production is induced, and the expressed polypeptides are immobilized to the filter at the location of the cell. A protein array can be contacted with a labeled target to determine the extent of binding of the target to each immobilized polypeptide. Information about the extent of binding at each address of the array can be stored as a profile, e.g., in a computer database. The protein array can be produced in replicates and used to compare binding profiles, e.g., of a target and a non-target.

FACS (Fluorescence Activated Cell Sorting). The MMP-14 binding protein can be used to label cells, e.g., cells in a sample (e.g., a patient sample). The binding protein is also attached (or attachable) to a fluorescent compound. The cells can then be sorted using fluorescence activated cell sorter (e.g., using a sorter available from Becton Dickinson Immunocytometry Systems, San Jose Calif.; see also U.S. Pat. Nos. 5,627,037; 5,030,002; and 5,137,809). As cells pass through the sorter, a laser beam excites the fluorescent compound while a detector counts cells that pass through and determines whether a fluorescent compound is attached to the cell by detecting fluorescence. The amount of label bound to each cell can be quantified and analyzed to characterize the sample.

The sorter can also deflect the cell and separate cells bound by the binding protein from those cells not bound by the binding protein. The separated cells can be cultured and/or characterized.

In vivo Imaging. Also featured is a method for detecting the presence of a MMP-14 expressing tissues in vivo. The method includes (i) administering to a subject (e.g., a patient having, e.g., a cancer (e.g., metastatic cancer, e.g., metastatic breast cancer), an inflammatory disease (e.g., synovitis, atherosclerosis), rheumatoid arthritis, osteoarthritis, an ocular condition (e.g., macular degeneration), diabetes, Alzheimer's Disease, cerebral ischemia, endometriosis, fibrin-invasive activity, angiogenesis, or capillary tube formation) an anti-MMP-14 antibody, conjugated to a detectable marker; (ii) exposing the subject to a means for detecting said detectable marker to the MMP-14 expressing tissues or cells. For example, the subject is imaged, e.g., by NMR or other tomographic means.

Examples of labels useful for diagnostic imaging include radiolabels such as $^{131}$I, $^{111}$In, $^{123}$I, $^{99m}$Tc, $^{32}$P, $^{125}$I, $^{3}$H, $^{14}$C, and $^{188}$Rh, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short range radiation emitters, such as isotopes detectable by short range detector probes can also be employed. The protein can be labeled with such reagents; for example, see Wensel and Meares, 1983, *Radioimmunoimaging and Radioimmunotherapy*, Elsevier, New York for techniques relating to the radiolabeling of antibodies and D. Colcher et al., 1986, *Meth. Enzymol.* 121: 802 816.

The binding protein can be labeled with a radioactive isotope (such as $^{14}C$, $^{3}H$, $^{35}S$, $^{125}I$, $^{32}P$, $^{131}I$). A radiolabeled binding protein can be used for diagnostic tests, e.g., an in vitro assay. The specific activity of a isotopically-labeled binding protein depends upon the half life, the isotopic purity of the radioactive label, and how the label is incorporated into the antibody.

In the case of a radiolabeled binding protein, the binding protein is administered to the patient, is localized to cells bearing the antigen with which the binding protein reacts, and is detected or "imaged" in vivo using known techniques such as radionuclear scanning using e.g., a gamma camera or emission tomography. See e.g., A. R. Bradwell et al., "Developments in Antibody Imaging", *Monoclonal Antibodies for Cancer Detection and Therapy*, R. W. Baldwin et al., (eds.), pp 65 85 (Academic Press 1985). Alternatively, a positron emission transaxial tomography scanner, such as designated Pet VI located at Brookhaven National Laboratory, can be used where the radiolabel emits positrons (e.g., $^{11}C$, $^{18}F$, $^{15}O$, and $^{13}N$).

MRI Contrast Agents. Magnetic Resonance Imaging (MRI) uses NMR to visualize internal features of living subject, and is useful for prognosis, diagnosis, treatment, and surgery. MRI can be used without radioactive tracer compounds for obvious benefit. Some MRI techniques are summarized in EP-A-0 502 814. Generally, the differences related to relaxation time constants T1 and T2 of water protons in different environments is used to generate an image. However, these differences can be insufficient to provide sharp high resolution images.

The differences in these relaxation time constants can be enhanced by contrast agents. Examples of such contrast agents include a number of magnetic agents paramagnetic agents (which primarily alter T1) and ferromagnetic or superparamagnetic (which primarily alter T2 response). Chelates (e.g., EDTA, DTPA and NTA chelates) can be used to attach (and reduce toxicity) of some paramagnetic substances (e.g., $Fe^{+3}$, $Mn^{+2}$, $Gd^{+3}$). Other agents can be in the form of particles, e.g., less than 10 mm to about 10 nM in diameter). Particles can have ferromagnetic, antiferromagnetic, or superparamagnetic properties. Particles can include, e.g., magnetite ($Fe_3O_4$), $\gamma$-$Fe_2O_3$, ferrites, and other magnetic mineral compounds of transition elements. Magnetic particles may include: one or more magnetic crystals with and without nonmagnetic material. The nonmagnetic material can include synthetic or natural polymers (such as sepharose, dextran, dextrin, starch and the like.

The MMP-14 binding protein can also be labeled with an indicating group containing of the NMR active $^{19}F$ atom, or a plurality of such atoms inasmuch as (i) substantially all of naturally abundant fluorine atoms are the $^{19}F$ isotope and, thus, substantially all fluorine containing compounds are NMR active; (ii) many chemically active polyfluorinated compounds such as trifluoracetic anhydride are commercially available at relatively low cost; and (iii) many fluorinated compounds have been found medically acceptable for use in humans such as the perfluorinated polyethers utilized to carry oxygen as hemoglobin replacements. After permitting such time for incubation, a whole body MRI is carried out using an apparatus such as one of those described by Pykett, 1982, *Sci. Am.* 246:78 88 to locate and image tissues expressing MMP-14.

The contents of all references, pending patent applications and published patents, cited throughout this application are hereby expressly incorporated by reference. The following examples provide further illustrate and are not limiting.

EXAMPLES

Example 1

Selection and Screening of Anti-MMP-14 Fabs and IgGs

Two strategies were employed to identify anti-MMP-14 antibodies.

Strategy I: A 100-fold excess of the FAB310 library (e.g., an amount of the library that should contain 100 copies of each library member) was depleted of streptavidin-binding antibodies by incubating the library with 200 µL of streptavidin beads for 1 hour at room temperature (RT) with rotation. 500 nM of biotinylated MMP-14 was coupled to streptavidin beads by incubation with 100 µL of streptavidin beads. The MMP-14 beads were then incubated with the streptavidin-depleted library for 1 hour at RT with rotation. The beads were then rinsed three times with 2% MTRIS/0.1% Tween, transferred to a fresh tube and washed an additional three times with 2% MTRIS/0.1% Tween, and transferred to a fresh tube and washed a final time with Round 1 TRIS buffer (50 mM TRIS; 50 mM $CaCl_2$; 150 mM NaCl, pH 7.5).

MMP-14 binding antibodies were eluted from the beads by re-suspension in 1 mL 2% MTRIS containing 2.5 µL TIMP-2 and incubation for 1 hour at RT with rotation. The beads were then washed three times with 2% MTRIS/0.1% Tween, transferred to a fresh tube and washed three times with TRIS/0.1% Tween, and transferred to a fresh tube and washed a final time with TRIS. 1 mL output was used for infection of 9 mL TG1 bacteria (grown to $OD_{600}$=0.5). The beads were further eluted by suspension in 1 mL 100 mM TEA for 10 minutes. The supernatant was neutralized with 500 µl TRIS/HCl pH 7.5. 1 mL of the second elution was used for infection of 9 mL TG1 bacteria (grown to $OD_{600}$=0.5).

Infections were carried out for 30 minutes at 37° C. in water bath, then amplified in a total volume of 25 mL 2×TY/AG at 30° C. overnight with 250 RPM shaking.

Two additional rounds of selection were carried out under the same conditions as the first round, except that the streptavidin beads were loaded with 100 nM biotinylated MMP-14 and the number of washes were doubled (6 times with 2% MTRIS/0.1% Tween, 6 times with TRIS/0.1% Tween and 2 times with TRIS), and Round 2/3 Tris buffer (50 mM TRIS; 5 mM $CaCl_2$; 150 mM NaCl pH=7.5) was used for incubation and wash.

Strategy II: Round 1-strategy II on bMMP-14 with depletion on Carboxilic beads-TIMP-2-bMMP-14 complex.

TIMP-2 was coupled to carboxylic beads, then complexed with a combination of biotinylated MMP-14 (500 nM each). The complexed beads were incubated with a 100 fold excess of FAB310 library that had been previously depleted by incubation with streptavidin beads and carboxylic beads. Elution/washing was carried out as for Strategy I.

Two additional rounds of selection were carried out, essentially as described for Strategy I, except that only 100 nM of each of MMP-14 were used in the bead complexes.

Pre Screening Phase ELISA 384-well plates were coated with biotinylated BSA (2 μg/ml in 50 mM TRIS; 5 mM $CaCl_2$; 150 mM NaCl, pH 7.5), then washed 3 times with 50 mM TRIS; 5 mM $CaCl_2$; 150 mM NaCl, pH 7.5; 0.1% Tween. Streptavidin was captured on the coated plates by incubation with 10 μg/mL streptavidin in 50 mM TRIS; 5 mM $CaCl_2$; 150 mM NaCl pH 7.5; 0.5% Gelatin, followed by a wash with 50 mM TRIS; 5 mM $CaCl_2$; 150 mM NaCl pH=7.5; 0.1% Tween. On the day the assay was to be performed, biotinylated MMP-14 (1 μg/ml) was captured in 50 mM TRIS; 5 mM $CaCl_2$; 150 mM NaCl, pH 7.5.

95 clones were picked from each of Round 2 and Round 3 of each selection strategy, producing 12 masterplates. ELISA was run on the MiniTrak-5 deck according to SOP.

TABLE 4

Phage on Fab ELISA pre-screening

| Round | Strategy | Hitrate >3BG |
|---|---|---|
| M0003 - R2 | I - TIMP elution | 61/95 |
| M0004 - R2 | I - TEA elution | 32/95 |
| M0006 - R2 | II | 27/95 |
| M0009 - R3 | I - TIMP elution | 86/95 |
| M0010 - R3 | I - TEA elution | 73/95 |
| M0012 - R3 | II | 63/95 |

Example 2

DNA Sequences of MMP-14 Binding Anti-MMP-14 Fabs

Exemplary Fabs that bind to human MMP-14 were identified and designated as: M0030-04, M0030-D08, M0031-A02, M0031-A04, M0031-C02, M0031-F01, M0031-H10, M0032-B07, M0032-B09, M0033-F02, M0033-H07, M0035-F02, M0036-D02, M0036-F02, M0036-H08, M0037-A08, M0037-B10, M0037-C03, M0037-C09, M0037-D01, M0037-H09, M0038-B06, M0038-C05, M0038-C06, M0038-D06, M0038-E05, M0038-E06, M0038-E12, M0038-F01, M0038-F08, M0038-H06, M0039-B07, M0039-D02, M0039-D10, M0039-G05, M0039-G07, M0039-H08, M0040-A03, M0040-A06, M0040-A08, M0040-A11, M0040-B06, M0040-B08, M0040-C10, M0040-D08, M0040-F03, M0040-G04, M0040-H04, M0040-H09, M0041-A05, M0041-B03, M0041-B11, M0041-C11, M0041-D03, M0041-D08, M0041-E11, M0041-H09, M0041-H11, M0042-B07, M0042-G12, M0043-A09, M0043-C03, M0043-F01, M0043-G01, M0043-G02, M0044-B03, M0044-D08, M0044-E01, and M0044-E05. The DNA sequences of these Fab light chain variable regions (LV) and heavy chain variable regions (HV) are shown in Table 5.

TABLE 5

DNA sequences of variable regions of MMP-14 binding antibodies

>M0030-A04 LV (SEQ ID NO:6)
CAG AGC GAA TTG ACT CAG CCA CCC TCA GCG TCT GGG ACC CCC GGG
CAG AGG GTC ACT ATC TCT TGT TCT GGA AGC AGC TCC AAC ATC GGA
ATT AAT TTT GTT ACC TGG TAC CAG CAG CTC CCA GGA ACG GCC CCC
AAA CTC CTC ATC TAT ACT AAT AAT CAG CGG CCC TCT GGG GTC CCT
GAC CGA TTC TCT GGC TCC AAG TCT GGC ACC TCA GCC TCC CTG GCC
ATC AGT GGG CTC CAG TCT GAG GAT GAG GCT GCT TAT TAC TGT GCA
GCA TGG GAT GAC AAC CTG AAC GGT CCG GTG TTC GGC GGC GGG ACC
AAG CTG ACC GTC CTA

>M0030-A04 HV (SEQ ID NO:7)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
GTT TAC GAG ATG AAT TGG GTT CGC CAA GCT CCT GGT AAA GGT TTG
GAG TGG GTT TCT TCT ATC TAT TCT TCT GGT GGC CGT ACT GAT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGA GAG GCC CAT TAC TAT GAT AGT
AGT GGT CCG CCT GAC TAC TGG GGC CAG GGA ACC CTG GTC ACC GTC
TCA AGC

>M0030-D08 LV (SEQ ID NO:8)
CAA GAC ATC CAG ATG ACC CAG TCT CCA TCC TCC CTG TCT GCA TCT
GTA GGA GAC AGA GTC ACC ATG ACT TGC CGG GCA GGT CAG AAC ATT
AAA TCC TAT TTA AAT TGG TAT CAG CAG AAG CCA GGG AAA GCC CCT
CAG GTC CTG ATC TAT GCT GCA TCC ACT TTA CAA AGT GGG GTC TCA
TCA GGT TTC GTG GCA GTG GAT CTG GGA CAT TTC ACT CTC ACC
ATC AGC GAT CTG CAA CCT GGA GAT TCT GCG ACT TAC TAC TGT CAA
CAA AGT TTC AGT ACC CCT CGC AGT TTT GGC CAG GGG ACC AAG CTG
GAG ATC AAA

TABLE 5-continued

DNA sequences of variable regions of
MMP-14 binding antibodies

>M0030-D08 HV (SEQ ID NO:9)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
ATT TAC CAG ATG TAT TGG GTT CGC CAA GCT CCT GGT AAA GGT TTG
GAG TGG GTT TCT TCT ATC GTT CCT TCT GGT GGC CTT ACT AAG TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGA GAG AGA TTA CGA TAT TTT GAC
TGG TCA GAT CGT GTG GGG GAA TCG GGT GAC TAC TGG GGC CAG GGA
ACC CTG GTC ACC GTC TCA AGC

>M0031-A02 LV (SEQ ID NO:10)
CAA GAC ATC CAG ATG ACC CAG TCT CCA TCC TCC CTG TCT GCA TCT
GTA GGA GAC AGA GTC ACC GTC ACT TGC CGG GCA AGT CAG AGC ATT
AGC AGT TAT TTA AAT TGG TAT CAG CAG AAA CCA GGG AAA GCC CCT
AAA CTC CTG ATC TAT GCT GCA TCC AGT TTG CAA AGT GGG GTC CCA
TCA AGG TTC AGT GGC AGT GGA TCT GGG ACA GAT TTC ACT CTC ACC
ATC AGC AGT CTG CAA CCT GAA GAT TTT GCA ACT TAC TAC TGT CAA
CAG AGT TAC AGT ATC CCG CTC ACT TTC GGC GGA GGG ACC AAG GTG
GCG ATC AAA

>M0031-A02 HV (SEQ ID NO:11)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
AAT TAC TGG ATG CTT TGG GTT CGC CAA GCT CCT GGT AAA GGT TTG
GAG TGG GTT TCT GGT ATC GTT TCT TCT GGT GGC CGT ACT AAT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGG TTT AGC AGC TCG TTA GGG GCT
TTT GAT ATC TGG GGC CAA GGG ACA ATG GTC ACC GTC TCA AGC

>M0031-A04 LV (SEQ ID NO:12)
CAA GAC ATC CAG ATG ACC CAG TCT CCA GGC ACC CTG TCA TTG TCT
CCA GGG GAA AGA GCC ACC CTC TCC TGC AGG GCC AGT CAG AGT CTT
AGG AAC AGC TAC TTA GCC TGG TAT CAG CAG AAA CCT GGC CAG GCT
CCC AGG CTC CTC ATC TAT GAT GCA TCC AAC AGG GCC ACT GGC ATC
CCA GCC AGG TTC AGT GGC AGT GGG TCT GGG ACA GAC TTC ACT CTC
ACC ATC AGC AGC CTA GAG CCT GAA GAT TTT GCA GTT TAT TAC TGT
CAG CAG CGT AGC AAC TGG CCT CCG TAC ACT TTT GGC CAG GGG ACC
AAG CTG GAG ATC AAA

>M0031-A04 HV (SEQ ID NO:13)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
AAT TAC GTT ATG CTT TGG GTT CGC CAA GCT CCT GGT AAA GGT TTG
GAG TGG GTT TCT TCT ATC CGT CCT TCT GGT GGC CCT ACT AAG TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCT AGG GAC TGG CCC TCT TAC TAC TAC
TAC GGT ATG GAC GTC TGG GGC CAA GGG ACC ACG GTC ACC GTC TCA
AGC

>M0031-C02 LV (SEQ ID NO:14)
CAA GAC ATC CAG ATG ACC CAG TCT CCA CTC TCC CTG CCC GTC ACC
CCT GGA GAG CCG GCC TCC ATC TCC TGC AGG TCT AGT CAG AGC CTC
CTG CAT AGT AAT GGA TAC TAC TAT TTG GAT TGG TAC CTG CAG AAG
CCA GGG CAG TCT CCA CAA CTC CTG ATC TAT TTG GGT TCT TAT CGG
GCC TCC GGG GTC CCT GAC AGG TTC AGT GGC AGT GGA TCA GGC ACA
GAT TTT ACA CTG AAA ATC AGC AGT GTG GAG GCT GAA GAT GTT GGG
GTT TAT TAC TGC ATG CAA GCT CTA CAA ACT CCT CTC ACT TTC GGC
GGA GGG ACC AGG GTG GAC ATC AAA

TABLE 5-continued

DNA sequences of variable regions of
MMP-14 binding antibodies

>M0031-C02 HV (SEQ ID NO:15)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CCT TAC CCT ATG GGT TGG GTT CGC CAA GCT CCT GGT AAA GGT TTG
GAG TGG GTT TCT TCT ATC GTT TCT TCT GGT GGC CTT ACT CTT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACT GCC GTG TAT TAC TGT GCG AGA GGG GGA CGG CTT TAC GAT ATT
TTG ACT GGT CAA GGG GCC CCG TTT GAC TAC TGG GGC CAG GGA ACC
CTG GTC ACC GTC TCA AGC

>M0031-F01 LV (SEQ ID NO:16)
CAG AGC GAA TTG ACT CAG CCA CCC TCA GTG TCT GGG ACC CCC GGG
CAG AGG GTC ACC ATC TCT TGT TCT GGA ACC AGC GCC AAC ATC GGA
CGT AAT GCT GTA CAC TGG TAC CAG CAG CTC CCA GGA ACG GCC CCC
AAA CTC CTC ATT CAT AGT AAT AAC CGG CGG CCC TCA GGG GTC CCT
GAC CGA TTC TCT GGC TCC AAG TCT GGC ACC TCA GCC TCC CTG GCC
ATC AGT GGG CTC CAG TCT GAG GAT GAG GCT GAT TAT TAC TGT GCA
GCA TGG GAG AAC AGC CTG AAT GCC TTT TAT GTC TTC GGA ACT GGG
ACC AAG GTC ACC GTC CTA

>M0031-F01 HV (SEQ ID NO:17)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
ACT TAC GAG ATG CAT TGG GTT CGC CAA GCT CCT GGT AAA GGT TTG
GAG TGG GTT TCT TCT ATC TAT TCT TCT GGT GGC TGG ACT GGT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGA TCT CAA CAG TAT TAC GAT TTT
TCC TCT CGC TAC TAC GGC ATG GAC GTC TGG GGC CAA GGG ACC ACG
GTC ACC GTC TCA AGC

>M0031-H10 LV (SEQ ID NO:18)
CAA GAC ATC CAG ATG ACC CAG TCT CCA TCC TCC CTG TCT GCA TCT
GTA GGA GAC AGA GTC ACC ATC ACT TGC CGG GCA AGT CAG AGC ATT
AGC AGC TAT TTA AAT TGG TAT CAG CAG AAA CCA GGG AAA GCC CCT
AAG CTC CTG ATC TAT GCT GCA TCC AGT TTG CAA AGT GGG GTC CCA
TCA AGG TTC AGT GGC AGT GGA TCT GGG ACA GAT TTC ACT CTC ACC
ATC AGC AGT CTG CAA CCT GAA GAT TTT GCA ACC TAC TTC TGC CAA
CAG AGT TAT AGT AAT CCT TTC ACT TTC GGC CCT GGG ACC AAA GTG
GAT ATC AAA

>M0031-H10 HV (SEQ ID NO:19)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CAG TAC GTT ATG TGG TGG GTT CGC CAA GCT CCT GGT AAA GGT TTG
GAG TGG GTT TCT TCT ATC GTT CCT TCT GGT GGC GTT ACT AAG TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AAA GAC GTC TTC GGT AGT ATT GGT
TAT TAC TAC GTA CCG TTT TTT GAC TAC TGG GGC CAG GGA ACC CTG
GTC ACC GTC TCA AGC

>M0032-B07 LV (SEQ ID NO:20)
CAG AGC GTC TTG ACT CAG GAG CCC TCA TTG ACT GTG TCC CCA GGA
GGG ACA GTC ACT CTC ACC TGT GCT TCC AAC ACT GGA GCA GTC ACC
AGT GGT TCC TAT GCA AAC TGG TTC CAG CAA AAA CCT GGA CTA ACA
CCC AGG GCA CTG ATT TAT AGT GGA ACT AAC AAA TAT TCG TGG ACC
CCT GCC CGA TTC TCA GGC TCC CTC TTT GGG GGC AAG GCA GCC CTG
ACA CTG TCA GGT GTG CTG CCT GAG GAC GAG GCT GAG TAT TAC TGC
CTC GTC TAC TAT GGT GGT GTT TGG GTG TTC GGC GGA GGG ACC AAG
CTG ACC GTC CTA

TABLE 5-continued

DNA sequences of variable regions of
MMP-14 binding antibodies

>M0032-B07 HV (SEQ ID NO:21)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CCT TAC CTT ATG CAT TGG GTT CGC CAA GCT CCT GGT AAA GGT TTG
GAG TGG GTT TCT TCT ATC TAT CCT TCT GGT GGC ATT ACT CAG TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGA TTT TTC CCT AGT CAC AGG GAC
TAT ACG GCG TTC GAC ACC TGG GGC CGG GGA ACC CTG GTC ACC GTC
TCA AGC

>M0032-B09 LV (SEQ ID NO:22)
CAA GAC ATC CAG ATG ACC CAG TCT CCA TCT TCC GTG TCT GCA TCT
GTT GGA GAC ACA GTC ACC ATC ACC TGT CGG GCG AGT CAG GGT ATT
AGC ACC TGG TTA GCC TGG TAT CAG CAC AAA CCA GGG AAA GCC CCT
AAA CTC CTC ATA TAT GCT GGA CCC AGT TTG CAG AGT GGG GTC CCA
TCA AGG TTC AGC GGC AGT GGA TCT GGG ACA GAA TTC ACT CTC ACA
ATC AGC AGC CTG CAC CCT GAA GAT TTT GCA ACT TAT TAC TGT CAA
CAA CTT AAT CAC TAC CCG ATG ACC TTC GGC CAA GGG ACA CGA CTG
GAG ATT AAA

>M0032-B09 HV (SEQ ID NO:23)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
ATT TAC AAG ATG GTT TGG GTT CGC CAA GCT CCT GGT AAA GGT TTG
GAG TGG GTT TCT TCT ATC GGT TCT TCT GGT GGC CAT ACT CGT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGA GCT CCT TAC TAC TAC TAC ATG
GAC GTC TGG GGC AAA GGG ACC ACG GTC ACC GTC TCA AGC

>M0033-F02 LV (SEQ ID NO:24)
CAG AGC GTC TTG ACT CAG CCT GCC TCC GTG TCT GGG TCT CCT GGA
CAG TCG ATC ACC ATC TCC TGC ACT GGA ACC AGC AGT GAC GTT GGT
GGT TAT AAC TAT GTC TCC TGG TAC CAA CAA CAC CCA GGC AAA GCC
CCC AAA CTC ATG ATT TAT GAT GTC AGT AAT GGG CCC TCA GGG GTT
TCT AAT CGC CTC TCT GGC TCC AAG TCT GGC AAC ACG GCC TCC CTG
ACC ATC TCT GGG CTC CAG GCT GAG GAC GAG GCT GAT TAT TAC TGC
AGC TCA TAT ACA AGC AGC AGC ACA GGT GTT CGG CGG AGG GAC CAA
GCT GAC CGT CCT A

>M0033-F02 HV (SEQ ID NO:25)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CAG TAC GCT ATG AAT TGG GTT CGC CAA GCT CCT GGT AAA GGT TTG
GAG TGG GTT TCT TGG ATC GTT TCT TCT GGT GGC TAT ACT CAT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ATG GCT GTG TAT TAC TGT GCG AGC CTC GTA GCA GCT CGT AAA CTT
GAC TAC TGG GGC CAG GGC ACC CTG GTC ACC GTC TCA AGC

>M0033-H07 LV (SEQ ID NO:26)
CAA GAC ATC CAG ATG ACC CAG TCT CCA TCC TCC CTG TCT GCA TCT
GTA GGA GAC AGA GTC ACC ATC ACT TGC CGG GCG AGT CAG GGC ATT
AGG AAT TTT TTA GCC TGG TAT CAG CAG AAA CCA GGG AAA GTT CCT
AAG CTC CTG GTC TTT GGT GCA TCC GCT TTG CAA TCG GGG GTC CCA
TCT CGG TTC AGT GGC AGT GGA TCT GGG ACA GAT TTC ACT CTC ACC
ATC AGC GGC CTG CAG CCT GAG GAT GTT GCA ACT TAT TAC TGT CAA
AAG TAT AAC GGT GTC CCG CTC ACT TTC GGC GGA GGG ACC AAG GTG
GAG ATC AAA

TABLE 5-continued

DNA sequences of variable regions of
MMP-14 binding antibodies

>M0033-H07 HV (SEQ ID NO:27)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
GTT TAC GGT ATG GTT TGG GTT CGC CAA GCT CCT GGT AAA GGT TTG
GAG TGG GTT TCT GTT ATC TCT TCT TCT GGT GGC TCT ACT TGG TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACC GCC TTG TAT TAC TGT GCG AGA CCG TTC AGT AGA AGA TAC GGC
GTC TTT GAC TAC TGG GGC CAG GGC ACC CTG GTC ACC GTC TCA AGC

>M0035-F02 LV (SEQ ID NO:28)
CAA GAC ATC CAG ATG ACC CAG TCT CCA GCC ACC CTG TCT TTG TCT
CCA GGG GAA AGA GCC ACC CTC TCC TGC AGG GCC AGT CAG AGT GTT
AGC AAT TAC TTA GCC TGG TAC CAA CAA AAA CCT GGC CAG GCT CCC
AGG CTC CTC ATC TAT GAT GCA TCC AAC AGG GCC ACT GGC ATC CCA
GCC AGG TTC AGT GGC AGT GGG TCT GGG ACA GAC TTC ACT CTC ACC
ATC AGC AGC CTA GAG CCT GAA GAT TTT GCA GTT TAT TAC TGT CAG
CAG CGT AGC AAC TGG CCG CTC ACT TTC GGC GGA GGG ACC AAG GTG
GAG ATC AAA

>M0035-F02 HV (SEQ ID NO:29)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
TTT TAC CGT ATG GAG TGG GTT CGC CAA GCT CCT GGT AAA GGT TTG
GAG TGG GTT TCT TCT ATC GTT CCT TCT GGT GGC TTT ACT CGT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGA TTT CAC GTA TTA CGA TAT TTT
GAC TGG TTT GGT AAC ACC AGG ATA CTG ATG CTT TTG ATA TCT GG
GGC CAG GGC ACC CTG GTC ACC GTC TCA AGC

>M0036-D02 LV (SEQ ID NO:30)
CAA GAC ATC CAG ATG ACC CAG TCT CCA GCC ACC CTG TCT TTG TCT
CCA GGG GAA AAA GCC ACC CTC TCC TGC AGG GCC AGT CAG ACT GTT
TAC AAC TAC TTA GCC TGG TAC CAG CAA AAA CCT GGC CAG GCT CCC
AGG CTC CTC ATC TAT GAC GCA TTC AAC AGG GCC ACT GGC ATC CCT
GCC AGG TTC AGT GGC AGT GGG TCT GGG ACA GAC TTC ACT CTC ACC
ATC AGC AGC CTG GAG CCT GAA GAT TTT GCA GTT TAT TAC TGT CAG
CAG CGT GGC AAC TGG CCC CGG ACG TTC GGC CAA GGG ACC AAG GTG
GAA ATC AAA

>M0036-D02 HV (SEQ ID NO:31)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
TTT TAC AAG ATG ACT TGG GTT CGC CAA GCT CCT GGT AAA GGT TTG
GAG TGG GTT TCT GGT ATC TAT CCT TCT GGT GGC CGT ACT GTT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACC GCC ATG TAT TAC TGT GCA AGA GGG CCC CAT TAC TAT GAT AGC
CCG GGT GCT TTT GAT ATC TGG GGC CAA GGG ACA ATG GTC ACC GTC
TCA AGC

>M0036-F02 LV (SEQ ID NO:32)
CAG TAC GAA TTG ACT CAG CCA CCC TCG TTG TCC GTG TCC CCA GGA
CAG ACA GCC AGC ATC ACC TGC TCT GGA GAG AAA TTG GGG GAA AAA
TTT GCT TCC TGG TAT CAA CGG AGG CCC GGC CAG TCT CCT CTA TTG
ATC ATC TAT CAG GAT AAC AAG CGG CCC TCA GGG ATC CCT GAG CGG
TTC TCT GGC TCC AAT TCT GGA AAC ACA GCC GCT CTG ACC ATC ACC
GGG ACC CAG GCT ATG GAT GAC GCT GAC TAT TAC TGT CAG GCG TGG
GAG AGC ACC ACA GCG GTC TTC GGC GGA GGG ACC AAG TTG ACC GTC
CTA

TABLE 5-continued

DNA sequences of variable regions of
MMP-14 binding antibodies

>M0036-F02 HV (SEQ ID NO:33)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CGT TAC ACT ATG GGT TGG GTT CGC CAA GCT CCT GGT AAA GGT TTG
GAG TGG GTT TCT CGT ATC TAT TCT TCT GGT GGC AAT ACT GTT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACA GCC ACA TAT TAC TGT GCA CGG ACC CGT AGA GAT GGC TAC AAC
CCC TTT GAC TAC TGG GGC CAG GGA ACC CTG GTC ACC GTC TCA AGC

>M0036-H08 LV (SEQ ID NO:34)
CAA GAC ATC CAG ATG ACC CAG TCT CCA TCC TCC CTG TCT GCA TCT
GTA GGA GAC AGA GTC ACC ATC ACT TGC CGG GCA AGT CAG AGC ATT
AGC AGC TAT TTA AAT TGG TAT CAG CAG AAA CCA GGG AAA GCC CCT
AAG CTC CTG ATC TAT GCT GCA TCC AGT TTG CAA AGT GGG GTC CCA
TCA AGG TTC AGT GGC AGT GGA TCT GGG ACA GAT TTC ACT CTC ACC
ATC AGC AGT CTG CAA CCT GAA GAT TTT GCA ACT TAC TAC TGT CAA
CAG AGT TAC AGT CTC CCC GTG ACG TTT GGC CAA GGG TCC AAG GTG
GAA ATC AAA CGA ACT

>M0036-H08 HV (SEQ ID NO:35)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CGT TAC TGG ATG GTT TGG GTT CGC CAA GCT CCT GGT AAA GGT TTG
GAG TGG GTT TCT TAT ATC TAT TCT TCT GGT GGC ATG ACT GGT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCA AGG GGG GGG GAA TAT AGT GGT TTC
TTA GGG GTT TGG GGC CAG GGC ACC CTG GTC ACC GTC TCA AGC

>M0037-A08 LV (SEQ ID NO:36)
CAA GAC ATC CAG ATG ACC CAG TCT CCA TCT TCC GTG TCT GCT TCT
GTA GGA GAC AGA GTC ACC ATC ACT TGT CGG GCG AGT CAG GGT GTT
AGC AGT TAC TTA GCC TGG TAT CAG CAG AAA CCA GGG AAA GCC CCT
AAG CTC CTG ATC TAT GGT GCA TCC ACT TTG CAA AAT GGG GTC CCA
TCA AGG TTC AGC GGC AGT GGA TCT GGG ACA GAT TTC ACT CTC ACC
ATC AGC AGC CTG CAG CCT GAA GAT TTT GCG ACT TAC CAT TGT CAA
CAG GTT CAC AGT TTC CCT CCG ACG TTC GGT CAG GGG ACC AAG GTG
GAA ATC AAA

>M0037-A08 HV (SEQ ID NO:37)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CAT TAC ATG ATG ATG TGG GTT CGC CAA GCT CCT GGT AAA GGT TTG
GAG TGG GTT TCT GGT ATC TCT TCT TCT GGT GGC CGT ACT GGT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGT TCG GGG AAT AGT GGG AGC TAC
TCT TGG CGT GCT TTT GAT ATC TGG GGC CAA GGG ACC ACG GTC ACC
GTC TCA AGC

>M0037-B10 LV (SEQ ID NO:38)
CAA GAC ATC CAG ATG ACC CAG TCT CCA TCC TCC CTG TCT GCA TCT
GTG GGA GAC AGA GTC GCC ATC ACT TGC CGC GCA AGT CAG AGC ATC
GAC ACC TAT TTA AAT TGG TAT CAG CAG AAA CCA GGG AAA GCC CCT
AAA CTC CTG ATC TAT GCT GCA TCC AAG TTG GAA GAC GGG GTC CCA
TCA AGA TTC AGT GGC AGT GGA ACT GGG ACA GAT TTC ACT CTC ACC
ATC AGA AGT CTG CAA CCT GAA GAT TTT GCA AGT TAT TTC TGT CAA
CAG AGC TAC TCT AGT CCA GGG ATC ACT TTC GGC CCT GGG ACC AAG
GTG GAG ATC AAA

TABLE 5-continued

DNA sequences of variable regions of
MMP-14 binding antibodies

>M0037-B10 HV (SEQ ID NO:39)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
GTT TAC TAT ATG GGT TGG GTT CGC CAA GCT CCT GGT AAA GGT TTG
GAG TGG GTT TCT TAT ATC GGT TCT TCT GGT GGC TGG ACT GAG TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGA GAC CTC TCG GCA GTG GCT GGT
CTA GGG GGT GCT TTT GAT ATC TGG GGC CAA GGG ACA ATG GTC ACC
GTC TCA AGC

>M0037-C03 LV (SEQ ID NO:40)
CAA GAC ATC CAG ATG ACC CAG TCT CCA TCT TCC GTG TCT GCA TCT
GTA GGA GAC AGA GTC ACC ATC ACT TGT CGG GCG AGT CAG GGT ATT
AGC AGC TGG TTA GCC TGG TAT CAG CAG AAA CCA GGG AAA GCC CCT
AAG CTC CTG ATC TAT GCT GCA TCC AGT TTG CAA AGT GGG GTC CCA
TCA AGG TTC AGC GGC AGT GGA TCT GGG ACA GAT TTC ACT CTC ACC
ATC AGC AGC CTG CAG CCT GAA GAT TTT GCA ACT TAC TAT TGT CAA
CAG GCT AAC AGT TTC CCC TTC GTA ACT TTT GGC CAG GGG ACC AAG
CTG GAG ATC AAA

>M0037-C03 HV (SEQ ID NO:41)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
ATG TAC CTT ATG ATT TGG GTT CGC CAA GCT CCT GGT AAA GGT TTG
GAG TGG GTT TCT GTT ATC TCT TCT TCT GGT GGC CAG ACT AAA TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGA ACC GAT TTG ACT GGT TAT TCA
GCG GGA GCT TTT GAT ATC TGG GGC CAA GGG ACA ATG GTC ACC GTC
TCA AGC

>M0037-C09 LV (SEQ ID NO:42)
CAA GAC ATC CAG ATG ACC CAG TCT CCA CTC TCC CTG CCC GTC ACC
CTT GGA GAG TCG GCC TCC GTC TCC TGC AGG TCT AGT CAG AGC CTC
CTT CAT GAA AAT GGA CAC AAC TAT TTG GAT TGG TAC CTG CAG AAG
CCA GGG CAG TCT CCA CAG CTC CTG ATC TAT TTG GGT TCT AAT CGG
GCC TCC GGG GTC CCT GAC AGG TTC AGT GGC AGT GGA TCA GGC ACA
GAT TTT ACA CTG AAA ATC AGC AGA GTG GAG GCT GAG GAT GTT GGG
GTT TAT TAC TGC ATG CAA TCT CTA AAG ACT CCT CCG ACG TTC GGC
CCA GGG ACC AAG GTG GAA ATC AAA

>M0037-C09 HV (SEQ ID NO:43)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CAT TAC GAG ATG TTT TGG GTT CGC CAA GCT CCT GGT AAA GGT TTG
GAG TGG GTT TCT TCT ATC TCT CCT TCT GGT GGC CAG ACT CAT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACT GCC GTG TAT TAC TGT GCC ACA GAT CGG ACG TAT TAC GAT TTT
TGG AGT GGT TAT GGG CCC CTG TGG TAC TGG GGC CAG GGA ACC CTG
GTC ACC GTC TCA AGC

>M0037-D01 LV (SEQ ID NO:44)
CAA GAC ATC CAG ATG ACC CAG TCT CCA TCC TCC CTG TCT GCA TCT
GTC GGA GAC AGA GTC ACC ATC ACT TGC CGG GCA AGT CAG GGC ATT
AGA AAT GAT TTA GGC TGG TAT CAG CAG AAA CCA GGG AAA GCC CCT
AAG CGC CTG ATC TAT GTT GCA TCC AGT TTG CAA AGT GGG GTC CCA
TCA AGG TTC AGC GGC AGT GGA TCT GGG ACA GAA TTC ACT CTC ACA
ATC AGC AGC CTG CAG CCT GAA GAT TTT GCA ACT TAT TAC TGT CTA
CAG CAT AAT AGT TAC CCG TGG ACG TTC GGC CAA GGG ACC AAG GTG
GAA ATC AAA

TABLE 5-continued

DNA sequences of variable regions of
MMP-14 binding antibodies

>M0037-D01 HV (SEQ ID NO:45)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
ATG TAC ATG ATG ATT TGG GTT CGC CAA GCT CCT GGT AAA GGT TTG
GAG TGG GTT TCT TCT ATC TAT CCT TCT GGT GGC AAT ACT ATG TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCC ACA GGT GTA TTA CGA TAT TTT GAC
TGG GAT GCT GGG AGC GGT ATG GAC GTC TGG GGC CAA GGG ACC ACG
GTC ACC GTC TCA AGC

>M0037-H09 LV (SEQ ID NO:46)
CAA GAC ATC CAG ATG ACC CAG TCT CCA CTC TCC CTG CCC GTC ACC
CCT GGA GAG CCG GCC TCC ATC TCC TGC AGG TCT AGT CAG AGC CTC
CTG CAT GGT AAT GGA AAC AAC TAT TTG GAT TGG TAC CTG CAG AAG
CCA GGG CAG TCT CCA CAA CTC CTG ATC TAT TTG GGT TCC AAT CGG
GCC TCC GGG GTC CCT GAC AGG TTC AGT GGC AGT GGA TCA GGC ACA
GAT TTT ACA CTG AAA ATC AGC AGT GTG GAG GCT GAA GAT GTT GGC
GTT TAT TAC TGC ATG CAA GGT CTA CAA ACT CCT CAC ACT TTT GGC
CAG GGG ACC CAG CTG GAG ATC AAA

>M0037-H09 HV (SEQ ID NO:47)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CGT TAC TGG ATG GAT TGG GTT CGC CAA GCT CCT GGT AAA GGT TTG
GAG TGG GTT TCT TCT ATC CGT TCT TCT GGT GGC ATG ACT GGT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGA CAC CGT ACG GGC CGC GGG GCT
TTT GAT ATC TGG GGC CAA GGG ACC ACG GTC ACC GTC TCA AGC

>M0038-B06 LV (SEQ ID NO:48)
CAA GAC ATC CAG ATG ACC CAG TCT CCA TCC TCC CTG TCT GCA TCT
GTA GGA GAC AGA GTC ACC ATC ACT TGC CGG GCA AGT CAG AGC ATT
AGC AGC TAT TTA AAT TGG TAT CAG CAG AAA CCA GGG AAA GCC CCT
AAG CTC CTG ATC TAT GCT GCA TCC AGT TTG CAA AGT GGG GTC CCA
TCA AGG TTC CGT GGC AGT GGA TCT GGG ACA GAT TTC AGT CTC ACC
ATC AGC AGT CTG CAA CCT GAA GAT TTT GCA ACT TAC TAC TGT CAA
CAG ACT TAC AGT GGC CTT CCC ACT TTT GGT GGA GGG ACC GTG GTG
GAG ATC AAA

>M0038-B06 HV (SEQ ID NO:49)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
TCT TAC GTT ATG GGT TGG GTT CGC CAA GCT CCT GGT AAA GGT TTG
GAG TGG GTT TCT GTT ATC TCT CCT TCT GGT GGC TGG ACT ACT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACA GCC ACA TAT TAC TGT GCG AGT CGG GGA GTG GTT ACC AAC CTT
GAC TAC TGG GGC CAG GGA ACC CTG GTC ACC GTC TCA AGC

>M0038-C05 LV (SEQ ID NO:50)
CAA GAC ATC CAG ATG ACC CAG TCT CCA TCC TCC CTG TCT GCA TCT
GTA GGA GAC AGA GTC ACC ATC ACT TGC CGG GCA AGT CAG AGC ATT
AGC AGC TAT TTA AAT TGG TAT CAG CAG AAA CCA GGG AAA GCC CCT
AAG CTC CTG ATC TAT GCT GCA TCC AGT TTG CAA AGT GGG GTC CCA
TCA AGG TTC AGT GGC AGT GGG TCT GGG ACA GAC TTC ACT CTC ACC
ATC AGC AGA CTG GAG CCT GAA GAT TTT GCA GTG TAT TAT TGT CAG
CAG TAT GGT AGC TCA CCC ACG TTC GGC CAA GGG ACC AAG GTG GAA
ATC AAA

TABLE 5-continued

DNA sequences of variable regions of
MMP-14 binding antibodies

>M0038-C05 HV (SEQ ID NO:51)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
TCT TAC ATT ATG GTT TGG GTT CGC CAA GCT CCT GGT AAA GGT TTG
GAG TGG GTT TCT GTT ATC TAT CCT TCT GGT GGC CCT ACT TAT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGG GAC CCC CGG CTG GAA CGT TTC
TAC TTT GAC TAC TGG GGC CAG GGC ACC CTG GTC ACC GTC TCA AGC

>M0038-C06 LV (SEQ ID NO:52)
CAA GAC ATC CAG ATG ACC CAG TCT CCA GGC ACC CTG TCT TTG TCT
CCA GGG GAC AGA GCC ACC CTC TCC TGC AGG GCC AGT CAG AGT GTT
GGC AGC GAC TAC TTA GCC TGG TAC CAG CAG AAA CCT GGC CAG GCT
CCC AGG CTC CTC ATC TTT GCT GCG TCC ACC AGG GCC ACC GGC ATC
CCA GAC AGG TTC AGT GGC AGT GGG TCT GCG ACA GAC TTC ACT CTC
ACC ATC AGC AGC CTG GAA CCT GAA GAT TTT GCA GTG TAT TTC TGT
CAG CAG TAT GCT AGC CCA CCT CGG ACG TTC GGC CAA GGG ACC AAG
GTG GAA ATC AAA

>M0038-C06 HV (SEQ ID NO:53)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
ATG TAC GGT ATG CAT TGG GTT CGC CAA GCT CCT GGT AAA GGT TTG
GAG TGG GTT TCT CTA TAT TCT TCT GGT GGC TAT ACT GGT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGG GGG AGG GCC GTT GAC CTC TGG
GGC CAG GGA ACC CTG GTC ACC GTC TCA AGC

>M0038-D06 LV (SEQ ID NO:54)
CAA GAC ATC CAG ATG ACC CAG TCT CCA GCC ACC CTG TCT TTG TCT
CCA GGG GAA AGA GCC ACC CTC TCC TGC AGG GCC AGT CAG AGT GTT
AGC AGC TAC TTA GCC TGG TAC CAA CAG AAA CCT GGC CAG GCT CCC
AGG CTC CTC ATC TAT GAT GCA TCC AAC AGG GCC ACT GGC ATC CCA
GCC AGG TTC AGT GGC AGT GGG TCT GGG ACA GAC TTC ACT CTC ACC
ATC AGC AGC CTA GAG CCT GAA GAT TTT GCA GTT TAT TAC TGT CAG
CAG CGT AGC AAC TGG CCT CTC ACC TTC GGC CAA GGG ACA CGA CTG
GAG ATT AAA

>M0038-D06 HV (SEQ ID NO:55)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
TGG TAC TAT ATG GGT TGG GTT CGC CAA GCT CCT GGT AAA GGT TTG
GAG TGG GTT TCT TAT ATC GGT TCT TCT GGT GGC ATG ACT GGT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACA GCC ACA TAT TAC TGT GCG ATG GTG GGC TTC CTC CCG ACC GTT
GAC TAC TGG GGC CAG GGA ACC CTG GTC ACC GTC TCA AGC

>M0038-E05 LV (SEQ ID NO:56)
CAA GAC ATC CAG ATG ACC CAG TCT CCA TCT TCT GTG TCT GCA TCT
GTA GGA GAC AGA GTC ACC ATC ACT TGT CGG GCG AGT CAG CAT ATT
AGC AAC TGG CTA GCC TGG TAT CAG CAG AAA CCA GGG GAG GCC CCT
AAA CTC CTG ATC TCT GCT GCA TCC AGT TTG CAA AGT GGG GTC CCA
TCA AGG TTC AGT GGC AGT GGA TCT GGG ACA GAT TTC ACT CTC ACC
ATC AGC AGT CTG CAA CCT GAA GAT TTT GCA ACT TAC TAC TGT CAA
CAG AGT TAC AGT ACC CCG CTC ACT TTC GGC GGA GGG ACC AAG GTG
GAG ATC AAA

TABLE 5-continued

DNA sequences of variable regions of
MMP-14 binding antibodies

>M0038-E05 HV (SEQ ID NO:57)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CCT TAC CAT ATG ACT TGG GTT CGC CAA GCT CCT GGT AAA GGT TTG
GAG TGG GTT TCT TCT ATC TCT TCT TCT GGT GGC CAT ACT GAG TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG ACA GCA TGG GCG GGA TTT ACT TTT
AAC GTC TGG GGC CAA GGG ACA ATG GTC ACC GTC TCA AGC

>M0038-E06 LV (SEQ ID NO:58)
CAA GAC ATC CAG ATG ACC CAG TCT CCA GGC ACC CTG TCC TTG TCT
CCA GGG GAC AGA GCC ACC CTC TCC TGC GGG GCC AGC CAG CTT GTT
GTC AGC AAC TAC ATA GCC TGG TAC CAG CAA AAA CCT GGC CAG GCT
CCC AGA CTC CTC ATG TAT GCT GGA TCC ATC AGG GCC ACT GGC ATC
CCA GAC AGG TTC AGT GGC AGT GGG TCT GGG ACA GAC TTC ACT CTC
ACC ATC AGC AGA CTA GAA CCT GAA GAT TTT GCA ATA TAT TAC TGT
CAG CAG CGT AGC AAC TGG CCT TGG ACG TTC GGC CAA GGG ACC AAG
GTG GAA ATC AAA

>M0038-E06 HV (SEQ ID NO:59)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CCT TAC GTT ATG CAT TGG GTT CGC CAA GCT CCT GGT AAA GGT TTG
GAG TGG GTT TCT TCT ATC TCT CCT TCT GGT GGC TGG ACT TAT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ATG GCT GTG TAT TAC TGT GCG AGA GGG ACT GGA GCC TAC GGT ATG
GAC GTC TGG GGC CAA GGG ACC ACG GTC ACC GTC TCA AGC

>M0038-E12 LV (SEQ ID NO:60)
CAA GAC ATC CAG ATG ACC CAG TCT CCA TCC TCC CTG TCT GCA TCT
GTA GGA GAC AGC GTC ACC ATC ACT TGC CGG GCA AGT CAG AAC ATT
AAC AGT TAT TTA AAT TGG TAT CAG CAG AAA CCA GGA AAA GCC CCT
AAG CTC CTG ATC TAT GTT GCA TCC AAT TTG CAA AGG GGG GTC CCA
TCA AGG TTC GGT GGC AGT GGA TCT GGG ACA GAT TTC ACT CTC ACC
ATC ACC AGT CTG CAA CCT GAA GAT TTT GCA ACT TAC TCC TGT CAG
CAG ACT TAC AGT ACC CCC CTC ACT TTC GGC GGA GGG ACC AAG GTG
GAG ATC AAA

>M0038-E12 HV (SEQ ID NO:61)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
AAG TAC TGG ATG ATG TGG GTT CGC CAA GCT CCT GGT AAA GGT TTG
GAG TGG GTT TCT GTT ATC TAT CCT TCT GGT GGC ATT ACT TAT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACT GCA GTC TAT TGT GCG AGA CTA CCT TCT TGG GGG TTT GAT
GCT CTT GAT ATC TGG GGC CAA GGG ACA ATG GTC ACC GTC TCA AGC

>M0038-F01 LV (SEQ ID NO:62)
CAA GAC ATC CAG ATG ACC CAG TCT CCA TCC TCC CTG TCT GCA TTT
GTA GGA GAC AAA GTC ACC ATC ACT TGC CGG GCA AGT CAG AGT GTT
GGC ACC TAT TTA AAT TGG TAT CAG CAG AAA GCA GGG AAA GCC CCT
GAG CTC CTG ATC TAT GCT ACA TCC AAT TTG CGA AGT GGG GTC CCA
TCA AGG TTC AGT GGC AGT GGA TCT GGG ACA GAT TTC ACT CTC ACC
ATC AAC ACT CTG CAA CCT GAA GAT TTT GCA ACT TAC TAC TGT CAA
CAG AGT TAC AGT ATC CCT CGG TTT ACT TTC GGC CCT GGG ACC AAA
GTG GAT ATC AAA

TABLE 5-continued

DNA sequences of variable regions of
MMP-14 binding antibodies

>M0038-F01 HV (SEQ ID NO:63)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CTT TAC TCT ATG AAT TGG GTT CGC CAA GCT CCT GGT AAA GGT TTG
GAG TGG GTT TCT TCT ATC TAT TCT TCT GGT GGC TCT ACT CTT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGA GGT CGG GCT TTT GAT ATC TGG
GGC CAA GGG ACA ATG GTC ACC GTC TCA AGC

>M0038-F08 LV (SEQ ID NO:64)
CAA GAC ATC CAG ATG ACC CAG TCT CCA GGC ACC CTG TCT TTG TCT
CCA GGG GAA AGA GCC ACC CTC TCC TGC AGG GCC AGT CAG AGT GTT
AGC AGC AGC TAC TTA GCC TGG TAC CAG CAG AAA CCT GGC CAG GCT
CCC AGG CTC CTC ATC TAT GGT GCA TCC AGC AGG GCC ACT GGC ATC
CCA GAC AGG TTC AGT GGC AGT GGG TCT GGG ACA GAC TTC ACT CTC
ACC ATC AGC AGA CTG GAG CCT GAA GAT TTT GCA GTG TAT TAC TGT
CAG CAC TAT GGT GGC TCA CAG GCT TTC GGC GGA GGG ACC AAG GTG
GAG ATC AAA

>M0038-F08 HV (SEQ ID NO:65)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CGT TAC AAG ATG TGG TGG GTT CGC CAA GCT CCT GGT AAA GGT TTG
GAG TGG GTT TCT GGT ATC CGT CCT TCT GGT GGC CTT ACT CGT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGA CGC GGT GAC TAC GTC GGG GGG
TTT GAC TAC TGG GGC CAG GGA ACC CTG GTC ACC GTC TCA AGC

>M0038-H06 LV (SEQ ID NO:66)
CAA GAC ATC CAG ATG ACC CAG TCT CCA GGC ACC CTG TCT TTG TCT
CCA GGG GAA GGA GCC ACC CTC TCC TGC AGG GCC AGT CAG ATT ATA
AAT CCT TTT TAC GTA GCC TGG TAT CAA CAG AGA CCT GGC CAG GCT
CCC AGG CTC CTC ATC TAT GCT TCA TCC AGG AGG GCC GGT GGC ATC
CCA GAC AGA TTC AGT GGC AGT GCG TCT GGG ACA GAC TTC ACT CTC
ACA ATC AGC AGA CTG GAG CCT GAA GAT TTT GCA GTC TAT TAC TGT
CAA TAC TTT TAT AAC TCC ATG TGG ACG TTC GGC CAA GGG GCC AAG
GTG GAG ATC AGA

>M0038-H06 HV (SEQ ID NO:67)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
TGG TAC AAT ATG ACT TGG GTT CGC CAA GCT CCT GGT AAA GGT TTG
GAG TGG GTT TCT CGT ATC TCT CCT TCT GGT GGC GAT ACT TTT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCT AGA GCT GCG ATA GCA CCT CGT CCG
TAC GGT ATG GAC GTC TGG GGC CAA GGG ACC ACG GTC ACC GTC TCA
AGC

>M0039-B07 LV (SEQ ID NO:68)
CAA GAC ATC CAG ATG ACC CAG TCT CCA CTC TCC CTG TCT GCA TCT
GTA GGA GAC AGA GTC ACC ATC ACT TGC CGG GCG AGT CAG GGC ATT
AGC AAT TAT TTA GCC TGG TAT CAG CAG AAA CCA GGG AAA GTT CCT
AAG CTC CTG ATC TAT GCT GCA TCC ACT TTG CAA TCA GGG GTC CCA
TCT CGG TTC AGT GGC AGT GGA TCT GGG ACA GAT TTC ACT CTC ACC
ATC AGC AGT CTG CAG CCT GAA GAT GTT GCA ACT TAT TAC TGT CAA
AAG TAT AAC AGT GCC CGC CTC ACT TTC GGC GGA GGG ACC AAG GTG
GAG ATC AAA

TABLE 5-continued

DNA sequences of variable regions of
MMP-14 binding antibodies

>M0039-B07 HV (SEQ ID NO:69)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CTT TAC CCT ATG CTT TGG GTT CGC CAA GCT CCT GGT AAA GGT TTG
GAG TGG GTT TCT GGT ATC TCT CCT TCT GGT GGC CAG ACT TTT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCA AGG ATG GCT TAT TAC TCT GGA TAC
TTC GAT CTC TGG GGC CGT GGC ACC CTG GTC ACC GTC TCA AGC

>M0039-D02 LV (SEQ ID NO:70)
CAA GAC ATC CAG ATG ACC CAG TCT CCA TCC TCC CTG TCT GCA TCT
GTA GGA GAC AGA GTC ACC ATC ACT TGC CGG GCA AGT CAG AGC ATT
AGC AGC TAT TTA AAT TGG TAT CAG CAG AAA CCA GGG AAA GCC CCT
AAG CTC CTG ATC TAC GAT GCA TCC AAT TTG GAA ACA GGG GTC CCA
TCA AGG TTC AGT GGA AGT GGA TCT GGG ACA GAT TTT ACT TTC ACC
ATC AGC AGC CTG CAG CCT GAA GAT ATT GCA ACA TAT TAC TGT CAA
CAG TTT GAT GAT CTC CCG CTC ACT TTC GCC GGA GGG ACG AAG GTG
GAG CTC AAA CGA ACT

>M0039-D02 HV (SEQ ID NO:71)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CTT TAC GTT ATG ATT TGG GTT CGC CAA GCT CCT GGT AAA GGT TTG
GAG TGG GTT TCT GGT ATC TAT TCT TCT GGT GGC GAT ACT TAT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGG GGG CAG CAG CTG GGG GGG GGT
GCT TTT GAT ATC TGG GGC CAA GGG ACA ATG GTC ACC GTC TCA AGC

>M0039-D10 LV (SEQ ID NO:72)
CAA GAC ATC CAG ATG ACC CAG TCT CCA GAC ACC GTG TCT TTC TCT
CCA GGG GAA AGA GCC TCC CTC TCA TGC CGG GCC AGT CAG AGT GTC
CGC AGC GAC TTA GCC TGG TAC CAA CAG AAG CCT GGC CAG GCT CCC
AGG CTG CTC ATC TAT GGT GCA TCC AAC AGG GCC ACT GGC ATC CCA
GTC AGG TTC AGT GGC AGT GGG TCT GGG ACA GAC TTC ACT CTC ACC
ATC AGC AGA CTG GAG CCT GAA GAT TTT GCA GTG TAT TAC TGT CAG
CAG TAT GGT AGC TCA CCC CTA TTC ACT TTC GGC CCT GGG ACC AAA
GTG GAT ATC AAA

>M0039-D10 HV (SEQ ID NO:73)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
ATG TAC AAT ATG GCT TGG GTT CGC CAA GCT CCT GGT AAA GGT TTG
GAG TGG GTT TCT TGG ATC TAT TCT TCT GGT GGC CTT ACT TTG TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTA TAT TAC TGT GCG AAA GGC TCC AAT ACG TAC TAC TTT
GAT GCT AGT GGC CTC GGT GCT TTT AAT ATG TGG GGC CAA GGG ACA
ATG GTC ACC GTC TCA AGC

>M0039-G05 LV (SEQ ID NO:74)
CAA GAC ATC CAG ATG ACC CAG TCT CCA TCC TTC CTG TCT GCA TCT
ATA GGA GAC AGA GTC ACC ATC ACT TGC CGG GCC AGT CAG GGC ATT
AAC ACT TTT TTA GCC TGG TAT CAG CAA AAA CCA GGG ATA GCC CCT
AAG CTC CTG ATC TAT GCT GCA TCC ACT CTG CAA AGT GGG GTC CCA
TCA AGG TTC AGC GGC AGT GGA TCT GGG ACA GAA TTC ACT CTC ACA
ATC AGC AGT CTG CAG CCT GAA GAT TTT GCA ACT TAT TAC TGT CAG
CAG CTT AAT GGT TAC CGC AGC TTC GGA CAA GGG ACA CGA CTA GAG
ATG AAA

TABLE 5-continued

DNA sequences of variable regions of
MMP-14 binding antibodies

>M0039-G05 HV (SEQ ID NO:75)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
AAT TAC GAG ATG GGT TGG GTT CGC CAA GCT CCT GGT AAA GGT TTG
GAG TGG GTT TCT TGG ATC TAT TCT TCT GGT GGC TAT ACT TCT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACA GCC ACG TAT TAC TGT GCG AGA GAT CCG TAT TAC TAT GAT AGT
AGT GGT TAT TAC TAC TAC TAC TAC TAC ATG GAC GTC TGG GGC
AAA GGG ACC ACG GTC ACC GTC TCA AGC

>M0039-G07 LV (SEQ ID NO:76)
CAA GAC ATC CAG ATG ACC CAG TCT CCA GGC ACC CTG TCT TTG TCT
CCA GGG GAA AGA GCC ACC CTC TCC TGC AGG GCC AGT CAG AGT GTT
AAC AGC AGG TTC TTG GCC TGG TAC CAG CAG AAA CCT GGC CAG GCT
CCC AGG CTC CTC ATC TAT AGT ACA TCC ACC AGG GCC ACT GGC ATC
CCA GCC AGG TTC AGT GGC AGT GGG TCC GGG ACA GAC TTC ACT CTC
ACC ATC AGC AGA CTG GAG CCT GAA GAT TTT GCG GTG TAT TAC TGT
CAG CGA TAT GGT AGC TCA CCT ACG TGG ACG TTC GGC CAA GGG ACC
AAG GTG GAA ATC AAA

>M0039-G07 HV (SEQ ID NO:77)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CGT TAC GTT ATG GAT TGG GTT CGC CAA GCT CCT GGT AAA GGT TTG
GAG TGG GTT TCT CGT ATC TCT CCT TCT GGT GGC CAT ACT GAT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCC AGA GAA ACG GTT CGG GGA GTT TAC
TTT GAC TAC TGG GGC CAG GGA ACC CTG GTC ACC GTC TCA AGC

>M0039-H08 LV (SEQ ID NO:78)
CAA GAC ATC CAG ATG ACC CAG TCT CCA GCC ACC CTG TCT GTG TCT
CCA GGG GAA AGA GCC ACC CTC TCC TGC AGG GCC AGT GAG AGT GTT
AAA AAC AAC TTA GCC TGG TAT CAG CAG AAA CCT GGC CAG GCT CCC
AGG CTC CTC ATC TAT GGT GTT TCC ACC AGG GCC CCT GGT ATC CCA
GCC AGG TTC AGT GGC AGT GGG TCT GGG ACA GAC TTC ACT CTC ACC
ATC AGC AGC CTA GAG CCT GAA GAT TTT GCA GTT TAT TAC TGT CAG
CAG CGT AGC AAC TGG CCT CCG GTC ACC TTC GGC CAA GGG ACA CGA
CTG GAG ATT AAA

>M0039-H08 HV (SEQ ID NO:79)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
GCT TAC AAT ATG GGT TGG GTT CGC CAA GCT CCT GGT AAA GGT TTG
GAG TGG GTT TCT TCT ATC TCT TCT TCT GGT GGC TAT ACT GGT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGA GAT CTT TAC AGG GGC TTT GAC
TAC TGG GGC CAG GGA ACC CTG GTC ACC GTC TCA AGC

>M0040-A03 LV (SEQ ID NO:80)
CAA GAC ATC CAG ATG ACC CAG TCT CCA TCT TTT GTG TCT GCA TCT
GTC GGA GAC AGA GTC ACC ATC TCT TGT CGG GCG AGT CAC AAT ATT
AAC ACC TGG TTA GCC TGG TAT CAG CAG AAA CCA GGG AAA GCC CCT
AAC CTC CTG ATC TAT TCT GCA TCC AAT TTG CAA GGT GGG GTC CCA
TCT AGG TTC AGC GGC AGT GGA TCT GGG ACA GAC TTC ACT CTC ACT
ATC AGC AGC CTG CAG CCT GGA GAT TTT GCG ACT TAC TAT TGT CAA
CAG GCT AGC AGT TTC CCT ATC ACC TTC GGC CAA GGG ACA CGA CTG
GAG ATT AAA

TABLE 5-continued

DNA sequences of variable regions of
MMP-14 binding antibodies

>M0040-A03 HV (SEQ ID NO:81)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
AAT TAC ATG ATG ATT TGG GTT CGC CAA GCT CCT GGT AAA GGT TTG
GAG TGG GTT TCT TGG ATC TCT CCT TCT GGT GGC TAT ACT TTT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGA GGA TAT TAC GAT ATT TTG ACT
GGT ATG GTG GGC GGC GGT GCT TTT GAT ATC TGG GGC CAA GGG ACC
ACG GTC ACC GTC TCA AGC

>M0040-A06 LV (SEQ ID NO:82)
CAG GAC ATC GTC ATG ACT CAA ACC CCT CCT AGT TTA CCG GTT AAC
CCG GGT GAA CCT GCC TCC ATC TCC TGC AGG TCT AGT CAG AGC CTC
CTG CAT AGA AAT GGA TAC AAC TAT TTG GAT TGG TAC CTG CAG AAG
CCA GGG CAG TCT CCA CAG CTC CTG ATC CAT TTG GGT TCT TAT CGG
GCC TCC GGG GTC CCT GAC AGG TTC AGT GGC AGT GGA TCA GCC ACA
GAT TTT ACA CTG AAA ATC AGC AGA GTG GAG GCT GAG GAT GTT GGG
GTT TAT TAC TGC ATG CAA CCT CTA CAA ACT CCA TTC ACT TTC GGC
CCT GGG ACC AAA GTG GAT ATC AAA

>M0040-A06 HV (SEQ ID NO:83)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
TAT TAC GGT ATG TAT TGG GTT CGC CAA GCT CCT GGT AAA GGT TTG
GAG TGG GTT TCT TCT ATC TCT TCT GGT GGC TAT ACT GAT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCA AGG AGG ATT AAG TAT TAC GAT ATT
GAA GGG GAA GGT GCT TTT GAT ATC TGG GGC CAA GGG ACA ATG GTC
ACC GTC TCA AGC

>M0040-A08 LV (SEQ ID NO:84)
CAA GAC ATC CAG ATG ACC CAG TCT CCA CTC TCC CTG CCC GTC ACC
CCT GGA GAG CCG GCC TCC ATC TCC TGC AGG TCT AGT CAG AGC CTC
CTG CAT AGT AAT GGA TAC AAC TAT TTG GAT TGG TAC CTG CAG AAG
CCA GGG CAG TCT CCA CAG CTC CTG ATC TAT TTG GGT TCT AAT CGG
GCC TCC GGG GTC CCT GAC AGG TTC AGT GGC AGT GGA TCA GGC ACA
GAT TTT ACA CTG AAA ATC AGC AGA GTG GAG GCT GAG GAT GTT GGG
GTT TAT TAC TGC ATG CAA GCT CTA CAA CCT TTC ACT TTC GGC GGA
GGG ACC AAG GTG GAG ATC AAA

>M0040-A08 HV (SEQ ID NO:85)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
GCT TAC ATG ATG GGT TGG GTT CGC CAA GCT CCT GGT AAA GGT TTG
GAG TGG GTT TCT GGT ATC TCT TCT TCT GGT GGC CTT ACT TCT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGA CCA GCG CTG ATT TAC TAT GAT
AGT AGT GGC CCA GTG ATG CTT TTT GAT ATC TGG GGC CAA GGG ACA
ATG GTC ACC GTC TCA AGC

>M0040-A11 LV (SEQ ID NO:86)
CAG AGC GCT TTG ACT CAG CCT CCC TCC GCG TCC GGG TCT CCT GGA
CAG TCA GTC ACC ATC TCC TGC ACT GGA ACC AGC AGT GAC GTT GGT
GCT TAT AAC TAT GTC TCC TGG TAC CAA CAG CAC CCA GAC AAA GCC
CCC AAA CTC ATT ATT TAT AAT GTC AAT GAG CGG CCC TCA GGG GTC
CCT GAT CGC TTC TCT GGC TCC AAG TCT GGC AAC ACG GCC TCC CTG
ACC GTC TCT GGG CTC CAG GCT GAG GAT GAG GCT GAT TAT TAC TGT
ACC TCA TAT GCA GGC AGC AAC AAA ATC GGG GTC TCC GGA ACT GGG
ACC AAG GTC ACC GTC CTA

TABLE 5-continued

DNA sequences of variable regions of
MMP-14 binding antibodies

>M0040-A11 HV (SEQ ID NO:87)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CAT TAC GTT ATG TTT TGG GTT CGC CAA GCT CCT GGT AAA GGT TTG
GAG TGG GTT TCT CGT ATC GTT CCT TCT GGT GGC GCT ACT ATG TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGA GAT CGA CCG CTC TAT GAT AGT
AGT GGT TAC GTT GAC TAC TGG GGC CAG GGA ACC CTG GTC ACC GTC
TCA AGC

>M0040-B06 LV (SEQ ID NO:88)
CAG TAC GAA TTG ACT CAG CCA CCC TCA GCG TCT GGG ACC CCC GGG
CAG AGG GTC ACC ATC TCT TGT TCT GGA AGC AGC TCC AAC ATC GGA
AGG AAT TAT GTA TAC TGG TAC CAG CAG GTC CCA GGA ACG GCC CCC
AAA CTC CTC ATC TAT AGT AAT AAT CAG CGG CCC TCA GGG GTC CCT
GAC CGA TTC TCT GGC TCC AAG TCT GGC ACC TCA GCC TCC CTG GTC
ATC AGT GGG CTC CGG TCC GAG GAT GAG GCT GAT TAT TAC TGT GCA
GCA TGG GAT GCC AGC CTG CGT GGG GTG TTC GGC GGA GGG ACC AAG
CTG ACC GTC CTA

>M0040-B06 HV (SEQ ID NO:89)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
GTT TAC CCT ATG GTT TGG GTT CGC CAA GCT CCT GGT AAA GGT TTG
GAG TGG GTT TCT TAT ATC TCT CCT TCT GGT GGC TTT ACT TTT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGA GTG CCC GGG GGC AGC AGA CAG
GAT TTT GAT ATC TGG GGC CAA GGG ACA ATG GTC ACC GTC TCA AGC

>M0040-B08 LV (SEQ ID NO:90)
CAA GAC ATC CAG ATG ACC CAG TCT CCA TCC TCC CTG TCT GCA TCT
GTA GGA GAC AGA GTC ACC ATC ACT TGC CGG GCA AGT CAG AGC ATT
AGC AGC TAT TTA AAT TGG TAT CAG CAG AAA CCA GGG AAA GCC CCT
AAG CTC CTG ATC TAT GCT GCA TCC AGT TTG CAA AGT GGG GTC CCA
TCA AGG TTC AGT GGC AGT GGA TCT GGG ACA GAT TTC ACT CTC ACC
ATC AGC AGT CTG CAA CCT GAA GAT TTT GCA ACT TAC TAC TGT CAA
CAG AGT TAC AGT ACC CCT CGA ACG TTC GGC CAA GGG ACC AAG GTG
GAA ATC AAA

>M0040-B08 HV (SEQ ID NO:91)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
TAT TAC AAT GAT ATG GCT TGG GTT CGC CAA GCT CCT GGT AAA GGT
TTG GAG TGG GTT TCT TCT ATC TCT CCT TCT GGT GGC AAG ACT GAG
TAT GCT GAC TCC GTT AAA GGT CGC TTC ACT ATC TCT AGA GAC AAC
TCT AAG AAT ACT CTC TAC TTG CAG ATG AAC AGC TTA AGG GCT GAG
GAC ACG GCC GTG TAT TAC TGT GCG AGG AGT GGA AGC TAC ACT CAA
CAT TTT GAC TAC TGG GGC CAG GGA ACC CTG GTC ACC GTC TCA AGC

>M0040-C10 LV (SEQ ID NO:92)
CAA GAC ATC CAG ATG ACC CAG TCT CCA GCC ACC CTG TCT GCA TCT
GTA GGA GAC AGA GTC ACC ATC ACT TGC CGG GCA AGT CAG ACC ATT
AGC ACC TAT TTA AAT TGG TAT CAA CAC AAA CCA GGG AAA GCC CCT
GAG CTC CTG ATT TAT GCT GCA TCC AGT TTG CAA AGT GGG GTC CCA
TCA AGG TTC AGT GGC AGT GGA TCT GGG ACA GAT TTC ACT CTC CGC
ATC AGC AGT CTG CAA CCT GAA GAT TTT GCA ACT TAC TAC TGT CAA
CAG AGT TAC ACT ACC CCG TGG ACG TTC GGC CAA GGG ACC AAG GTG
GAA ATC AAA

TABLE 5-continued

DNA sequences of variable regions of
MMP-14 binding antibodies

>M0040-C10 HV (SEQ ID NO:93)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CGT TAC ATG ATG GTT TGG GTT CGC CAA GCT CCT GGT AAA GGT TTG
GAG TGG GTT TCT TCT ATC GTT TCT TCT GGT GGC AAG ACT TGG TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACC GCC ATG TAT TAC TGT GCC AGA TGG GAC TGG GGA CCT TTT GAC
TAC TGG GGC CAG GGA ACC CTG GTC ACC GTC TCA AGC

>M0040-D08 LV (SEQ ID NO:94)
CAG AGC GCT TTG ACT CAA TCA CCC TCT GCC TCT GCT TCA CTG GGA
TCC TCG GTC AAG CTC ACC TGC ACT CTG GCC AGT GAG CAC AGT GGC
TAC ATC ATC GCA TGG CAT CAG CAG CAA CCA GGG AAG GCC CCT CGG
TTC TTG ATG AAA CTT GAC GGT ACT GGC AAC TTC AAC AAG GGC AGC
GGA GTT CCT GAT CGC TTC TCA GGC TAC AGC TCT GGG GCT GAC GCC
TAC CTC ACC ATC TCC AAC CTC CAG TCT GAG GAT GCT GAT TAT
TAC TGT GAG ACC TGG GAC AGT ACC ACT CTT TGG GTG TTC GGC GGG
GGG ACC AAG CTG ACC GTC CTA

>M0040-D08 HV (SEQ ID NO:95)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CAT TAC GGT ATG ACT TGG GTT CGC CAA GCT CCT GGT AAA GGT TTG
GAG TGG GTT TCT TCT ATC GTT CCT TCT GGT GGC TAT ACT GCT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACA GCC GTG TAT TAC TGT ACC ACA GGT CTC AGC AGC AGC GGT ACA
CGG TGG TTC GAC GCC TGG GGC CAG GGA ACC CTG GTC ACC GTC TCA
AGC

>M0040-F03 LV (SEQ ID NO:96)
CAA GAC ATC CAG ATG ACC CAG TCT CCA CTC TCC CTG CCC GTC ACC
CCT GGA GAG CCG GCC TCC ATC TCC TGC AGG TCT GGT CAG AGC CTC
CTG CAT AGT AAT GGA TAC AAC TAT TTG AAT TGG TAC CTG CAG AAG
CCA GGG CAG TCT CCA CAG CTC CTG ATC TAT TTG GGT TCT TAT CGG
GCC TCC GGG GTC CCT GAC AGG TTC AGT GGC AGT GGA TCA GGC ACA
GAT TTT ACA CTG AAA ATC AGC AGA GTG GAG GCT GAG GAT GTT GGG
CTT TAT TAC TGC ATG CAA GCT CTA CAA ACT CCT CTC ACT TTC GGC
GTA GGG ACC AAG GTG GAG ATC AAA

>M0040-F03 HV (SEQ ID NO:97)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
ATG TAC GTT ATG TCT TGG GTT CGC CAA GCT CCT GGT AAA GGT TTG
GAG TGG GTT TCT TCT ATC TCT TCT TCT GGT GGC AAT ACT GGT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AAG AGT TCG TTA TAT TAC GAT ATT
TTG GCT GGC CCT GGG TTT GAC TAC TGG GGC CAG GGA ACC CTG GTC
ACC GTC TCA AGC

>M0040-G04 LV (SEQ ID NO:98)
CAG AGC GTC TTG ACT CAG CCA CCC TCA GCG TCT GGG ACC CCC GGG
CAG AGG GTC ACC ATC TCA TGT TCT GGA AGC AGG ACC AAC ATC GGA
AGT GAT TAT GTA TAT TGG TAC CAG CAA CTC CCA GGA ACG GCC CCC
AAA CTC CTC ATC TAT AGG AAT AAT GAG CGG CCC TCA GGG GTC CCT
GAC CGA TTC TCT GGC TTC AAG TCT GGC ACC TCA GCC TCC CTG GCC
ATC AGT GGG CTC CGG TCC GAG GAT GAG GCT GAT TAT TAC TGT GCA
TCA TGG GAT GAC AGG CTG AGT GGT CCG GTT TTC GGC GGA GGG ACC
AAG CTG ACC GTC CTA

TABLE 5-continued

DNA sequences of variable regions of
MMP-14 binding antibodies

>M0040-G04 HV (SEQ ID NO:99)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CAG TAC CAT ATG CTT TGG GTT CGC CAA GCT CCT GGT AAA GGT TTG
GAG TGG GTT TCT GTT ATC GTT TCT TCT GGT GGC TTT ACT TTT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGA AGC TAC GGT GGA GAT GCT TTT
GAT ATC TGG GGC CAA GGG ACA ATG GTC ACC GTC TCA AGC

>M0040-H04 LV (SEQ ID NO:100)
CAA GAC ATC CAG ATG ACC CAG TCT CCA GAC TCC CTG GCT GTG TCT
CTG GGC GAG AGG GCC ACC CTC AAC TGC AGG TCC AGC CAG AGT GTT
TTA TAC AGC CCC AAC AAT AAG AAC TAC TTA GCT TGG TAC CAG CAG
AAA GCA GGA CAG CCA CCT AAG CTG CTC ATT TAC TGG GCA TCT TTC
CGG GAA TCC GGG GTC CCT GAG CGA TTC AGT GGC AGC GGG TCT GGG
ACA GAT TTC ACT CTC ACC ATC AGC AGC CTG GAG GCT GAA GAT GTG
GCA GTT TAT TAC TGT CAG CAA TAT CAT ACT CCT CCC TGG ACG TTC
GGC CAA GGG ACC AAG GTG GAA ATC AAA

>M0040-H04 HV (SEQ ID NO:101)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
TCT TAC GAT ATG GTT TGG GTT CGC CAA GCT CCT GGT AAA GGT TTG
GAG TGG GTT TCT TCT ATC TCT CCT TCT GGT GGC AAT ACT CAG TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AAA GTG GCA GCT ATG GCC CCG TGG
TAC TTT GAC TAC TGG GGC CAG GGA ACC CTG GTC ACC GTC TCA AGC

>M0040-H09 LV (SEQ ID NO:102)
CAG AGC GAA TTG ACT CAG GAC CCT GCT GTG TCT GTG GCC TTG GGA
CAG GCA GTC ATC ATC ACA TGC CAA GGA GAC AGC CTC AGA ACC TAT
TAT CCA AGC TGG TAC CAA CAG AAG CCA GGA CAG GCC CCT ACA CTT
CTC GTC TAT GGT AAA AAC AAG CGG CCC TCA GGG GTC CCA GAC CGA
TTC TCT GGC TCC AGG TCA GGA GAC ACA GCT TCC TTG ATC ATC ACT
GGG GCT CAG GCG GAA GAT GAC GCT GAC TAT TAT TGT AAC TCC CGG
GAC GGC AGT GGT CAC CTT TTT GTC TTC GGA CCT GGG ACC ACG GTC
ACC GTC CTC

>M0040-H09 HV (SEQ ID NO:103)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CTT TAC CCT ATG CAG TGG GTT CGC CAA GCT CCT GGT AAA GGT TTG
GAG TGG GTT TCT TAT ATC CGT TCT TCT GGT GGC AAG ACT CAT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCT GTG TAT TAC TGT GCG AGA GTA GGA ATG GGC AGT GGC TGG
TAC ACG GGG TAC TTC GAT CTC TGG GGC CGT GGC ACC CTG GTC ACC
GTC TCA AGC

>M0041-A05 LV (SEQ ID NO:104)
CAA GAC ATC CAG ATG ACC CAG TCT CCA TCC TCC CTG TCT GCA TCT
GTA GGA GAC AGA GTC ACC ATC ACT TGC CGG GCA AGT CAG AAC ATT
AAC AGC TAT TTA AAT TGG TAT CAG CAG AAA CCA GGG AAA GCC CCT
AAG CTC CTG ATC TAT GCT GCA TCC AGT TTG CAA AGT GGG GTC CCA
TCA AGG TTC AGT GGC AGT GGA TCT GGG ACA GAT TTC ACT CTC ACC
ATC AGC AGT CTG CAA CCT GAA GAT TTT GTA ACT TAC TAC TGT CAA
CAG AGT TAC AGT ACC CCT AAG ACG TTC GGC CAA GGG ACC AAG GTG
GAA ATC AAA

TABLE 5-continued

DNA sequences of variable regions of
MMP-14 binding antibodies

>M0041-A05 HV (SEQ ID NO:105)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
GTT TAC ACT ATG CAT TGG GTT CGC CAA GCT CCT GGT AAA GGT TTG
GAG TGG GTT TCT GTT ATC TAT CCT TCT GGT GGC TTA ACT ATT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCA CGG AAT AGG GGT TAC TAT GCC CCT
ATG GAC GTC TGG GGC CAA GGG ACC ACG GTC ACC GTC TCA AGC

>M0041-B03 LV (SEQ ID NO:106)
CAA GAC ATC CAG ATG ACC CAG TCT CCA GCC ACC CTG TCT GCA TCT
GTA GGA GAC AGA GTC ACC ATC TCT TGC CGG GCC AGT CAG AAT ATT
AGT AAT TGG TTG GCC TGG TAT CAG CAG AAG CCA GGC AAA GCC CCT
AAA CTC CTC ATC TAC ACT GCA TCC ACT TTG CAC CGT GGG GTC CCA
TCA AGG TTC AGC GGC AGT GGA TCT GGG ACA GAT TTC ACT CTC ACT
ATC ACC AGC CTG CAG CCT GAA GAT TTT GCA ACT TAC TAT TGT CAA
CAG GCT AAC ACT TTC CCT TGG ACG TTC GGC CAA GGG ACC AAG GTG
GAA ATC AAA

>M0041-B03 HV (SEQ ID NO:107)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
ATG TAC ATG ATG TGG GTT CGC CAA GCT CCT GGT AAA GGT TTG
GAG TGG GTT TCT GTT ATC TCT TCT TCT GGT GGC TTT ACT TCT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGA CTA GGT ACA GTA ATT TCG TA
GGC GGT CTG GAC GTC TGG GGC CAA GGG ACC ACG GTC ACC GTC TCA
AGC

>M0041-B11 LV (SEQ ID NO:108)
CAG AGC GTC TTG ACT CAG GAC CCT GCT GTG TCT GTG GCC TTG GGA
CAG ACA GTC AGG ATC ACA TGC CAA GGA GAC AGC CTC AGA AGC TAT
TCT GCA AGT TGG TAC CAG CGG AAG CCA GGA CAG GCC CCT TTA CTT
GTC ATC TAT CGT AAA ACC AAC CGG CCC TCA GGG ATC CCA GAC CGG
TTC TCT GGC TCC AGC TCA GGA AAC ACA GCT TCC TTG ACC ATC ACT
GGG GCT CAG GCG GAA GAT GAG TCT GAC TAT TAC TGT AAC TCC CGG
GAC AGC AGT GGT AAC CAC CTA TTC GGC GGA GGG ACC AAA CTG ACC
GTC CTA

>M0041-B11 HV (SEQ ID NO:109)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CAG TAC TCT ATG CAT TGG GTT CGC CAA GCT CCT GGT AAA GGT TTG
GAG TGG GTT TCT TCT ATC GTT TCT TCT GGT GGC ATG ACT GCT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AAA ATT TCA CGG GGA AAT GAT GCT
TTT GAT ATC TGG GGC CAA GGG ACA ATG GTC ACC GTC TCA AGC

>M0041-C11 LV (SEQ ID NO:110)
CAA GAC ATC CAG ATG ACC CAG TCT CCA TCC TCC CTG TCT GCA TCT
GTT GGA GAC AGA GTC ACC ATC ACT TGC CGG GCA AGT CAG CGA ATT
GGC AGC TAC TTG AAT TGG TAT CAG CAA AAT TCG GGA AAA GCC CCA
AGG CTC CTG ATC TAT GGT GCA TCC AAT TTG GAA AGT GGG GTC CCT
TCA AGG TTC AGT GGC CGT GGA TCT GGG ACA GAC TTC ACT CTC ACC
ATC AGC AGT CTG CAA CCT GAA GAT TTT GCG ACT TAC TAC TGT CAA
CAG AGT AAC AGT ACC CCT CAC ACG TTC GGC CAA GGG ACC AAG GTG
GAA ATC AAA

TABLE 5-continued

DNA sequences of variable regions of
MMP-14 binding antibodies

>M0041-C11 HV (SEQ ID NO:111)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CAG TAC CCT ATG TCT TGG GTT CGC CAA GCT CCT GGT AAA GGT TTG
GAG TGG GTT TCT TCT ATC GGT CCT GGT GGC TGG ACT TGG TAT GCT
GAC TCC GTT AAA GGT CGC TTC ACT ATC TCT AGA GAC AAC TCT AAG
AAT ACT CTC TAC TTG CAG ATG AAC AGC TTA AGG GCT GAG GAC ACT
GCA GTC TAC TAT TGT GCG AGG ACC GCT ACA CGG ATT TTT GGA GTG
GTT ATT ATG GGT CGC GCT TTT GAT ATC TGG GGC CAA GGG ACA ATG
GTC ACC GTC TCA AGC

>M0041-D03 LV (SEQ ID NO:112)
CAA GAC ATC CAG ATG ACC CAG TCT CCA TCT TCA CTG TCT GCA TCT
GTA GGA GAC AGA ATC ACC GTC ACT TGC CGG GCA AGT CAG AGC ATT
ACC AAC TAT TTA AAT TGG TAT CAG CAG AAA CCA GGG AAA GCC CCT
AAG CTC CTG ATC TAT GCT GCA TCC ACT TTG CAA TCT GGG GTC CCA
TCA AGG TTC AGT GGC AGT GGG TCT GGG ACA GAC TTC ACT CTC ACC
ATC AGC AGA CTG GAG CCT GAA GAT TTT GCA GTA TAT TAC TGT CAG
CAG TAT GGT AGC TCA CCG ACG TTC GGC CAA GGG ACC AAG GTG GAA
GTC AAA

>M0041-D03 HV (SEQ ID NO:113)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
TTT TAC AAT ATG ACT TGG GTT CGC CAA GCT CCT GGT AAA GGT TTG
GAG TGG GTT TCT TCT ATC TAT TCT TCT GGT GGC AAT ACT GAT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTA TAT TAC TGT GCT AGA GAT TCC CTC TCC CAC TAC TAC
TAC GGT ATG GAC GTC TGG GGC CAA GGG ACC ACG GTC ACC GTC TCA
AGC

>M0041-D08 LV (SEQ ID NO:114)
CAA GAC ATC CAG ATG ACC CAG TCT CCA GGC ACC CTG TCT TTG TCT
CCA GGG GAA AGA GCC ACC CTC TCC TGC AGG GCC AGT CAG AGT GTT
AGC AGC AGC TAC TTA GCC TGG TAC CAG CAG AAA CCT GGC CAG GCT
CCC AGG CTC CTC ATC TAT GGT GCA TCC AGC AGG GCC ACT GGC ATC
CCA GAC AGG TTC AGT GGC AGT GGG TCT GGG ACA GAC TTC ACT CTC
ACC ATC AGC AGA CTG GAG CCT GAA GAT TTT GCA GTG TAT TAC TGT
CAG CAG TAT GGT ACC TCA TCG ACG TTC GGC CAA GGG ACC AAG GTG
GAA ATC AAA

>M0041-D08 HV (SEQ ID NO:115)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
TCT TAC CGT ATG TCT TGG GTT CGC CAA GCT CCT GGT AAA GGT TTG
GAG TGG GTT TCT GGT ATC TCT TCT TCT GGT GGC TTT ACT ATG TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGG GAT ATT TGG ACT GGT TAT TCC
TAC GGT ATG GAC GTC TGG GGC CAA GGG ACC ACG GTC ACC GTC TCA
AGC

>M0041-E11 LV (SEQ ID NO:116)
CAA GAC ATC CAG ATG ACC CAG TCT CCA TCT TCC CTG TCT GCA TTT
GTA GGA GAC AGA GTC ATC ATC ACT TGC CGG GCA AGC CAG GAC ATT
AGT GTT TAT GTA AAT TGG TAT CAG CAG AGC TCA GGC AAA GCC CCT
AAA CTC CTA ATC TAT GGT GCA TCC AGT TTG CAA AGT GGG GTC CCA
TCA AGG TTC AGT GGC AGT GGA TCT GGG ACA GAT TTC ACT CTC ACC
ATC AGC AGT CTG CAA CCT GAA GAT TTT GCA AGT TAC TTC TGT CAA
CAG AGT TAT AAT TTG CCT TTC ACC TTC GGC GGA GGA ACC AAC GTG
CAG ATC AAA

TABLE 5-continued

DNA sequences of variable regions of
MMP-14 binding antibodies

>M0041-E11 HV (SEQ ID NO:117)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CAG TAC AAT ATG CAG TGG GTT CGC CAA GCT CCT GGT AAA GGT TTG
GAG TGG GTT TCT GGT ATC GTT CCT TCT GGT GGC TGG ACT CCT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCA AGA GGG GTG CGC TAC GGG CTT GAC
TAC TGG GGC CAG GGA ACC CTG GTC ACC GTC TCA AGC

>M0041-H09 LV (SEQ ID NO:118)
CAA GAC ATC CAG ATG ACC CAG TCT CCA GGC ACC CTG TCT TTG TCT
CCA GGG GAG AGA GCC ACC CTT TCC TGC AGG GCC AGT CAG AGT CTT
AGC GGC GAC TAC TTA GCC TGG TAT CAG CAG AAA ATT GGC CAG GCT
CCC AGG CTC CTC ATA TTT GGT GCA TCT AGG AGA CCC ACT GGC ATC
CCA GAC AGG TTC AGT GGC AGT GGG TCT GGG ACA GAC TTC GCT CTC
ACC ATC AGC AGA CTG GAG CCT GAA GAT TTT GCA GTG TAT TAC TGT
CAG CAG TAT GGT AGT TTA ATC ACC TTC GGC CAA GGG ACA CGG CTG
GAG ATT AAA

>M0041-H09 HV (SEQ ID NO:119)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
GTT TAC GAG ATG ACT TGG GTT CGC CAA GCT CCT GGT AAA GGT TTG
GAG TGG GTT TCT GGT ATC GGT TCT TCT GGT GGC ATG ACT TTT TAT
GCC GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCC CGG ATA AGG TAT AGT GGG AGC TAT
GGG TGG CAC TAC ATG GAC GTC TGG GGC AAA GGG ACC ACG GTC ACC
GTC TCA AGC

>M0041-H11 LV (SEQ ID NO:120)
CAG AGC GAA TTG ACT CAG GAC CCT GCT GTG TCT GTG GCC TTG GGA
CAG ACA GTC AGG ATC ACA TGC CAA GGA GAC AGC CTC AGA AGC TAT
TAT GCA AGC TGG TAC CAG CAG AAG CCA GGA CAG GCC CCT GTA CTT
GTC ATC TAT GGT AAA AAC AAC CGG CCC TCA GGG ATC CCA GAC CGA
TTC TCT GGC TCC AGC TCA GGA AAC ACA GCT TCC TTG ACC ATC ACT
GGG GCT CAG GCG GAA GAT GAG GCT GAC TAT TAC TGT AAC TCC CGG
GAC AGC AGT GGT AAC CAT GTG GTA TTC GGC GGA GGG ACC AAG CTG
ACC GTC CTA

>M0041-H11 HV (SEQ ID NO:121)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
ATG TAC CCT ATG AAT TGG GTT CGC CAA GCT CCT GGT AAA GGT TTG
GAG TGG GTT TCT TCT ATC TCT TCT TCT GGT GGC TGG ACT AAG TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGA GTT TTT TTC GGC TAT GAT AGT
AGT GGT TAC CCT TAC TAC TAC TAC GGT ATG GAC GTC TGG GGC CAA
GGG ACC ACG GTC ACC GTC TCA AGC

>M0042-B07 LV (SEQ ID NO:122)
CAA GAC ATC CAG ATG ACC CAG TCT CCA CTC TCC CTG CCC GTC ACC
CCT GGA GAG CCG GCC TCC ATC TCC TGC AGG TCT AGT CAG AGC CTC
CTA CAT AGT AAT GGA TAC AAC TAT TTG GAT TGG TAT GTG CAG AAG
CCA GGA CAG TCT CCA CAG CTC CTG ATC TAT TTG GGT TCT GGT CGG
GCC TCC GGG GTC CCT GAC AGG TTC AGT GGC AGT GGA TCA GGC ACA
GAT TTT ACA CTG AAA ATC AAC AGA GTG GAG GCT GAG GAT GTT GGG
GTT TAT TAC TGC ATG CAA GCT CTA CAA ACT CCG TGG ACG TTC GGC
CAA GGG ACC AAG GTG GAA ATC AAA

TABLE 5-continued

DNA sequences of variable regions of
MMP-14 binding antibodies

>M0042-B07 HV (SEQ ID NO:123)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CCT TAC TCT ATG TTT TGG GTT CGC CAA GCT CCT GGT AAA GGT TTG
GAG TGG GTT TCT GTT ATC TAT CCT TCT GGT GGC GGT ACT ATT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGA AGT AGA GAG TCT TGT GAT GCT
GAT ACT TGC TAC CAA TAT TTC CAG GAG TGG GGC CAG GGC ACC CTG
GTC ACC GTC TCA AGC

>M0042-G12 LV (SEQ ID NO:124)
CAA GAC ATC CAG ATG ACC CAG TCT CCA GGC ACC CTG TCT TTG TCT
CCA GGG GAA AGA GCC ACC CTC TCC TGC AGG GCC AGT CAG AGT GTT
AGC AGC AGC TAC TTA GCC TGG TAC CAG CAG AAA CCT GGC CAG GCT
CCC AGG CTC CTC ATC TAT GGT GCA TCC ATC AGG GCC ACT GGC ATC
CCA GAC AGG TTC AGT GGC AGT GGG TCT GGG ACA GAC TTC ACT CTC
ACC ATC AGC AGA CTG GAG CCT GAA GAT TTT GCA GTG TAT TAC TGT
CAG CAG TAT GGT AGC TCA CCC CCG TAC ACT TTT GGC CAG GGG ACC
AAG CTG GAG ATC AAA

>M0042-G12 HV (SEQ ID NO:125)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CAT TAC CCT ATG TTT TGG GTT CGC CAA GCT CCT GGT AAA GGT TTG
GAG TGG GTT TCT GGT ATC TCT TCT TCT GGT GGC TAT ACT ATT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGA GGG GGA AGA CGA CAG ACG CGG
CGT ACC AGC GAC TAC TAC TAC GGT ATG GAC GTC TGG GGC CAA GGG
ACC ACG GTC ACC GTC TCA AGC

>M0043-A09 LV (SEQ ID NO:126)
CAG AGC GTC TTG ACT CAG CCA CCC TCG GTG TCC AAG GAC TTG AGA
CAG ACC GCC ACA CTC ACC TGC ACT GGG AAC AGC AAC AAT GTT GGC
TAC CAA GGA GCA GCT TGG CTG CAG CAG CAC CAG GGC CAC CCT CCC
AAA GTC CTT TCG TAC AGG AAT AAC AAC CGG CCC TCA GGG ATC TCA
GAG AGA TTT TCT GCG TCC AGG TCA GGA AAT ACA GCC TCC CTG ACC
ATT ACT GGA CTC CAG CCT GAG GAC GAG GCT GAC TAT TAC TGC TCA
GCG TGG GAC AGC AGC CTC ACT GCT TGG GTC TTC GGC GGA GGG ACC
AAG CTG ACC GTC CTA

>M0043-A09 HV (SEQ ID NO:127)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
TTT TAC GAT ATG ACT TGG GTT CGC CAA GCT CCT GGT AAA GGT TTG
GAG TGG GTT TCT TCT ATC TGG TCT TCT GGT GGC GTT ACT GAT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACA GCC GTG TAT TAC TGT ACG AGA GCT AGT AGT GGT TAT TAT GAT
GCT TTT GAT ATC TGG GGC CAA GGG ACA ATG GTC ACC GTC TCA AGC

>M0043-C03 LV (SEQ ID NO:128)
CAA GAC ATC CAG ATG ACC CAG TCT CCA GCC TCC CTG TAT TTG TCT
CCA GGG GAA AGA GCC ACC CTC TCC TGC AGG GCC AGT CAG AGT GTT
AGC AGC AAC TTA GCC TGG TAC CAG CAG AAA CCT GGC CAG GCT CCC
AGG CTC CTC ATC TAT GGT GCA TCC ACC AGG GCC ACT GGT ATC CCA
GCC AGG TTC AGT GGC AGT GGG TCT GGG ACA GAG TTC ACT CTC ACC
ATC AGC AGC CTG CAG TCT GCA GAT TTT GCC GTT TAT TAC TGT CAG
CAG TAT GAT AAC TGG CCT CCC CTC ACT TTC GGC GGA GGG ACC AAG
GTG GAG ATC AAA

TABLE 5-continued

DNA sequences of variable regions of
MMP-14 binding antibodies

>M0043-C03 HV (SEQ ID NO:129)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
TAT TAC GCT ATG GAT TGG GTT CGC CAA GCT CCT GGT AAA GGT TTG
GAG TGG GTT TCT TCT ATC GGT TCT TCT GGT GGC GAT ACT GTT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACA GCC ACG TAT TAC TGT GCG AGA GAC CCT CGG CAG CCC GGA GTC
TTT GAC TAC TGG GGC CAG GGA ACC CTG GTC ACC GTC TCA AGC

>M0043-F01 LV (SEQ ID NO:130)
CAG AGC GCT TTG ACT CAG CCT GCT TCC GTG TCT GGG TCT CCT GGA
CAG TCG ATC ACC ATC TCC TGC ACT GGA ACC AGC AGT GAC ATT GGT
GCT TAT AGG TAT GTC TCC TGG TAC CAA CAG CGC CCA GGC AAA GCC
CCC AAA CTC ATG ATT TTT GAT GTC ACT AAG CGG CCC TCA GGG GTT
TCT AAT CGC TTC TCT GGC TTC AAG TCT GGC AAC ACG GCT TCC CTG
ACC ATC TCT GGG CTC CAG GCT GAG GAC GAG GCC GAT TAT TAC TGC
AGC TCA TTT ACA AGT GGC AGC ACT TTC GTC TTC GGA ACT GGG ACC
AAG GTC ACC GTC CTA

>M0043-F01 HV (SEQ ID NO:131)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
AAG TAC TCT ATG TAT TGG GTT CGC CAA GCT CCT GGT AAA GGT TTG
GAG TGG GTT TCT TCT ATC TCT TCT TCT GGT GGC TAT ACT GCT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACT GCC GTG TAT TAC TGT GCG ATT CCT TGG GGT AGT GGG AGT TCC
TGG GGC CAG GGA ACC CTG GTC ACC GTC TCA AGC

>M0043-G01 LV (SEQ ID NO:132)
CAA GAC ATC CAG ATG ACC CAG TCT CCA TCT GCC ATG TCT GCA TCT
GTA GGA GAC AGA GTC ACC ATC ACT TGT CGG GCG AGT CAG GGT ATT
AGC AGC TGG TTA GCC TGG TAT CAG CAG AAA CCA GGG AAA GCC CCT
AAG CTC CTG ATC TAT GCT GCA TCC AGT TTG CAA AGT GGG GTC CCA
TCA AGG TTC AGC GGC AGT GGA TCT GGG ACA GAT TTC ACT CTC ACC
ATC AGC AGC CTG CAG CCT GAA GAT TTT GCA ACT TAC TAT TGT CAA
CAG GCT AAC AGT TTC CCG CTC ACT TTC GGC GGA GGG ACC AAG GTG
GAG ATC AAA

>M0043-G01 HV (SEQ ID NO:133)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
TTT TAC TCT ATG CAT TGG GTT CGC CAA GCT CCT GGT AAA GGT TTG
GAG TGG GTT TCT GGT ATC TCT TCT TCT GGT GGC GTT ACT AAG TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGA GCA CGG TCA ACT CGT GGC TTT
GAC TAC TGG GGC CAG GGA ACC CTG GTC ACC GTC TCA AGC

>M0043-G02 LV (SEQ ID NO:134)
CAA GAC ATC CAG ATG ACC CAG TCT CCA GGC ACC CTG TCT TTG TCT
CCA GGG GAA AGA GCC ACC CTC TCC TGC AGG GCC AGT CAG AGT GTT
AGC AGC AGC TAC TTA GCC TGG TAC CAG CAG AAA CCT GGC CAG GCT
CCC AGG CTC CTC ATC TAT GGT GCA TCC AGC AGG GCC ACT GGC ATC
CCA GAC AGG TTC AGT GGC AGT GGG TCT GGG ACA GAC TTC ACT CTC
ACC ATC AGC AGA CTG GAG CCT GAA GAT TTT GCA GTG TAT TAC TGT
CAG TCG GGG GTC ACT TTC GGC GGA GGG ACC AAG GTG GAG ATC AAA

TABLE 5-continued

DNA sequences of variable regions of
MMP-14 binding antibodies

>M0043-G02 HV (SEQ ID NO:135)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
TGG TAC CCT ATG TTT TGG GTT CGC CAA GCT CCT GGT AAA GGT TTG
GAG TGG GTT TCT GGT ATC TAT TCT TCT GGT GGC CCT ACT GAT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCA AAA GAT ACC CTA GGG AGG TAT TAC
GAT TTT TGG AGT GGT TAT TCC TAC GGT ATG GAC GTC TGG GGC CAA
GGG ACC ACG GTC ACC GTC TCA AGC

>M0044-B03 LV (SEQ ID NO:136)
CAA GAC ATC CAG ATG ACC CAG TCT CCA TCT TCC GTG TCT GCA TCT
GTA GGA GAC AGA GTC ACC ATC ACT TGT AGG GCG AGT CAG AAT ATT
TAC AGT TGG TTA GCC TGG TAT CAG CAG AGA CCA GGG AAA GCC CCT
AAG CTC CTG ATC TAC GCT GCA TCC AGT TTA CAT AGT GGG GTC CCA
TCA AGG TTC AGC GGC AGT GGA TCT GGG ACA GAT TTC ACT CTC ACC
ATC AGC AGC CTG CAG CCT GAA GAT TTT GCA ACT TAC TAT TGT CAA
CAG GCT AAG AGT TTC CCT GTG ACT TTC GGC GGA GGG ACC AAG GTG
GAA ATC AAA

>M0044-B03 HV (SEQ ID NO:137)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CAG TAC CAT ATG ATG TGG GTT CGC CAA GCT CCT GGT AAA GGT TTG
GAG TGG GTT TCT TCT ATC GGT TCT TCT GGC TAT ACT AAG TAT GCT
GAC TCC GTT AAA GGT CGC TTC ACT ATC TCT AGA GAC AAC TCT AAG
AAT ACT CTC TAC TTG CAG ATG AAC AGC TTA AGG GCT GAG GAC ACG
GCC GTG TAT TAC TGT GCG GGA GCA GTG GCT GGT ACC GGG GCC TTT
GAC TAC TGG GGC CAG GGA ACC CTG GTC ACC GTC TCA AGC

>M0044-D08 LV (SEQ ID NO:138)
CAG TAC GAA TTG ACT CAG CCA CTC TCA GTC TCA GTG GCC CTG GGA
CAG ACG GCC AGT ATT TCC TGT TGG GGA CAT AAC ATT AGA ATT AAA
AAT GTA CAC TGG TAC CAG CAG AAG CCA GGC CAG GCC CCT GTG GTG
GTC ATG TAT ATC CCT GAG CGG TTC TCT GGC TCC ACC TCG GGG AAC
ACG GCC ACC CTG ACC ATC AGT GGA GCC CAA GCC GGG GAT GAG GCT
GAC TAT TAT TGT CAA GTG TGG GAC AGC AGC ACT GTG GTG TTC GGC
GGA GGG ACC AAG CTG ACC GTC CTA

>M0044-D08 HV (SEQ ID NO:139)
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
AAG TAC CCT ATG TCT TGG GTT CGC CAA GCT CCT GGT AAA GGT TTG
GAG TGG GTT TCT TCT ATC TGG TCT TCT GGT GGC CAT ACT TTT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AAA AAT CCC GGG CTA CGG TAT GCT
TTT GAT AAC TGG GGC CGA GGG ACA ATG GTC ACC GTC TCA AGC

>M0044-E01 LV (SEQ ID NO:140)
CAG TAC GAA TTG ACT CAG CCA CCC TCA ACG TCT GGG ACC CCC GGG
CAG ACG GTC ACC ATC TCT TGT TCT GGA AGC ATC TCC AAC ATC GGA
AGA AAT CTT GTA AAC TGG TAC CAG CAG CTC CCA GGA ACG GCC CCC
AAA CTC CTC ATG TTT AGG AAT AAT GAG CGG CCC TCA GGG GTC CCT
GAC CGA TTC TCT GGC TCC AAG TCT GGC ACC TCG GCC TCC CTG GCC
ATC AGT GGG CTC CGG TCC GAG GAT GAG GCT GAT TAT TAC TGT GCA
GCA TGG GGT GAC AGC CTG AGT GGT TCT TAT GTC TTC GGA ACT GGG
ACC AAG GTC ACC GTC CTA

TABLE 5-continued

DNA sequences of variable regions of
MMP-14 binding antibodies

>M0044-E01 HV (SEQ ID NO:141)
```
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
TAT TAC GCT ATG GGT TGG GTT CGC CAA GCT CCT GGT AAA GGT TTG
GAG TGG GTT TCT TAT ATC GTT CCT TCT GGT GGC GAG ACT CGT TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGA GAT GGT TAT TAC GAT TTT TGG
AGT GGT TAT TGG TCC TAC TAC TAC TAC GGT ATG GAC GTC TGG GGC
CAA GGG ACC ACG GTC ACC GTC TCA AGC
```

>M0044-E05 LV (SEQ ID NO:142)
```
CAA GAC ATC CAG ATG ACC CAG TCT CCA TCC TCC CTG TCT GCA TCT
GTG GGA GAC AGA GTC ACC ATC ACT TGC CGG GCA AGT CAG AGC ATT
AGC AGC TAT TTA AAT TGG TAT CAG CAA AAA CCA GGG GAA GCC CCT
AAG CTC CTC ATC TAT GCT GCA TCC GCT TTG CAA AGT GGG GTC CCG
TCA AGG TTC AGT GGC AGT GGA CTT GGG ACA GTT TTC ACT CTC ACC
ATC ACC AGC CTG CAA CCT GAA GAT TCT GCA ACT TAC TAT TGT CAA
CAG AGT TAC AGT CCC CCG GTC ACT TTC GGC GGA GGG ACC AAG GTG
GAT ATC AAA
```

>M0044-E05 HV (SEQ ID NO:143)
```
GAA GTT CAA TTG TTA GAG TCT GGT GGC GGT CTT GTT CAG CCT GGT
GGT TCT TTA CGT CTT TCT TGC GCT GCT TCC GGA TTC ACT TTC TCT
CGT TAC CCT ATG TCT TGG GTT CGC CAA GCT CCT GGT AAA GGT TTG
GAG TGG GTT TCT CGT ATC TCT TCT TCT GGT GGC TGG ACT CAG TAT
GCT GAC TCC GTT AAA GGT CGC TTC ACT ATC TCT AGA GAC AAC TCT
AAG AAT ACT CTC TAC TTG CAG ATG AAC AGC TTA AGG GCT GAG GAC
ACG GCC GTG TAT TAC TGT GCG AGA GAG GGT TCT AGT GGG AGC CGT
CGT GGT GAC TAC TGG GGC CAG GGA ACC CTG GTC ACC GTC TCA AGC
```

Example 3

DNA Sequences of MMP-14 Inhibiting Anti-MMP-14 Fabs

Exemplary Fabs that bind to and inhibit human MMP-14 were identified and include: M0031-C02, M0031-F01, M0033-H07, M0037-C09, M0037-D01, M0038-E06, M0038-F01, M0038-F08, M0039-H08, M0040-A06, M0040-A11, and M0043-G02. The DNA sequences of these antibodies are shown in Table 5.

Example 4

Amino Acid Sequences of MMP-14 Binding Fabs that Inhibit MMP-14

The amino acid sequences of exemplary Fab heavy chain (HC) and light chain (LC) variable regions that bind to and inhibit human MMP-14, the DNA sequence of which are provided in Example 3, are shown in Table 6. In Table 6, the standard numbering of the HC V domain is shown. The length of HC CDR3 varies considerably. By convention, the second cysteine is numbered 92 and the W of the conserved WG motif of FR4 is number 103. If there are more than 9 residues between C92 and W103, then residues after 102 are numbered 102a, 102b, etc. Table 7 shows the germline (GL) Vlight and Jlight assignments.

Table 8 shows the LCs of the 12 inhibitory Fabs aligned to their germline VJ genes. In the germline sequence, FR regions are bold. In the isolate sequences, departures from GL are shown bold. Table 9 shows the departures from GL as mutations from the isolate to GL, i.e. the mutation that is needed to restore GL sequence to the isolate. In one embodiment, the departures from germline in the FR regions are reverted to GL. Residues at or near the FR-CDR junctions may be involved in interactions with the antigen and so reversions of these residues is more likely to affect affinity than is the reversion of residues far from the junctions.

TABLE 6

Amino-acid sequences of Fabs that bind and inhibit human MMP-14

1 M0031-C02 SC = SC-001 Round = SC-001-SR-003
HC
```
       1     5    0     5    0     5    0     5    0     5    0
    1  EVQLLESGGG LVQPGGSLRL SCAASGFTFS PYPMGWVRQA PGKGLEWVSS
```

TABLE 6-continued

Amino-acid sequences of Fabs that bind
and inhibit human MMP-14

```
        5    5     6    6     7    7     8 8  8 8   8 8   9    9
        1 a  5     0    5     0    5     0 2abc3 5  7 9   2    5
 51  IVSSGGLTLY ADSVKGRFTI SRDNSKNTLY LQMNSLRAED TAVYYCARGG 1           1 1    1
        9    0           0 0    1
        7    2abcd efghi3 5     0
101  RLYDILTGQG APFDYWGQGT LVTVSS (SEQ ID NO:144)
LC 1  QDIQMTQSPL SLPVTPGEPA SISCRSSQSL LHSNGYYYLD WYLQKPGQSP
  51  QLLIYLGSYR ASGVPDRFSG SGSGTDFTLK ISSVEAEDVG VYYCMQALQT
 101  PLTFGGGTRV DIK (SEQ ID NO:145)

------
2 M0031-F01 SC = SC-001 Round = SC-001-SR-003
HC
   1  EVQLLESGGG LVQPGGSLRL SCAASGFTFS TYEMHWVRQA PGKGLEWVSS
  51  IYSSGGWTGY ADSVKGRFTI SRDNSKNTLY LQMNSLRAED TAVYYCARSQ
 101  QYYDFSSRYY GMDVWGQGTT VTVSS (SEQ ID NO:146)
LC 1  QSELTQPPSV SGTPGQRVTI SCSGTSANIG RNAVHWYQQL PGTAPKLLIH
  51  SNNRRPSGVP DRFSGSKSGT SASLAISGLQ SEDEADYYCA AWENSLNAFY
 101  VFGTGTKVTV L (SEQ ID NO:147)

------
3 M0033-H07 SC = SC-001 Round = SC-001-SR-003
HC
   1  EVQLLESGGG LVQPGGSLRL SCAASGFTFS VYGMVWVRQA PGKGLEWVSV
  51  ISSSGGSTWY ADSVKGRFTI SRDNSKNTLY LQMNSLRAED TALYYCARPF
 101  SRRYGVFDYW GQGTLVTVSS (SEQ ID NO:148)
LC 1  QDIQMTQSPS SLSASVGDRV TITCRASQGI RNFLAWYQQK PGKVPKLLVF
  51  GASALQSGVP SRFSGSGSGT DFTLTISGLQ PEDVATYYCQ KYNGVPLTFG
 101  GGTKVEIK (SEQ ID NO:149)

------
4 M0037-C09 SC = SC-001 Round = SC-001-SR-003
HC
   1  EVQLLESGGG LVQPGGSLRL SCAASGFTFS HYEMFWVRQA PGKGLEWVSS
  51  ISPSGGQTHY ADSVKGRFTI SRDNSKNTLY LQMNSLRAED TAVYYCATDR
 101  TYYDFWSGYG PLWYWGQGTL VTVSS (SEQ ID NO:150)
LC 1  QDIQMTQSPL SLPVTLGESA SVSCRSSQSL HENGHNYLD WYLQKPGQSP
  51  QLLIYLGSNR ASGVPDRFSG SGSGTDFTLK ISRVEAEDVG VYYCMQSLKT
 101  PPTFGPGTKV ElK (SEQ ID NO:151)

------
5 M0037-D01 SC = SC-001 Round = SC-001-SR-003
HC
   1  EVQLLESGGG LVQPGGSLRL SCAASGFTFS MYMMIWVRQA PGKGLEWVSS
  51  IYPSGGNTMY ADSVKGRFTI SRDNSKNTLY LQMNSLRAED TAVYYCATGV
 101  LRYFDWDAGS GMDVWGQGTT VTVSS (SEQ ID NO:152)
LC 1  QDIQMTQSPS SLSASVGDRV TITCRASQGI RNDLGWYQQK PGKAPKRLIY
  51  VASSLQSGVP SRFSGSGSGT EFTLTISSLQ PEDFATYYCL QHNSYPWTFG
 101  QGTKVEIK (SEQ ID NO:153)

------
6 M0038-E06 SC = SC-001 Round = SC-001-SR-003
HC
   1  EVQLLESGGG LVQPGGSLRL SCAASGFTFS PYVMHWVRQA PGKGLEWVSS
  51  ISPSGGWTYY ADSVKGRFTI SRDNSKNTLY LQMNSLRAED MAVYYCARGT
 101  GAYGMDVWGQ GTTVTVSS (SEQ ID NO:154)
LC 1  QDIQMTQSPG TLSLSPGDRA TLSCGASQLV VSNYIAWYQQ KPGQAPRLLM
  51  YAGSIRATGI PDRFSGSGSG TDFTLTISRL EPEDFAIYYC QQRSNWPWTF
 101  GQGTKVEIK (SEQ ID NO:155)

------
```

TABLE 6-continued

Amino-acid sequences of Fabs that bind
and inhibit human MMP-14

7 M0038-F01 SC = SC-001 Round = SC-001-SR-003
HC
  1 EVQLLESGGG LVQPGGSLRL SCAASGFTFS LYSMNWVRQA PGKGLEWVSS
 51 IYSSGGSTLY ADSVKGRFTI SRDNSKNTLY LQMNSLRAED TAVYYCARGR
101 AFDIWGQGTM VTVSS (SEQ ID NO:156)
LC 1 QDIQMTQSPS SLSAFVGDKV TITCRASQSV GTYLNWYQQK AGKAPELLIY
 51 ATSNLRSGVP SRFSGSGSGT DFTLTINTLQ PEDFATYYCQ QSYSIPRFTF
101 GPGTKVDIK (SEQ ID NO:157)

------

8 M0038-F08 SC = SC-001 Round = SC-001-SR-003
HC
  1 EVQLLESGGG LVQPGGSLRL SCAASGFTFS RYKMWWVRQA PGKGLEWVSG
 51 IRPSGGLTRY ADSVKGRFTI SRDNSKNTLY LQMNSLRAED TAVYYCARRG
101 DYVGGFDYWG QGTLVTVSS (SEQ ID NO:158)
LC 1 QDIQMTQSPG TLSLSPGERA TLSCRASQSV SSSYLAWYQQ KPGQAPRLLI
 51 YGASSRATGI PDRFSGSGSG TDFTLTISRL EPEDFAVYYC QHYGGSQAFG
101 GGTKVEIK (SEQ ID NO:159)

------

9 M0039-H08 SC = SC-001 Round = SC-001-SR-003
HC
  1 EVQLLESGGG LVQPGGSLRL SCAASGFTFS AYNMGWVRQA PGKGLEWVSS
 51 ISSSGGYTGY ADSVKGRFTI SRDNSKNTLY LQMNSLRAED TAVYYCARDL
101 YRGFDYWGQG TLVTVSS (SEQ ID NO:160)
LC 1 QDIQMTQSPA TLSVSPGERA TLSCRASESV KNNLAWYQQK PGQAPRLLIY
 51 GVSTRAPGIP ARFSGSGSGT DFTLTISSLE PEDFAVYYCQ QRSNWPPVTF
101 GQGTRLEIK (SEQ ID NO:161)

------

10 M0040-A06 SC = SC-001 Round = SC-001-SR-003
HC
  1 EVQLLESGGG LVQPGGSLRL SCAASGFTFS YYGMYWVRQA PGKGLEWVSS
 51 ISSSGGYTDY ADSVKGRFTI SRDNSKNTLY LQMNSLRAED TAVYYCARRI
101 KYYDIEGEGA FDIWGQGTMV TVSS (SEQ ID NO:162)
LC 1 QDIVMTQTPP SLPVNPGEPA SISCRSSQSL LHRNGYNYLD WYLQKPGQSP
 51 QLLIHLGSYR ASGVPDRFSG SGSGTDFTLK ISRVEAEDVG VYYCMQPLQT
101 PFTFGPGTKV DIK (SEQ ID NO:163)

------

11 M0040-A11 SC = SC-001 Round = SC-001-SR-003
HC
  1 EVQLLESGGG LVQPGGSLRL SCAASGFTFS HYVMFWVRQA PGKGLEWVSR
 51 IVPSGGATMY ADSVKGRFTI SRDNSKNTLY LQMNSLRAED TAVYYCARDR
101 PLYDSSGYVD YWGQGTLVTV SS (SEQ ID NO:164)
LC 1 QSALTQPPSA SGSPGQSVTI SCTGTSSDVG AYNYVSWYQQ HPDKAPKLII
 51 YNVNERPSGV PDRFSGSKSG NTASLTVSGL QAEDEADYYC TSYAGSNKIG
101 VSGTGTKVTV L (SEQ ID NO:165)

------

12 M0043-G02 SC = SC-001 Round = SC-001-SR-003
HC
  1 EVQLLESGGG LVQPGGSLRL SCAASGFTFS WYPMFWVRQA PGKGLEWVSG
 51 IYSSGGPTDY ADSVKGRFTI SRDNSKNTLY LQMNSLRAED TAVYYCAKDT
101 LGRYYDFWSG YSYGMDVWGQ GTTVTVSS (SEQ ID NO:166)
LC 1 QDIQMTQSPG TLSLSPGERA TLSCRASQSV SSSYLAWYQQ KPGQAPRLLI
 51 YGASSRATGI PDRFSGSGSG TDFTLTISRL EPEDFAVYYC QSGVTFGGGT
101 KVEIK (SEQ ID NO:167)

TABLE 7

Types of the light chains of inhibitory Fabs

| | Isolate | J | V_Class |
|---|---|---|---|
| 1 | M0031-C02 | JK4 | VK-A3-VK2_8_A3 |
| 2 | M0031-F01 | JL1 | VL1-16-VL1_1c |
| 3 | M0033-H07 | JK4 | VK-A20-VK1_5_A20 |
| 4 | M0037-C09 | JK1 | VK-A3-VK2_8_A3 |
| 5 | M0037-D01 | JK1 | VK-A30-VK1_6_A30 |
| 6 | M0038-E06 | JK1 | VK-A27-VK3_1_A27 |
| 7 | M0038-F01 | JK3 | VK-O2-VK1_2_O2 |

TABLE 7-continued

Types of the light chains of inhibitory Fabs

| | Isolate | J | V_Class |
|---|---|---|---|
| 8 | M0038-F08 | JK4 | VK-A27-VK3_1_A27 |
| 9 | M00390H08 | JK5 | VK-L6-VK3_5_L6 |
| 10 | M0040-A06 | JK3 | VK-A3-VK2_8_A3 |
| 11 | M0040-A11 | JL1 | VL2 2c |
| 12 | M0043-G02 | JK4 | VK-A27-VK3_1_A27 |

TABLE 8

Alignment of LCs of inhibitory Fabs with their germline sequences

```
                         FR1                    CDR1          FR2              CDR2
                                  1   1    2  2 2     33      3333   4    4    5
                          1   5   0   5    0  3 5     01ACDEF2345   0    5    0
VKIIA3-JK1               -DIVMTQSPLSLPVTPGEPASISCRSSQSLLHSNGYNYLDWYLQKPGQSPQLLIYLGSNR
M0037-C09                QDIQMTQSPLSLPVTLGESASVSCRSSQSLLHENGHNYLDWYLQKPGQSPQLLIYLGSNR

FR3                               CDR3     FR4
                                                                 1    1
                         5  5   6    6    7    7    8    8  8 9  9   0    0
                         5  7   0    5    0    5    0    5  8 0  5   0    5
VKIIA3-JK1               ASGVPDRFSGSGSGTDFTLKISRVEAEDVGVYYCMQALQTPWTFGQGTKVEIK
(SEQ ID NO:168)
M0037-C09                ASGVPDRFSGSGSGTDFTLKISRVEAEDVGVYYCMQSLKTPPTFGPGTKVEIK
(SEQ ID NO:151)

FR1                    CDR1          FR2              CDR2
                                  1   1    2  2 2     33      3333   4    4    5   5
                          1   5   0   5    0  3 5     01acdef2345   0    5    0   4
VKIIA3-JK4               -DIVMTQSPLSLPVTPGEPASISCRSSQSLLHSNGYNYLDWYLQKPGQSPQLLIYLGSNR
M0031-C02                QDIQMTQSPLSLPVTPGEPASISCRSSQSLLHSNGYYYLDWYLQKPGQSPQLLIYLGSYR FR3                               CDR3     FR4
                                                                 1    1
                         5  5   6    6    7    7    8    8  8 9  9   0    0
                         5  7   0    5    0    5    0    5  8 0  5   0    5
VKIIA3-JK4               ASGVPDRFSGSGSGTDFTLKISRVEAEDVGVYYCMQALQTPLTFGGGTKVEIK
(SEQ ID NO:169)
M0031-C02                ASGVPDRFSGSGSGTDFTLKISSVEAEDVGVYYCMQALQTPLTFGGGTRVDIK
(SEQ ID NO:145)

FR1                    CDR1          FR2              CDR2
                                  1   1    2  2 2     33      3333   4    4    5
                          1   5   0   5    0  3 5     01acdef2345   0    5    0
VKIIA3-JK3               -DIVMTQSPLSLPVTPGEPASISCRSSQSLLHSNGYNYLDWYLQKPGQSPQLLIYLGSNR
M0040-A06                QDIVMTQTPPSLPVNPGEPASISCRSSQSLLHRNGYNYLDWYLQKPGQSPQLLIHLGSYR FR3                               CDR3     FR4
                                                                 1    1
                         5  5   6    6    7    7    8    8  8 9  9   0    0
                         5  7   0    5    0    5    0    5  8 0  5   0    5
VKIIA3-JK3               ASGVPDRFSGSGSGTDFTLKISRVEAEDVGVYYCMQALQTPFTFGPGTKVDIK
(SEQ ID NO:170)
M0040-A06                ASGVPDRFSGSGSGTDFTLKISRVEAEDVGVYYCMQPLQTPFTFGPGTKVDIK
(SEQ ID NO:163)

FR1                    CDR1          FR2              CDR2
                                  1   1    2  2      3       3       4    4    5   5
                          1   5   0   5    0  3 5    0       5       0    5    0   4
VK3L6-JK5                -EIVLTQSPATLSLSPGERATLSCRASQSVSSYLAWYQQKPGQAPRLLIYDASNR
M0039-H08                QDIQMTQSPATLSVSPGERATLSCRASESVKNNLAWYQQKPGQAPRLLIYGVSTR

FR3                               CDR3     FR4
                                                                 1    1
                         5      6    6    7    7    8    8  9    9   0    0
                         5      0    5    0    5    0    5  0    5a  0    5
VK3L6-JK5                ATGIPARFSGSGSGTDFTLTISSLEPEDFAVYYCQQRSNWP-ITFGQGTRLEIK
(SEQ ID NO:171)
M0039-H08                APGIPARFSGSGSGTDFTLTISSLEPEDFAVYYCQQRSNWPPVTFGQGTRLEIK
(SEQ ID NO:145)
```

TABLE 8-continued

Alignment of LCs of inhibitory Fabs with their germline sequences

```
                       FR1                        CDR1             FR2              CDR2
                                 1    1    2   2            3       3     4    4      5   5
                1     5     0    5    0   3 5    01a        5       0     5    0      5   4
VKIIIA27-JK1    -EIVLTQSPGTLSLSPGERATLSCRASQSVSSSYLAWYQQKPGQAPRLLIYGASSR
M0038-E06        QDIQMTQSPGTLSLSPGDRATLSCGASQLVVSNYIAWYQQKPGQAPRLLMYAGSIR

FR3                                    CDR3      FR4
                                                                                 1   1
                5     6     6    7    7    8    8    9    9    0         0
                5     0     5    0    5    0    5    0    5    0         5
VKIIIA27-JK1    ATGIPDRFSGSGSGTDFTLTISRLEPEDFAVYYCQQYGSSPWTFGQGTKVEIK
(SEQ ID NO:172)
M0038-E06       ATGIPDRFSGSGSGTDFTLTISRLEPEDFAIYYCQQRSNWPWTFGQGTKVEIK
(SEQ ID NO:155)

FR1                        CDR1             FR2              CDR2
                                 1    1    2   2            3       3     4    4      5   5
                1     5     0    5    0   3 5    01a        5       0     5    0      5   4
VKIIIA27-JK4    -EIVLTQSPGTLSLSPGERATLSCRASQSVSSSYLAWYQQKPGQAPRLLIYGASSR
M0038-F08        QDIQMTQSPGTLSLSPGERATLSCRASQSVSSSYLAWYQQKPGQAPRLLIYGASSR
M0043-G02        QDIQMTQSPGTLSLSPGERATLSCRASQSVSSSYLAWYQQKPGQAPRLLIYGASSR

FR3                                    CDR3      FR4
                                                                                 1   1
                5     6     6    7    7    8    8    9    9    0         0
                5     0     5    0    5    0    5    0    5    0         5
VKIIIA27-JK4    ATGIPDRFSGSGSGTDFTLTISRLEPEDFAVYYCQQYGSSPLTFGGGTKVEIK
(SEQ ID NO:173)
M0038-F08       ATGIPDRFSGSGSGTDFTLTISRLEPEDFAVYYCQHYGGSQA-FGGGTKVEIK
(SEQ ID NO:159)
M0043-G02       ATGIPDRFSGSGSGTDFTLTISRLEPEDFAVYYCQS--GVT--FGGGTKVEIK
(SEQ ID NO:167)

FR1                        CDR1             FR2              CDR2
                                 1    1    2   2        3           3     4    4      5   5
                1     5     0    5    0   3 5    0                  5     0    5      0   4
VKIA20-JK4      -DIQMTQSPSSLSASVGDRVTITCRASQGISNYLAWYQQKPGKVPKLLIYAASTL
M0033-H07        QDIQMTQSPSSLSASVGDRVTITCRASQGIRNFLAWYQQKPGKVPKLLVFGASAL

FR3                                    CDR3      FR4
                                                                                 1   1
                5     6     6    7    7    8    8    9    9    0         0
                5     0     5    0    5    0    5    0    5    0         5
VKIA20-JK4      QSGVPSRFSGSGSGTDFTLTISSLQPEDVATYYCQKYNSAPLTFGGGTKVEIK
(SEQ ID NO:174)
M0033-H07       QSGVPSRFSGSGSGTDFTLTISGLQPEDVATYYCQKYNGVPLTFGGGTKVEIK
(SEQ ID NO:149)

FR1                        CDR1             FR2              CDR2
                                 1    1    2   2        3           3     4    4      5   5
                1     5     0    5    0   3 5    0                  5     0    5      0   4
VKIA30-JK1      -DIQMTQSPSSLSASVGDRVTITCRASQGIRNDLGWYQQKPGKAPKRLLIYAASSL
M0037-D01        QDIQMTQSPSSLSASVGDRVTITCRASQGIRNDLGWYQQKPGKAPKRLIYVASSL

FR3                                    CDR3      FR4
                                                                                 1   1
                5     6     6    7    7    8    8    9    9    0         0
                5     0     5    0    5    0    5    0    5    0         5
VKIA30-JK1      QSGVPSRFSGSGSGTEFTLTISSLQPEDFATYYCLQHNSYPWTFGQGTKVEIK
(SEQ ID NO:175)
M0037-D01       QSGVPSRFSGSGSGTEFTLTISSLQPEDFATYYCLQHNSYPWTFGQGTKVEIK
(SEQ ID NO:153)

FR1                        CDR1             FR2              CDR2
                                 1    1    2   2        3           3     4    4      5   5
                1     5     0    5    0   3 5    0                  5     0    5      0   4
VKI02-JK3       -DIQMTQSPSSLSASVGDRVTITCRASQSISSYLNWYQQKPGKAPKLLIYAASSL
M0038-F01        QDIQMTQSPSSLSAFVGDKVTITCRASQSVGTYLNWYQQKAGKAPELLIYATSNL

FR3                                    CDR3      FR4
                                                                                 1   1
                5     6     6    7    7    8    8    9    9    0         0
                5     0     5    0    5    0    5    0    5    0         5
VKI02-JK3       QSGVPSRFSGSGSGTDFTLTISSLQPEDFATYYCQQSYSTP-FTFGPGTKVDIK
(SEQ ID NO:176)
M0038-F01       RSGVPSRFSGSGSGTDFTLTINTLQPEDFATYYCQQSYSIPRFTFGPGTKVDIK
(SEQ ID NO:157)
```

TABLE 8-continued

Alignment of LCs of inhibitory Fabs with their germline sequences

```
                      FR1                    CDR1              FR2            CDR2
                              1   1     2  2  2     33  3   3        4     4    5    5
                      1   5   91  5     0  3  5     01ab2   5        0     5    0    4
VL1_1c-JL1            QSVLTQPPSASGTPGQRVTISCSGSSSNIGSNTVNWYQQLPGTAPKLLIYSNNQR
M0031-F01             QSELTQPPSVSGTPGQRVTISCSGTSANIGRNAVHWYQQLPGTAPKLLIHSNNRR

FR3                                CDR3            FR4
                                                                           1    1
                      5   6   6   7    7    8     8    9  9   0    0
                      5   0   5   0    5    0     5   5abc6   0    5
VL1_1c-JL1            PSGVPDRFSGSKSGTSASLAISGLQSEDEADYYCAAWDDSLNG-YVFGTGTKVTVL
(SEQ ID NO:177)
M0031-F01             PSGVPDRFSGSKSGTSASLAISGLQSEDEADYYCAAWENSLNAFYVFGTGTKVTVL
(SEQ ID NO:147)

FR1                    CDR1              FR2            CDR2
                              1   1     2  2  2     33  3   3        4     4    5    5
                      1   5   91  5     0  3  5     01abc2   5       0     5    0    4
VL2_2c-JL1            QSALTQPPSASGSPGQSVTISCTGTSSDVGGYNYVSWYQQHPGKAPKLMIYEVSKR
M0040-A11             QSALTQPPSASGSPGQSVTISCTGTSSDVGAYNYVSWYQQHPDKAPKLIIYNVNER FR3                                CDR3            FR4
                                                                           1    1
                      5   6   6   7    7    8     8    9   9  9    0    0
                      5   0   5   0    5    0     5    0  5ab6     0    4
VL2_2c-JL1            PSGVPDRFSGSKSGNTASLTVSGLQAEDEADYYCSSYAGSNNFYVFGTGTKVTVL
(SEQ ID NO:178)
M0040-A11             PSGVPDRFSGSKSGNTASLTVSGLQAEDEADYYCTSYAGSNKIGVSGTGTKVTVL
(SEQ ID NO:165)
```

TABLE 9

Non Germline Residues in Inhibitory Fabs

| Isolate | HC FR3 | LC FRs | LC CDRs |
| --- | --- | --- | --- |
| M0031-C02 |  | Q(-1)Δ, Q3V, S77R, R103K, D105E | Y31fN, Y53N |
| M0031-F01 |  | E3V, V11A, H49Y | T26S, A28S, R31aS, A32T, H34N, R53Q, E92D, N93D, A95bG, F95cΔ |
| M0033-H07 | V89L | Q(-1)Δ, V48I, F49Y, G77S | R30S, F32Y, G50A, A53T, G93S, V94A |
| M0037-C09 |  | Q(-1)Δ, Q3V, L15P, S18P, V21I, P96W, P100Q | E31aS, H31eY, S91A, K93Q |
| M0037-D01 |  | Q(-1)Δ | V50A |
| M0038-E06 | T87M | Q(-1)Δ, D1E, Q3V, M4L, D17E, M48I, I85V | G24R, L28S, N31aS, I33L, A50G, G51A, I53S, R91Y, S92G, N93S, W94S |
| M0038-F01 |  | Q(-1)Δ, F14S, K18R, A40P, E45K, N76S, T77S | V29I, G30S, T31S, T51A, N53S, I94T, R96Δ |
| M0038-F08 |  | Q(-1)Δ, D1E, Q3V, M4L | H90Q, Q95P, A96L, Δ97T |
| M0039-H08 |  | Q(-1)Δ, D1E, Q3V, M4L, V13L, V96I | E27Q, K30S, N31S, N32Y, G50D, V51A, T53N, P56T, P95aΔ |
| M0040-A06 |  | Q(-1)Δ, T7S, P9L, N14T, H49Y | R31aS, Y53N, P91A |
| M0040-A11 |  | D41G, I47M, S98F | A31aG, N50E, N52K, T89S, K95aN, I95bF, G96Y, |
| M0043-G02 |  | Q(-1)Δ, D1E, Q3V, M4L | S90Q, Δ91Y, Δ92G, Δ96L, Δ97T |

Example 5

IC$_{50}$ Values for MMP-14 Inhibition of MMP-14 Binding Fabs and IgGs

The IC$_{50}$ values for MMP-14 inhibition (MMP-14 was at 2 pM) of exemplary MMP-14 binding Fabs and IgGs are provided in Table 10.

TABLE 10

IC$_{50}$ Values

| M name | IC50 (nM) - Fab | IC50 (nM) - IgG |
| --- | --- | --- |
| M0040-A06 | 8.6 ± 1.3 | 1.7 ± 0.6 |
| M0040-A11 | 23.2 ± 2.4 | 6.7 ± 0.5 |
| M0031-C02 | 56.0 ± 4.6 | 8.0 ± 1.1 |
| M0037-C09 | 11.5 ± 1.9 | 4.2 ± 0.8 |
| M0037-D01 | 4.3 ± 0.8 | 1.7 ± 0.3 |
| M0038-E06 | 16.6 ± 1.2 | 7.2 ± 1.2 |
| M0031-F01 | 25.3 ± 4.0 | 15.2 ± 4.2 |
| M0038-F01 | 3.8 ± 0.3 | 2.0 ± 0.7 |
| M0038-F08 | 31.1 ± 3.7 | 23.0 ± 9.7 |
| M0043-G02 | 9.3 ± 1.1 | 0.3 ± 0.07 |
| M0033-H07 | 11.5 ± 1.2 | 5.1 ± 1.7 |
| M0039-H08 | 23.0 ± 2.8 | 7.4 ± 2.0 |

Example 6

K$_i$ Values for MMP-14 Inhibition by Anti-MMP-14 IgGs

The K$_i$ values for MMP-14 inhibition by exemplary IgGs are presented in Table 11. K$_i$ studies were performed using an enzymatic assay at substrate [Mca-Pro-Leu-Ala-Cys(Mob)-Trp-Ala-Arg-Dap(Dnp)-NH$_2$] concentrations of 10 μM, 14 μM and 18 μM. These concentrations were chosen based on the finding that the $K_m$ for the reaction was 6 μM, and that substrate inhibition occurred at 15-20 μM substrate. The concentration of MMP-14 was 2 nM.

Five MMP-14 binding IgGs were selected for $K_i$ studies: M0043-G02, M0037-D01, M037-C09, M0038-F01, M0033-H07. The results with each IgG is depicted in FIG. 1(a)-1(e), respectively. The highest $K_i$ measured for each of these antibodies is shown in Table 11.

TABLE 11

$K_i$ of Human Antibodies that inhibit MMP-14

| Isolate | $K_i$ |
|---|---|
| M0043-G02 | 1.2 nM |
| M0037-D01 | 2.9 nM |
| M0037-C09 | 8.6 nM |
| M0038-F01 | 1.2 nM |
| M0033-H07 | 4.0 nM |

Example 7

Cross-Reactivity of MMP-14 Binding IgGs and Fabs Against other MMPs and TACE

The cross-reactivity of exemplary anti-MMP-14 IgGs and Fabs with other human MMPs and TACE (TNF-alpha converting enzyme) was examined. MMP and TACE enzymatic activity was monitored in the absence and presence of 1 μM anti-MMP-14 IgG antibody. Inhibition (Y) of activity ranged from approximately 50-80% of the reaction rate observed in the absence of antibody. "X" indicates no inhibition was observed. Cross-reactivity was not determined for MMP-17 because protein activity could not be detected.

For the studies summarized in Table 12, six anti-MMP-14 IgGs were selected for cross-reactivity testings: M0043-G02, M0040-A06, M0037-D01, M037-C09, M0038-F01, M0033-H07. The results are shown in Tables 5-7.

TABLE 12

Cross Reactivity of Anti-MMP-14 IgGs with Other MMPs and TACE

| MMP | M0043-G02 | M0040-A06 | M0037-D01 | M0037-C09 | M0038-F01 | M0033-H07 |
|---|---|---|---|---|---|---|
| 1 | N | N | N | N | N | N |
| 2 | Y | Y | N | N | N | N |
| 3 | N | Y | N | N | N | N |
| 7 | N | Y | N | N | N | N |
| 8 | N | Y | N | N | N | N |
| 9 | Y | Y | N | N | N | N |
| 10 | N | N | N | N | N | N |
| 12 | Y | Y | N | N | N | N |
| 13 | Y | Y | N | N | N | N |
| 16 | Y | Y | Y | Y | Y | Y |
| 17 | — | — | — | — | — | — |
| 24 | Y | Y | Y | Y | N | Y |
| TACE | N | N | N | N | N | N |

TABLE 13

Anti hMMP-14 Fab cross-reactivity with MMP-16

| Anti MMP-14 Fab | MMP-16 |
|---|---|
| M0043-G02 | Y 70% inhibition |
| M0039-H08 | X |
| M0038-F08 | X |
| M0031-C02 | X |
| M0037-C09 | X |
| M0037-D01 | X |
| M0038-E06 | X |
| M0038-F01 | X |
| M0033-F01 | X |
| M0040-A11 | X |
| M0040-A06 | X |
| M0033-H07 | X |

X: Does not inhibit MMP-16 at [I] = 100 nM level

TABLE 14

Anti hMMP-14 IgG cross-reactivity against MMP-16

| Anti MMP-14 IgG | MMP-16 |
|---|---|
| M0043-G02 | Y 94% inhibition |
| M0039-H08 | X |
| M0038-F08 | X |
| M0031-C02 | X |
| M0037-C09 | X |
| M0037-D01 | X |
| M0038-E06 | X |
| M0038-F01 | X |
| M0033-F01 | X |
| M0040-A11 | X |
| M0040-A06 | X |
| M0033-H07 | X |

X: Does not inhibit MMP-16 at [I] = 100 nM level

Example 8

Cross-Reactivity of MMP-14 Binding Fabs and IgGs with MMP-16

For the studies summarized in Tables 13 and 14, 100 nM anti-MMP-14 Fab/IgG were incubated with 5 nM MMP16 for 30 minutes at 30° C., 10 μM of substrate was added, and the MMP-16 activity was measured.

Example 9

Cross-Reactivity of MMP-14 Binding Fabs with MMP-16 and MMP-24

For the studies summarized in Table 15, 1 μM of anti-MMP-14 Fab/IgG (100 nM final inhibitor concentration) were incubated with 5 nM of MMP-16 or 5 nM of MMP-24 for 30 minutes at 30° C., 10 μM of substrate was added, and the MMP-16 activity was measured.

TABLE 15

Anti-hMMP14 Fab Cross-reactivity Against MMP-16 and MMP-24

| Anti-MMP-14 Fab | MMP-16 | MMP-24 |
|---|---|---|
| M0043-G02 | X | Y 74% inhibition |
| M0039-H08 | X | X |
| M0038-F08 | X | X |
| M0031-C02 | X | Y 54% inhibition |
| M0037-C09 | X | Y 72% inhibition |
| M0037-D01 | X | Y 71% inhibition |
| M0038-E06 | X | X |
| M0038-F01 | X | X |
| M0033-F01 | X | X |
| M0040-A11 | X | Y 58% inhibition |
| M0040-A06 | X | Y 65% inhibition |
| M0033-H07 | X | X |

X: Do not inhibit MMP-16 or MMP-24 at [I] = 100 nM level
Y: partially inhibit at [I] = 100 nM level Example 10

Binding of MMP-14 IgGs to Tumor Cells Expressing MMP-14

The ability of twelve biotinylated-MMP-14 binding IgGs to bind to tumor cells expressing MMP-14 was evaluated using both immunocytochemistry (ICC) and flow cytometry. The cell lines tested were HT-1080 (a human fibrosarcoma cell line), LNCaP (human, prostate, carcinoma), MDA-MB-231 (human, Caucasian, breast, adenocarcinoma), or PC3 (Human prostatic cancer cells) cells. MMP-14 is expressed on HT-1080 cells (Cancer Res. (2005) 65(23):10959-69.). MMP-14 is expressed on PC-3 cells (Oncol Rep. (2006) 15(1):199-206). LNCaP express MMP-14 (Endocrinology (2003) 144(5):1656-1663) at a relatively low level. FGF-1 significantly induced MMP-14 expression in LNCaP prostate carcinoma cells (Prostate. (2004) 58(1):66-75). MMP-14 is expressed by MDA-MB-231 cells (Int J Cancer. (2005) 114 (4):544-554.).

Cells ($2 \times 10^5$) were cultivated on cell culture slides in complete medium. At confluency, cells were washed with PBS and fixed with 4% paraformaldehyde for 30 minutes at room temperature. Endogenous peroxidases were blocked with 3% hydrogen peroxide for 20 minutes. Nonspecific binding sites were blocked by incubation with 10% heat inactivated human serum 10% normal rabbit serum for 30 minutes at room temperature. Cells were then incubated with biotinylated or non-biotinylated MMP-14 binding proteins at 10 g/ml for 2 hours at room temperature. Streptavidin/HRP (1/200, where the MMP-14 binding proteins were biotinylated) or anti human IgG/HRP (1/200, for non-biotinylated MMP-14 binding proteins) was then added for 60 minutes at room temperature. Binding was detected with the substrate AEC+ (25 minutes at room temperature in the dark). Slides were then dried and mounted using Faramount mounting medium.

The results are summarized in Table 16.

TABLE 16

Binding of Anti-MMP-14 IgGs to Tumor Cells Expressing MMP-14

| | Antibody Staining |
|---|---|
| M0033-H07 | +++ |
| M0043-G02 | − |
| M0038-F08 | ++ |
| | (only positive in immunocytochemistry, ICC) |
| M0037-C09 | − |
| M0038-F01 | +++ |
| M0038-E06 | − |
| M0031-C02 | − |
| M0040-A06 | − |
| M0037-D01 | − |
| M0040-A11 | − |
| M0039-H08 | ++ |
| M0031-F01 | + |
| | (only positive in ICC) |

Example 11

Inhibition of Pro-MMP-2 Activation by MMP-14 by MMP-14 Binding IgGs

The ability of anti-MMP-14 IgGs to inhibit the activation of pro-MMP-2 by MMP-14 was examined by gelatin zymogram experiments performed with PMA-activated HT-1080 cells. M0033-H07 and M0038-F01 were tested for their ability to inhibit MMP-14 in this assay. HT1080 cells (well-known to express MMP-14 and MMP-2) were seeded at $5 \times 10^5$ cells/well at Day 0. At Day 1, the cells were cultured in a serum-free medium in presence of either GM6001 (a broad-spectrum hydroxamate-based matrix metalloproteinase inhibitor) at 10 μM, or a commercial polyclonal anti-human MMP-14 antibody (this antibody binds, but does not inhibit MMP-14) at 10 μg/ml (negative control), or M0038-F01 at 10 μg/ml, or M0033-H07 at 10 μg/ml. HT-1080 cells cultured in the presence of 20 ng/ml of PMA were used as a positive control.

Figure 2:
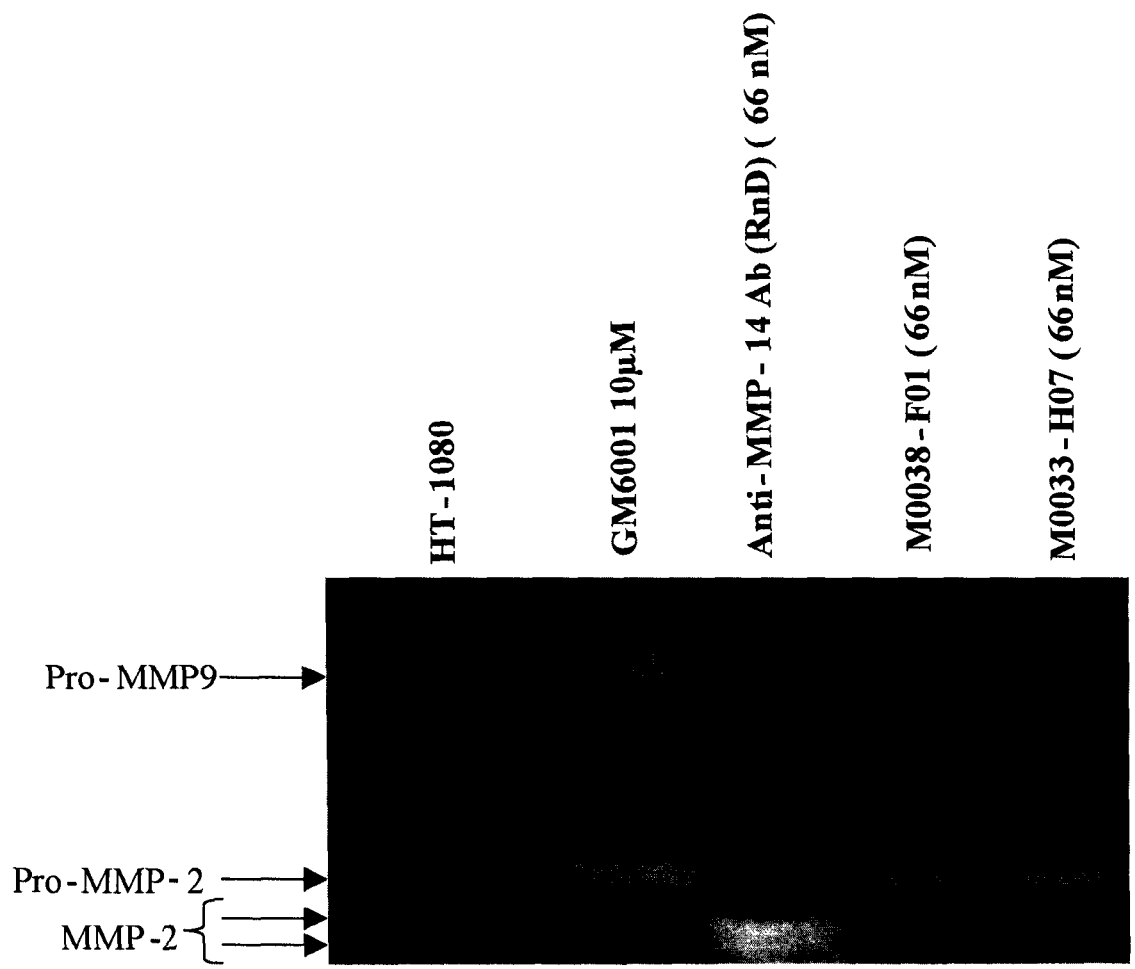
FIG. 2 is a reproduction of a gelatin zymogram.

After 3 days of incubation, conditioned media were collected and gelatinolytic activities were analyzed by gelatin zymography as described previously (Maquoi et al, J Biol Chem 2000; 275:11368-78). The results are shown in FIG. 2. When HT-1080 cells are activated with a phorbol ester, pro-MMP-2 is activated into MMP-2 (lane 1). In presence of GM6001 (10 μM) (lane 2), activation of pro-MMP-2 is completely abolished but expression of pro-MMP-9 is paradoxically stimulated, as described in the literature (Maquoi E et al, 1999, Ann N Y Acad Sci., 30878:744-6). As expected, the commercial polyclonal anti-MMP-14 antibody does not affect expression or activation of gelatinases (lane 3). Interestingly, M0038-F01 completely inhibits pro-MMP-2 activation by MMP-14 (lane 4), while M0033-H07 partly inhibited pro-MMP-14 activation by MMP-14 (lane 5). No stimulation of pro-MMP-9 expression was observed in both conditions.

Example 12

Germlining of M0038-F01 and M0033-H07

The sequences of M0038-F01 and M0033-H07 were compared with human germline sequence and modified where possible to achieve identity with the germline. Sequences of the germlined antibodies, designated M0038-F01 germline and M0033-H07 germline are shown in Table 17 (underlined portions indicate the signal sequence).

Germlined antibodies were tested for binding affinity and MMP-14 inhibitory activity in comparison with the parental antibodies.

Figure 3:
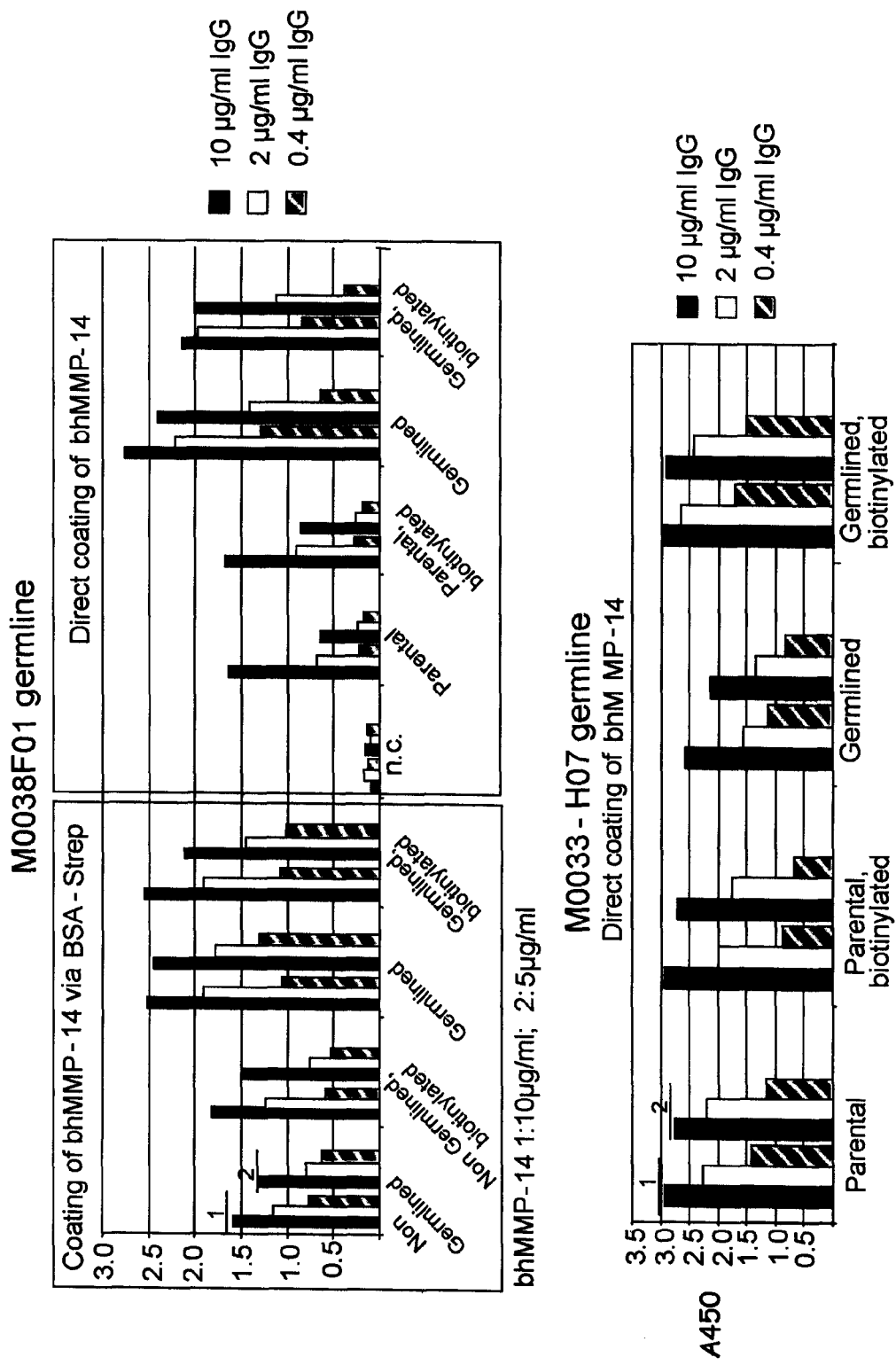
FIG. 3 shows a series of graphs depicting the binding of germlined antibodies (539C-M0038F01 Germline and 539C-M0033-H07 Germline) to MMP-14.

Binding of M0038F01 germline and 539C-M0033-H07 germline to biotinylated human MMP-14 (bhMMP-14) was tested in an ELISA format essentially as described in previous examples. 539C-M0038-F01 germline was tested against bhMMP-14 both directly adsorbed to the ELISA plate and bound to the plate via streptavidin. 539C-M0033-H07 germline was tested against directly adsorbed bhMMP-14 only. Results, shown in FIG. 3, indicate that both germlined antibodies retain binding to hMMP-14.

Figure 4:
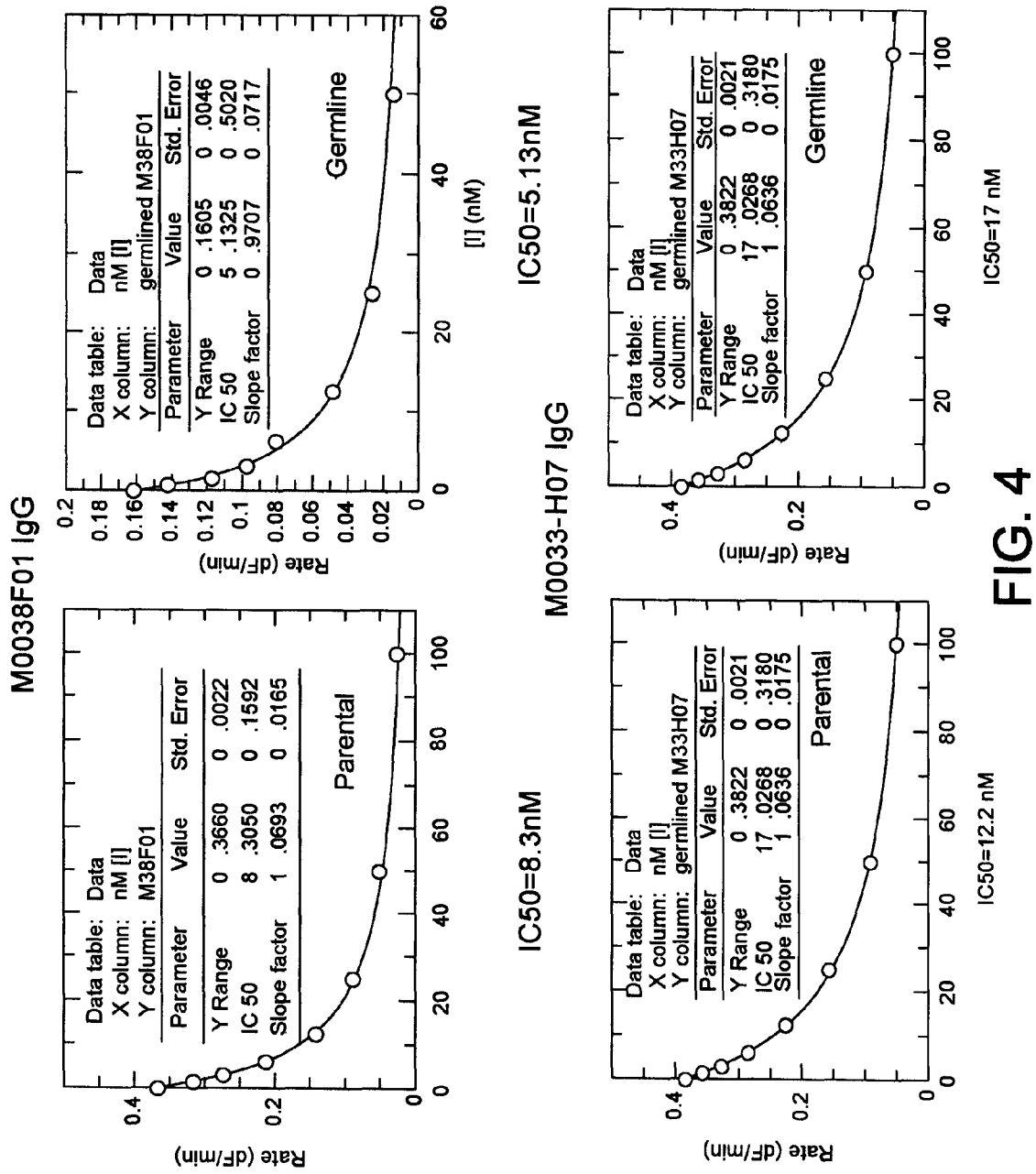
FIG. 4 shows a a series of graphs depicting the determination of IC50 values (against 2 pM hMMP-14) for two germlined antibodies (539C-M0038F01 Germline and 539C-M0033-H07 Germline ) as compared to the parental antibodies.

IC50's were determined for both germlined antibodies, using 2 pM MMP-14. Results, shown in FIG. 4, demonstrate that the IC50's of the germlined antibodies (the panels labeled "Germlined") are the similar to those of the parental antibodies, and that 539C-M0038F01 Germlined has an improved IC50 as compared to the parental antibody.

Figure 5:
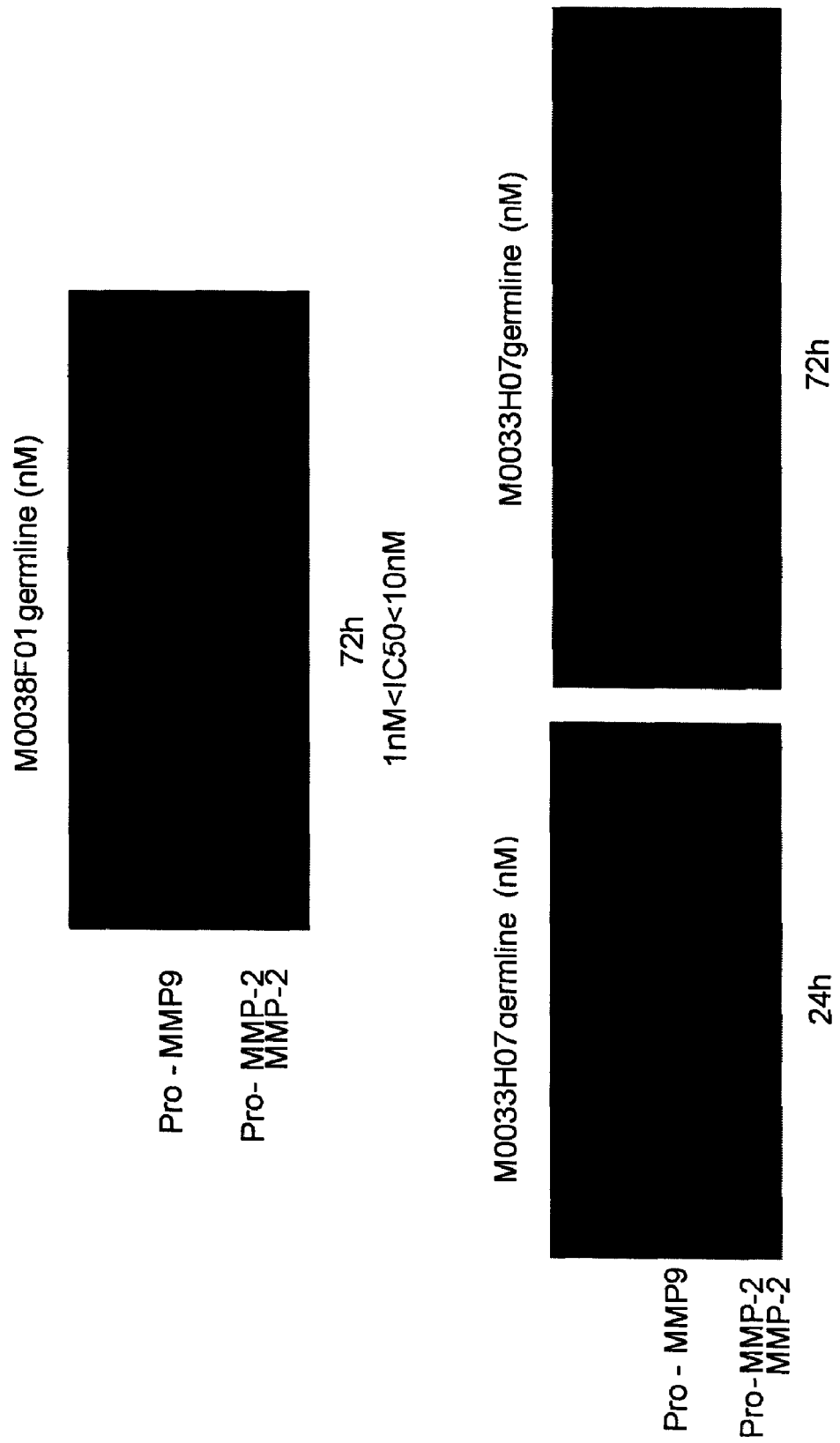
FIG. 5 shows reproductions of gelatin zymograms performed with germlined antibodies 539C-M0038F01 Geneart and 539C-M0033-H07 Geneart.

Inhibitory activity of the germlined antibodies was tested in the HT-1080 zymogram assay. Results are shown in FIG. 5 (lanes, from left to right, are no antibody, 100 nM antibody, 50 nM antibody, 10 nM antibody, 1 nM antibody, and 0.1 nM antibody). The ratio of pro-MMP-2:MMP-2 indicates the MMP-14 inhibitory activity of the antibody (higher ratios indicate greater inhibitory activity).

TABLE 17

Sequences of Germlined Antibodies

>MMP-14-M0033H07 germline-Light chain (SEQ ID NO:179)
MGWSCIILFLVATATGVHSDIQMTQSPSSLSASVGDRVTITCRASQGIRN
FLAWYQQKPGKVPKLLIYGASALQSGVPSRFSGSGSGTDFTLTISSLQPE
DVATYYCQKYNGVPLTFGGGTKVEIKRTVAAPSVFIFPPSDEQLKSGTAS
VVCLLNNFYPREAKVQWKVDNALQSGNSQESVTEQDSKDSTYSLSSTLTL
SKADYEKHKVYACEVTHQGLSSPVTKSFNRGEC >MMP-14-M0033H07 germline-Heavy chain (SEQ ID NO:180)
MGWSCIILFLVATATGAHSEVQLLESGGGLVQPGGSLRLSCAASGFTFSV
YGMVWVRQAPGKGLEWVSVISSSGGSTWYADSVKGRFTISRDNSKNTLYL
QMNSLRAEDTAVYYCARPFSRRYGVFDYWGQGTLVTVSSASTKGPSVFPL
APSSKSTSGGTAALGCLVKDYFPEPVTVSWNSGALTSGVHTFPAVLQSSG
LYSLSSXTVTVPSSSLGTQTYICNVNHKPSNTKVDKRVEPKSCDKTHTCP
PCPAPELLGGPSVFLFPPKPKDTLMISRTPEVTCVVVDVSHEDPEVKFNW
YVDGVEVHNAKTKPREEQYNSTYRXTVSVLTVLHQDWLNGKEYKCKVSNK
ALPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCS
VMHEALHNHYTQKSLSLSPGK >MMP-14-M0038f01 germline-Light chain (SEQ ID NO:181)
MGWSCIILFLVATATGVHSDIQMTQSPSSLSASVGDRVTITCRASQSVGT
YLNWYQQKPGKAPKLLIYATSNLRSGVPSRFSGSGSGTDFTLTISSLQPE
DFATYYCQQSYSIPRFTFGPGTKVDIKRTVAAPSVFIFPPSDEQLKSGTA
SXTVCLLNNFYPREAKVQWKVDNALQSGNSQESVTEQDSKDSTYSLSSTL
TLSKADYEKHKVYACEVTHQGLSSPVTKSFNRGEC >MMP-14-M0038f01 germline-Heavy chain (SEQ ID NO:182)
MGWSCIILFLVATATGAHSEVQLLESGGGLVQPGGSLRLSCAASGFTFSL
YSMNWVRQAPGKGLEWVSSIYSSGGSTLYADSVKGRFTISRDNSKNTLYL
QMNSLRAEDTAVYYCARGRAFDIWGQGTMVTVSSASTKGPSVFPLAPSSK
STSGGTAALGCLVKDYFPEPVTVSWNSGALTSGVHTFPAVLQSSGLYSLS
SXTVTVPSSSLGTQTYICNVNHKPSNTKVDKRVEPKSCDKTHTCPPCPAP
ELLGGPSVFLFPPKPKDTLMISRTPEVTCXTVVDVSHEDPEVKFNWYVDG
VEVHNAKTKPREEQYNSTYRVVSVLTVLHQDWLNGKEYKCKVSNKALPAP TABLE 17-continued Sequences of Germlined Antibodies IFKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEA
LHNHYTQKSLSLSPGK Example 13

Inhibition of Tube Formation by MMP-14 Binding IgGs

Human umbilical vascular endothelium cells (HUVECs) were seeded into MATRIGEL™ basement membrane extract-coated 96 well plates at 20,000 or 40,000 cells in 100 µl/well. The seeded cells were incubated for 30 minutes, then the various test articles were added (vehicle control, M0038-F01 at concentrations ranging from 1 nM to 250 nM, or suramin 8 mg/ml). The cells were incubated at 37° for 18 hours. 100 µl of calcein solution (8 µg/ml) was added 20 minutes prior to image capture. Representative photomicrographs are shown in FIG. 6A. Tube lengths were also quantified. Tube length measurements are summarized in FIG. 6B. M0038-F01 dose-dependently inhibits tube formation in the dose-range tested.

Example 14

Inhibition of MDA-MB-231 Tumor Growth and Metastasis by MMP-14 Binding IgGs

Human breast cancer cells MDA-MB-231 cells transfected with green fluorescent protein (MDA-MB-231-GFP) were inoculated into the mammary fat pad of female BALB/c nu/nu mice with Matrigel. Animals were monitored for tumor growth, and at week 4-5 post tumor cell inoculation, animals with tumors of 30-50 mm$^3$ were selected, randomized and divided into experimental groups. Animals were treated with vehicle alone (control, n=9) doxorubicin (DOX, 5 mg/kg, administered weekly by intraperitoneal (IP) injection for 5 weeks, n=9, although one animal died during the experiment, between weeks 5 and 6), MMP-14 binding antibody M0038-F01 (10 mg/kg, administered on alternating days (Q2d) by IP injection for five weeks, n=8), or an IgG isotype control antibody specific for streptavidin (A2, administered 10 mg/kg, Q2d by IP injection for five weeks, n=8). Tumor volume was measured weekly, starting at week 5. Additionally, tissue samples of lung, liver, and spleen were taken to assess metastasis.

Figure 7:
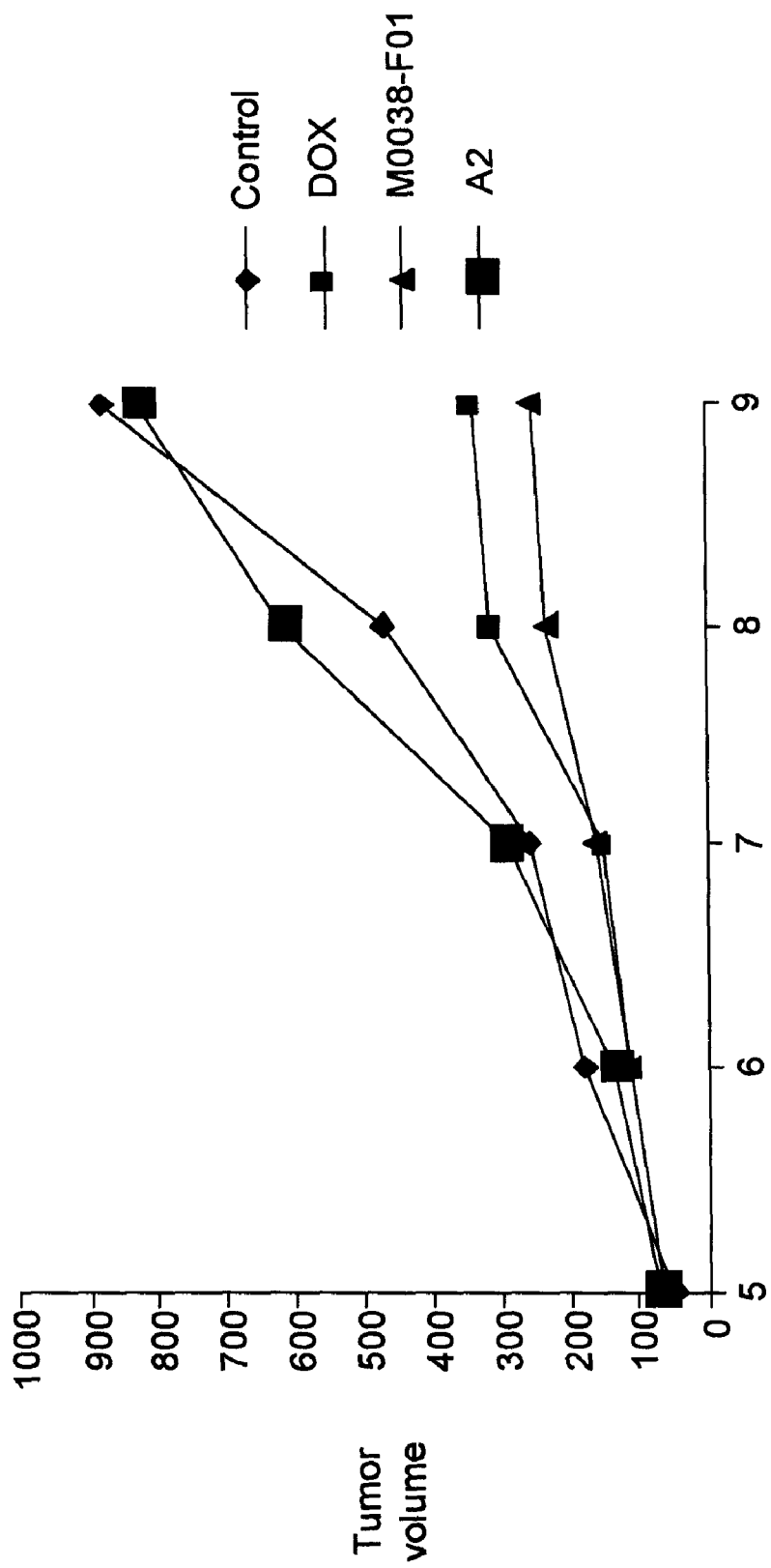
FIG. 7 shows a graph summarizing results of an experiment examining the effect of an MMP-14 binding antibody (M0038-F01) on growth of tumors derived from MDA-MB-231 cells orthotopically injected into the mammary fat pads of female Balb/c mice. The y-axis is tumor volume (in cubic millimeters) and the x-axis is time (in weeks), starting at initiation of dosing.

Tumor volume results are summarized in FIG. 7. Tumor volumes increased rapidly in animals treated with either vehicle or the isotype control (A2). Tumor growth was substantially inhibited in the animals treated with either DOX or M0038-F01.

There was a statistically significant reduction in lung and liver metastases in animals treated with DOX or M0038-F01 as compared to controls. Metastases to spleen were reduced in DOX and M0038-F01 treated animals, but the difference was not statistically significant in this experiment.

A dose-ranging experiment was performed to examine dose-response to MMP-14 binding antibody M0038-F01. Animals were inoculated with MDA-MB-231-GFP cells as described above, then selected and randomized, and divided into experimental groups of 8 animals each. Animals were treated with vehicle alone (control), DOX (5 mg/kg weekly by IP injection for 5 weeks), M0038-F01 (0.1, 1, or 10 mg/kg Q2d by IP injection for 5 weeks), or the IgG isotype control A2 (10 mg/kg Q2d by IP injection for five weeks). Tumor volume was measured weekly, starting at week 5.

Figure 8:
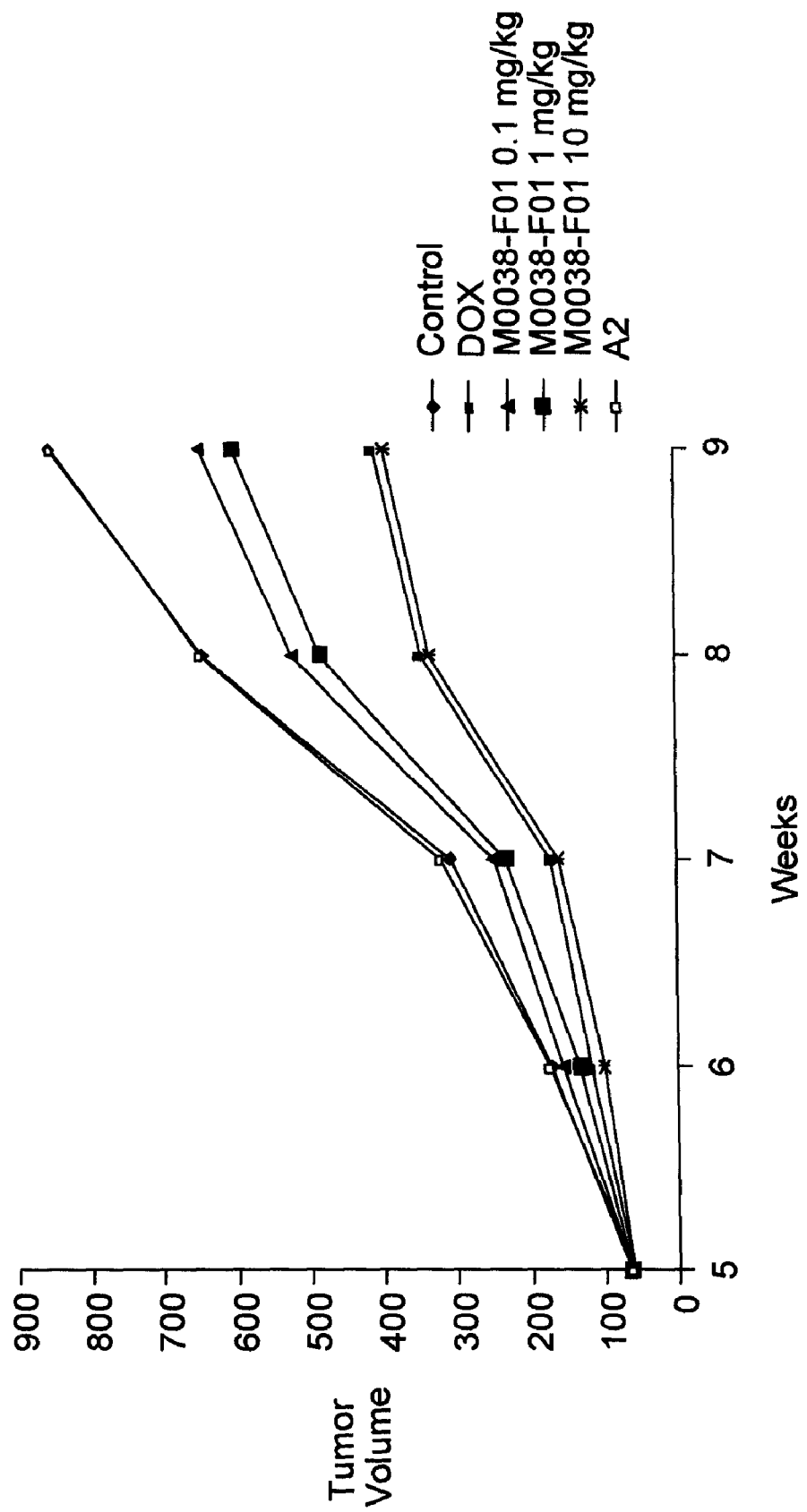
FIG. 8 shows a graph summarizing results of an experiment examining the effect of a range of doses of an MMP-14 binding antibody (M0038-F01) on growth of tumors derived from MDA-MB-231 cells orthotopically injected into the mammary fat pads of female Balb/c mice. The y-axis is tumor volume (in cubic millimeters) and the x-axis is time (in weeks), starting at initiation of dosing.

Results from the dose-ranging experiment are summarized in FIG. 8. As in the previous experiment, tumor volumes increased rapidly in animals treated with either vehicle or the isotype control (A2). Tumor growth was reduced in all M0038-F01 treated animals, with the 10 mg/kg dose being most effective, followed by the 1 mg/kg and 0.1 mg/kg doses.

Tumor tissue samples were collected on day 35 post-treatment for immunohistochemical analysis. Paraffin-embedded tissue samples were sectioned, stained with CD31 (Santa Cruz Biotechnology Inc., Santa Cruz, Calif., USA), Ki-67 (DAKO, Carpinteria, Calif., USA), MAPK, FAK, phospho-MAPK or phosphoFAK antibodies, visualized with biotinylated secondary antibodies using a VECTASTAIN® ABC (Vector Laboratories Inc., Burlingame, Calif., USA), and lightly counterstained with haemotoxylin.

Immunostaining was quantitated by computer-assisted image analysis (Khalili et al., 2005, Oncogene, 24: 6657-66). While CD31 and KI67 levels were slightly reduced in doxorubicin-treated tumors as compared to both vehicle and IgG isotype (A2) controls, M0038-F01-treated tumors had statistically significant (p<0.05) reductions in both CD31 and KI67. These data are summarized in Table 18. M0038-F01-treated tumors also had significantly reduced levels of phospho-MAP kinase and phospho-FAK (2.4±0.7 and 4±1.2, respectively) as compared to controls (7.4±0.7; 6.9±0.9 A.U.), but total MAP kinase and FAK levels were essentially the same as in control tumors. Doxorubicin treated resulted in statistically significant reductions (p<0.05) in levels of total MAP kinase (5.8±1.9 A.U.) and FAK (6±1 A.U.) as well as phospho-MAP kinase (5.8±1.9 A.U.) and phospho-FAK (4±1.2 A.U.).

TABLE 18

| Treatment | CD31 | Ki67 |
| --- | --- | --- |
| Vehicle | 5.2 ± 0.75 | 6 ± 1.38 |
| A2 | 4.7 ± 0.7 | 5.9 ± 1.64 |
| DOX | 4.08 ± 1.28 | 5.2 ± 0.84 |
| M0038-F01 | 2.0 ± 0.6 | 2.4 ± 1.2 |

A dose-ranging experiment was performed to examine dose-response to MMP-14 binding antibody M0038-F01. Animals were inoculated with MDA-MB-231-GFP cells as described above, then selected and randomized, and divided into experimental groups of 8 animals each. Animals were treated with vehicle alone (control), DOX (5 mg/kg weekly by IP injection for 5 weeks), M0038-F01 (0.1, 1, or 10 mg/kg Q2d by IP injection for 5 weeks), or the IgG isotype control A2 (10 mg/kg Q2d by IP injection for five weeks). Tumor volume was measured weekly, starting at week 5.

Results from the dose-ranging experiment are summarized in FIG. 8. As in the previous experiment, tumor volumes increased rapidly in animals treated with either vehicle or the isotype control (A2). Tumor growth was reduced in all M0038-F01 treated animals, with the 10 mg/kg dose being most effective, followed by the 1 mg/kg and 0.1 mg/kg doses.

Example 15

Inhibition of MDA-MB-435 Breast Tumor Growth by MMP-14 Binding IgGs

Fragments of MDA-MB-435 GFP (MDA-MB-435 cells expressing green fluorescent protein) tumors were transplanted by surgical orthotopic implantation (SOI) into the right second mammary gland. Treatment was started on day 15 after SOI when the volume of primary tumors reached about 85 mm$^3$. Animals were treated with vehicle alone (Control, n=10), taxotere (10 mg/kg, administered QW×3, i.v., n=10), MMP-14 binding antibody M0038-F01 (0.1, 1, or 10 mg/kg, administered on alternating days (Q2d) by IP injection for five weeks, n=10), or an IgG isotype control antibody specific for streptavidin (A2, administered 10 mg/kg Q2d by IP injection for five weeks, n=10). Tumor volume was measured weekly, starting at week 5.

Figure 9:
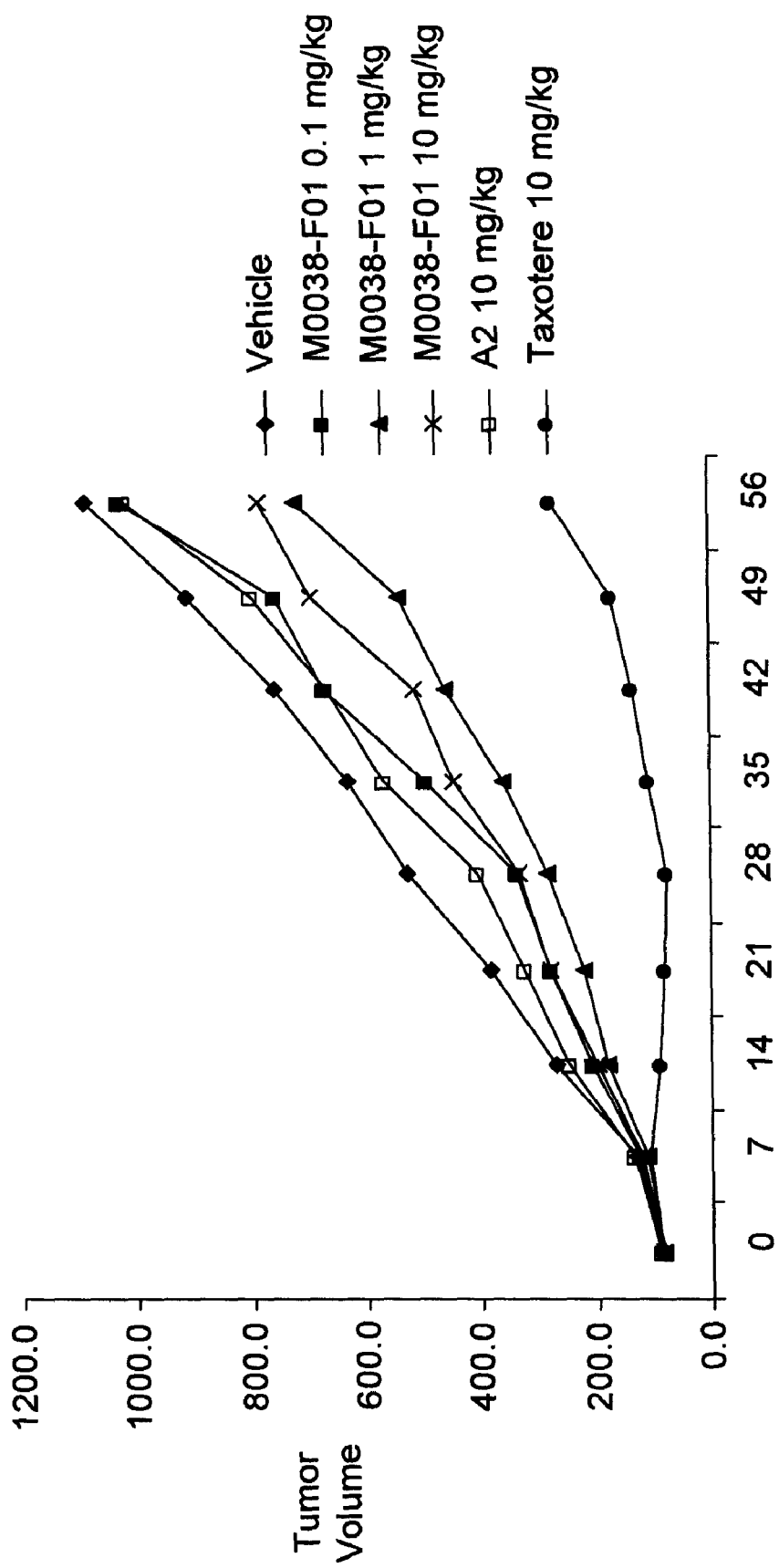
FIG. 9 shows a graph summarizing results of an experiment examining the effect of a range of doses of an MMP-14 binding antibody (M0038-F01) on growth of MDA-MB-435 GFP breast tumors orthotopically transplanted into the mammary fat pads of female Balb/c mice (described in Example 15). The y-axis is tumor volume (in cubic millimeters) and the x-axis is time (in weeks), starting at initiation of dosing

Mice were sacrificed at day 61 after the start of the treatment and tumors (primary and metastases) were identified by fluorescent imaging. Additionally, primary tumors were excised and weighed. The tumor volume results are summarized in FIG. 9. The administration of 1 or 10 mg/kg doses of M0038-F01 resulted in a reduction of tumor volume, as did administration of taxotere. Tumor mass results are summarized in Table 19 (asterisks indicate values that are significantly different (p≦0.05) compared to Control). Tumor mass results were comparable to tumor volume data. However, M0038-F01 was not effective in reducing lymph node or lung metastases in this experiment.

TABLE 19

| Group | Tumor Mass (±SD) |
| --- | --- |
| Control | 1.44 ± 0.85 |
| A2 | 1.34 ± 0.66 |
| F01 0.1 mg/kg | 1.54 ± 0.91 |
| F01 1 mg/kg | 0.86 ± 0.21* |
| F01 10 mg/kg | 0.82 ± 0.35* |
| Taxotere | 0.59 ± 0.59* |

Example 16

Inhibition of B16 Melanoma Tumor Growth by MMP-14 Binding Antibodies

B16F1 melanoma cells were implanted into Female C57/BL6 (CR) mice (4-6 Weeks old) mice by subcutaneous injection. Animals were monitored for tumor growth and, at day 11 post-implantation, animals were selected, randomized and divided into experimental groups. Animals were treated with vehicle alone (Control, n=8), doxorubicin (DOX, 5 mg/kg, administered weekly by intraperitoneal (IP) injection, n=8), MMP-14 binding antibody M0038-F01 (10, 1, or 0.1 mg/kg, administered on alternating days (Q2d) by IP injection, n=8), or an IgG isotype control antibody specific for streptavidin (A2, administered 10 mg/kg Q2d by IP injection, n=8).

Figure 10A:
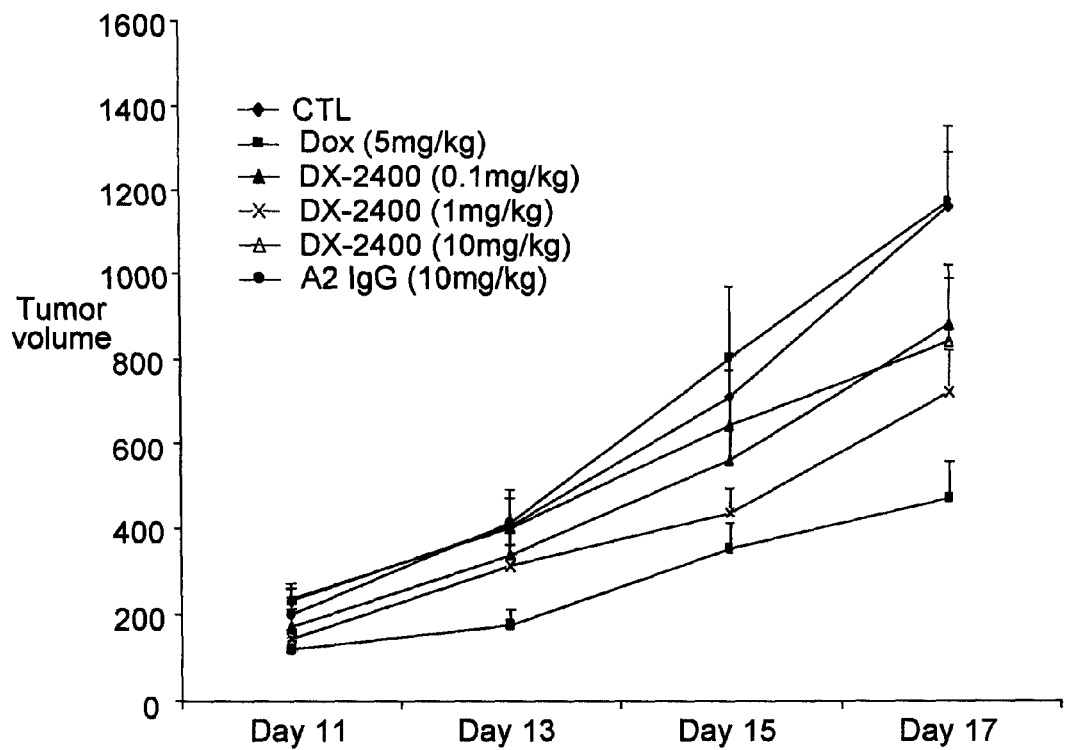
FIG. 10A shows a graph summarizing results of an experiment examining the effect of a range of doses of an MMP-14 binding antibody (M0038-F01) on growth of B16F1 melanoma tumors implanted subcutaneously (described in Example 16). The y-axis is tumor volume (in cubic millimeters) and the x-axis is time (in weeks), starting at initiation of dosing.

Results are summarized in FIG. 10A. All doses of M0038-F01 were effective in reducing tumor growth in this model, as was doxorubicin.

Figure 10B:
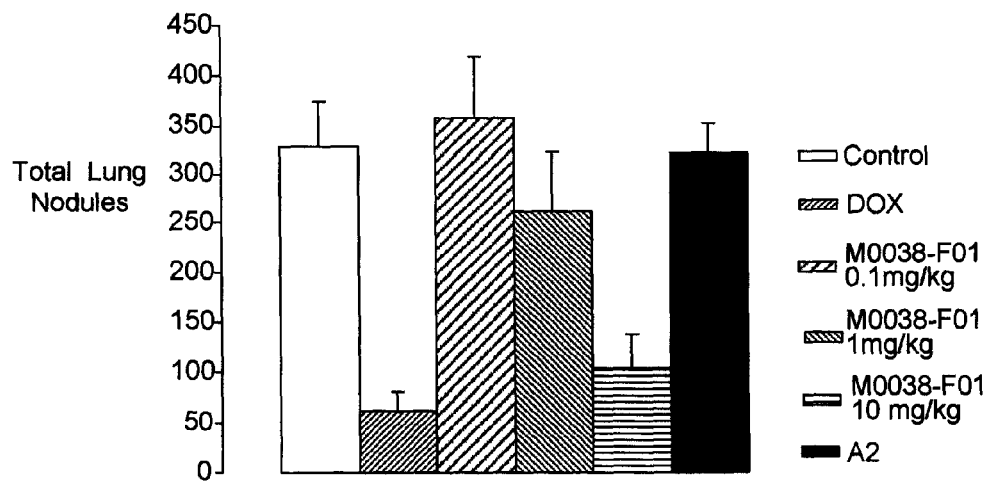
FIG. 10B shows the quantification of the lung nodules after treatment with Dox, M0038F01 and isotpype-matched antibody control on B16F1 melanoma metastasis. The y-axis is total number of lung nodules.

MMP-14 binding antibodies were also tested in a model of melanoma metastasis. B16F1 cells were grown in culture, harvested at 85% confluence and inoculated at 5×10$^5$ cells/ mouse in 100 µl saline by tail vein injection. Treatment started on Day 1, post inoculation, for 14 days. Animals were treated with vehicle alone (Control, n=8), doxorubicin (DOX, 5 mg/kg, administered weekly by intraperitoneal (IP) injection, n=8), MMP-14 binding antibody M0038-F01 (F01, 10 mg/kg, administered on alternating days (Q2d) by IP injection, n=8), or an IgG isotype control antibody specific for streptavidin (A2, administered 10 mg/kg Q2d by IP injection, n=8). On day 15, animals were sacrificed and lungs taken, fixed, and analyzed for the number of metastases (nodules). Results are summarized in FIG. 10B. MMP-14 binding antibody substantially reduced the number of lung melanoma tumors in a dose-dependent manner.

Example 17

Inhibition of Prostate Tumor Growth by MMP-14 Binding Antibodies

PC3 prostate cancer cells were implanted into male nude mice by subcutaneous injection. Animals were monitored for tumor growth, and at week 3 post tumor cell inoculation, animals with tumors of 50-100 mm$^3$ were selected, randomized and divided into experimental groups. Animals were treated with vehicle alone (Control, n=8), taxotere (10 mg/kg, administered weekly by IP injection, n=8), MMP-14 binding antibody M0038-F01 (10, 1, or 0.1 mg/kg, administered on alternating days (Q2d) by IP injection, n=8), or an IgG isotype control antibody specific for streptavidin (A2, administered 10 mg/kg Q2d, n=8). Tumor volume was measured weekly, starting at week 3.

Figure 11:
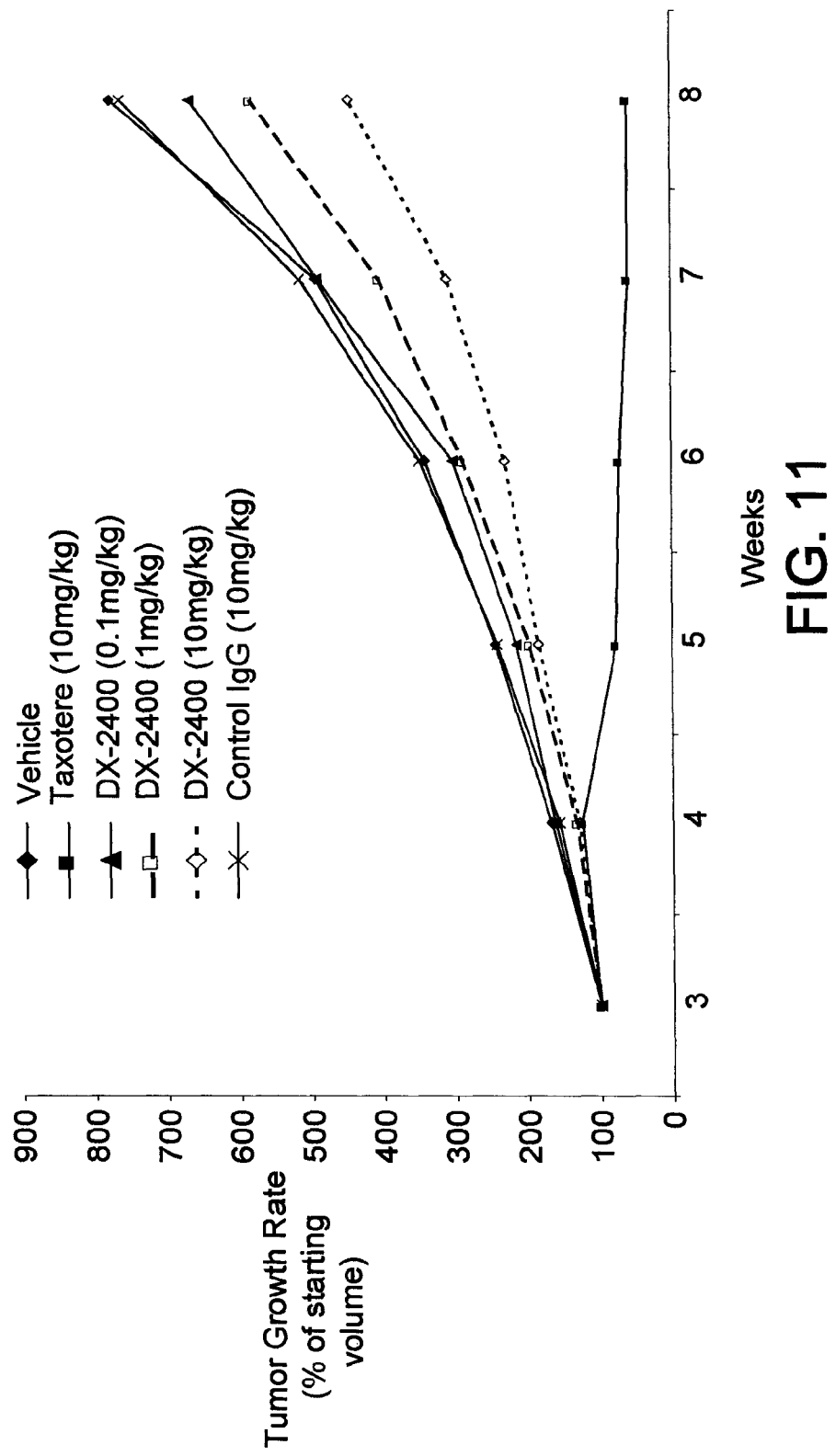
FIG. 11 shows a graph summarizing results from an experiment examining the effect of a range of doses of an MMP-14 binding antibody (M0038-F01) on growth of PC3 prostate tumors in mice (described in Example 17). The y-axis is tumor volume (in cubic millimeters) and the x-axis is time (in weeks), starting at initiation of dosing.

Results from the dose-ranging experiment are summarized in FIG. 11. As in the previous experiment, tumor volumes increased rapidly in animals treated with either vehicle or the isotype control (A2). Tumor growth was reduced in all M0038-F01 treated animals, with the 10 mg/kg dose being most effective, followed by the 1 mg/kg and 0.1 mg/kg doses. Taxotere was extremely effective in this model.

Example 18

Inhibition of BT747 Breast Tumor Growth by MMP-14 Binding Antibodies

Fragments (approximately 1 mm$^3$) of BT747 breast cancer tumor fragments were implanted into the flanks of female HRLN CB.17 SCID mice. Tumors were allowed to grow until they reached an average size of 80-120 mg, then animals were assorted into six experimental groups of ten animals each: vehicle alone (Vehicle), trastuzumab (HERCEPTIN®. 20 mg/kg), MMP-14 binding antibody M0038-F01 (10, 1, or 0.1 mg/kg, administered on alternating days (Q2d))or an IgG isotype control antibody specific for streptavidin (A2, 10 mg/kg Q2d). All groups were dosed by intraperitoneal (IP) injection. Tumor volume was measured biweekly.

Additionally, a seventh group of ten animals bearing large tumors (288 mm$^3$) was selected for testing with a combination therapy (M0038-F01, 10 mg/kg Q2d, starting at day 3 plus trastuzumab, 20 mg/kg biweekly, starting at day 4).

Figure 12:
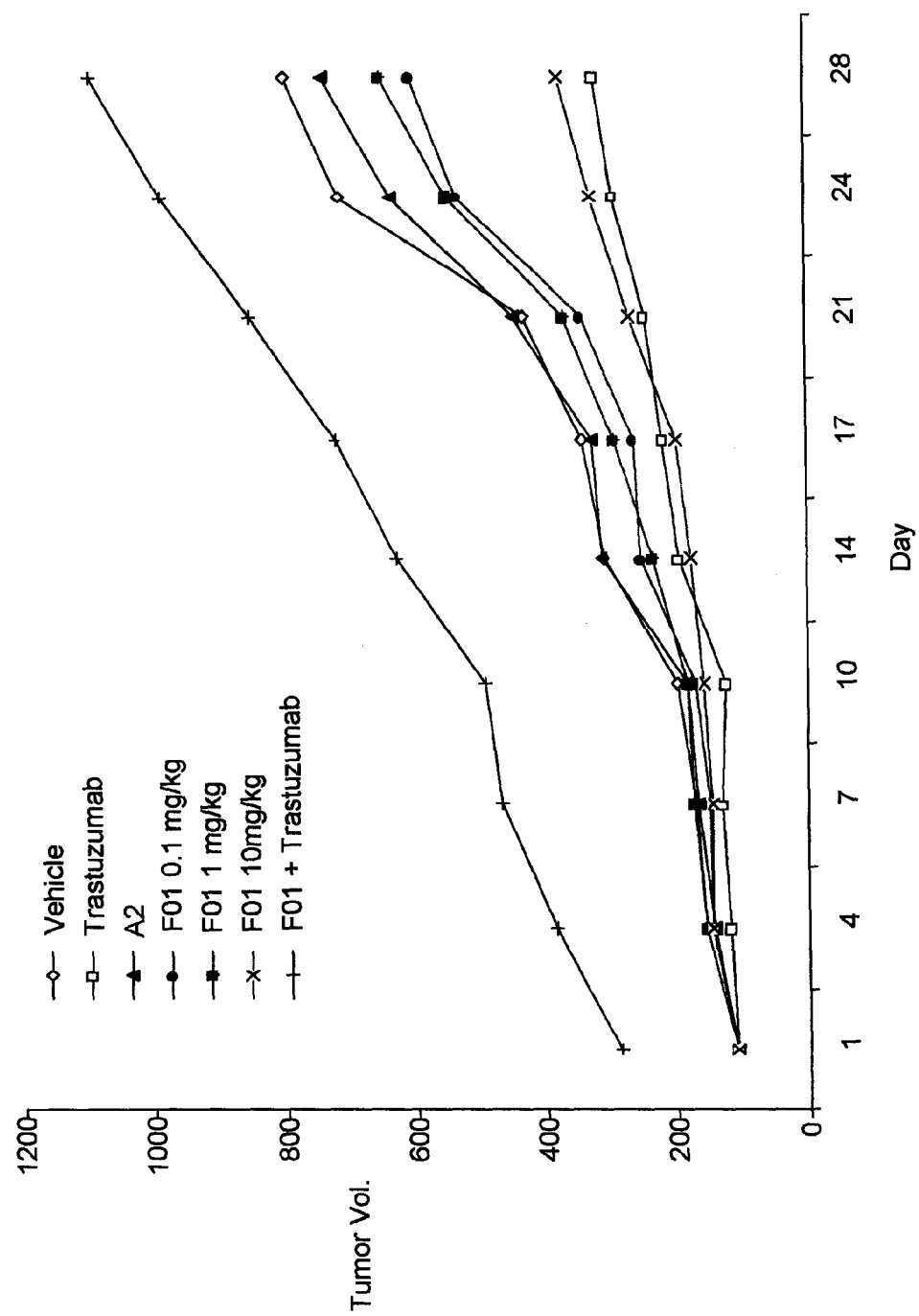
FIG. 12 shows a graph summarizing results from an experiment examining the effect of a range of doses of an MMP-14 binding antibody (M0038-F01 or "F01") on growth of BT474 breast tumors in mice (described in Example 18). The y-axis is tumor volume (in cubic millimeters) and the x-axis is time (in days), starting at initiation of dosing.

Data from the small initial tumor size groups (i.e., initial tumor size 80-120 mm$^3$) showed inhibition of tumor growth by MMP-14 binding antibody M0038-F01, with the highest dose resulting in the greatest inhibition of tumor growth. Trastuzumab inhibited tumor growth to an extent similar to 10 mg/kg M0038-F01. The effect of the combination of MMP-14 binding antibody M0038-F01 and trastuzumab on large tumors is unclear, as insufficient animals with large tumors were available to serve as controls for this group, however it was noted that the growth rate of tumors treated with M0038-F01 and trastuzumab was lower than the growth rate of controls of similar size (i. e., the vehicle and A2 controls. Results are summarized graphically in FIG. 12.

Example 19

MMP-14 in Mouse Models of Arthritis

Antigen-induced arthritis, a model of rheumatoid arthritis, was induced by intraarticular injection of *Streptococcus* cell wall (SCW, 25 mg/6 ml) into the knee joints of C57B16 mice at day 0, 7, 14 and 21.

MMP14 expression in acute phase SCW-induced arthritis (7 days after the first injection of SCW) was examined by immunohistochemical staining using M0038-F01. M0038-F01, but not an isotype-matched control, strongly stained synovial cells and chondrocytes, as well as macrophages in joint exudate.

Mice were assorted into groups of six animals each and treated (by IP injection) with M0038-F01 (2, 6, or 10 mg/kg), a control isotype-matched antibody (control, 20 mg/ml), or etanercept (ENBREL®, 5 mg/ml) at day 13, 16, 20, and 23. Joint swelling (measured by technecium uptake) was measured at day 15, 16, 22, 23 and 28. M0038-F01 did not have an effect on joint swelling in this experiment.

A number of embodiments of the invention have been described. Nevertheless, it will be understood that various modifications may be made without departing from the spirit and scope of the invention. Accordingly, other embodiments are within the scope of the following claims.

What is claimed is:

1. An isolated protein comprising a heavy chain (HC) immunoglobulin variable domain sequence and a light chain (LC) immunoglobulin variable domain sequence, wherein the HC and the LC immunoglobulin variable domain sequences form an antigen binding site that binds to a human membrane-type-matrix metalloproteinase 14 (MMP-14) and wherein the HC immunoglobulin variable domain comprises HC complementarity determining region (CDR) 1, CDR2, and CDR3, wherein the HC CDR1 sequence comprises residues 31-35 of SEQ ID NO:156, the HC CDR2 sequence comprises residues 50-66 of SEQ ID NO:156, and the HC CDR3 sequence comprises residues 99-104 of SEQ ID NO:156; and the LC immunoglobulin variable domain comprises LC CDR1, CDR2, and CDR3, wherein the LC CDR1 sequence comprises residues 25-35 of SEQ ID NO:157, the LC CDR2 sequence comprises residues 51-57 of SEQ ID NO:157, and the LC CDR3 sequence comprises residues 90-99 of SEQ ID NO:157.

2. The protein of claim 1, wherein the protein inhibits human MMP-14 enzymatic activity.

3. The protein of claim 1, wherein the HC and LC variable domain sequences are components of the same polypeptide chain.

4. The protein of claim 1, wherein the protein comprises a human antibody framework region.

5. A pharmaceutical composition comprising the protein of claim 1 and a pharmaceutically acceptable carrier.

6. The protein of claim 1, wherein the protein is a primate antibody.

7. The protein of claim 1, wherein the protein comprises a primate antibody framework region.

8. The protein of claim 1, wherein the protein is a humanized antibody.

9. The protein of claim 1, wherein the HC immunoglobulin variable domain sequence comprises a sequence that has less than 10 conservative mutations in the framework regions relative to SEQ ID NO:156.

10. The protein of claim 1, wherein the HC immunoglobulin variable domain sequence comprises SEQ ID NO:156.

11. The protein of claim 1, wherein the LC immunoglobulin variable domain sequence comprises a sequence that has less than 10 conservative mutations in the framework regions relative to SEQ ID NO:157.

12. The protein of claim 1, wherein the LC immunoglobulin variable domain sequence comprises SEQ ID NO:157.

13. The protein of claim 1, wherein the HC immunoglobulin variable domain sequence comprises a sequence that has less than 10 conservative mutations in the framework regions relative to SEQ ID NO:156 and the LC immunoglobulin variable domain sequence comprises a sequence that is has less than 10 conservative mutations in the framework regions relative to SEQ ID NO:157.

14. The protein of claim 1, wherein the HC immunoglobulin variable domain sequence comprises SEQ ID NO:156 and the LC immunoglobulin variable domain sequence comprises SEQ ID NO:157.

15. The protein of claim 1, wherein the protein comprises a sequence that is at least 90% identical to residues 20 to 464 of SEQ ID NO:182 in the framework regions.

16. The protein of claim 1, wherein the protein comprises residues 20 to 464 of SEQ ID NO:182.

17. The protein of claim 1, wherein the protein comprises a sequence that is at least 90% identical to residues 20 to 234 of SEQ ID NO:181 in the framework regions.

18. The protein of claim 1, wherein the protein comprises residues 20 to 234 of SEQ ID NO:181.

19. The protein of claim 1, wherein the protein comprises a sequence that is at least 90% identical to residues 20 to 464 of SEQ ID NO:182 in the framework regions and a sequence that is at least 90% identical to residues 20 to 234 of SEQ ID NO:181 in the framework regions.

20. The protein of claim 1, wherein the protein comprises residues 20 to 464 of SEQ ID NO:182 and residues 20 to 234 of SEQ ID NO:181.

21. A pharmaceutical composition comprising the protein of claim 14 and a pharmaceutically acceptable carrier.

22. A pharmaceutical composition comprising the protein of claim 20 and a pharmaceutically acceptable carrier.

23. The protein of claim 1, wherein the protein binds to human MMP-14.

24. The protein of claim 1, wherein the protein comprises a sequence that has less than 10 conservative mutations in the framework regions relative to residues 20 to 464 of SEQ ID NO:182.

25. The protein of claim 1, wherein the protein comprises a sequence that has less than 10 conservative mutations in the framework regions relative to residues 20 to 234 of SEQ ID NO:181.

26. The protein of claim 1, wherein the protein comprises a sequence that has less than 10 conservative mutations in the framework regions relative to residues 20 to 464 of SEQ ID NO:182 and a sequence that that has less than 10 conservative mutations in the framework regions relative to residues 20 to 234 of SEQ ID NO:181.

27. The protein of claim 1, wherein the protein comprises a sequence that has less than 5 conservative mutations in the framework regions relative to residues 20 to 464 of SEQ ID NO:182.

28. The protein of claim 1, wherein the protein comprises a sequence that has less than 5 conservative mutations in the framework regions relative to residues 20 to 234 of SEQ ID NO:181.

29. The protein of claim 1, wherein the protein comprises a sequence that has less than 5 conservative mutations in the framework regions relative to residues 20 to 464 of SEQ ID NO:182 and a sequence that that has less than 5 conservative mutations in the framework regions relative to residues 20 to 234 of SEQ ID NO:181.

30. The protein of claim 1, wherein the HC immunoglobulin variable domain sequence comprises a sequence that has less than 5 conservative mutations in the framework regions relative to SEQ ID NO:156.

31. The protein of claim 1, wherein the LC immunoglobulin variable domain sequence comprises a sequence that has less than 5 conservative mutations in the framework regions relative to SEQ ID NO:157.

32. The protein of claim 1, wherein the HC immunoglobulin variable domain sequence comprises a sequence that has less than 5 conservative mutations in the framework regions relative to SEQ ID NO:156 and the LC immunoglobulin variable domain sequence comprises a sequence that is has less than 5 conservative mutations in the framework regions relative to SEQ ID NO:157.

* * * * *

SEQUENCE LISTING

<160> NUMBER OF SEQ ID NOS: 182

<210> SEQ ID NO 1
<211> LENGTH: 580
<212> TYPE: PRT
<213> ORGANISM: Homo sapiens

<400> SEQUENCE: 1

Met Ser Pro Ala Pro Arg Pro Pro Arg Cys Leu Leu Leu Pro Leu Leu
1               5                   10                  15

Thr Leu Gly Thr Ala Leu Ala Ser Leu Gly Ser Ala Gln Ser Ser Ser

```
                    20                  25                  30
Phe Ser Pro Glu Ala Trp Leu Gln Gln Tyr Gly Tyr Leu Pro Pro Gly
         35                  40                  45

Asp Leu Arg Thr His Thr Gln Arg Ser Pro Gln Ser Leu Ser Ala Ala
 50                  55                  60

Ile Ala Ala Met Gln Lys Phe Tyr Gly Leu Gln Val Thr Gly Lys Ala
 65                  70                  75                  80

Asp Ala Asp Thr Met Lys Ala Met Arg Arg Pro Arg Cys Gly Val Pro
                 85                  90                  95

Asp Lys Phe Gly Ala Glu Ile Lys Ala Asn Val Arg Arg Lys Arg Tyr
            100                 105                 110

Ala Ile Gln Gly Leu Lys Trp Gln His Asn Glu Ile Thr Phe Cys Ile
        115                 120                 125

Gln Asn Tyr Thr Pro Lys Val Gly Glu Tyr Ala Thr Tyr Glu Ala Ile
    130                 135                 140

Arg Lys Ala Phe Arg Val Trp Glu Ser Ala Thr Pro Leu Arg Phe Arg
145                 150                 155                 160

Glu Val Pro Tyr Ala Tyr Ile Arg Glu Gly His Glu Lys Gln Ala Asp
                165                 170                 175

Ile Met Ile Phe Phe Ala Glu Gly Phe His Gly Asp Ser Thr Pro Phe
            180                 185                 190

Asp Gly Glu Gly Gly Phe Leu Ala His Ala Tyr Phe Pro Gly Pro Asn
        195                 200                 205

Ile Gly Gly Asp Thr His Phe Asp Ser Ala Glu Pro Trp Thr Val Arg
    210                 215                 220

Asn Glu Asp Leu Asn Gly Asn Asp Ile Phe Leu Val Ala Val His Glu
225                 230                 235                 240

Leu Gly His Ala Leu Gly Leu Glu His Ser Ser Asp Pro Ser Ala Ile
                245                 250                 255

Met Ala Pro Phe Tyr Gln Trp Met Asp Thr Glu Asn Phe Val Leu Pro
            260                 265                 270

Asp Asp Asp Arg Arg Gly Ile Gln Gln Leu Tyr Gly Gly Glu Ser Gly
        275                 280                 285

Phe Pro Thr Lys Met Pro Pro Gln Pro Arg Thr Thr Ser Arg Pro Ser
    290                 295                 300

Val Pro Asp Lys Pro Lys Asn Pro Thr Tyr Gly Pro Asn Ile Cys Asp
305                 310                 315                 320

Gly Asn Phe Asp Thr Val Ala Met Leu Arg Gly Glu Met Phe Val Phe
                325                 330                 335

Lys Glu Arg Trp Phe Trp Arg Val Arg Asn Asn Gln Val Met Asp Gly
            340                 345                 350

Tyr Pro Met Pro Ile Gly Gln Phe Trp Arg Gly Leu Pro Ala Ser Ile
        355                 360                 365

Asn Thr Ala Tyr Glu Arg Lys Asp Gly Lys Phe Val Phe Phe Lys Gly
    370                 375                 380

Asp Lys His Trp Val Phe Asp Glu Ala Ser Leu Glu Pro Gly Tyr Pro
385                 390                 395                 400

Lys His Ile Lys Glu Leu Gly Arg Gly Leu Pro Thr Asp Lys Ile Asp
                405                 410                 415

Ala Ala Leu Phe Trp Met Pro Asn Gly Lys Thr Tyr Phe Phe Arg Gly
            420                 425                 430

Asn Lys Tyr Tyr Arg Phe Asn Glu Glu Leu Arg Ala Val Asp Ser Glu
        435                 440                 445
```

```
Tyr Pro Lys Asn Ile Lys Val Trp Glu Gly Ile Pro Glu Ser Pro Arg
        450                 455                 460

Gly Ser Phe Met Gly Ser Asp Glu Val Phe Thr Tyr Phe Tyr Lys Gly
465                 470                 475                 480

Asn Lys Tyr Trp Lys Phe Asn Asn Gln Lys Leu Lys Val Glu Pro Gly
                485                 490                 495

Tyr Pro Lys Ser Ala Leu Arg Asp Trp Met Gly Cys Pro Ser Gly Gly
            500                 505                 510

Arg Pro Asp Glu Gly Thr Glu Glu Thr Glu Val Ile Ile Ile Glu
                515                 520                 525

Val Asp Glu Glu Gly Gly Ala Val Ser Ala Ala Val Val Leu
    530                 535                 540

Pro Val Leu Leu Leu Leu Val Leu Ala Val Gly Leu Ala Val Phe
545                 550                 555                 560

Phe Phe Arg Arg His Gly Thr Pro Arg Arg Leu Leu Tyr Cys Gln Arg
                565                 570                 575

Ser Leu Leu Asp
            580

<210> SEQ ID NO 2
<211> LENGTH: 582
<212> TYPE: PRT
<213> ORGANISM: Homo sapiens

<400> SEQUENCE: 2

Met Ser Pro Ala Pro Arg Pro Pro Arg Cys Leu Leu Leu Pro Leu Leu
1               5                   10                  15

Thr Leu Gly Thr Ala Leu Ala Ser Leu Gly Ser Ala Gln Ser Ser Ser
            20                  25                  30

Phe Ser Pro Glu Ala Trp Leu Gln Gln Tyr Gly Tyr Leu Pro Pro Gly
        35                  40                  45

Asp Leu Arg Thr His Thr Gln Arg Ser Pro Gln Ser Leu Ser Ala Ala
    50                  55                  60

Ile Ala Ala Met Gln Lys Phe Tyr Gly Leu Gln Val Thr Gly Lys Ala
65                  70                  75                  80

Asp Ala Asp Thr Met Lys Ala Met Arg Arg Pro Arg Cys Gly Val Pro
                85                  90                  95

Asp Lys Phe Gly Ala Glu Ile Lys Ala Asn Val Arg Arg Lys Arg Tyr
            100                 105                 110

Ala Ile Gln Gly Leu Lys Trp Gln His Asn Glu Ile Thr Phe Cys Ile
        115                 120                 125

Gln Asn Tyr Thr Pro Lys Val Gly Glu Tyr Ala Thr Tyr Glu Ala Ile
    130                 135                 140

Arg Lys Ala Phe Arg Val Trp Glu Ser Ala Thr Pro Leu Arg Phe Arg
145                 150                 155                 160

Glu Val Pro Tyr Ala Tyr Ile Arg Glu Gly His Glu Lys Gln Ala Asp
                165                 170                 175

Ile Met Ile Phe Phe Ala Glu Gly Phe His Gly Asp Ser Thr Pro Phe
            180                 185                 190

Asp Gly Glu Gly Gly Phe Leu Ala His Ala Tyr Phe Pro Gly Pro Asn
        195                 200                 205

Ile Gly Gly Asp Thr His Phe Asp Ser Ala Glu Pro Trp Thr Val Arg
    210                 215                 220

Asn Glu Asp Leu Asn Gly Asn Asp Ile Phe Leu Val Ala Val His Glu
```

-continued

```
             225                 230                 235                 240

Leu Gly His Ala Leu Gly Leu Glu His Ser Ser Asp Pro Ser Ala Ile
                245                 250                 255

Met Ala Pro Phe Tyr Gln Trp Met Asp Thr Glu Asn Phe Val Leu Pro
                260                 265                 270

Asp Asp Arg Arg Gly Ile Gln Gln Leu Tyr Gly Gly Glu Ser Gly
                275                 280                 285

Phe Pro Thr Lys Met Pro Gln Pro Arg Thr Thr Ser Arg Pro Ser
    290                 295                 300

Val Pro Asp Lys Pro Lys Asn Pro Thr Tyr Gly Pro Asn Ile Cys Asp
305                 310                 315                 320

Gly Asn Phe Asp Thr Val Ala Met Leu Arg Gly Glu Met Phe Val Phe
                325                 330                 335

Lys Glu Arg Trp Phe Trp Arg Val Arg Asn Asn Gln Val Met Asp Gly
                340                 345                 350

Tyr Pro Met Pro Ile Gly Gln Phe Trp Arg Gly Leu Pro Ala Ser Ile
                355                 360                 365

Asn Thr Ala Tyr Glu Arg Lys Asp Gly Lys Phe Val Phe Phe Lys Gly
                370                 375                 380

Asp Lys His Trp Val Phe Asp Glu Ala Ser Leu Glu Pro Gly Tyr Pro
385                 390                 395                 400

Lys His Ile Lys Glu Leu Gly Arg Gly Leu Pro Thr Asp Lys Ile Asp
                405                 410                 415

Ala Ala Leu Phe Trp Met Pro Asn Gly Lys Thr Tyr Phe Phe Arg Gly
                420                 425                 430

Asn Lys Tyr Tyr Arg Phe Asn Glu Glu Leu Arg Ala Val Asp Ser Glu
                435                 440                 445

Tyr Pro Lys Asn Ile Lys Val Trp Glu Gly Ile Pro Glu Ser Pro Arg
                450                 455                 460

Gly Ser Phe Met Gly Ser Asp Glu Val Phe Thr Tyr Phe Tyr Lys Gly
465                 470                 475                 480

Asn Lys Tyr Trp Lys Phe Asn Asn Gln Lys Leu Lys Val Glu Pro Gly
                485                 490                 495

Tyr Pro Lys Ser Ala Leu Arg Asp Trp Met Gly Cys Pro Ser Gly Gly
                500                 505                 510

Arg Pro Asp Glu Gly Thr Glu Glu Thr Glu Val Ile Ile Ile Glu
                515                 520                 525

Val Asp Glu Glu Gly Gly Gly Ala Val Ser Ala Ala Val Val Leu
                530                 535                 540

Pro Val Leu Leu Leu Leu Leu Val Leu Ala Val Gly Leu Ala Val Phe
545                 550                 555                 560

Phe Phe Arg Arg His Gly Thr Pro Arg Arg Leu Leu Tyr Cys Gln Arg
                565                 570                 575

Ser Leu Leu Asp Lys Val
                580

<210> SEQ ID NO 3
<211> LENGTH: 580
<212> TYPE: PRT
<213> ORGANISM: Mus musculus

<400> SEQUENCE: 3

Met Ser Pro Ala Pro Arg Pro Ser Arg Ser Leu Leu Leu Pro Leu Leu
 1               5                  10                  15
```

-continued

```
Thr Leu Gly Thr Ala Leu Ala Ser Leu Gly Trp Ala Gln Gly Ser Asn
            20                  25                  30
Phe Ser Pro Glu Ala Trp Leu Gln Gln Tyr Gly Tyr Leu Pro Pro Gly
        35                  40                  45
Asp Leu Arg Thr His Thr Gln Arg Ser Pro Gln Ser Leu Ser Ala Ala
    50                  55                  60
Ile Ala Ala Met Gln Lys Phe Tyr Gly Leu Gln Val Thr Gly Lys Ala
65                  70                  75                  80
Asp Leu Ala Thr Met Met Ala Met Arg Arg Pro Arg Cys Gly Val Pro
            85                  90                  95
Asp Lys Phe Gly Thr Glu Ile Lys Ala Asn Val Arg Arg Lys Arg Tyr
        100                 105                 110
Ala Ile Gln Gly Leu Lys Trp Gln His Asn Glu Ile Thr Phe Cys Ile
    115                 120                 125
Gln Asn Tyr Thr Pro Lys Val Gly Glu Tyr Ala Thr Phe Glu Ala Ile
130                 135                 140
Arg Lys Ala Phe Arg Val Trp Glu Ser Ala Thr Pro Leu Arg Phe Arg
145                 150                 155                 160
Glu Val Pro Tyr Ala Tyr Ile Arg Glu Gly His Glu Lys Gln Ala Asp
            165                 170                 175
Ile Met Ile Leu Phe Ala Glu Gly Phe His Gly Asp Ser Thr Pro Phe
        180                 185                 190
Asp Gly Glu Gly Gly Phe Leu Ala His Ala Tyr Phe Pro Gly Pro Asn
    195                 200                 205
Ile Gly Gly Asp Thr His Phe Asp Ser Ala Glu Pro Trp Thr Val Gln
210                 215                 220
Asn Glu Asp Leu Asn Gly Asn Asp Ile Phe Leu Val Ala Val His Glu
225                 230                 235                 240
Leu Gly His Ala Leu Gly Leu Glu His Ser Asn Asp Pro Ser Ala Ile
            245                 250                 255
Met Ser Pro Phe Tyr Gln Trp Met Asp Thr Glu Asn Phe Val Leu Pro
        260                 265                 270
Asp Asp Asp Arg Arg Gly Ile Gln Gln Leu Tyr Gly Ser Lys Ser Gly
    275                 280                 285
Ser Pro Thr Lys Met Pro Pro Gln Pro Arg Thr Thr Ser Arg Pro Ser
290                 295                 300
Val Pro Asp Lys Pro Lys Asn Pro Ala Tyr Gly Pro Asn Ile Cys Asp
305                 310                 315                 320
Gly Asn Phe Asp Thr Val Ala Met Leu Arg Gly Glu Met Phe Val Phe
            325                 330                 335
Lys Glu Arg Trp Phe Trp Arg Val Arg Asn Asn Gln Val Met Asp Gly
        340                 345                 350
Tyr Pro Met Pro Ile Gly Gln Phe Trp Arg Gly Leu Pro Ala Ser Ile
    355                 360                 365
Asn Thr Ala Tyr Glu Arg Lys Asp Gly Lys Phe Val Phe Phe Lys Gly
370                 375                 380
Asp Lys His Trp Val Phe Asp Glu Ala Ser Leu Glu Pro Gly Tyr Pro
385                 390                 395                 400
Lys His Ile Lys Glu Leu Gly Arg Gly Leu Pro Thr Asp Lys Ile Asp
            405                 410                 415
Ala Ala Leu Phe Trp Met Pro Asn Gly Lys Thr Tyr Phe Phe Arg Gly
        420                 425                 430
Asn Lys Tyr Tyr Arg Phe Asn Glu Glu Phe Arg Ala Val Asp Ser Glu
```

```
                    435                 440                 445
Tyr Pro Lys Asn Ile Lys Val Trp Glu Gly Ile Pro Glu Ser Pro Arg
    450                 455                 460

Gly Ser Phe Met Gly Ser Asp Glu Val Phe Thr Tyr Phe Tyr Lys Gly
465                 470                 475                 480

Asn Lys Tyr Trp Lys Phe Asn Asn Gln Lys Leu Lys Val Glu Pro Gly
                485                 490                 495

Tyr Pro Lys Ser Ala Leu Arg Asp Trp Met Gly Cys Pro Ser Gly Arg
        500                 505                 510

Arg Pro Asp Glu Gly Thr Glu Glu Thr Glu Val Ile Ile Ile Glu
        515                 520                 525

Val Asp Glu Glu Gly Ser Gly Ala Val Ser Ala Ala Val Val Leu
    530                 535                 540

Pro Val Leu Leu Leu Leu Val Leu Ala Val Gly Leu Ala Val Phe
545                 550                 555                 560

Phe Phe Arg Arg His Gly Thr Pro Lys Arg Leu Leu Tyr Cys Gln Arg
                565                 570                 575

Ser Leu Leu Asp
            580

<210> SEQ ID NO 4
<211> LENGTH: 582
<212> TYPE: PRT
<213> ORGANISM: Mus musculus

<400> SEQUENCE: 4

Met Ser Pro Ala Pro Arg Pro Ser Arg Ser Leu Leu Pro Leu Leu
  1               5                  10                  15

Thr Leu Gly Thr Ala Leu Ala Ser Leu Gly Trp Ala Gln Gly Ser Asn
                 20                  25                  30

Phe Ser Pro Glu Ala Trp Leu Gln Gln Tyr Gly Tyr Leu Pro Pro Gly
             35                  40                  45

Asp Leu Arg Thr His Thr Gln Arg Ser Pro Gln Ser Leu Ser Ala Ala
         50                  55                  60

Ile Ala Ala Met Gln Lys Phe Tyr Gly Leu Gln Val Thr Gly Lys Ala
 65                  70                  75                  80

Asp Leu Ala Thr Met Met Ala Met Arg Arg Pro Arg Cys Gly Val Pro
                 85                  90                  95

Asp Lys Phe Gly Thr Glu Ile Lys Ala Asn Val Arg Arg Lys Arg Tyr
            100                 105                 110

Ala Ile Gln Gly Leu Lys Trp Gln His Asn Glu Ile Thr Phe Cys Ile
        115                 120                 125

Gln Asn Tyr Thr Pro Lys Val Gly Glu Tyr Ala Thr Phe Glu Ala Ile
    130                 135                 140

Arg Lys Ala Phe Arg Val Trp Glu Ser Ala Thr Pro Leu Arg Phe Arg
145                 150                 155                 160

Glu Val Pro Tyr Ala Tyr Ile Arg Glu Gly His Glu Lys Gln Ala Asp
                165                 170                 175

Ile Met Ile Leu Phe Ala Glu Gly Phe His Gly Asp Ser Thr Pro Phe
            180                 185                 190

Asp Gly Glu Gly Gly Phe Leu Ala His Ala Tyr Phe Pro Gly Pro Asn
        195                 200                 205

Ile Gly Gly Asp Thr His Phe Asp Ser Ala Glu Pro Trp Thr Val Gln
    210                 215                 220
```

-continued

Asn Glu Asp Leu Asn Gly Asn Asp Ile Phe Leu Val Ala Val His Glu
225                 230                 235                 240

Leu Gly His Ala Leu Gly Leu Glu His Ser Asn Asp Pro Ser Ala Ile
            245                 250                 255

Met Ser Pro Phe Tyr Gln Trp Met Asp Thr Glu Asn Phe Val Leu Pro
        260                 265                 270

Asp Asp Asp Arg Arg Gly Ile Gln Gln Leu Tyr Gly Ser Lys Ser Gly
        275                 280                 285

Ser Pro Thr Lys Met Pro Pro Gln Pro Arg Thr Thr Ser Arg Pro Ser
    290                 295                 300

Val Pro Asp Lys Pro Lys Asn Pro Ala Tyr Gly Pro Asn Ile Cys Asp
305                 310                 315                 320

Gly Asn Phe Asp Thr Val Ala Met Leu Arg Gly Glu Met Phe Val Phe
                325                 330                 335

Lys Glu Arg Trp Phe Trp Arg Val Arg Asn Asn Gln Val Met Asp Gly
            340                 345                 350

Tyr Pro Met Pro Ile Gly Gln Phe Trp Arg Gly Leu Pro Ala Ser Ile
        355                 360                 365

Asn Thr Ala Tyr Glu Arg Lys Asp Gly Lys Phe Val Phe Phe Lys Gly
    370                 375                 380

Asp Lys His Trp Val Phe Asp Glu Ala Ser Leu Glu Pro Gly Tyr Pro
385                 390                 395                 400

Lys His Ile Lys Glu Leu Gly Arg Gly Leu Pro Thr Asp Lys Ile Asp
                405                 410                 415

Ala Ala Leu Phe Trp Met Pro Asn Gly Lys Thr Tyr Phe Phe Arg Gly
            420                 425                 430

Asn Lys Tyr Tyr Arg Phe Asn Glu Glu Phe Arg Ala Val Asp Ser Glu
        435                 440                 445

Tyr Pro Lys Asn Ile Lys Val Trp Glu Gly Ile Pro Glu Ser Pro Arg
    450                 455                 460

Gly Ser Phe Met Gly Ser Asp Glu Val Phe Thr Tyr Phe Tyr Lys Gly
465                 470                 475                 480

Asn Lys Tyr Trp Lys Phe Asn Asn Gln Lys Leu Lys Val Glu Pro Gly
                485                 490                 495

Tyr Pro Lys Ser Ala Leu Arg Asp Trp Met Gly Cys Pro Ser Gly Arg
            500                 505                 510

Arg Pro Asp Glu Gly Thr Glu Glu Thr Glu Val Ile Ile Ile Glu
        515                 520                 525

Val Asp Glu Glu Gly Ser Gly Ala Val Ser Ala Ala Ala Val Val Leu
530                 535                 540

Pro Val Leu Leu Leu Leu Leu Val Leu Ala Val Gly Leu Ala Val Phe
545                 550                 555                 560

Phe Phe Arg Arg His Gly Thr Pro Lys Arg Leu Leu Tyr Cys Gln Arg
                565                 570                 575

Ser Leu Leu Asp Lys Val
            580

<210> SEQ ID NO 5
<211> LENGTH: 58
<212> TYPE: PRT
<213> ORGANISM: Artificial Sequence
<220> FEATURE:
<223> OTHER INFORMATION: Naturally occurring peptide

<400> SEQUENCE: 5

```
Met His Ser Phe Cys Ala Phe Lys Ala Glu Thr Gly Pro Cys Arg Ala
 1               5                  10                  15

Arg Phe Asp Arg Trp Phe Phe Asn Ile Phe Thr Arg Gln Cys Glu Glu
             20                  25                  30

Phe Ile Tyr Gly Gly Cys Glu Gly Asn Gln Asn Arg Phe Glu Ser Leu
             35                  40                  45

Glu Glu Cys Lys Lys Met Cys Thr Arg Asp
 50                  55
```

<210> SEQ ID NO 6
<211> LENGTH: 330
<212> TYPE: DNA
<213> ORGANISM: Artificial Sequence
<220> FEATURE:
<223> OTHER INFORMATION: Synthetically generated oligonucleotide

<400> SEQUENCE: 6

```
cagagcgaat tgactcagcc accctcagcg tctgggaccc ccgggcagag ggtcactatc    60
tcttgttctg gaagcagctc caacatcgga attaattttg ttacctggta ccagcagctc   120
ccaggaacgg ccccccaaact cctcatctat actaataatc agcggccctc tggggtccct   180
gaccgattct ctagctccaa gtctggcgcc tcagcctccc tggccatcag tgggctccag   240
tctgaggatg aggctgctta ttactgtgca gcatgggatg acaacctgaa cggtccggtg   300
ttcggcggcg ggaccaagct gaccgtccta                                    330
```

<210> SEQ ID NO 7
<211> LENGTH: 366
<212> TYPE: DNA
<213> ORGANISM: Artificial Sequence
<220> FEATURE:
<223> OTHER INFORMATION: Synthetically generated oligonucleotide

<400> SEQUENCE: 7

```
gaagttcaat tgttagagtc tggtggcggt cttgttcagc ctggtggttc tttacgtctt    60
tcttgcgctg cttccggatt cactttctct gtttacgaga tgaattgggt tcgccaagct   120
cctggtaaag gtttggagtg ggtttcttct atctattctt ctggtggccg tactgattat   180
gctgactccg ttaaaggtcg cttcactatc tctagagaca actctaagaa tactctctac   240
ttgcagatga acagcttaag ggctgaggac acggccgtgt attactgtgc gagagaggcc   300
cattactatg atagtagtgg tccgcctgac tactggggcc agggaaccct ggtcaccgtc   360
tcaagc                                                              366
```

<210> SEQ ID NO 8
<211> LENGTH: 323
<212> TYPE: DNA
<213> ORGANISM: Artificial Sequence
<220> FEATURE:
<223> OTHER INFORMATION: Synthetically generated oligonucleotide

<400> SEQUENCE: 8

```
caagacatcc agatgaccca gtctccatcc tccctgtctg catctgtagg agacagagtc    60
accatgactt gccgggcagg tcagaacatt aaatcctatt taaattggta tcagcagaag   120
ccagggaaag cccctcaggt cctgatctat gctgcatcca ctttacaaag tggggtctca   180
tcaaggttcc gtggcagtgg atctgggaca catttcactc tcaccatcag cgatctgcaa   240
cctggagatt ctgcgactta ctactgtcaa caaagtttca gtaccctcg cagttttggc    300 caggggacaa gctggagatc aaa                                           323
```

<210> SEQ ID NO 9
<211> LENGTH: 381
<212> TYPE: DNA
<213> ORGANISM: Artificial Sequence
<220> FEATURE:
<223> OTHER INFORMATION: Synthetically generated oligonucleotide

<400> SEQUENCE: 9

```
gaagttcaat tgttagagtc tggtggcggt cttgttcagc ctggtggttc tttacgtctt    60
tcttgcgctg cttccggatt cactttctct atttaccaga tgtattgggt tcgccaagct   120
cctggtaaag gtttggagtg ggtttcttct atcgttcctt ctggtggcct tactaagtat   180
gctgactccg ttaaaggtcg cttcactatc tctagagaca actctaagaa tactctctac   240
ttgcagatga acagcttaag ggctgaggac acggccgtgt attactgtgc gagagagaga   300
ttacgatatt ttgactggtc agatcgtgtg ggggaatcgg gtgactactg gggccaggga   360
accctggtca ccgtctcaag c                                             381
```

<210> SEQ ID NO 10
<211> LENGTH: 323
<212> TYPE: DNA
<213> ORGANISM: Artificial Sequence
<220> FEATURE:
<223> OTHER INFORMATION: Synthetically generated oligonucleotide

<400> SEQUENCE: 10

```
caagacatcc agatgaccca gtctccatcc tccctgtctg catctgtagg agacagagtc    60
accgtcactt gccgggaagt cagagcatta gcagttattt aaattggtat cagcagaaac   120
cagggaaagc ccctaaactc ctgatctatg ctgcatccag tttgcaaagt ggggtcccat   180
caaggttcag tggcagtgga tctgggacag atttcactct caccatcagc agtctgcaac   240
ctgaagattt tgcaacttac tactgtcaac agagttacag tatcccgctc actttcggcg   300
gagggaccaa ggtggcgatc aaa                                           323
```

<210> SEQ ID NO 11
<211> LENGTH: 357
<212> TYPE: DNA
<213> ORGANISM: Artificial Sequence
<220> FEATURE:
<223> OTHER INFORMATION: Synthetically generated oligonucleotide

<400> SEQUENCE: 11

```
gaagttcaat tgttagagtc tggtggcggt cttgttcagc ctggtggttc tttacgtctt    60
tcttgcgctg cttccggatt cactttctct aattactgga tgctttgggt tcgccaagct   120
cctggtaaag gtttggagtg ggtttctggt atcgtttctt ctggtggccg tactaattat   180
gctgactccg ttaaaggtcg cttcactatc tctagagaca actctaagaa tactctctac   240
ttgcagatga acagcttaag ggctgaggac acggccgtgt attactgtgc gaggtttagc   300
agctcgttag ggcttttga tatctggggc caagggacaa tggtcaccgt ctcaagc       357
```

<210> SEQ ID NO 12
<211> LENGTH: 330
<212> TYPE: DNA
<213> ORGANISM: Artificial Sequence
<220> FEATURE:
<223> OTHER INFORMATION: Synthetically generated oligonucleotide

<400> SEQUENCE: 12

```
caagacatcc agatgaccca gtctccaggc accctgtcat tgtctccagg ggaaagagcc    60
accctctcct gcagggccag tcagagtctt aggaacagct acttagcctg gtatcagcag   120
aaacctggcc aggctcccag gctcctcatc tatgatgcat ccaacagggc cactggcatc   180
ccagccaggt tcagtggcag tgggtctggg acagacttca ctctcaccat cagcagccta   240
gagcctgaag attttgcagt ttattactgt cagcagcgta gcaactggcc tccgtacact   300
tttggccagg ggaccaagct ggagatcaaa                                    330

<210> SEQ ID NO 13
<211> LENGTH: 363
<212> TYPE: DNA
<213> ORGANISM: Artificial Sequence
<220> FEATURE:
<223> OTHER INFORMATION: Synthetically generated oligonucleotide

<400> SEQUENCE: 13
gaagttcaat tgttagagtc tggtggcggt cttgttcagc ctggtggttc tttacgtctt    60
tcttgcgctg cttccggatt cactttctct aattacgtta tgctttgggt tcgccaagct   120
cctggtaaag gtttggagtg gtttcttcct atccgtcctt ctggtggccc tactaagtat   180
gctgactccg ttaaaggtcg cttcactatc tctagagaca actctaagaa tactctctac   240
ttgcagatga acagcttaag ggctgaggac acggccgtgt attactgtgc tagggactgg   300
ccctcttact actactacgg tatggacgtc tggggccaag gaccacggt caccgtctca   360 agc                                                                363

<210> SEQ ID NO 14
<211> LENGTH: 339
<212> TYPE: DNA
<213> ORGANISM: Artificial Sequence
<220> FEATURE:
<223> OTHER INFORMATION: Synthetically generated oligonucleotide

<400> SEQUENCE: 14
caagacatcc agatgaccca gtctccactc tccctgcccg tcaccctgg agagccggcc    60 tccatctcct gcaggtctag tcagagcctc ctgcatagta tggatacta ctatttggat   120 tggtacctgc agaagccagg gcagtctcca caactcctga tctatttggg ttcttatcgg   180
gcctccgggg tccctgacag gttcagtggc agtggatcag gcacagattt tacactgaaa   240
atcagcagtg tggaggctga agatgttggg gtttattact gcatgcaagc tctacaaact   300
cctctcactt tcggcggagg gaccagggtg gacatcaaa                          339

<210> SEQ ID NO 15
<211> LENGTH: 378
<212> TYPE: DNA
<213> ORGANISM: Artificial Sequence
<220> FEATURE:
<223> OTHER INFORMATION: Synthetically generated oligonucleotide

<400> SEQUENCE: 15
gaagttcaat tgttagagtc tggtggcggt cttgttcagc ctggtggttc tttacgtctt    60
tcttgcgctg cttccggatt cactttctct ccttacccta tgggttgggt tcgccaagct   120
cctggtaaag gtttggagtg gtttcttcct atcgtttctt ctggtggcct tactctttat   180
gctgactccg ttaaaggtcg cttcactatc tctagagaca actctaagaa tactctctac   240
ttgcagatga acagcttaag ggctgaggac actgccgtgt attactgtgc gagaggggga   300
cggctttacg atattttgac tggtcaaggg gccccgtttg actactgggg ccagggaacc   360
```
ctggtcaccg tctcaagc                                                    378

<210> SEQ ID NO 16
<211> LENGTH: 333
<212> TYPE: DNA
<213> ORGANISM: Artificial Sequence
<220> FEATURE:
<223> OTHER INFORMATION: Synthetically generated oligonucleotide

<400> SEQUENCE: 16
cagagcgaat tgactcagcc accctcagtg tctgggaccc ccgggcagag ggtcaccatc      60
tcttgttctg gaaccagcgc caacatcgga cgtaatgctg tacactggta ccagcagctc     120
ccaggaacgg cccccaaact cctcattcat agtaataacc ggcggccctc agggtccct      180 gaccgattct ctggctccaa gtctggcacc tcagcctccc tggccatcag tgggctccag     240
tctgaggatg aggctgatta ttactgtgca gcatgggaga acagcctgaa tgccttttat     300
gtcttcggaa ctgggaccaa ggtcaccgtc cta                                  333

<210> SEQ ID NO 17
<211> LENGTH: 375
<212> TYPE: DNA
<213> ORGANISM: Artificial Sequence
<220> FEATURE:
<223> OTHER INFORMATION: Synthetically generated oligonucleotide

<400> SEQUENCE: 17
gaagttcaat tgttagagtc tggtggcggt cttgttcagc ctggtggttc tttacgtctt      60
tcttgcgctg cttccggatt cactttctct acttacgaga tgcattgggt tcgccaagct     120
cctggtaaag gtttggagtg ggtttcttct atctattctt ctggtggctg gactggttat     180
gctgactccg ttaaaggtcg cttcactatc tctagagaca actctaagaa tactctctac     240
ttgcagatga acagcttaag ggctgaggac acggccgtgt attactgtgc gagatctcaa     300
cagtattacg attttttcctc tcgctactac ggcatggacg tctggggcca agggaccacg     360
gtcaccgtct caagc                                                      375

<210> SEQ ID NO 18
<211> LENGTH: 324
<212> TYPE: DNA
<213> ORGANISM: Artificial Sequence
<220> FEATURE:
<223> OTHER INFORMATION: Synthetically generated oligonucleotide

<400> SEQUENCE: 18
caagacatcc agatgaccca gtctccatcc tccctgtctg catctgtagg agacagagtc      60
accatcactt gccgggcaag tcagagcatt agcagctatt taaattggta tcagcagaaa     120
ccagggaaag cccctaagct cctgatctat gctgcatcca gtttgcaaag tggggtccca     180
tcaaggttca gtggcagtgg atctgggaca gatttcactc tcaccatcag cagtctgcaa     240
cctgaagatt ttgcaaccta cttctgccaa cagagttata gtaatccttt cactttcggc     300
cctgggacca aagtggatat caaa                                            324

<210> SEQ ID NO 19
<211> LENGTH: 375
<212> TYPE: DNA
<213> ORGANISM: Artificial Sequence
<220> FEATURE:
<223> OTHER INFORMATION: Synthetically generated oligonucleotide -continued

```
<400> SEQUENCE: 19
gaagttcaat tgttagagtc tggtggcggt cttgttcagc ctggtggttc tttacgtctt    60
tcttgcgctg cttccggatt cactttctct cagtacgtta tgtggtgggt tcgccaagct   120
cctggtaaag gtttggagtg ggtttcttct atcgttcctt ctggtggcgt tactaagtat   180
gctgactccg ttaaaggtcg cttcactatc tctagagaca actctaagaa tactctctac   240
ttgcagatga acagcttaag ggctgaggac acggccgtgt attactgtgc gaaagacgtc   300
ttcggtagta ttggttatta ctacgtaccg ttttttgact actggggcca gggaaccctg   360
gtcaccgtct caagc                                                    375

<210> SEQ ID NO 20
<211> LENGTH: 327
<212> TYPE: DNA
<213> ORGANISM: Artificial Sequence
<220> FEATURE:
<223> OTHER INFORMATION: Synthetically generated oligonucleotide

<400> SEQUENCE: 20
cagagcgtct tgactcagga gccctcattg actgtgtccc caggagggac agtcactctc    60
acctgtgctt ccaacactgg agcagtcacc agtggttcct atgcaaactg gttccagcaa   120
aaacctggac taacacccag ggcactgatt tatagtggaa ctaacaaata ttcgtggacc   180
cctgcccgat tctcaggctc cctctttggg ggcaaggcag ccctgacact gtcaggtgtg   240
ctgcctgagg acgaggctga gtattactgc ctcgtcactact atggtggtgt ttgggtgttc   300
ggcggaggga ccaagctgac cgtccta                                       327

<210> SEQ ID NO 21
<211> LENGTH: 366
<212> TYPE: DNA
<213> ORGANISM: Artificial Sequence
<220> FEATURE:
<223> OTHER INFORMATION: Synthetically generated oligonucleotide

<400> SEQUENCE: 21
gaagttcaat tgttagagtc tggtggcggt cttgttcagc ctggtggttc tttacgtctt    60
tcttgcgctg cttccggatt cactttctct ccttacctta tgcattgggt tcgccaagct   120
cctggtaaag gtttggagtg ggtttcttct atctatcctt ctggtggcat tactcagtat   180
gctgactccg ttaaaggtcg cttcactatc tctagagaca actctaagaa tactctctac   240
ttgcagatga acagcttaag ggctgaggac acggccgtgt attactgtgc gagatttttc   300
cctagtcaca gggactatac ggcgttcgac acctggggcc ggggaaccct ggtcaccgtc   360
tcaagc                                                              366

<210> SEQ ID NO 22
<211> LENGTH: 324
<212> TYPE: DNA
<213> ORGANISM: Artificial Sequence
<220> FEATURE:
<223> OTHER INFORMATION: Synthetically generated oligonucleotide

<400> SEQUENCE: 22
caagacatcc agatgaccca gtctccatct tccgtgtctg catctgttgg agacacagtc    60
accatcacct gtcgggcgag tcagggtatt agcacctggt tagcctggta tcagcacaaa   120
ccagggaaag cccctaaact cctcatatat gctggaccca gtttgcagag tggggtccca   180
tcaaggttca gcggcagtgg atctgggaca gaattcactc tcacaatcag cagcctgcac   240
```

```
cctgaagatt ttgcaactta ttactgtcaa caacttaatc actacccgat gaccttcggc    300
caagggacac gactggagat taaa                                           324

<210> SEQ ID NO 23
<211> LENGTH: 354
<212> TYPE: DNA
<213> ORGANISM: Artificial Sequence
<220> FEATURE:
<223> OTHER INFORMATION: Synthetically generated oligonucleotide

<400> SEQUENCE: 23
gaagttcaat tgttagagtc tggtggcggt cttgttcagc ctggtggttc tttacgtctt     60
tcttgcgctg cttccggatt cactttctct atttacaaga tggtttgggt tcgccaagct    120
cctggtaaag gtttggagtg ggtttcttct atcggttctt ctggtggcca tactcgttat    180
gctgactccg ttaaaggtcg cttcactatc tctagagaca actctaagaa tactctctac    240
ttgcagatga acagcttaag ggctgaggac acggccgtgt attactgtgc gagagctcct    300
tactactact acatggacgt ctggggcaaa gggaccacgg tcaccgtctc aagc          354

<210> SEQ ID NO 24
<211> LENGTH: 328
<212> TYPE: DNA
<213> ORGANISM: Artificial Sequence
<220> FEATURE:
<223> OTHER INFORMATION: Synthetically generated oligonucleotide

<400> SEQUENCE: 24
cagagcgtct tgactcagcc tgcctccgtg tctgggtctc ctggacagtc gatcaccatc     60
tcctgcactg gaaccagcag tgacgttggt ggttataact atgtctcctg gtaccaacaa    120
cacccaggca agccccccaa actcatgatt tatgatgtca gtaatgggcc ctcagggggtt   180 tctaatcgcc tctctggctc caagtctggc aacacggcct ccctgaccat ctctgggctc    240
caggctgagg acgaggctga ttattactgc agctcatata caagcagcag cacaggtgtt    300
cggcggaggg accaagctga ccgtccta                                       328

<210> SEQ ID NO 25
<211> LENGTH: 354
<212> TYPE: DNA
<213> ORGANISM: Artificial Sequence
<220> FEATURE:
<223> OTHER INFORMATION: Synthetically generated oligonucleotide

<400> SEQUENCE: 25
gaagttcaat tgttagagtc tggtggcggt cttgttcagc ctggtggttc tttacgtctt     60
tcttgcgctg cttccggatt cactttctct cagtacgcta tgaattgggt tcgccaagct    120
cctggtaaag gtttggagtg ggtttcttgg atcgtttctt ctggtggcta tactcattat    180
gctgactccg ttaaaggtcg cttcactatc tctagagaca actctaagaa tactctctac    240
ttgcagatga acagcttaag ggctgaggac atgctgtgt attactgtgc gagcctcgta    300
gcagctcgta aacttgacta ctgggggccag ggcacccctgg tcaccgtctc aagc         354

<210> SEQ ID NO 26
<211> LENGTH: 324
<212> TYPE: DNA
<213> ORGANISM: Artificial Sequence
<220> FEATURE:
<223> OTHER INFORMATION: Synthetically generated oligonucleotide
```

```
<400> SEQUENCE: 26
caagacatcc agatgaccca gtctccatcc tccctgtctg catctgtagg agacagagtc    60
accatcactt gccgggcgag tcagggcatt aggaattttt tagcctggta tcagcagaaa   120
ccagggaaag ttcctaagct cctggtcttt ggtgcatccg ctttgcaatc ggggtccca    180 tctcggttca gtggcagtgg atctgggaca gatttcactc tcaccatcag cggcctgcag   240
cctgaggatg ttgcaactta ttactgtcaa aagtataacg gtgtcccgct cactttcggc   300
ggagggacca aggtggagat caaa                                         324

<210> SEQ ID NO 27
<211> LENGTH: 360
<212> TYPE: DNA
<213> ORGANISM: Artificial Sequence
<220> FEATURE:
<223> OTHER INFORMATION: Synthetically generated oligonucleotide

<400> SEQUENCE: 27
gaagttcaat tgttagagtc tggtggcggt cttgttcagc ctggtggttc tttacgtctt    60
tcttgcgctg cttccggatt cactttctct gtttacggta tggtttgggt tcgccaagct   120
cctggtaaag gtttggagtg gtttctgtt atctcttctt ctggtggctc tacttggtat   180
gctgactccg ttaaaggtcg cttcactatc tctagagaca actctaagaa tactctctac   240
ttgcagatga acagcttaag ggctgaggac accgccttgt attactgtgc gagaccgttc   300
agtagaagat acggcgtctt tgactactgg ggccagggca ccctggtcac cgtctcaagc   360

<210> SEQ ID NO 28
<211> LENGTH: 324
<212> TYPE: DNA
<213> ORGANISM: Artificial Sequence
<220> FEATURE:
<223> OTHER INFORMATION: Synthetically generated oligonucleotide

<400> SEQUENCE: 28
caagacatcc agatgaccca gtctccagcc accctgtctt tgtctccagg ggaaagagcc    60
accctctcct gcagggccag tcagagtgtt agcaattact tagcctggta ccaacaaaaa   120
cctggccagg ctcccaggct cctcatctat gatgcatcca cagggccac tggcatccca    180 gccaggttca gtggcagtgg gtctgggaca gacttcactc tcaccatcag cagcctagag   240
cctgaagatt ttgcagttta ttactgtcag cagcgtagca actggccgct cactttcggc   300
ggagggacca aggtggagat caaa                                         324

<210> SEQ ID NO 29
<211> LENGTH: 390
<212> TYPE: DNA
<213> ORGANISM: Artificial Sequence
<220> FEATURE:
<223> OTHER INFORMATION: Synthetically generated oligonucleotide

<400> SEQUENCE: 29
gaagttcaat tgttagagtc tggtggcggt cttgttcagc ctggtggttc tttacgtctt    60
tcttgcgctg cttccggatt cactttctct ttttaccgta tggagtgggt tcgccaagct   120
cctggtaaag gtttggagtg gtttcttcct atcgttcctt ctggtggctt tactcgttat   180
gctgactccg ttaaaggtcg cttcactatc tctagagaca actctaagaa tactctctac   240
ttgcagatga acagcttaag ggctgaggac acggccgtgt attactgtgc gagatttcac   300
gtattacgat attttgactg gtttggtaac acccaggata ctgatgcttt tgatatctgg   360
```

```
ggccagggca ccctggtcac cgtctcaagc                                       390

<210> SEQ ID NO 30
<211> LENGTH: 324
<212> TYPE: DNA
<213> ORGANISM: Artificial Sequence
<220> FEATURE:
<223> OTHER INFORMATION: Synthetically generated oligonucleotide

<400> SEQUENCE: 30
caagacatcc agatgaccca gtctccagcc accctgtctt tgtctccagg ggaaaaagcc        60
accctctcct gcagggccag tcagactgtt acaactact agcctggta ccagcaaaaa         120 cctggccagg ctcccaggct cctcatctat gacgcattca acagggccac tggcatccct       180
gccaggttca gtggcagtgg gtctgggaca gacttcactc tcaccatcag cagcctggag       240
cctgaagatt ttgcagttta ttactgtcag cagcgtggca actggccccg gacgttcggc       300
caagggacca aggtggaaat caaa                                              324

<210> SEQ ID NO 31
<211> LENGTH: 366
<212> TYPE: DNA
<213> ORGANISM: Artificial Sequence
<220> FEATURE:
<223> OTHER INFORMATION: Synthetically generated oligonucleotide

<400> SEQUENCE: 31
gaagttcaat tgttagagtc tggtggcggt cttgttcagc ctggtggttc tttacgtctt        60
tcttgcgctg cttccggatt cactttctct ttttacaaga tgacttgggt tcgccaagct       120
cctggtaaag gtttggagtg ggtttctggt atctatcctt ctggtggccg tactgttat        180 gctgactccg ttaaaggtcg cttcactatc tctagagaca actctaagaa tactctctac       240
ttgcagatga acagcttaag ggctgaggac accgccatgt attactgtgc aagagggccc       300
cattactatg atagcccggg tgcttttgat atctggggcc aagggacaat ggtcaccgtc       360
tcaagc                                                                  366

<210> SEQ ID NO 32
<211> LENGTH: 318
<212> TYPE: DNA
<213> ORGANISM: Artificial Sequence
<220> FEATURE:
<223> OTHER INFORMATION: Synthetically generated oligonucleotide

<400> SEQUENCE: 32
cagtacgaat tgactcagcc accctcgttg tccgtgtccc caggacagac agccagcatc        60
acctgctctg gagagaaatt gggggaaaaa tttgcttcct ggtatcaacg gaggcccggc       120
cagtctcctc tattgatcat ctatcaggat aacaagcggc cctcagggat ccctgagcgg       180
ttctctggct ccaattctgg aaacacagcc gctctgacca tcacgggac ccaggctatg        240 gatgacgctg actattactg tcaggcgtgg gagagcacca cagcggtctt cggcggaggg       300
accaagttga ccgtcccta                                                    318

<210> SEQ ID NO 33
<211> LENGTH: 360
<212> TYPE: DNA
<213> ORGANISM: Artificial Sequence
<220> FEATURE:
<223> OTHER INFORMATION: Synthetically generated oligonucleotide
```

```
<400> SEQUENCE: 33
gaagttcaat tgttagagtc tggtggcggt cttgttcagc ctggtggttc tttacgtctt      60
tcttgcgctg cttccggatt cactttctct cgttacacta tggggttgggt tcgccaagct    120 cctggtaaag gtttggagtg ggtttctcgt atctattctt ctggtggcaa tactgtttat    180
gctgactccg ttaaaggtcg cttcactatc tctagagaca actctaagaa tactctctac    240
ttgcagatga acagcttaag ggctgaggac acagccacat attactgtgc acggacccgt    300
agagatggct acaacccctt tgactactgg ggccagggaa ccctggtcac cgtctcaagc    360

<210> SEQ ID NO 34
<211> LENGTH: 330
<212> TYPE: DNA
<213> ORGANISM: Artificial Sequence
<220> FEATURE:
<223> OTHER INFORMATION: Synthetically generated oligonucleotide

<400> SEQUENCE: 34
caagacatcc agatgaccca gtctccatcc tccctgtctg catctgtagg agacagagtc      60
accatcactt gccgggcaag tcagagcatt agcagctatt taaattggta tcagcagaaa    120
ccagggaaag cccctaagct cctgatctat gctgcatcca gtttgcaaag tggggtccca    180
tcaaggttca gtggcagtgg atctgggaca gatttcactc tcaccatcag cagtctgcaa    240
cctgaagatt ttgcaactta ctactgtcaa cagagttaca gtctccccgt gacgtttggc    300
caagggtcca aggtggaaat caaacgaact                                      330

<210> SEQ ID NO 35
<211> LENGTH: 357
<212> TYPE: DNA
<213> ORGANISM: Artificial Sequence
<220> FEATURE:
<223> OTHER INFORMATION: Synthetically generated oligonucleotide

<400> SEQUENCE: 35
gaagttcaat tgttagagtc tggtggcggt cttgttcagc ctggtggttc tttacgtctt      60
tcttgcgctg cttccggatt cactttctct cgttactgga tggtttgggt tcgccaagct    120
cctggtaaag gtttggagtg ggtttcttat atctattctt ctggtggcat gactggttat    180
gctgactccg ttaaaggtcg cttcactatc tctagagaca actctaagaa tactctctac    240
ttgcagatga acagcttaag ggctgaggac acggccgtgt attactgtgc aaggggggggg    300 gaatatagtg gtttcttagg ggtttgggggc cagggcaccc tggtcaccgt ctcaagc       357

<210> SEQ ID NO 36
<211> LENGTH: 324
<212> TYPE: DNA
<213> ORGANISM: Artificial Sequence
<220> FEATURE:
<223> OTHER INFORMATION: Synthetically generated oligonucleotide

<400> SEQUENCE: 36
caagacatcc agatgaccca gtctccatct tccgtgtctg cttctgtagg agacagagtc      60
accatcactt gtcgggcgag tcagggtgtt agcagttact tagcctggta tcagcagaaa    120
ccagggaaag cccctaagct cctgatctat ggtgcatcca ctttgcaaaa tggggtccca    180
tcaaggttca gcggcagtgg atctgggaca gatttcactc tcaccatcag cagcctgcag    240
cctgaagatt ttgcgactta ccattgtcaa caggttcaca gtttccctcc gacgttcggt    300
caggggacca aggtggaaat caaa                                            324
```

<210> SEQ ID NO 37
<211> LENGTH: 369
<212> TYPE: DNA
<213> ORGANISM: Artificial Sequence
<220> FEATURE:
<223> OTHER INFORMATION: Synthetically generated oligonucleotide

<400> SEQUENCE: 37

```
gaagttcaat tgttagagtc tggtggcggt cttgttcagc ctggtggttc tttacgtctt    60
tcttgcgctg cttccggatt cactttctct cattacatga tgatgtgggt tcgccaagct   120
cctggtaaag gtttggagtg ggtttctggt atctcttctt ctggtggccg tactggttat   180
gctgactccg ttaaaggtcg cttcactatc tctagagaca actctaagaa tactctctac   240
ttgcagatga acagcttaag ggctgaggac acggccgtgt attactgtgc gagtttcggg   300
aatagtggga gctactcttg gcgtgctttt gatatctggg gccaagggac cacggtcacc   360
gtctcaagc                                                          369
```

<210> SEQ ID NO 38
<211> LENGTH: 326
<212> TYPE: DNA
<213> ORGANISM: Artificial Sequence
<220> FEATURE:
<223> OTHER INFORMATION: Synthetically generated oligonucleotide

<400> SEQUENCE: 38

```
caagacatcc agatgaccca gtctccatcc tccctgtctg catctgtggg agacagagtc    60
gccatcactt gccgcgcaag tcagagcatc gacacctatt taaattggta tcagcagaaa   120
ccagggaaag cccctaaact cctgatctat gctgcatcca gtttggaaga cggggtccca   180
tcaagattca gtggcagtgg aactgggaca gatttcactc tcacatcaga agtctgcaac   240
ctgaagattt tgcaagttat ttctgtcaac agagctactc tagtccaggg atcactttcg   300
gccctgggac caaggtggag atcaaa                                       326
```

<210> SEQ ID NO 39
<211> LENGTH: 369
<212> TYPE: DNA
<213> ORGANISM: Artificial Sequence
<220> FEATURE:
<223> OTHER INFORMATION: Synthetically generated oligonucleotide

<400> SEQUENCE: 39

```
gaagttcaat tgttagagtc tggtggcggt cttgttcagc ctggtggttc tttacgtctt    60
tcttgcgctg cttccggatt cactttctct gtttactata tggggttgggt tcgccaagct   120
cctggtaaag gtttggagtg ggtttcttat atcggttctt ctggtggctg gactgagtat   180
gctgactccg ttaaaggtcg cttcactatc tctagagaca actctaagaa tactctctac   240
ttgcagatga acagcttaag ggctgaggac acggccgtgt attactgtgc gagagacctc   300
tcggcagtgg ctggtctagg gggtgctttt gatatctggg gccaagggac aatggtcacc   360
gtctcaagc                                                          369
```

<210> SEQ ID NO 40
<211> LENGTH: 327
<212> TYPE: DNA
<213> ORGANISM: Artificial Sequence
<220> FEATURE:
<223> OTHER INFORMATION: Synthetically generated oligonucleotide

<400> SEQUENCE: 40

```
caagacatcc agatgaccca gtctccatct tccgtgtctg catctgtagg agacagagtc      60
accatcactt gtcgggcgag tcagggtatt agcagctggt tagcctgta tcagcagaaa     120 ccagggaaag cccctaagct cctgatctat gctgcatcca gtttgcaaag tggggtccca    180
tcaaggttca gcggcagtgg atctgggaca gatttcactc tcaccatcag cagcctgcag    240
cctgaagatt ttgcaactta ctattgtcaa caggctaaca gttccccctt cgtaactttt    300
ggccagggga ccaagctgga gatcaaa                                         327
```

<210> SEQ ID NO 41
<211> LENGTH: 366
<212> TYPE: DNA
<213> ORGANISM: Artificial Sequence
<220> FEATURE:
<223> OTHER INFORMATION: Synthetically generated oligonucleotide

<400> SEQUENCE: 41

```
gaagttcaat tgttagagtc tggtggcggt cttgttcagc ctggtggttc tttacgtctt      60
tcttgcgctg cttccggatt cactttctct atgtacctta tgatttgggt tcgccaagct    120
cctggtaaag gtttggagtg ggtttctgtt atctcttctt ctggtggcca gactaaatat    180
gctgactccg ttaaaggtcg cttcactatc tctagagaca actctaagaa tactctctac    240
ttgcagatga acagcttaag ggctgaggac acggccgtgt attactgtgc gagaaccgat    300
ttgactggtt attcagcggg agcttttgat atctggggcc aagggacaat ggtcaccgtc    360
tcaagc                                                                366
```

<210> SEQ ID NO 42
<211> LENGTH: 339
<212> TYPE: DNA
<213> ORGANISM: Artificial Sequence
<220> FEATURE:
<223> OTHER INFORMATION: Synthetically generated oligonucleotide

<400> SEQUENCE: 42

```
caagacatcc agatgaccca gtctccactc tccctgcccg tcacccttgg agagtcggcc      60
tccgtctcct gcaggtctag tcagagcctc cttcatgaaa atggacacaa ctatttggat    120
tggtacctgc agaagccagg gcagtctcca cagctcctga tctatttggg ttctaatcgg    180
gcctccgggg tccctgacag gttcagtggc agtggatcag gcacagattt tacactgaaa    240
atcagcagag tggaggctga ggatgttggg gtttattact gcatgcaatc tctaaagact    300
cctccgacgt tcggcccagg gaccaaggtg gaaatcaaa                            339
```

<210> SEQ ID NO 43
<211> LENGTH: 375
<212> TYPE: DNA
<213> ORGANISM: Artificial Sequence
<220> FEATURE:
<223> OTHER INFORMATION: Synthetically generated oligonucleotide

<400> SEQUENCE: 43

```
gaagttcaat tgttagagtc tggtggcggt cttgttcagc ctggtggttc tttacgtctt      60
tcttgcgctg cttccggatt cactttctct cattacgaga tgttttgggt tcgccaagct    120
cctggtaaag gtttggagtg ggtttcttct atctctcctt ctggtggcca gactcattat    180
gctgactccg ttaaaggtcg cttcactatc tctagagaca actctaagaa tactctctac    240
ttgcagatga acagcttaag ggctgaggac actgccgtgt attactgtgc cacagatcgg    300
```

```
acgtattacg attttttggag tggttatggg cccctgtggt actggggcca gggaaccctg    360
gtcaccgtct caagc                                                      375

<210> SEQ ID NO 44
<211> LENGTH: 324
<212> TYPE: DNA
<213> ORGANISM: Artificial Sequence
<220> FEATURE:
<223> OTHER INFORMATION: Synthetically generated oligonucleotide

<400> SEQUENCE: 44
caagacatcc agatgaccca gtctccatcc tccctgtctg catctgtcgg agacagagtc    60
accatcactt gccgggcaag tcagggcatt agaaatgatt taggctggta tcagcagaaa    120
ccagggaaag cccctaagcg cctgatctat gttgcatcca gtttgcaaag tggggtccca    180
tcaaggttca gcggcagtgg atctgggaca gaattcactc tcacaatcag cagcctgcag    240
cctgaagatt ttgcaactta ttactgtcta cagcataata gttacccgtg gacgttcggc    300
caagggacca aggtggaaat caaa                                            324

<210> SEQ ID NO 45
<211> LENGTH: 375
<212> TYPE: DNA
<213> ORGANISM: Artificial Sequence
<220> FEATURE:
<223> OTHER INFORMATION: Synthetically generated oligonucleotide

<400> SEQUENCE: 45
gaagttcaat tgttagagtc tggtggcggt cttgttcagc ctggtggttc tttacgtctt    60
tcttgcgctg cttccggatt cactttctct atgtacatga tgatttgggt tcgccaagct    120
cctggtaaag gtttggagtg gtttcttcct atctatcctt ctggtggcaa tactatgtat    180
gctgactccg ttaaaggtcg cttcactatc tctagagaca actctaagaa tactctctac    240
ttgcagatga acagcttaag ggctgaggac acggccgtgt attactgtgc cacaggtgta    300
ttacgatatt ttgactggga tgctgggagc ggtatggacg tctggggcca agggaccacg    360
gtcaccgtct caagc                                                      375

<210> SEQ ID NO 46
<211> LENGTH: 339
<212> TYPE: DNA
<213> ORGANISM: Artificial Sequence
<220> FEATURE:
<223> OTHER INFORMATION: Synthetically generated oligonucleotide

<400> SEQUENCE: 46
caagacatcc agatgaccca gtctccactc tccctgcccg tcaccctgg agagccggcc     60 tccatctcct gcaggtctag tcagagcctc ctgcatggta atggaaacaa ctatttggat    120
tggtacctgc agaagccagg gcagtctcca caactcctga tctatttggg ttccaatcgg    180
gcctccgggg tccctgacag gttcagtggc agtggatcag gcacagattt tacactgaaa    240
atcagcagtg tggaggctga agatgttggc gtttattact gcatgcaagg tctacaaact    300
cctcacactt ttggccaggg gacccagctg gagatcaaa                            339

<210> SEQ ID NO 47
<211> LENGTH: 357
<212> TYPE: DNA
<213> ORGANISM: Artificial Sequence
<220> FEATURE:
```

<223> OTHER INFORMATION: Synthetically generated oligonucleotide

<400> SEQUENCE: 47

```
gaagttcaat tgttagagtc tggtggcggt cttgttcagc ctggtggttc tttacgtctt      60
tcttgcgctg cttccggatt cactttctct cgttactgga tggattgggt tcgccaagct     120
cctggtaaag gtttggagtg ggtttcttct atccgttctt ctggtggcat gactggttat     180
gctgactccg ttaaaggtcg cttcactatc tctagagaca actctaagaa tactctctac     240
ttgcagatga acagcttaag ggctgaggac acggccgtgt attactgtgc gagacaccgt     300
acgggccgcg gggcttttga tatctggggc caagggacca cggtcaccgt ctcaagc        357
```

<210> SEQ ID NO 48
<211> LENGTH: 324
<212> TYPE: DNA
<213> ORGANISM: Artificial Sequence
<220> FEATURE:
<223> OTHER INFORMATION: Synthetically generated oligonucleotide

<400> SEQUENCE: 48

```
caagacatcc agatgaccca gtctccatcc tccctgtctg catctgtagg agacagagtc      60
accatcactt gccgggcaag tcagagcatt agcagctatt taaattggta tcagcagaaa     120
ccagggaaag cccctaagct cctgatctat gctgcatcca gtttgcaaag tggggtccca     180
tcaaggttcc gtggcagtgg atctgggaca gatttcagtc tcaccatcag cagtctgcaa     240
cctgaagatt ttgcaactta ctactgtcaa cagacttaca gtggccttcc cactttggt     300
ggagggaccg tggtggagat caaa                                             324
```

<210> SEQ ID NO 49
<211> LENGTH: 354
<212> TYPE: DNA
<213> ORGANISM: Artificial Sequence
<220> FEATURE:
<223> OTHER INFORMATION: Synthetically generated oligonucleotide

<400> SEQUENCE: 49

```
gaagttcaat tgttagagtc tggtggcggt cttgttcagc ctggtggttc tttacgtctt      60
tcttgcgctg cttccggatt cactttctct tcttacgtta tggttgggt tcgccaagct     120
cctggtaaag gtttggagtg ggtttctgtt atctctcctt ctggtggctg gactacttat     180
gctgactccg ttaaaggtcg cttcactatc tctagagaca actctaagaa tactctctac     240
ttgcagatga acagcttaag ggctgaggac acagccacat attactgtgc gagtcgggga     300
gtggttacca accttgacta ctggggccag ggaaccctgg tcaccgtctc aagc           354
```

<210> SEQ ID NO 50
<211> LENGTH: 321
<212> TYPE: DNA
<213> ORGANISM: Artificial Sequence
<220> FEATURE:
<223> OTHER INFORMATION: Synthetically generated oligonucleotide

<400> SEQUENCE: 50

```
caagacatcc agatgaccca gtctccatcc tccctgtctg catctgtagg agacagagtc      60
accatcactt gccgggcaag tcagagcatt agcagctatt taaattggta tcagcagaaa     120
ccagggaaag cccctaagct cctgatctat gctgcatcca gtttgcaaag tggggtccca     180
tcaaggttca gtggcagtgg gtctgggaca gacttcactc tcaccatcag cagactggag     240
cctgaagatt ttgcagtgta ttattgtcag cagtatggta gctcacccac gttcggccaa     300
```

```
<210> SEQ ID NO 51
<211> LENGTH: 360
<212> TYPE: DNA
<213> ORGANISM: Artificial Sequence
<220> FEATURE:
<223> OTHER INFORMATION: Synthetically generated oligonucleotide

<400> SEQUENCE: 51
gaagttcaat tgttagagtc tggtggcggt cttgttcagc ctggtggttc tttacgtctt      60
tcttgcgctg cttccggatt cactttctct tcttacatta tggtttgggt tcgccaagct     120
cctggtaaag gtttggagtg ggtttctgtt atctatcctt ctggtggccc tacttattat     180
gctgactccg ttaaaggtcg cttcactatc tctagagaca actctaagaa tactctctac     240
ttgcagatga acagcttaag ggctgaggac acggccgtgt attactgtgc gagggacccc     300
cggctggaac gtttctactt tgactactgg ggccagggca ccctggtcac cgtctcaagc     360

<210> SEQ ID NO 52
<211> LENGTH: 327
<212> TYPE: DNA
<213> ORGANISM: Artificial Sequence
<220> FEATURE:
<223> OTHER INFORMATION: Synthetically generated oligonucleotide

<400> SEQUENCE: 52
caagacatcc agatgaccca gtctccaggc accctgtctt tgtctccagg ggacagagcc      60
accctctcct gcagggccag tcagagtgtt ggcagcgact acttagcctg gtaccagcag     120
aaacctggcc aggctcccag gctcctcatc tttgctgcgt ccaccagggc caccggcatc     180
ccagacaggt tcagtggcag tgggtctgcg acagacttca ctctcaccat cagcagcctg     240
gaacctgaag attttgcagt gtatttctgt cagcagtatg ctagcccacc tcggacgttc     300
ggccaaggga ccaaggtgga aatcaaa                                         327

<210> SEQ ID NO 53
<211> LENGTH: 345
<212> TYPE: DNA
<213> ORGANISM: Artificial Sequence
<220> FEATURE:
<223> OTHER INFORMATION: Synthetically generated oligonucleotide

<400> SEQUENCE: 53
gaagttcaat tgttagagtc tggtggcggt cttgttcagc ctggtggttc tttacgtctt      60
tcttgcgctg cttccggatt cactttctct atgtacggta tgcattgggt tcgccaagct     120
cctggtaaag gtttggagtg ggtttcttct atctattctt ctggtggcta tactggttat     180
gctgactccg ttaaaggtcg cttcactatc tctagagaca actctaagaa tactctctac     240
ttgcagatga acagcttaag ggctgaggac acggccgtgt attactgtgc gagggggagg     300
gccgttgacc tctggggcca gggaaccctg gtcaccgtct caagc                     345

<210> SEQ ID NO 54
<211> LENGTH: 324
<212> TYPE: DNA
<213> ORGANISM: Artificial Sequence
<220> FEATURE:
<223> OTHER INFORMATION: Synthetically generated oligonucleotide

<400> SEQUENCE: 54
```

```
caagacatcc agatgaccca gtctccagcc accctgtctt tgtctccagg ggaaagagcc      60
accctctcct gcagggccag tcagagtgtt agcagctact tagcctggta ccaacagaaa     120
cctggccagg ctcccaggct cctcatctat gatgcatcca acagggccac tggcatccca     180
gccaggttca gtggcagtgg gtctgggaca gacttcactc tcaccatcag cagcctagag     240
cctgaagatt ttgcagttta ttactgtcag cagcgtagca actggcctct caccttcggc     300
caagggacac gactggagat taaa                                            324

<210> SEQ ID NO 55
<211> LENGTH: 354
<212> TYPE: DNA
<213> ORGANISM: Artificial Sequence
<220> FEATURE:
<223> OTHER INFORMATION: Synthetically generated oligonucleotide

<400> SEQUENCE: 55
gaagttcaat tgttagagtc tggtggcggt cttgttcagc ctggtggttc tttacgtctt      60
tcttgcgctg cttccggatt cactttctct tggtactata tgggttgggt tcgccaagct     120
cctggtaaag gtttggagtg gtttcttat atcggttctt ctggtggcat gactggttat      180
gctgactccg ttaaaggtcg cttcactatc tctagagaca actctaagaa tactctctac     240
ttgcagatga acagcttaag ggctgaggac acagccacat attactgtgc gatggtgggc     300
ttcctcccga ccgttgacta ctggggccag ggaaccctgg tcaccgtctc aagc           354

<210> SEQ ID NO 56
<211> LENGTH: 324
<212> TYPE: DNA
<213> ORGANISM: Artificial Sequence
<220> FEATURE:
<223> OTHER INFORMATION: Synthetically generated oligonucleotide

<400> SEQUENCE: 56
caagacatcc agatgaccca gtctccatct tctgtgtctg catctgtagg agacagagtc      60
accatcactt gtcgggcgag tcagcatatt agcaactggc tagcctggta tcagcagaaa     120
ccaggggagg cccctaaact cctgatctct gctgcatcca gtttgcaaag tggggtccca     180
tcaaggttca gtggcagtgg atctgggaca gatttcactc tcaccatcag cagtctgcaa     240
cctgaagatt ttgcaactta ctactgtcaa cagagttaca gtaccccgct cactttcggc     300
ggagggacca aggtggagat caaa                                            324

<210> SEQ ID NO 57
<211> LENGTH: 354
<212> TYPE: DNA
<213> ORGANISM: Artificial Sequence
<220> FEATURE:
<223> OTHER INFORMATION: Synthetically generated oligonucleotide

<400> SEQUENCE: 57
gaagttcaat tgttagagtc tggtggcggt cttgttcagc ctggtggttc tttacgtctt      60
tcttgcgctg cttccggatt cactttctct ccttaccata tgacttgggt tcgccaagct     120
cctggtaaag gtttggagtg gtttcttct atctcttctt ctggtggcca tactgagtat      180
gctgactccg ttaaaggtcg cttcactatc tctagagaca actctaagaa tactctctac     240
ttgcagatga acagcttaag ggctgaggac acggccgtgt attactgtgc gacagcatgg     300
gcgggattta cttttaacgt ctggggccaa gggacaatgg tcaccgtctc aagc           354
```

<210> SEQ ID NO 58
<211> LENGTH: 327
<212> TYPE: DNA
<213> ORGANISM: Artificial Sequence
<220> FEATURE:
<223> OTHER INFORMATION: Synthetically generated oligonucleotide

<400> SEQUENCE: 58

| | | | | | |
|---|---|---|---|---|---|
| caagacatcc | agatgaccca | gtctccaggc | accctgtcct | tgtctccagg | ggacagagcc | 60 |
| accctctcct | gcggggccag | ccagcttgtt | gtcagcaact | acatagcctg | gtaccagcaa | 120 |
| aaacctggcc | aggctcccag | actcctcatg | tatgctggat | ccatcagggc | cactggcatc | 180 |
| ccagacaggt | tcagtggcag | tgggtctggg | acagacttca | ctctcaccat | cagcagacta | 240 |
| gaacctgaag | attttgcaat | atattactgt | cagcagcgta | gcaactggcc | ttggacgttc | 300 |
| ggccaaggga | ccaaggtgga | aatcaaa | | | | 327 |

<210> SEQ ID NO 59
<211> LENGTH: 354
<212> TYPE: DNA
<213> ORGANISM: Artificial Sequence
<220> FEATURE:
<223> OTHER INFORMATION: Synthetically generated oligonucleotide

<400> SEQUENCE: 59

| | | | | | |
|---|---|---|---|---|---|
| gaagttcaat | tgttagagtc | tggtggcggt | cttgttcagc | ctggtggttc | tttacgtctt | 60 |
| tcttgcgctg | cttccggatt | cactttctct | ccttacgtta | tgcattgggt | tcgccaagct | 120 |
| cctggtaaag | gtttggagtg | ggtttcttct | atctctcctt | ctggtggctg | gacttattat | 180 |
| gctgactccg | ttaaaggtcg | cttcactatc | tctagagaca | actctaagaa | tactctctac | 240 |
| ttgcagatga | acagcttaag | ggctgaggac | atggctgtgt | attactgtgc | gagagggact | 300 |
| ggagcctacg | gtatggacgt | ctggggccaa | gggaccacgg | tcaccgtctc | aagc | 354 |

<210> SEQ ID NO 60
<211> LENGTH: 324
<212> TYPE: DNA
<213> ORGANISM: Artificial Sequence
<220> FEATURE:
<223> OTHER INFORMATION: Synthetically generated oligonucleotide

<400> SEQUENCE: 60

| | | | | | |
|---|---|---|---|---|---|
| caagacatcc | agatgaccca | gtctccatcc | tccctgtctg | catctgtagg | agacagcgtc | 60 |
| accatcactt | gccgggcaag | tcagaacatt | aacagttatt | taaattggta | tcagcagaaa | 120 |
| ccaggaaaag | cccctaagct | cctgatctat | gttgcatcca | atttgcaaag | gggggtccca | 180 |
| tcaaggttcg | gtggcagtgg | atctgggaca | gatttcactc | tcaccatcac | cagtctgcaa | 240 |
| cctgaagatt | ttgcaactta | ctcctgtcag | cagacttaca | gtaccccccct | cactttcggc | 300 |
| ggagggacca | aggtggagat | caaa | | | | 324 |

<210> SEQ ID NO 61
<211> LENGTH: 360
<212> TYPE: DNA
<213> ORGANISM: Artificial Sequence
<220> FEATURE:
<223> OTHER INFORMATION: Synthetically generated oligonucleotide

<400> SEQUENCE: 61

| | | | | | |
|---|---|---|---|---|---|
| gaagttcaat | tgttagagtc | tggtggcggt | cttgttcagc | ctggtggttc | tttacgtctt | 60 |
| tcttgcgctg | cttccggatt | cactttctct | aagtactgga | tgatgtgggt | tcgccaagct | 120 |

-continued

```
cctggtaaag gtttggagtg ggtttctgtt atctatcctt ctggtggcat tacttattat    180
gctgactccg ttaaaggtcg cttcactatc tctagagaca actctaagaa tactctctac    240
ttgcagatga acagcttaag ggctgaggac actgcagtct actattgtgc gagactacct    300
tcttgggggt tgatgctct tgatatctgg ggccaaggga caatggtcac cgtctcaagc    360
```

<210> SEQ ID NO 62
<211> LENGTH: 327
<212> TYPE: DNA
<213> ORGANISM: Artificial Sequence
<220> FEATURE:
<223> OTHER INFORMATION: Synthetically generated oligonucleotide

<400> SEQUENCE: 62

```
caagacatcc agatgaccca gtctccatcc tccctgtctg catttgtagg agacaaagtc     60
accatcactt gccgggcaag tcagagtgtt ggcacctatt taaattggta tcagcagaaa    120
gcagggaaag cccctgagct cctgatctat gctacatcca atttgcgaag tggggtccca    180
tcaaggttca gtggcagtgg atctgggaca gatttcactc tcaccatcaa cactctgcaa    240
cctgaagatt ttgcaactta ctactgtcaa cagagttaca gtatccctcg gtttactttc    300
ggccctggga ccaaagtgga tatcaaa                                        327
```

<210> SEQ ID NO 63
<211> LENGTH: 344
<212> TYPE: DNA
<213> ORGANISM: Artificial Sequence
<220> FEATURE:
<223> OTHER INFORMATION: Synthetically generated oligonucleotide

<400> SEQUENCE: 63

```
gaagttcaat tgttagagtc tggtggcggt cttgttcagc ctggtggttc tttacgtctt     60
tcttgcgctg cttccggatt cactttctct ctttactcta tgaattgggt tcgccaagct    120
cctggtaaag gtttggagtg ggtttcttct atctattctt ctggtggctc tactctttat    180
gctgactccg ttaaaggtcg cttcactatc tctagagaca actctaagaa actctctact    240
tgcagatgaa cagcttaagg gctgaggaca cggccgtgta ttactgtgcg agaggtcggg    300
cttttgatat ctggggccaa gggacaatgg tcaccgtctc aagc                    344
```

<210> SEQ ID NO 64
<211> LENGTH: 324
<212> TYPE: DNA
<213> ORGANISM: Artificial Sequence
<220> FEATURE:
<223> OTHER INFORMATION: Synthetically generated oligonucleotide

<400> SEQUENCE: 64

```
caagacatcc agatgaccca gtctccaggc accctgtctt tgtctccagg ggaaagagcc     60
accctctcct gcagggccag tcagagtgtt agcagcagct acttagcctg gtaccagcag    120
aaacctggcc aggctcccag gctcctcatc tatggtgcat ccagcagggc cactggcatc    180
ccagacaggt tcagtggcag tgggtctggg acagacttca ctctcaccat cagcagactg    240
gagcctgaag attttgcagt gtattactgt cagcactatg gtggctcaca ggctttcggc    300
ggagggacca aggtggagat caaa                                           324
```

<210> SEQ ID NO 65
<211> LENGTH: 357
<212> TYPE: DNA
<213> ORGANISM: Artificial Sequence
<220> FEATURE:
<223> OTHER INFORMATION: Synthetically generated oligonucleotide

<400> SEQUENCE: 65

```
gaagttcaat tgttagagtc tggtggcggt cttgttcagc ctggtggttc tttacgtctt    60
tcttgcgctg cttccggatt cactttctct cgttacaaga tgtggtgggt tcgccaagct   120
cctggtaaag gtttggagtg ggtttctggt atccgtcctt ctggtggcct tactcgttat   180
gctgactccg ttaaaggtcg cttcactatc tctagagaca actctaagaa tactctctac   240
ttgcagatga acagcttaag ggctgaggac acggccgtgt attactgtgc gagacgcggt   300
gactacgtcg gggggtttga ctactggggc cagggaaccc tggtcaccgt ctcaagc      357
```

<210> SEQ ID NO 66
<211> LENGTH: 327
<212> TYPE: DNA
<213> ORGANISM: Artificial Sequence
<220> FEATURE:
<223> OTHER INFORMATION: Synthetically generated oligonucleotide

<400> SEQUENCE: 66

```
caagacatcc agatgaccca gtctccaggc accctgtctt tgtctccagg ggaaggagcc    60
accctctcct gcagggccag tcagattata aatccttttt acgtagcctg gtatcaacag   120
agacctggcc aggctcccag gctcctcatc tatgcttcat ccaggagggc cggtggcatc   180
ccagacagat tcagtggcag tgcgtctggg acagacttca ctctcacaat cagcagactg   240
gagcctgaag attttgcagt ctattactgt caatacttttt ataactccat gtggacgttc   300
```
(note above line: caatacttt t ataactccat)
```
ggccaagggg ccaaggtgga gatcaga                                         327
```

<210> SEQ ID NO 67
<211> LENGTH: 363
<212> TYPE: DNA
<213> ORGANISM: Artificial Sequence
<220> FEATURE:
<223> OTHER INFORMATION: Synthetically generated oligonucleotide

<400> SEQUENCE: 67

```
gaagttcaat tgttagagtc tggtggcggt cttgttcagc ctggtggttc tttacgtctt    60
tcttgcgctg cttccggatt cactttctct tggtacaata tgacttgggt tcgccaagct   120
cctggtaaag gtttggagtg ggtttctcgt atctctcctt ctggtggcga tacttttat    180
gctgactccg ttaaaggtcg cttcactatc tctagagaca actctaagaa tactctctac   240
ttgcagatga acagcttaag ggctgaggac acggccgtgt attactgtgc tagagctgcg   300
atagcacctc gtccgtacgg tatggacgtc tggggccaag gaccacggt caccgtctca    360
agc                                                                   363
```

<210> SEQ ID NO 68
<211> LENGTH: 324
<212> TYPE: DNA
<213> ORGANISM: Artificial Sequence
<220> FEATURE:
<223> OTHER INFORMATION: Synthetically generated oligonucleotide

<400> SEQUENCE: 68

```
caagacatcc agatgaccca gtctccactc tccctgtctg catctgtagg agacagagtc    60
accatcactt gccgggcgag tcagggcatt agcaattatt tagcctggta tcagcagaaa   120
ccagggaaag ttcctaagct cctgatctat gctgcatcca ctttgcaatc aggggtccca   180
```

```
tctcggttca gtggcagtgg atctgggaca gatttcactc tcaccatcag cagtctgcag    240
cctgaagatg ttgcaactta ttactgtcaa aagtataaca gtgcccgcct cactttcggc    300
ggagggacca aggtggagat caaa                                           324
```

<210> SEQ ID NO 69
<211> LENGTH: 357
<212> TYPE: DNA
<213> ORGANISM: Artificial Sequence
<220> FEATURE:
<223> OTHER INFORMATION: Synthetically generated oligonucleotide

<400> SEQUENCE: 69

```
gaagttcaat tgttagagtc tggtggcggt cttgttcagc ctggtggttc tttacgtctt     60
tcttgcgctg cttccggatt cactttctct ctttacccta tgctttgggt tcgccaagct    120
cctggtaaag gtttggagtg ggtttctggt atctctcctt ctggtggcca gacttttat    180 gctgactccg ttaaaggtcg cttcactatc tctagagaca actctaagaa tactctctac    240
ttgcagatga acagcttaag ggctgaggac acggccgtgt attactgtgc aaggatggct    300
tattactctg gatacttcga tctctggggc cgtggcaccc tggtcaccgt ctcaagc       357
```

<210> SEQ ID NO 70
<211> LENGTH: 330
<212> TYPE: DNA
<213> ORGANISM: Artificial Sequence
<220> FEATURE:
<223> OTHER INFORMATION: Synthetically generated oligonucleotide

<400> SEQUENCE: 70

```
caagacatcc agatgaccca gtctccatcc tccctgtctg catctgtagg agacagagtc     60
accatcactt gccgggcaag tcagagcatt agcagctatt taaattggta tcagcagaaa    120
ccagggaaag cccctaagct cctgatctac gatgcatcca atttggaaac agggtctcca    180
tcaaggttca gtggaagtgg atctgggaca gattttactt tcaccatcag cagcctgcag    240
cctgaagata ttgcaacata ttactgtcaa cagtttgatg atctcccgct cactttcgcc    300
ggagggacga aggtggagct caaacgaact                                     330
```

<210> SEQ ID NO 71
<211> LENGTH: 360
<212> TYPE: DNA
<213> ORGANISM: Artificial Sequence
<220> FEATURE:
<223> OTHER INFORMATION: Synthetically generated oligonucleotide

<400> SEQUENCE: 71

```
gaagttcaat tgttagagtc tggtggcggt cttgttcagc ctggtggttc tttacgtctt     60
tcttgcgctg cttccggatt cactttctct ctttacgtta tgatttgggt tcgccaagct    120
cctggtaaag gtttggagtg ggtttctggt atctattctt ctggtggcga tacttattat    180
gctgactccg ttaaaggtcg cttcactatc tctagagaca actctaagaa tactctctac    240
ttgcagatga acagcttaag ggctgaggac acggccgtgt attactgtgc gagggggcag    300
cagctggggg ggggtgcttt tgatatctgg ggccaaggga caatggtcac cgtctcaagc    360
```

<210> SEQ ID NO 72
<211> LENGTH: 327
<212> TYPE: DNA
<213> ORGANISM: Artificial Sequence
<220> FEATURE:
<223> OTHER INFORMATION: Synthetically generated oligonucleotide

<400> SEQUENCE: 72

```
caagacatcc agatgaccca gtctccagac accgtgtctt tctctccagg ggaaagagcc    60
tccctctcat gccgggccag tcagagtgtc cgcagcgact tagcctggta ccaacagaag   120
cctggccagg ctcccaggct gctcatctat ggtgcatcca cagggccac tggcatccca    180
gtcaggttca gtggcagtgg gtctgggaca gacttcactc tcaccatcag cagactggag   240
cctgaagatt ttgcagtgta ttactgtcag cagtatggta gctcacccct attcactttc   300
ggccctggga ccaaagtgga tatcaaa                                       327
```

<210> SEQ ID NO 73
<211> LENGTH: 378
<212> TYPE: DNA
<213> ORGANISM: Artificial Sequence
<220> FEATURE:
<223> OTHER INFORMATION: Synthetically generated oligonucleotide

<400> SEQUENCE: 73

```
gaagttcaat tgttagagtc tggtggcggt cttgttcagc ctggtggttc tttacgtctt    60
tcttgcgctg cttccggatt cactttctct atgtacaata tggcttgggt tcgccaagct   120
cctggtaaag gtttggagtg ggtttcttgg atctattctt ctggtggcct tactttgtat   180
gctgactccg ttaaaggtcg cttcactatc tctagagaca actctaagaa tactctctac   240
ttgcagatga acagcttaag ggctgaggac acggccgtat attactgtgc gaaaggctcc   300
aatacgtact actttgatgc tagtggcctc ggtgctttta atatgtgggg ccaagggaca   360
atggtcaccg tctcaagc                                                  378
```

<210> SEQ ID NO 74
<211> LENGTH: 321
<212> TYPE: DNA
<213> ORGANISM: Artificial Sequence
<220> FEATURE:
<223> OTHER INFORMATION: Synthetically generated oligonucleotide

<400> SEQUENCE: 74

```
caagacatcc agatgaccca gtctccatcc ttcctgtctg catctatagg agacagagtc    60
accatcactt gccgggccag tcagggcatt aacacttttt tagcctggta tcagcaaaaa   120
ccagggatag cccctaagct cctgatctat gctgcatcca ctctgcaaag tggggtccca   180
tcaaggttca gcggcagtgg atctgggaca gaattcactc tcacaatcag cagtctgcag   240
cctgaagatt ttgcaactta ttactgtcag cagcttaatg gttaccgcag cttcggacaa   300
gggacacgac tagagatgaa a                                             321
```

<210> SEQ ID NO 75
<211> LENGTH: 387
<212> TYPE: DNA
<213> ORGANISM: Artificial Sequence
<220> FEATURE:
<223> OTHER INFORMATION: Synthetically generated oligonucleotide

<400> SEQUENCE: 75

```
gaagttcaat tgttagagtc tggtggcggt cttgttcagc ctggtggttc tttacgtctt    60
tcttgcgctg cttccggatt cactttctct aattacgaga tgggttgggt tcgccaagct   120
cctggtaaag gtttggagtg ggtttcttgg atctattctt ctggtggcta tacttcttat   180
gctgactccg ttaaaggtcg cttcactatc tctagagaca actctaagaa tactctctac   240
```

```
ttgcagatga acagcttaag ggctgaggac acagccacgt attactgtgc gagagatccg      300
tattactatg atagtagtgg ttattactac tactactact actacatgga cgtctggggc      360
aaagggacca cggtcaccgt ctcaagc                                          387
```

<210> SEQ ID NO 76
<211> LENGTH: 330
<212> TYPE: DNA
<213> ORGANISM: Artificial Sequence
<220> FEATURE:
<223> OTHER INFORMATION: Synthetically generated oligonucleotide

<400> SEQUENCE: 76

```
caagacatcc agatgaccca gtctccaggc accctgtctt tgtctccagg ggaaagagcc      60
accctctcct gcagggccag tcagagtgtt aacagcaggt tcttggcctg gtaccagcag      120
aaacctggcc aggctcccag gctcctcatc tatagtacat ccaccagggc cactggcatc      180
ccagacaggt tcagtggcag tgggtccggg acagacttca ctctcaccat cagcagactg      240
gagcctgaag attttgcggt gtattactgt cagcgatatg gtagctcacc tacgtggacg      300
ttcggccaag ggaccaaggt ggaaatcaaa                                       330
```

<210> SEQ ID NO 77
<211> LENGTH: 357
<212> TYPE: DNA
<213> ORGANISM: Artificial Sequence
<220> FEATURE:
<223> OTHER INFORMATION: Synthetically generated oligonucleotide

<400> SEQUENCE: 77

```
gaagttcaat tgttagagtc tggtggcggt cttgttcagc ctggtggttc tttacgtctt      60
tcttgcgctg cttccggatt cactttctct cgttacgtta tggattgggt tcgccaagct      120
cctggtaaag gtttggagtg gtttctcgt atctctcctt ctggtggcca tactgattat      180
gctgactccg ttaaaggtcg cttcactatc tctagagaca actctaagaa tactctctac      240
ttgcagatga acagcttaag ggctgaggac acggccgtgt attactgtgc cagagaaacg      300
gttcggggag tttactttga ctactggggc cagggaaccc tggtcaccgt ctcaagc        357
```

<210> SEQ ID NO 78
<211> LENGTH: 327
<212> TYPE: DNA
<213> ORGANISM: Artificial Sequence
<220> FEATURE:
<223> OTHER INFORMATION: Synthetically generated oligonucleotide

<400> SEQUENCE: 78

```
caagacatcc agatgaccca gtctccagcc accctgtctg tgtctccagg ggaaagagcc      60
accctctcct gcagggccag tgagagtgtt aaaaacaact tagcctggta tcagcagaaa      120
cctggccagg ctcccaggct cctcatctat ggtgtttcca ccagggcccc tggtatccca      180
gccaggttca gtggcagtgg gtctgggaca gacttcactc tcaccatcag cagcctagag      240
cctgaagatt ttgcagttta ttactgtcag cagcgtagca actggcctcc ggtcaccttc      300
ggccaaggga cacgactgga gattaaa                                          327
```

<210> SEQ ID NO 79
<211> LENGTH: 351
<212> TYPE: DNA
<213> ORGANISM: Artificial Sequence
<220> FEATURE:
<223> OTHER INFORMATION: Synthetically generated oligonucleotide

<400> SEQUENCE: 79

```
gaagttcaat tgttagagtc tggtggcggt cttgttcagc ctggtggttc tttacgtctt    60
tcttgcgctg cttccggatt cactttctct gcttacaata tgggttgggt tcgccaagct   120
cctggtaaag gtttggagtg ggtttcttct atctcttctt ctggtggcta tactggttat   180
gctgactccg ttaaaggtcg cttcactatc tctagagaca actctaagaa tactctctac   240
ttgcagatga acagcttaag ggctgaggac acggccgtgt attactgtgc gagagatctt   300
tacaggggct tgactactg gggccaggga accctggtca ccgtctcaag c             351
```

<210> SEQ ID NO 80
<211> LENGTH: 324
<212> TYPE: DNA
<213> ORGANISM: Artificial Sequence
<220> FEATURE:
<223> OTHER INFORMATION: Synthetically generated oligonucleotide

<400> SEQUENCE: 80

```
caagacatcc agatgaccca gtctccatct tttgtgtctg catctgtcgg agacagagtc    60
accatctctt gtcgggcgag tcacaatatt aacacctggt tagcctggta tcagcagaaa   120
ccagggaaag cccctaacct cctgatctat tctgcatcca atttgcaagg tggggtccca   180
tctaggttca gcggcagtgg atctgggaca gacttcactc tcactatcag cagcctgcag   240
cctggagatt ttgcgactta ctattgtcaa caggctagca gtttccctat caccttcggc   300
caagggacac gactggagat taaa                                           324
```

<210> SEQ ID NO 81
<211> LENGTH: 378
<212> TYPE: DNA
<213> ORGANISM: Artificial Sequence
<220> FEATURE:
<223> OTHER INFORMATION: Synthetically generated oligonucleotide

<400> SEQUENCE: 81

```
gaagttcaat tgttagagtc tggtggcggt cttgttcagc ctggtggttc tttacgtctt    60
tcttgcgctg cttccggatt cactttctct aattacatga tgatttgggt tcgccaagct   120
cctggtaaag gtttggagtg ggtttcttgg atctctcctt ctggtggcta tacttttat    180
gctgactccg ttaaaggtcg cttcactatc tctagagaca actctaagaa tactctctac   240
ttgcagatga acagcttaag ggctgaggac acggccgtgt attactgtgc gagaggatat   300
tacgatattt tgactggtat ggtgggcggc ggtgcttttg atatctgggg ccaagggacc   360
acggtcaccg tctcaagc                                                  378
```

<210> SEQ ID NO 82
<211> LENGTH: 339
<212> TYPE: DNA
<213> ORGANISM: Artificial Sequence
<220> FEATURE:
<223> OTHER INFORMATION: Synthetically generated oligonucleotide

<400> SEQUENCE: 82

```
caggacatcg tcatgactca aaccnctcct agtttaccgg ttaacccggg tgaacctgcc    60
tccatctcct gcaggtctag tcagagcctc ctgcatagaa atggatacaa ctatttggat   120
tggtacctgc agaagccagg gcagtctcca cagctcctga tccatttggg ttcttatcgg   180
gcctccgggg tccctgacag gttcagtggc agtggatcag gcacagattt tacactgaaa   240
```

```
atcagcagag tggaggctga ggatgttggg gtttattact gcatgcaacc tctacaaact    300
ccattcactt tcggccctgg gaccaaagtg gatatcaaa                           339

<210> SEQ ID NO 83
<211> LENGTH: 372
<212> TYPE: DNA
<213> ORGANISM: Artificial Sequence
<220> FEATURE:
<223> OTHER INFORMATION: Synthetically generated oligonucleotide

<400> SEQUENCE: 83
gaagttcaat tgttagagtc tggtggcggt cttgttcagc ctggtggttc tttacgtctt     60
tcttgcgctg cttccggatt cactttctct tattacggta tgtattgggt tcgccaagct    120
cctggtaaag gtttggagtg gtttcttcct atctcttctt ctggtggcta tactgattat    180
gctgactccg ttaaaggtcg cttcactatc tctagagaca actctaagaa tactctctac    240
ttgcagatga acagcttaag ggctgaggac acggccgtgt attactgtgc aaggaggatt    300
aagtattacg atattgaagg ggaaggtgct tttgatatct ggggccaagg acaatggtc     360 accgtctcaa gc                                                        372

<210> SEQ ID NO 84
<211> LENGTH: 336
<212> TYPE: DNA
<213> ORGANISM: Artificial Sequence
<220> FEATURE:
<223> OTHER INFORMATION: Synthetically generated oligonucleotide

<400> SEQUENCE: 84
caagacatcc agatgaccca gtctccactc tccctgcccg tcacccctgg agagccggcc     60
tccatctcct gcaggtctag tcagagcctc ctgcatagta tggatacaa ctatttggat    120 tggtacctgc agaagccagg gcagtctcca cagctcctga tctatttggg ttctaatcgg    180
gcctccgggg tccctgacag gttcagtggc agtggatcag gcacagattt tacactgaaa    240
atcagcagag tggaggctga ggatgttggg gtttattact gcatgcaagc tctacaacct    300
ttcactttcg gcggagggac caaggtggag atcaaa                              336

<210> SEQ ID NO 85
<211> LENGTH: 378
<212> TYPE: DNA
<213> ORGANISM: Artificial Sequence
<220> FEATURE:
<223> OTHER INFORMATION: Synthetically generated oligonucleotide

<400> SEQUENCE: 85
gaagttcaat tgttagagtc tggtggcggt cttgttcagc ctggtggttc tttacgtctt     60
tcttgcgctg cttccggatt cactttctct gcttacatga tgggttgggt tcgccaagct    120
cctggtaaag gtttggagtg gtttctggt atctcttctt ctggtggcct tacttcttat    180
gctgactccg ttaaaggtcg cttcactatc tctagagaca actctaagaa tactctctac    240
ttgcagatga acagcttaag ggctgaggac acggccgtgt attactgtgc gagaccagcg    300
ctgatttact atgatagtag tggcccaagt gatgcttttg atatctgggg ccaagggaca    360
atggtcaccg tctcaagc                                                  378

<210> SEQ ID NO 86
<211> LENGTH: 333
<212> TYPE: DNA
<213> ORGANISM: Artificial Sequence
```

```
<220> FEATURE:
<223> OTHER INFORMATION: Synthetically generated oligonucleotide

<400> SEQUENCE: 86
cagagcgctt tgactcagcc tccctccgcg tccgggtctc ctggacagtc agtcaccatc    60
tcctgcactg gaaccagcag tgacgttggt gcttataact atgtctcctg gtaccaacag   120
cacccagaca aagcccccaa actcattatt tataatgtca atgagcggcc ctcaggggtc   180
cctgatcgct tctctggctc caagtctggc aacacggcct ccctgaccgt ctctgggctc   240
caggctgagg atgaggctga ttattactgt acctcatatg caggcagcaa caaaatcggg   300
gtctccggaa ctgggaccaa ggtcaccgtc cta                                333

<210> SEQ ID NO 87
<211> LENGTH: 366
<212> TYPE: DNA
<213> ORGANISM: Artificial Sequence
<220> FEATURE:
<223> OTHER INFORMATION: Synthetically generated oligonucleotide

<400> SEQUENCE: 87
gaagttcaat tgttagagtc tggtggcggt cttgttcagc ctggtggttc tttacgtctt    60
tcttgcgctg cttccggatt cactttctct cattacgtta tgttttgggt tcgccaagct   120
cctggtaaag gtttggagtg ggtttctcgt atcgttcctt ctggtggcgc tactatgtat   180
gctgactccg ttaaaggtcg cttcactatc tctagagaca actctaagaa tactctctac   240
ttgcagatga acagcttaag ggctgaggac acggccgtgt attactgtgc gagagatcga   300
ccgctctatg atagtagtgg ttacgttgac tactggggcc agggaaccct ggtcaccgtc   360
tcaagc                                                             366

<210> SEQ ID NO 88
<211> LENGTH: 327
<212> TYPE: DNA
<213> ORGANISM: Artificial Sequence
<220> FEATURE:
<223> OTHER INFORMATION: Synthetically generated oligonucleotide

<400> SEQUENCE: 88
cagtacgaat tgactcagcc accctcagcg tctgggaccc ccgggcagag ggtcaccatc    60
tcttgttctg gaagcagctc caacatcgga aggaattatg tatactggta ccagcaggtc   120
ccaggaacgg cccccaaact cctcatctat agtaataatc agcggccctc agggtccct    180 gaccgattct ctggctccaa gtctggcacc tcagcctccc tggtcatcag tgggctccgg   240
tccgaggatg aggctgatta ttactgtgca gcatgggatg ccagcctgcg tggggtgttc   300
ggcggaggga ccaagctgac cgtccta                                      327

<210> SEQ ID NO 89
<211> LENGTH: 360
<212> TYPE: DNA
<213> ORGANISM: Artificial Sequence
<220> FEATURE:
<223> OTHER INFORMATION: Synthetically generated oligonucleotide

<400> SEQUENCE: 89
gaagttcaat tgttagagtc tggtggcggt cttgttcagc ctggtggttc tttacgtctt    60
tcttgcgctg cttccggatt cactttctct gtttacccta tggtttgggt tcgccaagct   120
cctggtaaag gtttggagtg ggtttcttat atctctcctt ctggtggctt tactttttat   180
```

```
gctgactccg ttaaaggtcg cttcactatc tctagagaca actctaagaa tactctctac    240
ttgcagatga acagcttaag ggctgaggac acggccgtgt attactgtgc gagagtgccc    300
gggggcagca gacaggattt tgatatctgg ggccaaggga caatggtcac cgtctcaagc    360
```

<210> SEQ ID NO 90
<211> LENGTH: 324
<212> TYPE: DNA
<213> ORGANISM: Artificial Sequence
<220> FEATURE:
<223> OTHER INFORMATION: Synthetically generated oligonucleotide

<400> SEQUENCE: 90

```
caagacatcc agatgaccca gtctccatcc tccctgtctg catctgtagg agacagagtc     60
accatcactt gccgggcaag tcagagcatt agcagctatt taaattggta tcagcagaaa    120
ccagggaaag cccctaagct cctgatctat gctgcatcca gtttgcaaag tggggtccca    180
tcaaggttca gtggcagtgg atctgggaca gatttcactc tcaccatcag cagtctgcaa    240
cctgaagatt ttgcaactta ctactgtcaa cagagttaca gtacccctcg aacgttcggc    300
caagggacca aggtggaaat caaa                                           324
```

<210> SEQ ID NO 91
<211> LENGTH: 360
<212> TYPE: DNA
<213> ORGANISM: Artificial Sequence
<220> FEATURE:
<223> OTHER INFORMATION: Synthetically generated oligonucleotide

<400> SEQUENCE: 91

```
gaagttcaat tgttagagtc tggtggcggt cttgttcagc ctggtggttc tttacgtctt     60
tcttgcgctg cttccggatt cactttctct tattacaatg atatggcttg ggttcgccaa    120
gctcctggta aaggtttgga gtgggttttct tctatctctc cttctggtgg caagactgag    180
tatgctgact ccgttaaagg tcgcttcact atctctagag acaactctaa gaatactctc    240
tacttgcaga tgaacagctt aagggctgag gacacggccg tgtattactg tgcgaggagt    300
ggaagctaca ctcaacattt tgactactgg ggccaggaa ccctggtcac cgtctcaagc     360
```

<210> SEQ ID NO 92
<211> LENGTH: 324
<212> TYPE: DNA
<213> ORGANISM: Artificial Sequence
<220> FEATURE:
<223> OTHER INFORMATION: Synthetically generated oligonucleotide

<400> SEQUENCE: 92

```
caagacatcc agatgaccca gtctccagcc accctgtctg catctgtagg agacagagtc     60
accatcactt gccgggcaag tcagaccatt agcacctatt taaattggta tcaacacaaa    120
ccagggaaag cccctgagct cctgatttat gctgcatcca gtttgcaaag tggggtccca    180
tcaaggttca gtggcagtgg atctgggaca gatttcactc tccgcatcag cagtctgcaa    240
cctgaagatt ttgcaactta ctactgtcaa cagagttaca ctaccccgtg gacgttcggc    300
caagggacca aggtggaaat caaa                                           324
```

<210> SEQ ID NO 93
<211> LENGTH: 351
<212> TYPE: DNA
<213> ORGANISM: Artificial Sequence
<220> FEATURE:
<223> OTHER INFORMATION: Synthetically generated oligonucleotide

<400> SEQUENCE: 93

```
gaagttcaat tgttagagtc tggtggcggt cttgttcagc ctggtggttc tttacgtctt    60
tcttgcgctg cttccggatt cactttctct cgttacatga tggtttgggt tcgccaagct   120
cctggtaaag gtttggagtg ggtttcttct atcgtttctt ctggtggcaa gacttggtat   180
gctgactccg ttaaaggtcg cttcactatc tctagagaca actctaagaa tactctctac   240
ttgcagatga acagcttaag ggctgaggac accgccatgt attactgtgc cagatgggac   300
tggggacctt tgactactg gggccaggga accctggtca ccgtctcaag c             351
```

<210> SEQ ID NO 94
<211> LENGTH: 336
<212> TYPE: DNA
<213> ORGANISM: Artificial Sequence
<220> FEATURE:
<223> OTHER INFORMATION: Synthetically generated oligonucleotide

<400> SEQUENCE: 94

```
cagagcgctt tgactcaatc accctctgcc tctgcttcac tgggatcctc ggtcaagctc    60
acctgcactc tggccagtga gcacagtggc tacatcatcg catggcatca gcagcaacca   120
gggaaggccc ctcggttctt gatgaaactt gacggtactg gcaacttcaa caagggcagc   180
ggagttcctg atcgcttctc aggctacagc tctgggctg accgctacct caccatctcc    240
aacctccagt ctgaggatga ggctgattat tactgtgaga cctgggacag taccactctt   300
tgggtgttcg gcggggggac caagctgacc gtccta                              336
```

<210> SEQ ID NO 95
<211> LENGTH: 363
<212> TYPE: DNA
<213> ORGANISM: Artificial Sequence
<220> FEATURE:
<223> OTHER INFORMATION: Synthetically generated oligonucleotide

<400> SEQUENCE: 95

```
gaagttcaat tgttagagtc tggtggcggt cttgttcagc ctggtggttc tttacgtctt    60
tcttgcgctg cttccggatt cactttctct cattacggta tgacttgggt tcgccaagct   120
cctggtaaag gtttggagtg ggtttcttct atcgttcctt ctggtggcta tactgcttat   180
gctgactccg ttaaaggtcg cttcactatc tctagagaca actctaagaa tactctctac   240
ttgcagatga acagcttaag ggctgaggac acagccgtgt attactgtac cacaggtctc   300
agcagcagcg gtacacggtg gttcgacgcc tggggccagg gaaccctggt caccgtctca   360
agc                                                                  363
```

<210> SEQ ID NO 96
<211> LENGTH: 339
<212> TYPE: DNA
<213> ORGANISM: Artificial Sequence
<220> FEATURE:
<223> OTHER INFORMATION: Synthetically generated oligonucleotide

<400> SEQUENCE: 96

```
caagacatcc agatgaccca gtctccactc tccctgcccg tcaccctgg agagccggcc     60
tccatctcct gcaggtctgg tcagagcctc ctgcatagta atggatacaa ctatttgaat   120
tggtacctgc agaagccagg gcagtctcca cagctcctga tctatttggg ttcttatcgg   180
gcctccgggg tccctgacag gttcagtggc agtggatcag gcacagattt tacactgaaa   240
```

-continued

| | |
|---|---|
| atcagcagag tggaggctga ggatgttggg ctttattact gcatgcaagc tctacaaact | 300 |
| cctctcactt tcggcgtagg gaccaaggtg gagatcaaa | 339 |

<210> SEQ ID NO 97
<211> LENGTH: 372
<212> TYPE: DNA
<213> ORGANISM: Artificial Sequence
<220> FEATURE:
<223> OTHER INFORMATION: Synthetically generated oligonucleotide

<400> SEQUENCE: 97

| | |
|---|---|
| gaagttcaat tgttagagtc tggtggcggt cttgttcagc ctggtggttc tttacgtctt | 60 |
| tcttgcgctg cttccggatt cactttctct atgtacgtta tgtcttgggt tcgccaagct | 120 |
| cctggtaaag gtttggagtg gtttcttct atctcttctt ctggtggcaa tactggttat | 180 |
| gctgactccg ttaaaggtcg cttcactatc tctagagaca actctaagaa tactctctac | 240 |
| ttgcagatga acagcttaag ggctgaggac acggccgtgt attactgtgc gaagagttcg | 300 |
| ttatattacg atattttggc tggccctggg tttgactact ggggccaggg aaccctggtc | 360 |
| accgtctcaa gc | 372 |

<210> SEQ ID NO 98
<211> LENGTH: 330
<212> TYPE: DNA
<213> ORGANISM: Artificial Sequence
<220> FEATURE:
<223> OTHER INFORMATION: Synthetically generated oligonucleotide

<400> SEQUENCE: 98

| | |
|---|---|
| cagagcgtct tgactcagcc accctcagcg tctgggaccc ccgggcagag ggtcaccatc | 60 |
| tcatgttctg gaagcaggac caacatcgga agtgattatg tatattggta ccagcaactc | 120 |
| ccaggaacgg cccccaaact cctcatctat aggaataatg agcggccctc aggggtccct | 180 |
| gaccgattct ctggcttcaa gtctggcacc tcagcctccc tggccatcag tgggctccgg | 240 |
| tccgaggatg aggctgatta ttactgtgca tcatgggatg acaggctgag tggtccggtt | 300 |
| ttcggcggag ggaccaagct gaccgtccta | 330 |

<210> SEQ ID NO 99
<211> LENGTH: 354
<212> TYPE: DNA
<213> ORGANISM: Artificial Sequence
<220> FEATURE:
<223> OTHER INFORMATION: Synthetically generated oligonucleotide

<400> SEQUENCE: 99

| | |
|---|---|
| gaagttcaat tgttagagtc tggtggcggt cttgttcagc ctggtggttc tttacgtctt | 60 |
| tcttgcgctg cttccggatt cactttctct cagtaccata tgctttgggt tcgccaagct | 120 |
| cctggtaaag gtttggagtg gtttctgtt atcgtttctt ctggtggctt tacttttat | 180 |
| gctgactccg ttaaaggtcg cttcactatc tctagagaca actctaagaa tactctctac | 240 |
| ttgcagatga acagcttaag ggctgaggac acggccgtgt attactgtgc gagaagctac | 300 |
| ggtggagatg cttttgatat ctggggccaa gggacaatgg tcaccgtctc aagc | 354 |

<210> SEQ ID NO 100
<211> LENGTH: 342
<212> TYPE: DNA
<213> ORGANISM: Artificial Sequence
<220> FEATURE:
<223> OTHER INFORMATION: Synthetically generated oligonucleotide

<400> SEQUENCE: 100

```
caagacatcc agatgaccca gtctccagac tccctggctg tgtctctggg cgagagggcc    60
accctcaact gcaggtccag ccagagtgtt ttatacagcc caacaataa gaactactta    120
gcttggtacc agcagaaagc aggacagcca cctaagctgc tcatttactg ggcatctttc    180
cgggaatccg gggtccctga gcgattcagt ggcagcgggt ctgggacaga tttcactctc    240
accatcagca gcctgcaggc tgaagatgtg gcagtttatt actgtcagca atatcatact    300
cctcccctgga cgttcggcca agggaccaag gtggaaatca aa                     342
```

<210> SEQ ID NO 101
<211> LENGTH: 360
<212> TYPE: DNA
<213> ORGANISM: Artificial Sequence
<220> FEATURE:
<223> OTHER INFORMATION: Synthetically generated oligonucleotide

<400> SEQUENCE: 101

```
gaagttcaat tgttagagtc tggtggcggt cttgttcagc ctggtggttc tttacgtctt    60
tcttgcgctg cttccggatt cactttctct tcttacgata tggtttgggt tcgccaagct    120
cctggtaaag gtttggagtg gtttcttct atctctcctt ctggtggcaa tactcagtat    180
gctgactccg ttaaaggtcg cttcactatc tctagagaca actctaagaa tactctctac    240
ttgcagatga acagcttaag ggctgaggac acggccgtgt attactgtgc gaaagtggca    300
gctatggccc cgtggtactt tgactactgg ggccagggaa ccctggtcac cgtctcaagc    360
```

<210> SEQ ID NO 102
<211> LENGTH: 324
<212> TYPE: DNA
<213> ORGANISM: Artificial Sequence
<220> FEATURE:
<223> OTHER INFORMATION: Synthetically generated oligonucleotide

<400> SEQUENCE: 102

```
cagagcgaat tgactcagga ccctgctgtg tctgtggcct gggacaggc agtcatcatc    60
acatgccaag agacagcct cagaacctat tatccaagct ggtaccaaca gaagccagga    120
caggccccta cacttctcgt ctatggtaaa aacaagcggc cctcagggt cccagaccga    180
ttctctggct ccaggtcagg agacacagct tccttgatca tcactggggc tcaggcggaa    240
gatgacgctg actattattg taactcccgg gacggcagtg gtcaccttt tgtcttcgga    300
cctgggacca cggtcaccgt cctc                                         324
```

<210> SEQ ID NO 103
<211> LENGTH: 369
<212> TYPE: DNA
<213> ORGANISM: Artificial Sequence
<220> FEATURE:
<223> OTHER INFORMATION: Synthetically generated oligonucleotide

<400> SEQUENCE: 103

```
gaagttcaat tgttagagtc tggtggcggt cttgttcagc ctggtggttc tttacgtctt    60
tcttgcgctg cttccggatt cactttctct ctttaccta tgcagtgggt tcgccaagct    120
cctggtaaag gtttggagtg gtttcttat atccgttctt ctggtggcaa gactcattat    180
gctgactccg ttaaaggtcg cttcactatc tctagagaca actctaagaa tactctctac    240
ttgcagatga acagcttaag ggctgaggac acggctgtgt attactgtgc gagagtagga    300
```

```
atgggcagtg gctggtacac ggggtacttc gatctctggg gccgtggcac cctggtcacc    360
gtctcaagc                                                            369
```

<210> SEQ ID NO 104
<211> LENGTH: 324
<212> TYPE: DNA
<213> ORGANISM: Artificial Sequence
<220> FEATURE:
<223> OTHER INFORMATION: Synthetically generated oligonucleotide

<400> SEQUENCE: 104

```
caagacatcc agatgaccca gtctccatcc tccctgtctg catctgtagg agacagagtc     60
accatcactt gccgggcaag tcagaacatt aacagctatt taaattggta tcagcagaaa    120
ccagggaaag cccctaagct cctgatctat gctgcatccg gtttgcaaag tggggtccca    180
tcaaggttca gtggcagtgg atctgggaca gatttcactc tcaccatcag cagtctgcaa    240
cctgaagatt ttgtaactta ctactgtcaa cagagttaca gtacccctaa gacgttcggc    300
caagggacca aggtggaaat caaa                                            324
```

<210> SEQ ID NO 105
<211> LENGTH: 357
<212> TYPE: DNA
<213> ORGANISM: Artificial Sequence
<220> FEATURE:
<223> OTHER INFORMATION: Synthetically generated oligonucleotide

<400> SEQUENCE: 105

```
gaagttcaat tgttagagtc tggtggcggt cttgttcagc ctggtggttc tttacgtctt     60
tcttgcgctg cttccggatt cactttctct gtttacacta tgcattgggt tcgccaagct    120
cctggtaaag gtttggagtg ggtttctgtt atctatcctt ctggtggcct tactatttat    180
gctgactccg ttaaaggtcg cttcactatc tctagagaca actctaagaa tactctctac    240
ttgcagatga acagcttaag ggctgaggac acggccgtgt attactgtgc acggaatagg    300
ggttactatg cccctatgga cgtctggggc caagggacca cggtcaccgt ctcaagc       357
```

<210> SEQ ID NO 106
<211> LENGTH: 324
<212> TYPE: DNA
<213> ORGANISM: Artificial Sequence
<220> FEATURE:
<223> OTHER INFORMATION: Synthetically generated oligonucleotide

<400> SEQUENCE: 106

```
caagacatcc agatgaccca gtctccagcc accctgtctg catctgtagg agacagagtc     60
accatctctt gccgggccag tcagaatatt agtaattggt tggcctggta tcagcagaag    120
ccaggcaaag cccctaaact cctcatctac actgcatcca ctttgcaccg tggggtccca    180
tcaaggttca gcggcagtgg atctgggaca gatttcactc tcactatcac cagcctgcag    240
cctgaagatt ttgcaactta ctattgtcaa caggctaaca cttccccttg gacgttcggc    300
caagggacca aggtggaaat caaa                                            324
```

<210> SEQ ID NO 107
<211> LENGTH: 363
<212> TYPE: DNA
<213> ORGANISM: Artificial Sequence
<220> FEATURE:
<223> OTHER INFORMATION: Synthetically generated oligonucleotide

<400> SEQUENCE: 107

-continued
gaagttcaat tgttagagtc tggtggcggt cttgttcagc ctggtggttc tttacgtctt 60
tcttgcgctg cttccggatt cactttctct atgtacatga tgtggtgggt tcgccaagct 120
cctggtaaag gtttggagtg ggtttctgtt atctcttctt ctggtggctt tacttcttat 180
gctgactccg ttaaaggtcg cttcactatc tctagagaca actctaagaa tactctctac 240
ttgcagatga acagcttaag ggctgaggac acggccgtgt attactgtgc gagactaagg 300
tacagtaatt tcgtaggcgg tctggacgtc tggggccaag ggaccacggt caccgtctca 360
agc 363

<210> SEQ ID NO 108
<211> LENGTH: 321
<212> TYPE: DNA
<213> ORGANISM: Artificial Sequence
<220> FEATURE:
<223> OTHER INFORMATION: Synthetically generated oligonucleotide
<400> SEQUENCE: 108
cagagcgtct tgactcagga ccctgctgtg tctgtggcct tgggacagac agtcaggatc 60
acatgccaag gagacagcct cagaagctat tctgcaagtt ggtaccagcg gaagccagga 120
caggcccctt tacttgtcat ctatcgtaaa accaaccggc cctcagggat cccagaccgg 180
ttctctggct ccagctcagg aaacacagct tccttgacca tcactggggc tcaggcggaa 240
gatgagtctg actattactg taactcccgg gacagcagtg gtaaccacct attcggcgga 300
gggaccaaac tgaccgtcct a 321

<210> SEQ ID NO 109
<211> LENGTH: 357
<212> TYPE: DNA
<213> ORGANISM: Artificial Sequence
<220> FEATURE:
<223> OTHER INFORMATION: Synthetically generated oligonucleotide
<400> SEQUENCE: 109
gaagttcaat tgttagagtc tggtggcggt cttgttcagc ctggtggttc tttacgtctt 60
tcttgcgctg cttccggatt cactttctct cagtactcta tgcattgggt tcgccaagct 120
cctggtaaag gtttggagtg ggtttcttct atcgttcctt ctggtggcat gactgcttat 180
gctgactccg ttaaaggtcg cttcactatc tctagagaca actctaagaa tactctctac 240
ttgcagatga acagcttaag ggctgaggac acggccgtgt attactgtgc gaaaatttca 300
cggggaaatg atgcttttga tatctggggc caagggacaa tggtcaccgt ctcaagc 357

<210> SEQ ID NO 110
<211> LENGTH: 324
<212> TYPE: DNA
<213> ORGANISM: Artificial Sequence
<220> FEATURE:
<223> OTHER INFORMATION: Synthetically generated oligonucleotide
<400> SEQUENCE: 110
caagacatcc agatgaccca gtctccatcc tccctgtctg catctgttgg agacagagtc 60
accatcactt gccgggcaag tcagcgaatt ggcagctact tgaattggta tcagcaaaat 120
tcgggaaaag ccccaaggct cctgatctat ggtgcatcca atttggaaag tggggtccct 180
tcaaggttca gtggccgtgg atctgggaca gacttcactc tcaccatcag cagtctgcaa 240
cctgaagatt ttgcgactta ctactgtcaa cagagtaaca gtacccctca cacgttcggc 300


```
caagggacca aggtggaaat caaa                                          324
```

<210> SEQ ID NO 111
<211> LENGTH: 375
<212> TYPE: DNA
<213> ORGANISM: Artificial Sequence
<220> FEATURE:
<223> OTHER INFORMATION: Synthetically generated oligonucleotide

<400> SEQUENCE: 111

```
gaagttcaat tgttagagtc tggtggcggt cttgttcagc ctggtggttc tttacgtctt    60
tcttgcgctg cttccggatt cactttctct cagtacccta tgtcttgggt tcgccaagct   120
cctggtaaag gtttggagtg ggtttcttct atcggtcctg gtggctggac ttggtatgct   180
gactccgtta aaggtcgctt cactatctct agagacaact ctaagaatac tctctacttg   240
cagatgaaca gcttaagggc tgaggacact gcagtctact attgtgcgag gaccgctaca   300
cggattttg gagtggttat tatgggtcgc gcttttgata tctggggcca agggacaatg   360
gtcaccgtct caagc                                                    375
```

<210> SEQ ID NO 112
<211> LENGTH: 321
<212> TYPE: DNA
<213> ORGANISM: Artificial Sequence
<220> FEATURE:
<223> OTHER INFORMATION: Synthetically generated oligonucleotide

<400> SEQUENCE: 112

```
caagacatcc agatgaccca gtctccatct tcactgtctg catctgtagg agacagaatc    60
accgtcactt gccgggcaag tcagagcatt accaactatt taaattggta tcagcagaaa   120
ccagggaaag cccctaagct cctgatctat gctgcatcca ctttgcaaag tggggtccca   180
tcaaggttca gtggcagtgg gtctgggaca gacttcactc tcaccatcag cagactggag   240
cctgaagatt ttgcagtata ttactgtcag cagtatggta gctcaccgac gttcggccaa   300
gggaccaagg tggaagtcaa a                                             321
```

<210> SEQ ID NO 113
<211> LENGTH: 363
<212> TYPE: DNA
<213> ORGANISM: Artificial Sequence
<220> FEATURE:
<223> OTHER INFORMATION: Synthetically generated oligonucleotide

<400> SEQUENCE: 113

```
gaagttcaat tgttagagtc tggtggcggt cttgttcagc ctggtggttc tttacgtctt    60
tcttgcgctg cttccggatt cactttctct ttttacaata tgacttgggt tcgccaagct   120
cctggtaaag gtttggagtg ggtttcttct atctattctt ctggtggcaa tactgattat   180
gctgactccg ttaaaggtcg cttcactatc tctagagaca actctaagaa tactctctac   240
ttgcagatga acagcttaag ggctgaggac acggccgtat attactgtgc tagagattcc   300
ctctcccact actactacgg tatggacgtc tggggccaag gaccacggt caccgtctca   360
agc                                                                 363
```

<210> SEQ ID NO 114
<211> LENGTH: 324
<212> TYPE: DNA
<213> ORGANISM: Artificial Sequence
<220> FEATURE:
<223> OTHER INFORMATION: Synthetically generated oligonucleotide

<400> SEQUENCE: 114

```
caagacatcc agatgaccca gtctccaggc accctgtctt tgtctccagg ggaaagagcc      60
accctctcct gcagggccag tcagagtgtt agcagcagct acttagcctg gtaccagcag     120
aaacctggcc aggctcccag gctcctcatc tatggtgcat ccagcagggc cactggcatc     180
ccagacaggt tcagtggcag tgggtctggg acagacttca ctctcaccat cagcagactg     240
gagcctgaag attttgcagt gtattactgt cagcagtatg gtacctcatc gacgttcggc     300
caagggacca aggtggaaat caaa                                            324
```

<210> SEQ ID NO 115
<211> LENGTH: 363
<212> TYPE: DNA
<213> ORGANISM: Artificial Sequence
<220> FEATURE:
<223> OTHER INFORMATION: Synthetically generated oligonucleotide

<400> SEQUENCE: 115

```
gaagttcaat tgttagagtc tggtggcggt cttgttcagc ctggtggttc tttacgtctt      60
tcttgcgctg cttccggatt cactttctct tcttaccgta tgtcttgggt tcgccaagct     120
cctggtaaag gtttggagtg ggtttctggt atctcttctt ctggtggctt tactatgtat     180
gctgactccg ttaaaggtcg cttcactatc tctagagaca actctaagaa tactctctac     240
ttgcagatga acagcttaag ggctgaggac acggccgtgt attactgtgc gagggatatt     300
ttgactggtt attcctacgg tatggacgtc tggggccaag gaccacggt caccgtctca     360
agc                                                                   363
```

<210> SEQ ID NO 116
<211> LENGTH: 324
<212> TYPE: DNA
<213> ORGANISM: Artificial Sequence
<220> FEATURE:
<223> OTHER INFORMATION: Synthetically generated oligonucleotide

<400> SEQUENCE: 116

```
caagacatcc agatgaccca gtctccatct tccctgtctg catttgtagg agacagagtc      60
atcatcactt gccgggcaag ccaggacatt agtgtttatg taaattggta tcagcagagc     120
tcaggcaaag cccctaaact cctaatctat ggtgcatcca gtttgcaaag tggggtccca     180
tcaaggttca gtggcagtgg atctgggaca gatttcactc tcaccatcag cagtctgcaa     240
cctgaagatt ttgcaagtta cttctgtcaa cagagttata atttgccttt caccttcggc     300
ggaggaacca acgtgcagat caaa                                            324
```

<210> SEQ ID NO 117
<211> LENGTH: 351
<212> TYPE: DNA
<213> ORGANISM: Artificial Sequence
<220> FEATURE:
<223> OTHER INFORMATION: Synthetically generated oligonucleotide

<400> SEQUENCE: 117

```
gaagttcaat tgttagagtc tggtggcggt cttgttcagc ctggtggttc tttacgtctt      60
tcttgcgctg cttccggatt cactttctct cagtacaata tgcagtgggt tcgccaagct     120
cctggtaaag gtttggagtg ggtttctggt atcgttcctt ctggtggctg gactccttat     180
gctgactccg ttaaaggtcg cttcactatc tctagagaca actctaagaa tactctctac     240
```

```
ttgcagatga acagcttaag ggctgaggac acggccgtgt attactgtgc aagaggggtg    300
cgctacgggc ttgactactg gggccaggga accctggtca ccgtctcaag c             351

<210> SEQ ID NO 118
<211> LENGTH: 324
<212> TYPE: DNA
<213> ORGANISM: Artificial Sequence
<220> FEATURE:
<223> OTHER INFORMATION: Synthetically generated oligonucleotide

<400> SEQUENCE: 118
caagacatcc agatgaccca gtctccaggc accctgtctt tgtctccagg ggagagagcc     60 acccttttcct gcagggccag tcagagtctt agcggcgact acttagcctg gtatcagcag   120
aaaattggcc aggctcccag gctcctcata tttggtgcat ctaggagacc cactggcatc    180
ccagacaggt tcagtggcag tgggtctggg acagacttcg ctctcaccat cagcagactg    240
gagcctgaag attttgcagt gtattactgt cagcagtatg gtagtttaat caccttcggc    300
caagggacac ggctggagat taaa                                           324

<210> SEQ ID NO 119
<211> LENGTH: 369
<212> TYPE: DNA
<213> ORGANISM: Artificial Sequence
<220> FEATURE:
<223> OTHER INFORMATION: Synthetically generated oligonucleotide

<400> SEQUENCE: 119
gaagttcaat tgttagagtc tggtggcggt cttgttcagc ctggtggttc tttacgtctt     60
tcttgcgctg cttccggatt cactttctct gtttacgaga tgacttgggt tcgccaagct   120
cctggtaaag gtttggagtg ggtttctggt atcggttctt ctggtggcat gacttttat    180 gccgactccg ttaaaggtcg cttcactatc tctagagaca actctaagaa tactctctac    240
ttgcagatga acagcttaag ggctgaggac acggccgtgt attactgtgc ccggataagg    300
tatagtggga gctatgggtg gcactacatg gacgtctggg gcaaagggac cacggtcacc    360
gtctcaagc                                                            369

<210> SEQ ID NO 120
<211> LENGTH: 324
<212> TYPE: DNA
<213> ORGANISM: Artificial Sequence
<220> FEATURE:
<223> OTHER INFORMATION: Synthetically generated oligonucleotide

<400> SEQUENCE: 120
cagagcgaat tgactcagga ccctgctgtg tctgtggcct gggacagac agtcaggatc      60 acatgccaag agacagcct cagaagctat tatgcaagct ggtaccagca gaagccagga    120
caggcccctg tacttgtcat ctatggtaaa acaaccggc cctcagggat cccagaccga    180
ttctctggct ccagctcagg aaacacagct tccttgacca tcactggggc tcaggcggaa    240
gatgaggctg actattactg taactcccgg gacagcagtg gtaaccatgt ggtattcggc    300
ggagggacca agctgaccgt ccta                                           324

<210> SEQ ID NO 121
<211> LENGTH: 384
<212> TYPE: DNA
<213> ORGANISM: Artificial Sequence
<220> FEATURE:
<223> OTHER INFORMATION: Synthetically generated oligonucleotide
```

<400> SEQUENCE: 121

```
gaagttcaat tgttagagtc tggtggcggt cttgttcagc ctggtggttc tttacgtctt    60
tcttgcgctg cttccggatt cactttctct atgtacccta tgaattgggt tcgccaagct   120
cctggtaaag gtttggagtg ggtttcttct atctcttctt ctggtggctg gactaagtat   180
gctgactccg ttaaaggtcg cttcactatc tctagagaca actctaagaa tactctctac   240
ttgcagatga acagcttaag ggctgaggac acggccgtgt attactgtgc gagagttttt   300
ttcggctatg atagtagtgg ttacccttac tactactacg gtatggacgt ctggggccaa   360
gggaccacgg tcaccgtctc aagc                                          384
```

<210> SEQ ID NO 122
<211> LENGTH: 339
<212> TYPE: DNA
<213> ORGANISM: Artificial Sequence
<220> FEATURE:
<223> OTHER INFORMATION: Synthetically generated oligonucleotide

<400> SEQUENCE: 122

```
caagacatcc agatgaccca gtctccactc tccctgcccg tcaccctgg agagccggcc     60
tccatctcct gcaggtctag tcagagcctc ctacatagta atggatacaa ctatttggat   120
tggtatgtgc agaagccagg acagtctcca cagctcctga tctatttggg ttctggtcgg   180
gcctccgggg tccctgacag gttcagtggc agtggatcag gcacagattt tacactgaaa   240
atcaacagag tggaggctga ggatgttggg gtttattact gcatgcaagc tctacaaact   300
ccgtggacgt tcggccaagg gaccaaggtg gaaatcaaa                          339
```

<210> SEQ ID NO 123
<211> LENGTH: 375
<212> TYPE: DNA
<213> ORGANISM: Artificial Sequence
<220> FEATURE:
<223> OTHER INFORMATION: Synthetically generated oligonucleotide

<400> SEQUENCE: 123

```
gaagttcaat tgttagagtc tggtggcggt cttgttcagc ctggtggttc tttacgtctt    60
tcttgcgctg cttccggatt cactttctct ccttactcta tgttttgggt tcgccaagct   120
cctggtaaag gtttggagtg ggtttctgtt atctatcctt ctggtggcgg tactatttat   180
gctgactccg ttaaaggtcg cttcactatc tctagagaca actctaagaa tactctctac   240
ttgcagatga acagcttaag ggctgaggac acggccgtgt attactgtgc gagaagtaga   300
gagtcttgtg atgctgatac ttgctaccaa tatttccagg agtggggcca gggcaccctg   360
gtcaccgtct caagc                                                    375
```

<210> SEQ ID NO 124
<211> LENGTH: 330
<212> TYPE: DNA
<213> ORGANISM: Artificial Sequence
<220> FEATURE:
<223> OTHER INFORMATION: Synthetically generated oligonucleotide

<400> SEQUENCE: 124

```
caagacatcc agatgaccca gtctccaggc accctgtctt tgtctccagg ggaaagagcc    60
accctctcct gcagggccag tcagagtgtt agcagcagct acttagcctg gtaccagcag   120
aaacctggcc aggctcccag gctcctcatc tatggtgcat ccatcagggc cactggcatc   180
```

```
ccagacaggt tcagtggcag tgggtctggg acagacttca ctctcaccat cagcagactg    240
gagcctgaag attttgcagt gtattactgt cagcagtatg gtagctcacc cccgtacact    300
tttggccagg ggaccaagct ggagatcaaa                                     330
```

<210> SEQ ID NO 125
<211> LENGTH: 381
<212> TYPE: DNA
<213> ORGANISM: Artificial Sequence
<220> FEATURE:
<223> OTHER INFORMATION: Synthetically generated oligonucleotide

<400> SEQUENCE: 125

```
gaagttcaat tgttagagtc tggtggcggt cttgttcagc ctggtggttc tttacgtctt     60
tcttgcgctg cttccggatt cactttctct cattacccta tgttttgggt tcgccaagct    120
cctggtaaag gtttggagtg gtttctggt atctcttctt ctggtggcta tactatttat    180
gctgactccg ttaaaggtcg cttcactatc tctagagaca actctaagaa tactctctac    240
ttgcagatga acagcttaag ggctgaggac acggccgtgt attactgtgc gagaggggga    300
agacgacaga cgcggcgtac cagcgactac tactacggta tggacgtctg gggccaaggg    360
accacggtca ccgtctcaag c                                              381
```

<210> SEQ ID NO 126
<211> LENGTH: 330
<212> TYPE: DNA
<213> ORGANISM: Artificial Sequence
<220> FEATURE:
<223> OTHER INFORMATION: Synthetically generated oligonucleotide

<400> SEQUENCE: 126

```
cagagcgtct tgactcagcc accctcggtg tccaaggact gagacagac cgccacactc      60 acctgcactg ggaacagcaa caatgttggc taccaaggag cagcttggct gcagcagcac    120
cagggccacc ctcccaaagt cctttcgtac aggaataaca accggccctc agggatctca    180
gagagatttt ctgcgtccag gtcaggaaat acagcctccc tgaccattac tggactccag    240
cctgaggacg aggctgacta ttactgctca gcgtgggaca gcagcctcac tgcttgggtc    300
ttcggcggag ggaccaagct gaccgtccta                                     330
```

<210> SEQ ID NO 127
<211> LENGTH: 360
<212> TYPE: DNA
<213> ORGANISM: Artificial Sequence
<220> FEATURE:
<223> OTHER INFORMATION: Synthetically generated oligonucleotide

<400> SEQUENCE: 127

```
gaagttcaat tgttagagtc tggtggcggt cttgttcagc ctggtggttc tttacgtctt     60
tcttgcgctg cttccggatt cactttctct tttacgata tgacttgggt tcgccaagct    120
cctggtaaag gtttggagtg gtttcttct atctggtctt ctggtggcgt tactgattat    180
gctgactccg ttaaaggtcg cttcactatc tctagagaca actctaagaa tactctctac    240
ttgcagatga acagcttaag ggctgaggac acagccgtgt attactgtac gagagctagt    300
agtggttatt atgatgcttt tgatatctgg ggccaaggga caatggtcac cgtctcaagc    360
```

<210> SEQ ID NO 128
<211> LENGTH: 327
<212> TYPE: DNA
<213> ORGANISM: Artificial Sequence
<220> FEATURE:
<223> OTHER INFORMATION: Synthetically generated oligonucleotide

<400> SEQUENCE: 128

| | |
|---|---|
| caagacatcc agatgaccca gtctccagcc tccctgtatt tgtctccagg ggaaagagcc | 60 |
| accctctcct gcagggccag tcagagtgtt agcagcaact tagcctggta ccagcagaaa | 120 |
| cctggccagg ctcccaggct cctcatctat ggtgcatcca ccagggccac tggtatccca | 180 |
| gccaggttca gtggcagtgg gtctgggaca gagttcactc tcaccatcag cagcctgcag | 240 |
| tctgcagatt ttgccgttta ttactgtcag cagtatgata actggcctcc cctcactttc | 300 |
| ggcggaggga ccaaggtgga gatcaaa | 327 |

<210> SEQ ID NO 129
<211> LENGTH: 357
<212> TYPE: DNA
<213> ORGANISM: Artificial Sequence
<220> FEATURE:
<223> OTHER INFORMATION: Synthetically generated oligonucleotide

<400> SEQUENCE: 129

| | |
|---|---|
| gaagttcaat tgttagagtc tggtggcggt cttgttcagc ctggtggttc tttacgtctt | 60 |
| tcttgcgctg cttccggatt cactttctct tattacgcta tggattgggt tcgccaagct | 120 |
| cctggtaaag gtttggagtg gtttcttcct atcggttctt ctggtggcga tactgtttat | 180 |
| gctgactccg ttaaaggtcg cttcactatc tctagagaca actctaagaa tactctctac | 240 |
| ttgcagatga acagcttaag ggctgaggac acagccacgt attactgtgc gagagaccct | 300 |
| cggcagcccg gagtctttga ctactggggc cagggaaccc tggtcaccgt ctcaagc | 357 |

<210> SEQ ID NO 130
<211> LENGTH: 330
<212> TYPE: DNA
<213> ORGANISM: Artificial Sequence
<220> FEATURE:
<223> OTHER INFORMATION: Synthetically generated oligonucleotide

<400> SEQUENCE: 130

| | |
|---|---|
| cagagcgctt tgactcagcc tgcttccgtg tctgggtctc ctggacagtc gatcaccatc | 60 |
| tcctgcactg gaaccagcag tgacattggt gcttataggt atgtctcctg gtaccaacag | 120 |
| cgcccaggca aagcccccaa actcatgatt tttgatgtca ctaagcggcc ctcaggggtt | 180 |
| tctaatcgct tctctggctt caagtctggc aacacggctt ccctgaccat ctctgggctc | 240 |
| caggctgagg acgaggccga ttattactgc agctcattta caagtggcag cactttcgtc | 300 |
| ttcggaactg ggaccaaggt caccgtccta | 330 |

<210> SEQ ID NO 131
<211> LENGTH: 348
<212> TYPE: DNA
<213> ORGANISM: Artificial Sequence
<220> FEATURE:
<223> OTHER INFORMATION: Synthetically generated oligonucleotide

<400> SEQUENCE: 131

| | |
|---|---|
| gaagttcaat tgttagagtc tggtggcggt cttgttcagc ctggtggttc tttacgtctt | 60 |
| tcttgcgctg cttccggatt cactttctct aagtactcta tgtattgggt tcgccaagct | 120 |
| cctggtaaag gtttggagtg gtttcttcct atctcttctt ctggtggcta tactgcttat | 180 |
| gctgactccg ttaaaggtcg cttcactatc tctagagaca actctaagaa tactctctac | 240 |

```
ttgcagatga acagcttaag ggctgaggac actgccgtgt attactgtgc gattccttgg    300
ggtagtggga gttcctgggg ccagggaacc ctggtcaccg tctcaagc                 348
```

<210> SEQ ID NO 132
<211> LENGTH: 324
<212> TYPE: DNA
<213> ORGANISM: Artificial Sequence
<220> FEATURE:
<223> OTHER INFORMATION: Synthetically generated oligonucleotide

<400> SEQUENCE: 132

```
caagacatcc agatgaccca gtctccatct gccatgtctg catctgtagg agacagagtc     60
accatcactt gtcgggcgag tcagggtatt agcagctggt tagcctggta tcagcagaaa    120
ccagggaaag cccctaagct cctgatctat gctgcatcca gtttgcaaag tggggtccca    180
tcaaggttca gcggcagtgg atctgggaca gatttcactc tcaccatcag cagcctgcag    240
cctgaagatt ttgcaactta ctattgtcaa caggctaaca gtttcccgct cactttcggc    300
ggagggacca aggtggagat caaa                                           324
```

<210> SEQ ID NO 133
<211> LENGTH: 354
<212> TYPE: DNA
<213> ORGANISM: Artificial Sequence
<220> FEATURE:
<223> OTHER INFORMATION: Synthetically generated oligonucleotide

<400> SEQUENCE: 133

```
gaagttcaat tgttagagtc tggtggcggt cttgttcagc ctggtggttc tttacgtctt     60
tcttgcgctg cttccggatt cactttctct ttttactcta tgcattgggt tcgccaagct    120
cctggtaaag gtttggagtg ggtttctggt atctcttctt ctggtggcgt tactaagtat    180
gctgactccg ttaaaggtcg cttcactatc tctagagaca actctaagaa tactctctac    240
ttgcagatga acagcttaag ggctgaggac acggccgtgt attactgtgc gagagcacgg    300
tcaactcgtg gctttgacta ctggggccag ggaaccctgg tcaccgtctc aagc          354
```

<210> SEQ ID NO 134
<211> LENGTH: 315
<212> TYPE: DNA
<213> ORGANISM: Artificial Sequence
<220> FEATURE:
<223> OTHER INFORMATION: Synthetically generated oligonucleotide

<400> SEQUENCE: 134

```
caagacatcc agatgaccca gtctccaggc accctgtctt tgtctccagg ggaaagagcc     60
accctctcct gcagggccag tcagagtgtt agcagcagct acttagcctg gtaccagcag    120
aaacctggcc aggctcccag gctcctcatc tatggtgcat ccagcagggc cactggcatc    180
ccagacaggt tcagtggcag tgggtctggg acagacttca ctctcaccat cagcagactg    240
gagcctgaag attttgcagt gtattactgt cagtcggggg tcactttcgg cggagggacc    300
aaggtggaga tcaaa                                                     315
```

<210> SEQ ID NO 135
<211> LENGTH: 384
<212> TYPE: DNA
<213> ORGANISM: Artificial Sequence
<220> FEATURE:
<223> OTHER INFORMATION: Synthetically generated oligonucleotide

<400> SEQUENCE: 135

```
gaagttcaat tgttagagtc tggtggcggt cttgttcagc ctggtggttc tttacgtctt    60
tcttgcgctg cttccggatt cactttctct tggtacccta tgttttgggt tcgccaagct   120
cctggtaaag gtttggagtg ggtttctggt atctattctt ctggtggccc tactgattat   180
gctgactccg ttaaaggtcg cttcactatc tctagagaca actctaagaa tactctctac   240
ttgcagatga acagcttaag ggctgaggac acggccgtgt attactgtgc aaaagatacc   300
ctagggaggt attacgattt ttggagtggt tattcctacg gtatggacgt ctggggccaa   360
gggaccacgg tcaccgtctc aagc                                          384
```

<210> SEQ ID NO 136
<211> LENGTH: 324
<212> TYPE: DNA
<213> ORGANISM: Artificial Sequence
<220> FEATURE:
<223> OTHER INFORMATION: Synthetically generated oligonucleotide

<400> SEQUENCE: 136

```
caagacatcc agatgaccca gtctccatct tccgtgtctg catctgtagg agacagagtc    60
accatcactt gtagggcgag tcagaatatt tacagttggt tagcctggta tcagcagaga   120
ccagggaaag cccctaagct cctgatctac gctgcatcca gtttacatag tggggtccca   180
tcaaggttca gcggcagtgg atctgggaca gatttcactc tcaccatcag cagcctgcag   240
cctgaagatt ttgcaactta ctattgtcaa caggctaaga gtttccctgt gactttcggc   300
ggagggacca aggtggaaat caaa                                          324
```

<210> SEQ ID NO 137
<211> LENGTH: 354
<212> TYPE: DNA
<213> ORGANISM: Artificial Sequence
<220> FEATURE:
<223> OTHER INFORMATION: Synthetically generated oligonucleotide

<400> SEQUENCE: 137

```
gaagttcaat gttagagtc tggtggcggt cttgttcagc ctggtggttc tttacgtctt     60
tcttgcgctg cttccggatt cactttctct cagtaccata tgatgtgggt tcgccaagct   120
cctggtaaag gtttggagtg ggtttcttct atcggttctt ctggctatac taagtatgct   180
gactccgtta aggtcgctt cactatctct agagacaact ctaagaatac tctctacttg   240
cagatgaaca gcttaagggc tgaggacacg gccgtgtatt actgtgcggg agcagtggct   300
ggtaccgggg cctttgacta ctggggccag ggaaccctgg tcaccgtctc aagc         354
```

<210> SEQ ID NO 138
<211> LENGTH: 294
<212> TYPE: DNA
<213> ORGANISM: Artificial Sequence
<220> FEATURE:
<223> OTHER INFORMATION: Synthetically generated oligonucleotide

<400> SEQUENCE: 138

```
cagtacgaat tgactcagcc actctcagtc tcagtggccc tgggacagac ggccagtatt    60
tcctgtgggg gacataacat tagaattaaa aatgtacact ggtaccagca gaagccaggc   120
caggcccctg tggtggtcat gtatatccct gagcggttct ctggctccac ctcggggaac   180
acggccaccc tgaccatcag tggagcccaa gccggggatg aggctgacta ttattgtcaa   240
gtgtgggaca gcagcactgt ggtgttcggc ggagggacca agctgaccgt ccta         294
```

<210> SEQ ID NO 139
<211> LENGTH: 357
<212> TYPE: DNA
<213> ORGANISM: Artificial Sequence
<220> FEATURE:
<223> OTHER INFORMATION: Synthetically generated oligonucleotide

<400> SEQUENCE: 139

```
gaagttcaat tgttagagtc tggtggcggt cttgttcagc ctggtggttc tttacgtctt        60
tcttgcgctg cttccggatt cactttctct aagtacccta tgtcttgggt tcgccaagct       120
cctggtaaag gtttggagtg gtttcttct atctggcctt ctggtggcca tacttttat        180
gctgactccg ttaaaggtcg cttcactatc tctagagaca actctaagaa tactctctac       240
ttgcagatga acagcttaag ggctgaggac acggccgtgt attactgtgc gaaaaatccc       300
gggctacggt atgcttttga taactgggc cgagggacaa tggtcaccgt ctcaagc          357
```

<210> SEQ ID NO 140
<211> LENGTH: 333
<212> TYPE: DNA
<213> ORGANISM: Artificial Sequence
<220> FEATURE:
<223> OTHER INFORMATION: Synthetically generated oligonucleotide

<400> SEQUENCE: 140

```
cagtacgaat tgactcagcc accctcaacg tctgggaccc ccgggcagac ggtcaccatc        60
tcttgttctg gaagcatctc caacatcgga agaaattctg taaactggta ccagcagctc       120
ccaggaacgg cccccaaact cctcatgttt aggaataatg agcggccctc aggggtccct       180
gaccgattct ctggctccaa gtctggcacc tcggcctccc tggccatcag tgggctccgg       240
tccgaggatg aggctgatta ttactgtgca gcatggggtg acagcctgag tggttcttat       300
gtcttcggaa ctgggaccaa ggtcaccgtc cta                                    333
```

<210> SEQ ID NO 141
<211> LENGTH: 386
<212> TYPE: DNA
<213> ORGANISM: Artificial Sequence
<220> FEATURE:
<223> OTHER INFORMATION: Synthetically generated oligonucleotide

<400> SEQUENCE: 141

```
gaagttcaat tgttagagtc tggtggcggt cttgttcagc ctggtggttc tttacgtctt        60
tcttgcgctg cttccggatt cactttctct tattacgcta tgggttgggt tcgccaagct       120
cctggtaaag gtttggagtg gtttcttat atcttccttc tggtggcgag actcgttatg       180
ctgactccgt taaaggtcgc ttcactatct ctagagacaa ctctaagaat actctctact       240
tgcagatgaa cagcttaagg gctgaggaca cggccgtgta ttactgtgcg agagatggtt       300
attacgattt ttggagtggt tattggtcct actactacta cggtatggac gtctggggcc       360
aagggaccac ggtcaccgtc tcaagc                                            386
```

<210> SEQ ID NO 142
<211> LENGTH: 324
<212> TYPE: DNA
<213> ORGANISM: Artificial Sequence
<220> FEATURE:
<223> OTHER INFORMATION: Synthetically generated oligonucleotide

<400> SEQUENCE: 142

```
caagacatcc agatgaccca gtctccatcc tccctgtctg catctgtggg agacagagtc        60
```

```
accatcactt gccgggcaag tcagagcatt agcagctatt taaattggta tcagcaaaaa    120
ccaggggaag cccctaagct cctcatctat gctgcatccg ctttgcaaag tggggtcccg    180
tcaaggttca gtggcagtgg acttgggaca gttttcactc tcaccatcac cagcctgcaa    240
cctgaagatt ctgcaactta ctattgtcaa cagagttaca gtcccccggt cactttcggc    300
ggagggacca aggtggatat caaa                                          324
```

<210> SEQ ID NO 143
<211> LENGTH: 359
<212> TYPE: DNA
<213> ORGANISM: Artificial Sequence
<220> FEATURE:
<223> OTHER INFORMATION: Synthetically generated oligonucleotide

<400> SEQUENCE: 143

```
gaagttcaat tgttagagtc tggtggcggt cttgttcagc ctggtggttc tttacgtctt     60
tcttgcgctg cttccggatt cactttctct cgttacccta tgtcttgggt tcgccaagct    120
cctggtaaag gtttggagtg ggtttctcgt atctcttctt ctggtggctg gactcagtat    180
gctgactccg ttaaaggtcg cttcactatc tctagagaca actctaagaa actctctact    240
tgcagatgaa cagcttaagg gctgaggaca cggccgtgta ttactgtgcg agagagggtt    300
ctagtgggag ccgtcgtggt gactactggg gccagggaac cctggtcacc gtctcaagc    359
```

<210> SEQ ID NO 144
<211> LENGTH: 126
<212> TYPE: PRT
<213> ORGANISM: Artificial Sequence
<220> FEATURE:
<223> OTHER INFORMATION: Synthetically generated peptide

<400> SEQUENCE: 144

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Pro Tyr
            20                  25                  30

Pro Met Gly Trp Val Arg Gln Ala Pro Gly Lys Gly Leu Glu Trp Val
        35                  40                  45

Ser Ser Ile Val Ser Ser Gly Gly Leu Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Leu Tyr Asp Ile Leu Thr Gly Gln Gly Ala Pro
            100                 105                 110

Phe Asp Tyr Trp Gly Gln Gly Thr Leu Val Thr Val Ser Ser
        115                 120                 125

<210> SEQ ID NO 145
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 145

Gln Asp Ile Gln Met Thr Gln Ser Pro Leu Ser Leu Pro Val Thr Pro
 1               5                  10                  15

Gly Glu Pro Ala Ser Ile Ser Cys Arg Ser Ser Gln Ser Leu Leu His
            20                  25                  30

Ser Asn Gly Tyr Tyr Tyr Leu Asp Trp Tyr Leu Gln Lys Pro Gly Gln
        35                  40                  45

Ser Pro Gln Leu Leu Ile Tyr Leu Gly Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Ser Val Glu Ala Glu Asp Val Gly Val Tyr Tyr Cys Met Gln
                85                  90                  95

Ala Leu Gln Thr Pro Leu Thr Phe Gly Gly Gly Thr Arg Val Asp Ile
            100                 105                 110

Lys

<210> SEQ ID NO 146
<211> LENGTH: 125
<212> TYPE: PRT
<213> ORGANISM: Artificial Sequence
<220> FEATURE:
<223> OTHER INFORMATION: Synthetically generated peptide

<400> SEQUENCE: 146

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Glu Met His Trp Val Arg Gln Ala Pro Gly Lys Gly Leu Glu Trp Val
        35                  40                  45

Ser Ser Ile Tyr Ser Ser Gly Gly Trp Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gln Gln Tyr Tyr Asp Phe Ser Ser Arg Tyr Tyr Gly Met
            100                 105                 110

Asp Val Trp Gly Gln Gly Thr Thr Val Thr Val Ser Ser
        115                 120                 125

<210> SEQ ID NO 147
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 147

Gln Ser Glu Leu Thr Gln Pro Pro Ser Val Ser Gly Thr Pro Gly Gln
1               5                   10                  15

Arg Val Thr Ile Ser Cys Ser Gly Thr Ser Ala Asn Ile Gly Arg Asn
            20                  25                  30

Ala Val His Trp Tyr Gln Gln Leu Pro Gly Thr Ala Pro Lys Leu Leu
        35                  40                  45

Ile His Ser Asn Asn Arg Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Glu Asn Ser Leu
                85                  90                  95

Asn Ala Phe Tyr Val Phe Gly Thr Gly Thr Lys Val Thr Val Leu
            100                 105                 110

<210> SEQ ID NO 148
<211> LENGTH: 120
<212> TYPE: PRT
<213> ORGANISM: Artificial Sequence
<220> FEATURE:
<223> OTHER INFORMATION: Synthetically generated peptide

<400> SEQUENCE: 148

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Val Tyr
             20                  25                  30

Gly Met Val Trp Val Arg Gln Ala Pro Gly Lys Gly Leu Glu Trp Val
         35                  40                  45

Ser Val Ile Ser Ser Ser Gly Gly Ser Thr Trp Tyr Ala Asp Ser Val
     50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Arg Pro Phe Ser Arg Arg Tyr Gly Val Phe Asp Tyr Trp Gly Gln
            100                 105                 110

Gly Thr Leu Val Thr Val Ser Ser
        115                 120

<210> SEQ ID NO 149
<211> LENGTH: 108
<212> TYPE: PRT
<213> ORGANISM: Artificial Sequence
<220> FEATURE:
<223> OTHER INFORMATION: Synthetically generated peptide

<400> SEQUENCE: 149

Gln Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Gly Ile Arg Asn
             20                  25                  30

Phe Leu Ala Trp Tyr Gln Gln Lys Pro Gly Lys Val Pro Lys Leu Leu
         35                  40                  45

Val Phe Gly Ala Ser Ala Leu Gln Ser Gly Val Pro Ser Arg Phe Ser
     50                  55                  60

Gly Ser Gly Ser Gly Thr Asp Phe Thr Leu Thr Ile Ser Gly Leu Gln
65                  70                  75                  80

Pro Glu Asp Val Ala Thr Tyr Tyr Cys Gln Lys Tyr Asn Gly Val Pro
                85                  90                  95

Leu Thr Phe Gly Gly Gly Thr Lys Val Glu Ile Lys
            100                 105

<210> SEQ ID NO 150
<211> LENGTH: 125
<212> TYPE: PRT
<213> ORGANISM: Artificial Sequence
<220> FEATURE:
<223> OTHER INFORMATION: Synthetically generated peptide -continued

<400> SEQUENCE: 150

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Glu Met Phe Trp Val Arg Gln Ala Pro Gly Lys Gly Leu Glu Trp Val
        35                  40                  45

Ser Ser Ile Ser Pro Ser Gly Gly Gln Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Asp Arg Thr Tyr Tyr Asp Phe Trp Ser Gly Tyr Gly Pro Leu
            100                 105                 110

Trp Tyr Trp Gly Gln Gly Thr Leu Val Thr Val Ser Ser
        115                 120                 125

<210> SEQ ID NO 151
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 151

Gln Asp Ile Gln Met Thr Gln Ser Pro Leu Ser Leu Pro Val Thr Leu
1               5                   10                  15

Gly Glu Ser Ala Ser Val Ser Cys Arg Ser Ser Gln Ser Leu Leu His
            20                  25                  30

Glu Asn Gly His Asn Tyr Leu Asp Trp Tyr Leu Gln Lys Pro Gly Gln
        35                  40                  45

Ser Pro Gln Leu Leu Ile Tyr Leu Gly Ser Asn Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ser Leu Lys Thr Pro Pro Thr Phe Gly Pro Gly Thr Lys Val Glu Ile
            100                 105                 110

Lys

<210> SEQ ID NO 152
<211> LENGTH: 127
<212> TYPE: PRT
<213> ORGANISM: Artificial Sequence
<220> FEATURE:
<223> OTHER INFORMATION: Synthetically generated peptide

<400> SEQUENCE: 152

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

Met Met Ile Trp Val Arg Gln Ala Pro Gly Lys Gly Leu Glu Trp Val
        35                  40                  45

```
Ser Ser Ile Tyr Pro Ser Gly Gly Asn Thr Met Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Val Leu Arg Tyr Phe Asp Trp Asp Ala Gly Ser Gly Met
            100                 105                 110

Asp Val Trp Gly Gln Gly Thr Thr Val Thr Val Ser Ser Leu Cys
            115                 120                 125

<210> SEQ ID NO 153
<211> LENGTH: 108
<212> TYPE: PRT
<213> ORGANISM: Artificial Sequence
<220> FEATURE:
<223> OTHER INFORMATION: Synthetically generated peptide

<400> SEQUENCE: 153

Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Arg Asn
            20                  25                  30

Asp Leu Gly Trp Tyr Gln Gln Lys Pro Gly Lys Ala Pro Lys Arg Leu
        35                  40                  45

Ile Tyr Val Ala Ser Ser Leu Gln Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gln His Asn Ser Tyr Pro
                85                  90                  95

Trp Thr Phe Gly Gln Gly Thr Lys Val Glu Ile Lys
            100                 105

<210> SEQ ID NO 154
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 154

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Val Met His Trp Val Arg Gln Ala Pro Gly Lys Gly Leu Glu Trp Val
        35                  40                  45

Ser Ser Ile Ser Pro Ser Gly Gly Trp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Met Ala Val Tyr Tyr Cys
                85                  90                  95

Ala Arg Gly Thr Gly Ala Tyr Gly Met Asp Val Trp Gly Gln Gly Thr
            100                 105                 110

Thr Val Thr Val Ser Ser
            115
```

US 7,745,587 B2
227                                                         228
-continued
<210> SEQ ID NO 155
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 155

Gln Asp Ile Gln Met Thr Gln Ser Pro Gly Thr Leu Ser Leu Ser Pro
1               5                   10                  15

Gly Asp Arg Ala Thr Leu Ser Cys Gly Ala Ser Gln Leu Val Val Ser
            20                  25                  30

Asn Tyr Ile Ala Trp Tyr Gln Gln Lys Pro Gly Gln Ala Pro Arg Leu
        35                  40                  45

Leu Met Tyr Ala Gly Ser Ile Arg Ala Thr Gly Ile Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Ile Tyr Tyr Cys Gln Gln Arg Ser Asn Trp
                85                  90                  95

Pro Trp Thr Phe Gly Gln Gly Thr Lys Val Glu Ile Lys
            100                 105

<210> SEQ ID NO 156
<211> LENGTH: 115
<212> TYPE: PRT
<213> ORGANISM: Artificial Sequence
<220> FEATURE:
<223> OTHER INFORMATION: Synthetically generated peptide

<400> SEQUENCE: 156

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Ser Met Asn Trp Val Arg Gln Ala Pro Gly Lys Gly Leu Glu Trp Val
        35                  40                  45

Ser Ser Ile Tyr Ser Ser Gly Gly Ser Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ala Phe Asp Ile Trp Gly Gln Gly Thr Met Val Thr
            100                 105                 110

Val Ser Ser
        115

<210> SEQ ID NO 157
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 157

Gln Asp Ile Gln Met Thr Gln Ser Pro Ser Ser Leu Ser Ala Phe Val
1               5                   10                  15

```
Gly Asp Lys Val Thr Ile Thr Cys Arg Ala Ser Gln Ser Val Gly Thr
            20                  25                  30

Tyr Leu Asn Trp Tyr Gln Gln Lys Ala Gly Lys Ala Pro Glu Leu Leu
        35                  40                  45

Ile Tyr Ala Thr Ser Asn Leu Arg Ser Gly Val Pro Ser Arg Phe Ser
 50                  55                  60

Gly Ser Gly Ser Gly Thr Asp Phe Thr Leu Thr Ile Asn Thr Leu Gln
 65                  70                  75                  80

Pro Glu Asp Phe Ala Thr Tyr Tyr Cys Gln Gln Ser Tyr Ser Ile Pro
                85                  90                  95

Arg Phe Thr Phe Gly Pro Gly Thr Lys Val Asp Ile Lys
            100                 105
```

<210> SEQ ID NO 158
<211> LENGTH: 119
<212> TYPE: PRT
<213> ORGANISM: Artificial Sequence
<220> FEATURE:
<223> OTHER INFORMATION: Synthetically generated peptide

<400> SEQUENCE: 158

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Arg Tyr
             20                  25                  30

Lys Met Trp Trp Val Arg Gln Ala Pro Gly Lys Gly Leu Glu Trp Val
         35                  40                  45

Ser Gly Ile Arg Pro Ser Gly Gly Leu Thr Arg Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Arg Gly Asp Tyr Val Gly Gly Phe Asp Tyr Trp Gly Gln Gly
            100                 105                 110

Thr Leu Val Thr Val Ser Ser
        115
```

<210> SEQ ID NO 159
<211> LENGTH: 108
<212> TYPE: PRT
<213> ORGANISM: Artificial Sequence
<220> FEATURE:
<223> OTHER INFORMATION: Synthetically generated peptide

<400> SEQUENCE: 159

```
Gln Asp Ile Gln Met Thr Gln Ser Pro Gly Thr Leu Ser Leu Ser Pro
  1               5                  10                  15

Gly Glu Arg Ala Thr Leu Ser Cys Arg Ala Ser Gln Ser Val Ser Ser
             20                  25                  30

Ser Tyr Leu Ala Trp Tyr Gln Gln Lys Pro Gly Gln Ala Pro Arg Leu
         35                  40                  45

Leu Ile Tyr Gly Ala Ser Ser Arg Ala Thr Gly Ile Pro Asp Arg Phe
 50                  55                  60

Ser Gly Ser Gly Ser Gly Thr Asp Phe Thr Leu Thr Ile Ser Arg Leu
 65                  70                  75                  80

Glu Pro Glu Asp Phe Ala Val Tyr Cys Gln His Tyr Gly Gly Ser
                85                  90                  95
```

```
Gln Ala Phe Gly Gly Gly Thr Lys Val Glu Ile Lys
            100                 105

<210> SEQ ID NO 160
<211> LENGTH: 117
<212> TYPE: PRT
<213> ORGANISM: Artificial Sequence
<220> FEATURE:
<223> OTHER INFORMATION: Synthetically generated peptide

<400> SEQUENCE: 160

Glu Val Gln Leu Leu Glu Ser Gly Gly Leu Val Gln Pro Gly Gly
  1               5                  10                  15

Ser Leu Arg Leu Ser Cys Ala Ala Ser Gly Phe Thr Phe Ser Ala Tyr
            20                  25                  30

Asn Met Gly Trp Val Arg Gln Ala Pro Gly Lys Gly Leu Glu Trp Val
        35                  40                  45

Ser Ser Ile Ser Ser Gly Gly Tyr Thr Gly Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Tyr Arg Gly Phe Asp Tyr Trp Gly Gln Gly Thr Leu
            100                 105                 110

Val Thr Val Ser Ser
        115

<210> SEQ ID NO 161
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 161

Gln Asp Ile Gln Met Thr Gln Ser Pro Ala Thr Leu Ser Val Ser Pro
  1               5                  10                  15

Gly Glu Arg Ala Thr Leu Ser Cys Arg Ala Ser Glu Ser Val Lys Asn
            20                  25                  30

Asn Leu Ala Trp Tyr Gln Gln Lys Pro Gly Gln Ala Pro Arg Leu Leu
        35                  40                  45

Ile Tyr Gly Val Ser Thr Arg Ala Pro Gly Ile Pro Ala Arg Phe Ser
 50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Arg Ser Asn Trp Pro
                85                  90                  95

Pro Val Thr Phe Gly Gln Gly Thr Arg Leu Glu Ile Lys
            100                 105

<210> SEQ ID NO 162
<211> LENGTH: 124
<212> TYPE: PRT
<213> ORGANISM: Artificial Sequence
<220> FEATURE:
<223> OTHER INFORMATION: Synthetically generated peptide

<400> SEQUENCE: 162
```

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Tyr Tyr
            20                  25                  30

Gly Met Tyr Trp Val Arg Gln Ala Pro Gly Lys Gly Leu Glu Trp Val
        35                  40                  45

Ser Ser Ile Ser Ser Ser Gly Gly Tyr Thr Asp Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ile Lys Tyr Tyr Asp Ile Glu Gly Glu Gly Ala Phe Asp
            100                 105                 110

Ile Trp Gly Gln Gly Thr Met Val Thr Val Ser Ser
            115                 120
```

<210> SEQ ID NO 163
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 163

```
Gln Asp Ile Val Met Thr Gln Thr Pro Pro Ser Leu Pro Val Asn Pro
 1               5                  10                  15

Gly Glu Pro Ala Ser Ile Ser Cys Arg Ser Ser Gln Ser Leu Leu His
            20                  25                  30

Arg Asn Gly Tyr Asn Tyr Leu Asp Trp Tyr Leu Gln Lys Pro Gly Gln
        35                  40                  45

Ser Pro Gln Leu Leu Ile His Leu Gly Ser Tyr Arg Ala Ser Gly Val
50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Pro Leu Gln Thr Pro Phe Thr Phe Gly Pro Gly Thr Lys Val Asp Ile
            100                 105                 110

Lys
```

<210> SEQ ID NO 164
<211> LENGTH: 122
<212> TYPE: PRT
<213> ORGANISM: Artificial Sequence
<220> FEATURE:
<223> OTHER INFORMATION: Synthetically generated peptide

<400> SEQUENCE: 164

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser His Tyr
            20                  25                  30

Val Met Phe Trp Val Arg Gln Ala Pro Gly Lys Gly Leu Glu Trp Val
        35                  40                  45

Ser Arg Ile Val Pro Ser Gly Gly Ala Thr Met Tyr Ala Asp Ser Val
50                  55                  60
```

-continued

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Pro Leu Tyr Asp Ser Ser Gly Tyr Val Asp Tyr Trp
            100                 105                 110

Gly Gln Gly Thr Leu Val Thr Val Ser Ser
            115                 120

<210> SEQ ID NO 165
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 165

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Ala Tyr
                20                  25                  30

Asn Tyr Val Ser Trp Tyr Gln Gln His Pro Asp Lys Ala Pro Lys Leu
            35                  40                  45

Ile Ile Tyr Asn Val Asn Glu Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Thr Ser Tyr Ala Gly Ser
                85                  90                  95

Asn Lys Ile Gly Val Ser Gly Thr Gly Thr Lys Val Thr Val Leu
            100                 105                 110

<210> SEQ ID NO 166
<211> LENGTH: 128
<212> TYPE: PRT
<213> ORGANISM: Artificial Sequence
<220> FEATURE:
<223> OTHER INFORMATION: Synthetically generated peptide

<400> SEQUENCE: 166

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
                20                  25                  30

Pro Met Phe Trp Val Arg Gln Ala Pro Gly Lys Gly Leu Glu Trp Val
            35                  40                  45

Ser Gly Ile Tyr Ser Ser Gly Pro Thr Asp Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Thr Leu Gly Arg Tyr Tyr Asp Phe Trp Ser Gly Tyr Ser
            100                 105                 110

Tyr Gly Met Asp Val Trp Gly Gln Gly Thr Thr Val Thr Val Ser Ser
            115                 120                 125

<210> SEQ ID NO 167

```
<211> LENGTH: 105
<212> TYPE: PRT
<213> ORGANISM: Artificial Sequence
<220> FEATURE:
<223> OTHER INFORMATION: Synthetically generated peptide

<400> SEQUENCE: 167

Gln Asp Ile Gln Met Thr Gln Ser Pro Gly Thr Leu Ser Leu Ser Pro
1               5                   10                  15

Gly Glu Arg Ala Thr Leu Ser Cys Arg Ala Ser Gln Ser Val Ser Ser
            20                  25                  30

Ser Tyr Leu Ala Trp Tyr Gln Gln Lys Pro Gly Gln Ala Pro Arg Leu
        35                  40                  45

Leu Ile Tyr Gly Ala Ser Ser Arg Ala Thr Gly Ile Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Gln Ser Gly Val Thr Phe
                85                  90                  95

Gly Gly Gly Thr Lys Val Glu Ile Lys
            100                 105

<210> SEQ ID NO 168
<211> LENGTH: 112
<212> TYPE: PRT
<213> ORGANISM: Artificial Sequence
<220> FEATURE:
<223> OTHER INFORMATION: Synthetically generated peptide

<400> SEQUENCE: 168

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 169
<211> LENGTH: 112
<212> TYPE: PRT
<213> ORGANISM: Artificial Sequence
<220> FEATURE:
<223> OTHER INFORMATION: Synthetically generated peptide

<400> SEQUENCE: 169

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45
```

Pro Gln Leu Leu Ile Tyr Leu Gly Ser Asn Arg Ala Ser Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Leu Thr Phe Gly Gly Gly Thr Lys Val Glu Ile Lys
            100                 105                 110

<210> SEQ ID NO 170
<211> LENGTH: 112
<212> TYPE: PRT
<213> ORGANISM: Artificial Sequence
<220> FEATURE:
<223> OTHER INFORMATION: Synthetically generated peptide

<400> SEQUENCE: 170

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Phe Thr Phe Gly Pro Gly Thr Lys Val Asp Ile Lys
            100                 105                 110

<210> SEQ ID NO 171
<211> LENGTH: 107
<212> TYPE: PRT
<213> ORGANISM: Artificial Sequence
<220> FEATURE:
<223> OTHER INFORMATION: Synthetically generated peptide

<400> SEQUENCE: 171

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Ile
                 85                  90                  95

Thr Phe Gly Gln Gly Thr Arg Leu Glu Ile Lys
            100                 105

<210> SEQ ID NO 172
<211> LENGTH: 108
<212> TYPE: PRT
<213> ORGANISM: Artificial Sequence

```
<220> FEATURE:
<223> OTHER INFORMATION: Synthetically generated peptide

<400> SEQUENCE: 172

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 173
<211> LENGTH: 108
<212> TYPE: PRT
<213> ORGANISM: Artificial Sequence
<220> FEATURE:
<223> OTHER INFORMATION: Synthetically generated peptide

<400> SEQUENCE: 173

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 174
<211> LENGTH: 107
<212> TYPE: PRT
<213> ORGANISM: Artificial Sequence
<220> FEATURE:
<223> OTHER INFORMATION: Synthetically generated peptide

<400> SEQUENCE: 174

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro Leu
                 85                  90                  95

Thr Phe Gly Gly Gly Thr Lys Val Glu Ile Lys
            100                 105

<210> SEQ ID NO 175
<211> LENGTH: 107
<212> TYPE: PRT
<213> ORGANISM: Artificial Sequence
<220> FEATURE:
<223> OTHER INFORMATION: Synthetically generated peptide

<400> SEQUENCE: 175

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
                 20                  25                  30

Leu Gly Trp Tyr Gln Gln Lys Pro Gly Lys Ala Pro Lys Arg Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Val Glu Ile Lys
            100                 105

<210> SEQ ID NO 176
<211> LENGTH: 107
<212> TYPE: PRT
<213> ORGANISM: Artificial Sequence
<220> FEATURE:
<223> OTHER INFORMATION: Synthetically generated peptide

<400> SEQUENCE: 176

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Phe
                 85                  90                  95

Thr Phe Gly Pro Gly Thr Lys Val Asp Ile Lys
            100                 105

<210> SEQ ID NO 177
<211> LENGTH: 110
<212> TYPE: PRT
<213> ORGANISM: Artificial Sequence
<220> FEATURE:
<223> OTHER INFORMATION: Synthetically generated peptide
```

```
<400> SEQUENCE: 177

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65              70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu
            100                 105                 110

<210> SEQ ID NO 178
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 178

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65              70                  75                  80

Gln Ala Glu Asp Glu Ala Asp Tyr Tyr Cys Ser Ser Tyr Ala Gly Ser
                85                  90                  95

Asn Asn Phe Tyr Val Phe Gly Thr Gly Thr Lys Val Thr Val Leu
            100                 105                 110

<210> SEQ ID NO 179
<211> LENGTH: 233
<212> TYPE: PRT
<213> ORGANISM: Artificial Sequence
<220> FEATURE:
<223> OTHER INFORMATION: Synthetically generated peptide

<400> SEQUENCE: 179

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
                20                  25                  30

Ser Val Gly Asp Arg Val Thr Ile Thr Cys Arg Ala Ser Gln Gly Ile
            35                  40                  45

Arg Asn Phe Leu Ala Trp Tyr Gln Gln Lys Pro Gly Lys Val Pro Lys
    50                  55                  60

Leu Leu Ile Tyr Gly Ala Ser Ala Leu Gln Ser Gly Val Pro Ser Arg
65              70                  75                  80
```

-continued

```
Phe Ser Gly Ser Gly Ser Gly Thr Asp Phe Thr Leu Thr Ile Ser Ser
             85                  90                  95

Leu Gln Pro Glu Asp Val Ala Thr Tyr Tyr Cys Gln Lys Tyr Asn Gly
            100                 105                 110

Val Pro Leu Thr Phe Gly Gly Gly Thr Lys Val Glu Ile Lys Arg Thr
            115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
            165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230

<210> SEQ ID NO 180
<211> LENGTH: 469
<212> TYPE: PRT
<213> ORGANISM: Artificial Sequence
<220> FEATURE:
<223> OTHER INFORMATION: Synthetically generated peptide

<400> SEQUENCE: 180

Met Gly Trp Ser Cys Ile Ile Leu Phe Leu Val Ala Thr Ala Thr Gly
1               5                   10                  15

Ala His Ser Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Val Tyr Gly Met Val Trp Val Arg Gln Ala Pro Gly Lys Gly Leu
50                  55                  60

Glu Trp Val Ser Val Ile Ser Ser Gly Gly Ser Thr Trp Tyr Ala
65                  70                  75                  80

Asp Ser Val Lys Gly Arg Phe Thr Ile Ser Arg Asp Asn Ser Lys Asn
            85                  90                  95

Thr Leu Tyr Leu Gln Met Asn Ser Leu Arg Ala Glu Asp Thr Ala Val
            100                 105                 110

Tyr Tyr Cys Ala Arg Pro Phe Ser Arg Arg Tyr Gly Val Phe Asp Tyr
            115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
            165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205
```

```
Thr Val Pro Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 181
<211> LENGTH: 234
<212> TYPE: PRT
<213> ORGANISM: Artificial Sequence
<220> FEATURE:
<223> OTHER INFORMATION: Synthetically generated peptide

<400> SEQUENCE: 181

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Ser Val
        35                  40                  45

Gly Thr Tyr Leu Asn Trp Tyr Gln Gln Lys Pro Gly Lys Ala Pro Lys
    50                  55                  60

Leu Leu Ile Tyr Ala Thr Ser Asn Leu Arg Gly Val Pro Ser Arg
65                  70                  75                  80

Phe Ser Gly Ser Gly Ser Gly Thr Asp Phe Thr Leu Thr Ile Ser Ser
                85                  90                  95
```

```
Leu Gln Pro Glu Asp Phe Ala Thr Tyr Tyr Cys Gln Gln Ser Tyr Ser
            100                 105                 110

Ile Pro Arg Phe Thr Phe Gly Pro Gly Thr Lys Val Asp Ile Lys Arg
            115                 120                 125

Thr Val Ala Ala Pro Ser Val Phe Ile Phe Pro Ser Asp Glu Gln
            130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 182
<211> LENGTH: 464
<212> TYPE: PRT
<213> ORGANISM: Artificial Sequence
<220> FEATURE:
<223> OTHER INFORMATION: Synthetically generated peptide

<400> SEQUENCE: 182

Met Gly Trp Ser Cys Ile Ile Leu Phe Leu Val Ala Thr Ala Thr Gly
1               5                   10                  15

Ala His Ser Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Leu Tyr Ser Met Asn Trp Val Arg Gln Ala Pro Gly Lys Gly Leu
    50                  55                  60

Glu Trp Val Ser Ser Ile Tyr Ser Ser Gly Gly Ser Thr Leu Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gly Arg Ala Phe Asp Ile Trp Gly Gln Gly Thr
            115                 120                 125

Met Val Thr Val Ser Ser Ala Ser Thr Lys Gly Pro Ser Val Phe Pro
            130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
            195                 200                 205

Ser Leu Gly Thr Gln Thr Tyr Ile Cys Asn Val Asn His Lys Pro Ser
210                 215                 220
```

-continued

```
Asn Thr Lys Val Asp Lys Arg Val Glu Pro Lys Ser Cys Asp Lys Thr
225                 230                 235                 240

His Thr Cys Pro Pro Cys Pro Ala Pro Glu Leu Leu Gly Gly Pro Ser
            245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
            275                 280                 285

Glu Val Lys Phe Asn Trp Tyr Val Asp Gly Val Glu Val His Asn Ala
        290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
                340                 345                 350

Ile Ser Lys Ala Lys Gly Gln Pro Arg Glu Pro Gln Val Tyr Thr Leu
        355                 360                 365

Pro Pro Ser Arg Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460
```